(12) United States Patent
Sebhat et al.

(10) Patent No.: US 11,512,065 B2
(45) Date of Patent: Nov. 29, 2022

(54) GPR119 AGONISTS

(71) Applicant: Kallyope, Inc., New York, NY (US)

(72) Inventors: Iyassu Sebhat, Jersey City, NJ (US); Shuwen He, Fanwood, NJ (US); Christopher Moyes, Westfield, NJ (US)

(73) Assignee: KALLYOPE, INC., New York, NY (US)

( * ) Notice: Subject to any disclaimer, the term of this patent is extended or adjusted under 35 U.S.C. 154(b) by 0 days.

(21) Appl. No.: 17/592,348

(22) Filed: Feb. 3, 2022

(65) Prior Publication Data

US 2022/0153719 A1   May 19, 2022

Related U.S. Application Data

(63) Continuation of application No. PCT/US2020/054403, filed on Oct. 6, 2020.

(60) Provisional application No. 62/911,833, filed on Oct. 7, 2019.

(51) Int. Cl.
| | |
|---|---|
| *C07D 401/04* | (2006.01) |
| *C07D 401/14* | (2006.01) |
| *C07D 405/14* | (2006.01) |
| *A61K 31/4525* | (2006.01) |
| *A61K 31/454* | (2006.01) |
| *A61K 31/4545* | (2006.01) |
| *A61P 3/04* | (2006.01) |
| *A61P 3/10* | (2006.01) |

(52) U.S. Cl.
CPC ......... *C07D 401/04* (2013.01); *C07D 401/14* (2013.01); *C07D 405/14* (2013.01)

(58) Field of Classification Search
CPC ... C07D 401/04; C07D 401/14; C07D 405/14
See application file for complete search history.

(56) References Cited

U.S. PATENT DOCUMENTS

| 5,846,514 A | 12/1998 | Foster et al. |
| 6,334,997 B1 | 1/2002 | Foster et al. |
| 7,750,048 B2 | 7/2010 | Kuo et al. |
| 8,153,635 B2 | 4/2012 | Alper et al. |
| 2006/0177438 A1 | 8/2006 | Kopin et al. |

FOREIGN PATENT DOCUMENTS

| EP | 0697403 A1 | 2/1996 |
| EP | 2399914 A1 | 12/2011 |
| GB | 2498976 A | 8/2013 |
| KR | 101726819 B1 | 4/2017 |
| WO | WO-9314066 A1 | 7/1993 |
| WO | WO-9316982 A1 | 9/1993 |
| WO | WO-9424151 A1 | 10/1994 |
| WO | WO-9528391 A1 | 10/1995 |
| WO | WO-9528399 A1 | 10/1995 |
| WO | WO-9528419 A1 | 10/1995 |
| WO | WO-9611691 A1 | 4/1996 |
| WO | WO-9611940 A1 | 4/1996 |
| WO | WO-9632414 A1 | 10/1996 |
| WO | WO-9739031 A1 | 10/1997 |
| WO | WO-9851686 A1 | 11/1998 |
| WO | WO-9915525 A1 | 4/1999 |
| WO | WO-0068209 A2 | 11/2000 |
| WO | WO-0234743 A1 | 5/2002 |
| WO | WO-0244150 A1 | 6/2002 |
| WO | WO-02066511 A2 | 8/2002 |
| WO | WO-03104816 A1 | 12/2003 |
| WO | WO-2004041813 A1 | 5/2004 |
| WO | WO-2005035793 A2 | 4/2005 |
| WO | WO-2005051890 A1 | 6/2005 |
| WO | WO-2005095338 A1 | 10/2005 |
| WO | WO-2005116034 A1 | 12/2005 |
| WO | WO-2006011615 A1 | 2/2006 |
| WO | WO-2006083612 A1 | 8/2006 |
| WO | WO-2006083781 A1 | 8/2006 |
| WO | WO-2006117565 A2 | 11/2006 |
| WO | WO-2006128803 A1 | 12/2006 |
| WO | WO-2007067828 A2 | 6/2007 |
| WO | WO-2007088857 A1 | 8/2007 |
| WO | WO-2007120655 A2 | 10/2007 |
| WO | WO-2007120688 A2 | 10/2007 |
| WO | WO-2007123225 A1 | 11/2007 |
| WO | WO-2007136572 A2 | 11/2007 |
| WO | WO-2008028117 A2 | 3/2008 |
| WO | WO-2008054674 A2 | 5/2008 |
| WO | WO-2008054675 A2 | 5/2008 |
| WO | WO-2008056155 A1 | 5/2008 |
| WO | WO-2008063768 A2 | 5/2008 |
| WO | WO-2008067219 A2 | 6/2008 |

(Continued)

OTHER PUBLICATIONS

Berge et al. Pharmaceutical Salts. Journal of Pharmaceutical Sciences 66(1):1-19 (Jan. 1977).
Bundgard, H. Design of Prodrugs. 1985; pp. 7-9, 21-24 (Elsevier, Amsterdam).
Evans. Synthesis of radiolabeled compounds. J Radioanal Chem 64(1-2):9-32 (1981).
Kabalka et al. The Synthesis of Radiolabeled Compounds via Organometallic Intermediates. Tetrahedron 45(21):6601-6621 (1989).
PCT/US2020/054403 International Search Report and Written Opinion dated Jan. 22, 2021.
Zhu et al. Discovery of phenyl acetamides as potent and selective GPR119 agonists. Bioorg Med Chem Lett. 27(5):1124-1128 (2017).
PCT/US2022/023481 International Search Report and Written Opinion dated Jul. 25, 2022.

*Primary Examiner* — John M Mauro
(74) *Attorney, Agent, or Firm* — Wilson Sonsini Goodrich & Rosati

(57) ABSTRACT

This disclosure is directed, at least in part, to GPR119 agonists useful for the treatment of conditions or disorders involving the gut-brain axis. In some embodiments, the GPR119 agonists are gut-restricted compounds. In some embodiments, the condition or disorder is a metabolic disorder, such as diabetes, obesity, nonalcoholic steatohepatitis (NASH), or a nutritional disorder such as short bowel syndrome.

20 Claims, No Drawings

(56) References Cited

FOREIGN PATENT DOCUMENTS

| | | |
|---|---|---|
| WO | WO-2008067222 A1 | 6/2008 |
| WO | WO-2008091540 A2 | 7/2008 |
| WO | WO-2008091631 A1 | 7/2008 |
| WO | WO-2008097976 A1 | 8/2008 |
| WO | WO-2009026241 A1 | 2/2009 |
| WO | WO-2009034388 A1 | 3/2009 |
| WO | WO-2009039942 A1 | 4/2009 |
| WO | WO-2009039943 A1 | 4/2009 |
| WO | WO-2009050309 A1 | 4/2009 |
| WO | WO-2009054390 A1 | 4/2009 |
| WO | WO-2009054423 A1 | 4/2009 |
| WO | WO-2009054468 A1 | 4/2009 |
| WO | WO-2009054479 A1 | 4/2009 |
| WO | WO-2009058237 A1 | 5/2009 |
| WO | WO-2009106565 A1 | 9/2009 |
| WO | WO-2009119733 A1 | 10/2009 |
| WO | WO-2009126535 A1 | 10/2009 |
| WO | WO-2010004347 A1 | 1/2010 |
| WO | WO-2010014739 A2 | 2/2010 |
| WO | WO-2010014836 A2 | 2/2010 |
| WO | WO-2010016846 A1 | 2/2010 |
| WO | WO-2010042145 A1 | 4/2010 |
| WO | WO-2010056717 A1 | 5/2010 |
| WO | WO-2010059853 A1 | 5/2010 |
| WO | WO-2010059859 A1 | 5/2010 |
| WO | WO-2010067233 A1 | 6/2010 |
| WO | WO-2010085522 A1 | 7/2010 |
| WO | WO-2010085525 A1 | 7/2010 |
| WO | WO-2010085528 A1 | 7/2010 |
| WO | WO-2010091176 A1 | 8/2010 |
| WO | WO-2010093845 A1 | 8/2010 |
| WO | WO-2010123016 A1 | 10/2010 |
| WO | WO-2010123017 A1 | 10/2010 |
| WO | WO-2010143733 A1 | 12/2010 |
| WO | WO-2011046851 A1 | 4/2011 |
| WO | WO-2011050174 A1 | 4/2011 |
| WO | WO-2011052756 A1 | 5/2011 |
| WO | WO-2011066183 A1 | 6/2011 |
| WO | WO-2011071565 A1 | 6/2011 |
| WO | WO-2011078371 A1 | 6/2011 |
| WO | WO-2011146324 A1 | 11/2011 |
| WO | WO-2011161030 A1 | 12/2011 |
| WO | WO-2012004269 A1 | 1/2012 |
| WO | WO-2012004270 A1 | 1/2012 |
| WO | WO-2012010413 A1 | 1/2012 |
| WO | WO-2012011125 A1 | 1/2012 |
| WO | WO-2012024183 A1 | 2/2012 |
| WO | WO-2012028602 A1 | 3/2012 |
| WO | WO-2012046869 A1 | 4/2012 |
| WO | WO-2012070554 A1 | 5/2012 |
| WO | WO-2012072691 A1 | 6/2012 |
| WO | WO-2012082947 A1 | 6/2012 |
| WO | WO-2012111849 A1 | 8/2012 |
| WO | WO-2012138919 A2 | 10/2012 |
| WO | WO-2012147518 A1 | 11/2012 |
| WO | WO-2012149236 A1 | 11/2012 |
| WO | WO-2013025424 A1 | 2/2013 |
| WO | WO-2013040093 A2 | 3/2013 |
| WO | WO-2013054338 A1 | 4/2013 |
| WO | WO-2013057743 A1 | 4/2013 |
| WO | WO-2013096771 A1 | 6/2013 |
| WO | WO-2013104257 A1 | 7/2013 |
| WO | WO-2013122028 A1 | 8/2013 |
| WO | WO-2013122029 A1 | 8/2013 |
| WO | WO-2013128378 A1 | 9/2013 |
| WO | WO-2013144097 A1 | 10/2013 |
| WO | WO-2013154163 A1 | 10/2013 |
| WO | WO-2013164292 A1 | 11/2013 |
| WO | WO-2013164484 A1 | 11/2013 |
| WO | WO-2013178575 A1 | 12/2013 |
| WO | WO-2014019186 A1 | 2/2014 |
| WO | WO-2014066819 A1 | 5/2014 |
| WO | WO-2014073904 A1 | 5/2014 |
| WO | WO-2014082918 A1 | 6/2014 |
| WO | WO-2014085474 A1 | 6/2014 |
| WO | WO-2014086712 A1 | 6/2014 |
| WO | WO-2014096440 A2 | 6/2014 |
| WO | WO-2014100021 A1 | 6/2014 |
| WO | WO-2014100025 A1 | 6/2014 |
| WO | WO-2014122067 A1 | 8/2014 |
| WO | WO-2014130608 A1 | 8/2014 |
| WO | WO-2014146604 A1 | 9/2014 |
| WO | WO-2014169817 A1 | 10/2014 |
| WO | WO-2014170842 A2 | 10/2014 |
| WO | WO-2014187343 A1 | 11/2014 |
| WO | WO-2014200349 A1 | 12/2014 |
| WO | WO-2015000412 A1 | 1/2015 |
| WO | WO-2015010655 A1 | 1/2015 |
| WO | WO-2015017710 A1 | 2/2015 |
| WO | WO-2015020184 A1 | 2/2015 |
| WO | WO-2015024448 A1 | 2/2015 |
| WO | WO-2015024526 A1 | 2/2015 |
| WO | WO-2015028960 A1 | 3/2015 |
| WO | WO-2015032328 A1 | 3/2015 |
| WO | WO-2015044073 A1 | 4/2015 |
| WO | WO-2015051496 A1 | 4/2015 |
| WO | WO-2015052910 A1 | 4/2015 |
| WO | WO-2015062486 A1 | 5/2015 |
| WO | WO-2015073342 A1 | 5/2015 |
| WO | WO-2015078802 A1 | 6/2015 |
| WO | WO-2015084692 A1 | 6/2015 |
| WO | WO-2015088868 A1 | 6/2015 |
| WO | WO-2015089809 A1 | 6/2015 |
| WO | WO-2015097713 A1 | 7/2015 |
| WO | WO-2015105779 A1 | 7/2015 |
| WO | WO-2015105786 A1 | 7/2015 |
| WO | WO-2015119899 A1 | 8/2015 |
| WO | WO-2015160772 A1 | 10/2015 |
| WO | WO-2015176267 A1 | 11/2015 |
| WO | WO-2015181275 A1 | 12/2015 |
| WO | WO-2015183794 A1 | 12/2015 |
| WO | WO-2015198199 A1 | 12/2015 |
| WO | WO-2016000771 A1 | 1/2016 |
| WO | WO-2016019587 A1 | 2/2016 |
| WO | WO-2016022446 A1 | 2/2016 |
| WO | WO-2016022448 A1 | 2/2016 |
| WO | WO-2016022742 A1 | 2/2016 |
| WO | WO-2016032120 A1 | 3/2016 |
| WO | WO-2016054208 A1 | 4/2016 |
| WO | WO-2016057731 A1 | 4/2016 |
| WO | WO-2016066818 A1 | 5/2016 |
| WO | WO-2016073767 A1 | 5/2016 |
| WO | WO-2016086115 A1 | 6/2016 |
| WO | WO-2016130809 A1 | 8/2016 |
| WO | WO-2016161003 A1 | 10/2016 |
| WO | WO-2016205032 A1 | 12/2016 |
| WO | WO-2016205475 A2 | 12/2016 |
| WO | WO-2017002786 A1 | 1/2017 |
| WO | WO-2017005765 A1 | 1/2017 |
| WO | WO-2017025368 A1 | 2/2017 |
| WO | WO-2017027309 A1 | 2/2017 |
| WO | WO-2017027310 A1 | 2/2017 |
| WO | WO-2017027312 A1 | 2/2017 |
| WO | WO-2017027396 A1 | 2/2017 |
| WO | WO-2017042121 A1 | 3/2017 |
| WO | WO-2017053826 A1 | 3/2017 |
| WO | WO-2017079062 A1 | 5/2017 |
| WO | WO-2017106818 A1 | 6/2017 |
| WO | WO-2017147137 A1 | 8/2017 |
| WO | WO-2017147159 A1 | 8/2017 |
| WO | WO-2017147174 A1 | 8/2017 |
| WO | WO-2017147742 A1 | 9/2017 |
| WO | WO-2017172505 A1 | 10/2017 |
| WO | WO-2017180571 A1 | 10/2017 |
| WO | WO-2017180577 A1 | 10/2017 |
| WO | WO-2018005794 A2 | 1/2018 |
| WO | WO-2018005801 A2 | 1/2018 |
| WO | WO-2018009778 A1 | 1/2018 |
| WO | WO-2018064441 A1 | 4/2018 |
| WO | WO-2018071493 A1 | 4/2018 |
| WO | WO-2018077699 A1 | 5/2018 |
| WO | WO-2018081047 A1 | 5/2018 |
| WO | WO-2018095877 A1 | 5/2018 |

(56) References Cited

FOREIGN PATENT DOCUMENTS

| | | |
|---|---|---|
| WO | WO-2018103868 A1 | 6/2018 |
| WO | WO-2018104558 A1 | 6/2018 |
| WO | WO-2018104559 A1 | 6/2018 |
| WO | WO-2018104560 A1 | 6/2018 |
| WO | WO-2018104561 A1 | 6/2018 |
| WO | WO-2018106518 A1 | 6/2018 |
| WO | WO-2018111012 A1 | 6/2018 |
| WO | WO-2018118670 A1 | 6/2018 |
| WO | WO-2018138026 A1 | 8/2018 |
| WO | WO-2018138027 A1 | 8/2018 |
| WO | WO-2018138028 A1 | 8/2018 |
| WO | WO-2018138029 A1 | 8/2018 |
| WO | WO-2018138030 A1 | 8/2018 |
| WO | WO-2018142363 A1 | 8/2018 |
| WO | WO-2018146008 A1 | 8/2018 |
| WO | WO-2018172727 A1 | 9/2018 |
| WO | WO-2018181847 A1 | 10/2018 |
| WO | WO-2018182050 A1 | 10/2018 |
| WO | WO-2018219204 A1 | 12/2018 |
| WO | WO-2018222701 A1 | 12/2018 |
| WO | WO-2018226724 A1 | 12/2018 |
| WO | WO-2018229252 A1 | 12/2018 |
| WO | WO-2018237350 A1 | 12/2018 |
| WO | WO-2019040399 A1 | 2/2019 |
| WO | WO-2019086559 A1 | 5/2019 |
| WO | WO-2019090209 A1 | 5/2019 |
| WO | WO-2019099315 A1 | 5/2019 |
| WO | WO-2019134984 A1 | 7/2019 |
| WO | WO-2020197926 A1 | 10/2020 |
| WO | WO-2020242943 A1 | 12/2020 |
| WO | WO-2021071837 A1 | 4/2021 |
| WO | WO-2021113362 A1 | 6/2021 |
| WO | WO-2021113363 A1 | 6/2021 |
| WO | WO-2021113368 A1 | 6/2021 |
| WO | WO-2021174046 A1 | 9/2021 |
| WO | WO-2021174048 A1 | 9/2021 |

GPR119 AGONISTS

CROSS-REFERENCE TO RELATED APPLICATIONS

This application is a continuation of International Application Serial No. PCT/US2020/054403, filed Oct. 6, 2020, which claims the benefit of U.S. Provisional Application No. 62/911,833 filed on Oct. 7, 2019, which is incorporated herein by reference in its entirety.

BRIEF SUMMARY OF THE INVENTION

Disclosed herein, in certain embodiments, are G protein-coupled receptor 119 (GPR119) agonists useful for the treatment of conditions or disorders involving the gut-brain axis. In some embodiments, the GPR119 agonists are gut-restricted or selectively modulate GPR119 located in the gut. In some embodiments, the condition is selected from the group consisting of: central nervous system (CNS) disorders including mood disorders, anxiety, depression, affective disorders, schizophrenia, malaise, cognition disorders, addiction, autism, epilepsy, neurodegenerative disorders, Alzheimer's disease, and Parkinson's disease, Lewy Body dementia, episodic cluster headache, migraine, pain; metabolic conditions including diabetes and its complications such as chronic kidney disease/diabetic nephropathy, diabetic retinopathy, diabetic neuropathy, and cardiovascular disease, metabolic syndrome, obesity, dyslipidemia, and nonalcoholic steatohepatitis (NASH); eating and nutritional disorders including hyperphagia, cachexia, anorexia nervosa, short bowel syndrome, intestinal failure, intestinal insufficiency and other eating disorders; inflammatory disorders and autoimmune diseases such as inflammatory bowel disease, ulcerative colitis, Crohn's disease, psoriasis, celiac disease, and enteritis, including chemotherapy-induced enteritis or radiation-induced enteritis; necrotizing enterocolitis; diseases/disorders of gastrointestinal barrier dysfunction including environmental enteric dysfunction, spontaneous bacterial peritonitis; functional gastrointestinal disorders such as irritable bowel syndrome, functional dyspepsia, functional abdominal bloating/distension, functional diarrhea, functional constipation, and opioid-induced constipation; gastroparesis; nausea and vomiting; disorders related to microbiome dysbiosis, and other conditions involving the gut-brain axis.

Disclosed herein, in certain embodiments, is a compound of Formula (I):

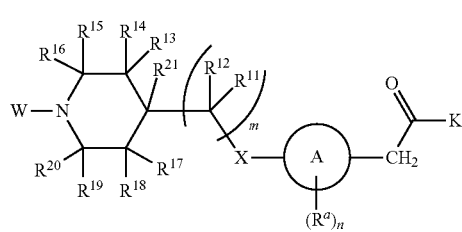

Formula (I)

or a pharmaceutically acceptable salt, solvate, stereoisomer, or prodrug thereof, wherein:

K is

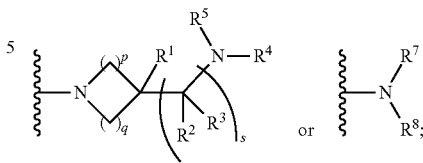

$R^1$ is hydrogen, —OH, $C_{1-8}$ alkyl, $C_{3-8}$ cycloalkyl, or 3- to 8-membered heterocycloalkyl, wherein the alkyl, cycloalkyl, and heterocycloalkyl are unsubstituted or substituted by 1-3 substituents independently selected from halogen, —OH, and —O($C_{1-6}$ alkyl);

each $R^2$ and $R^3$ is independently hydrogen, $C_{1-6}$ alkyl, or $C_{1-6}$ fluoroalkyl;

or $R^2$ and $R^3$ on the same carbon atom are taken together to form =O;

$R^4$ is hydrogen, $C_{1-8}$ alkyl, $C_{1-8}$ fluoroalkyl, $C_{2-8}$ alkenyl, $C_{2-8}$ alkynyl, $C_{3-8}$ cycloalkyl, $C_{5-8}$ cycloalkenyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein each alkyl, fluoroalkyl, alkenyl, alkynyl, cycloalkyl, cycloalkenyl, and 4- to 8-membered heterocycloalkyl is unsubstituted or substituted by 1-6 R$^c$ groups;

$R^5$ is $C_{1-8}$ alkyl, $C_{1-8}$ fluoroalkyl, $C_{2-8}$ alkenyl, $C_{2-8}$ alkynyl, $C_{3-8}$ cycloalkyl, $C_{5-8}$ cycloalkenyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$;

wherein each alkyl, fluoroalkyl, alkenyl, alkynyl, cycloalkyl, cycloalkenyl, and 4- to 8-membered heterocycloalkyl is substituted by 1-6 R$^c$ groups;

each Z is independently —CH$_2$O—, —CH$_2$NR$^d$—, —CH$_2$N$^+$(R$^d$)$_2$—, —NH—C(=O)—NH—, —C(=O)NH—, —CH$_2$S(=O)$_2$—, or —CH$_2$S(=O)—;

each r is independently 1-6;

each t is independently 1-6;

$R^6$ is hydrogen, $C_{1-8}$ alkyl, $C_{1-8}$ fluoroalkyl, $C_{2-8}$ alkenyl, $C_{2-8}$ alkynyl, $C_{3-8}$ cycloalkyl, $C_{5-8}$ cycloalkenyl, or 4- to 8-membered heterocycloalkyl, wherein the alkyl, fluoroalkyl, alkenyl, alkynyl, cycloalkyl, cycloalkenyl, or 4- to 8-membered heterocycloalkyl is unsubstituted or substituted by 1-6 R$^c$ groups;

or $R^4$ and $R^5$ are taken together with the nitrogen to which they are attached to form a 4- to 8-membered heterocycloalkyl, which is unsubstituted or substituted by 1-6 R$^c$ groups;

$R^7$ is hydrogen, $C_{1-4}$ alkyl, or $C_{1-4}$ fluoroalkyl;

$R^8$ is $C_{1-8}$ alkyl, $C_{1-8}$ fluoroalkyl, $C_{2-8}$ alkenyl, $C_{2-8}$ alkynyl, $C_{3-8}$ cycloalkyl, $C_{5-8}$ cycloalkenyl, 4- to 8-membered heterocycloalkyl, —[(CH$_2$)$_r$—Z]$_t$—R$^6$, —[(CHR$^d$)$_r$—Z]$_t$—R$^6$, or —[(CR$^d_2$)$_r$—Z]$_t$—R$^6$;

wherein each alkyl, fluoroalkyl, alkenyl, alkynyl, cycloalkyl, cycloalkenyl, and 4- to 8-membered heterocycloalkyl is substituted by 1-6 R$^c$ groups;

or $R^8$ is —(C$_{1-8}$ alkyl)-NH—R$^9$, —(C$_{1-8}$ alkyl)-C(=O)NH—R$^9$, —(C$_{1-8}$ alkyl)-C(=O)—N(R$^9$)$_2$, or —(C$_{1-8}$ alkyl)-NHC(=O)NH—R$^9$; wherein the alkyl is unsubstituted or substituted by 1-6 R$^c$ groups; each R$^9$ is independently $C_{1-8}$ alkyl, or $C_{1-8}$ fluoroalkyl which is substituted by 1-6 R$^c$ groups; or two R$^9$ are taken together with the nitrogen to which they are attached to form a 4- to 6-membered heterocycloalkyl, which is substituted by 1-6 R$^c$ groups;

each R$^c$ is independently —OH, —CH$_2$OH, —CH$_2$CH$_2$OH, —NH$_2$, —CH$_2$NH$_2$, —NH(R$^d$), —CH$_2$NH(R$^d$), —N(R$^d$)$_2$, —CH$_2$N(R$^d$)$_2$, —N(R$^d$)$_3^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), —P(=O)(OH)(OR$^d$), —B(OH)$_2$, —B(OR$^d$)(OH), —NHCONHS(=O)$_2$(R$^d$), —N(R$^d$)CONHS(=O)$_2$(R$^d$), —NHCON(R$^d$)S(=O)$_2$(R$^d$), —C(=O)NHS(=O)$_2$(R$^d$), —S(=O)$_2$NHC(=O)R$^d$, —NHC(=NH)NH$_2$, —NHC(=NH)NHR$^d$, —NHC(=NH)N(R$^d$)$_2$, —N(R$^d$)C(=NH)NH$_2$, —N(R$^d$)C(=NH)NH(R$^d$), —N(R$^d$)C(=NH)N(R$^d$)$_2$, —NHC(=N(R$^d$))NH$_2$, —NHC(=N(R$^d$))NHR$^d$, —NHC(=N(R$^d$))N(R$^d$)$_2$, —N(R$^d$)C(=N(R$^d$))NH$_2$, —N(R$^d$)C(=N(R$^d$))NHR$^d$, —N(R$^d$)C(=N(R$^d$))N(R$^d$)$_2$, —NHC(=NH)NHC(=NH)NH$_2$, —N(R$^d$)C(=NH)NHC(=NH)NH$_2$,

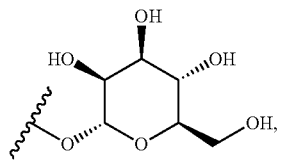

or a 4- to 6-membered heterocycle which is unsubstituted or substituted with 1, 2, 3, or 4 substituents selected from $C_{1-6}$ alkyl, —O—($C_{1-6}$ alkyl), —OH, =O and =S;

each R$^d$ is independently $C_{1-6}$ alkyl, $C_{1-6}$ fluoroalkyl, or $C_{3-6}$ cycloalkyl;

each R$^e$ is independently —OH, —CH$_2$OH, —CH$_2$CH$_2$OH, —N(R$^d$)$_3^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), —P(=O)(OH)(OR$^d$), —B(OH)$_2$, —B(OR$^d$)(OH), —NHCONHS(=O)$_2$(R$^d$), —N(R$^d$)CONHS(=O)$_2$(R$^d$), —NHCON(R$^d$)S(=O)$_2$(R$^d$), —C(=O)NHS(=O)$_2$(R$^d$), —S(O)$_2$NHC(O)R$^d$, —NHC(=NH)NH$_2$, —NHC(=NH)NHR$^d$, —NHC(=NH)N(R$^d$)$_2$, —N(R$^d$)C(=NH)NH$_2$, N(R$^d$)C(=NH)NH(R$^d$), —N(R$^d$)C(=NH)N(R$^d$)$_2$, —NHC(=N(R$^d$))NH$_2$, —NHC(=N(R$^d$))NHR$^d$, —NHC(=N(R$^d$))N(R$^d$)$_2$, —N(R$^d$)C(=N(R$^d$))NH$_2$, —N(R$^d$)C(=N(R$^d$))NHR$^d$, —N(R$^d$)C(=N(R$^d$))N(R$^d$)$_2$, —NHC(=NH)NHC(=NH)NH$_2$, N(R$^d$)C(=NH)NHC(=NH)NH$_2$,

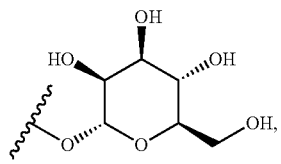

or a 4- to 6-membered heterocycle which is unsubstituted or substituted with 1, 2, 3, or 4 substituents selected from $C_{1-6}$ alkyl, —O—($C_{1-6}$ alkyl), —OH, =O and =S;

Ring A is phenyl or 5-6 membered monocyclic heteroaryl;

each R$^a$ is independently halogen, —CN, $C_{1-6}$ alkyl, $C_{1-6}$ fluoroalkyl, or $C_{3-6}$ cycloalkyl;

X, when K is

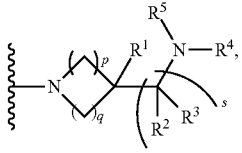

is —O—, —NR$^N$—, *—CH$_2$O—, *—CH$_2$NR$^N$—, *—C(=O)O—, *—C(=O)NR$^N$—, *—CH$_2$C(=O)O—, *—CH$_2$C(=O)NR$^N$—, *—OC(=O)—, *—NR$^N$C(=O)—, *—CH$_2$OC(=O)—, or *—CH$_2$NR$^N$C(=O)—, where * represents the attachment point to Ring A;

R$^N$ is hydrogen or $C_{1-4}$ alkyl;

or X, when K is

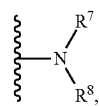

is —O—, —NR$^N$—, *—CH$_2$O—, *—CH$_2$NR$^N$—, *—C(=O)O—, *—C(=O)NR$^N$—, *—CH$_2$C(=O)O—, *—CH$_2$C(=O)NR$^N$—, *—OC(=O)—, *—CH$_2$OC(=O)—, or *—CH$_2$NR$^N$C(=O)—, where * represents the attachment point to Ring A;

R$^N$ is hydrogen or $C_{1-4}$ alkyl;

each R$^{11}$ is independently hydrogen, fluorine, —OH, $C_{1-6}$ alkyl, or $C_{1-6}$ alkoxy;

each R$^{12}$ is independently hydrogen, fluorine, or $C_{1-6}$ alkyl;

or, when K is

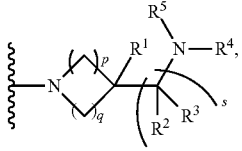

two R$^{11}$ are taken together with the intervening atoms to which they are attached to form a $C_{3-6}$ cycloalkyl;

or, when K is

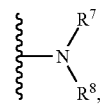

two R$^{11}$ are taken together with the intervening atoms to which they are attached to form a $C_{4-6}$ cycloalkyl;

R$^{13}$, R$^{14}$, R$^{15}$, R$^{16}$, R$^{17}$, R$^{18}$, R$^{19}$, and R$^{20}$ are each independently hydrogen, $C_{1-6}$ alkyl, $C_{1-6}$ alkoxy, or $C_{1-6}$ fluoroalkyl;

or R$^{13}$ and R$^{17}$ or R$^{13}$ and R$^{19}$ or R$^{15}$ and R$^{19}$ are taken together with the intervening atoms to which they are attached to form a ring;

R$^{21}$ is hydrogen, $C_{1-6}$ alkyl, or $C_{1-6}$ fluoroalkyl;

or R$^{21}$ and one R$^{11}$ are taken together with the intervening atoms to which they are attached to form a $C_{3-6}$ cycloalkyl;

W is phenyl or 5-6 membered monocyclic heteroaryl, wherein the phenyl or heteroaryl is unsubstituted or substituted with 1, 2, or 3 substituents selected from R$^b$;

each $R^b$ is independently halogen, —OH, —CN, —C(O)OH, —C(O)O($C_{1-6}$ alkyl), $C_{1-6}$ alkyl, $C_{1-6}$ alkoxy, $C_{3-6}$ cycloalkyl, phenyl, or 5- to 6-membered heteroaryl; wherein each alkyl, alkoxy, and cycloalkyl is unsubstituted or substituted with 1, 2, or 3 substituents selected from halogen, —OH, $C_{1-6}$ alkyl, and $C_{1-6}$ alkoxy;

or W is —C(=O)O—$R^{22}$;

$R^{22}$ is $C_{1-6}$ alkyl, $C_{3-6}$ cycloalkyl, or 3- to 6-membered heterocycloalkyl, wherein the alkyl, cycloalkyl, and heterocycloalkyl are unsubstituted or substituted by 1-3 substituents independently selected from fluorine, —OH, $C_{1-6}$ alkyl, $C_{1-6}$ haloalkyl or $C_{3-6}$ cycloalkyl;

m is 1-4;
n is 0-4;
p is 1 or 2;
q is 1 or 2; and
s is 1 or 2

In some embodiments, the compound of Formula (I) is a compound of Formula (Ia):

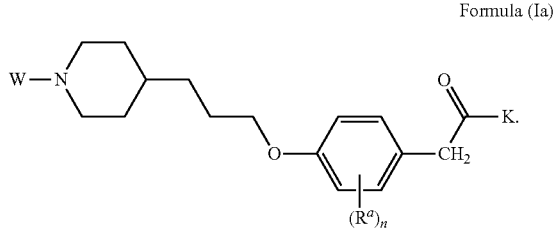

Formula (Ia)

or a pharmaceutically acceptable salt, solvate, stereoisomer, or prodrug thereof.

In some embodiments, the compound of Formula (I) is a compound of Formula (Ib):

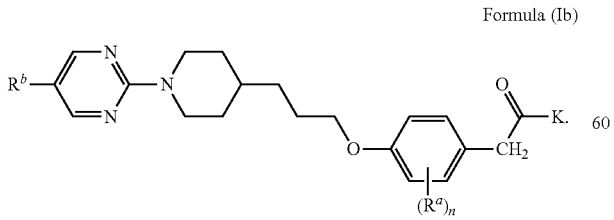

Formula (Ib)

or a pharmaceutically acceptable salt, solvate, stereoisomer, or prodrug thereof.

In some embodiments, the compound of Formula (I) is a compound of Formula (II):

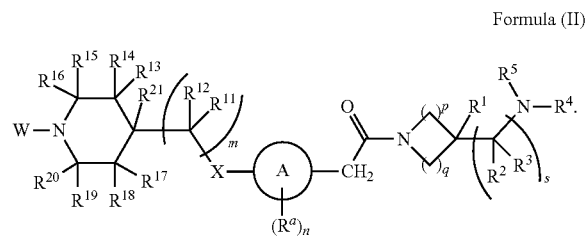

Formula (II)

or a pharmaceutically acceptable salt, solvate, stereoisomer, or prodrug thereof.

In some embodiments, the compound of Formula (II) is a compound of Formula (IIa):

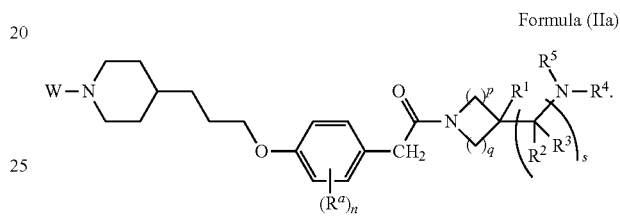

Formula (IIa)

or a pharmaceutically acceptable salt, solvate, stereoisomer, or prodrug thereof.

In some embodiments, the compound of Formula (II) is a compound of Formula (IIb):

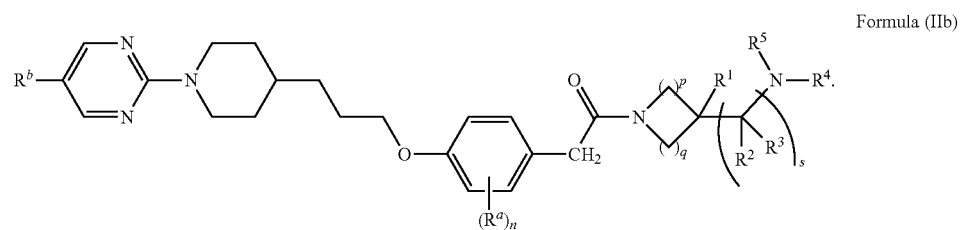

Formula (IIb)

or a pharmaceutically acceptable salt, solvate, stereoisomer, or prodrug thereof.

In some embodiments, the compound of Formula (II) is a compound of Formula (IIc) or Formula (IId):

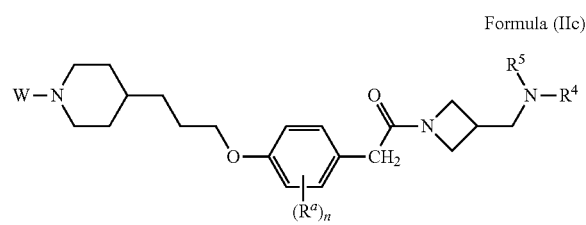

Formula (IIc)

-continued

Formula (IId)

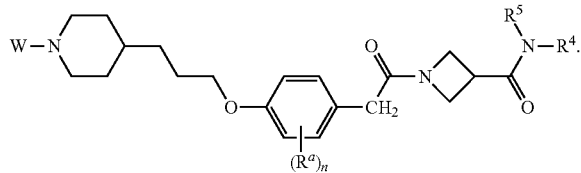

or a pharmaceutically acceptable salt, solvate, stereoisomer, or prodrug thereof.

In some embodiments, the compound of Formula (I) is a compound of Formula (III):

Formula (III)

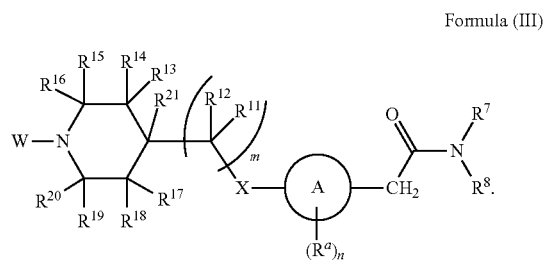

or a pharmaceutically acceptable salt, solvate, stereoisomer, or prodrug thereof.

In some embodiments, the compound of Formula (III) is a compound of Formula (IIIa):

Formula (IIIa)

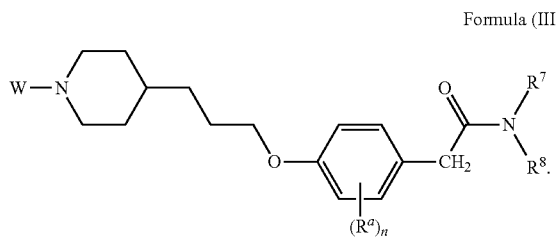

or a pharmaceutically acceptable salt, solvate, stereoisomer, or prodrug thereof.

In some embodiments, the compound of Formula (III) is a compound of Formula (IIIb):

Formula (IIIb)

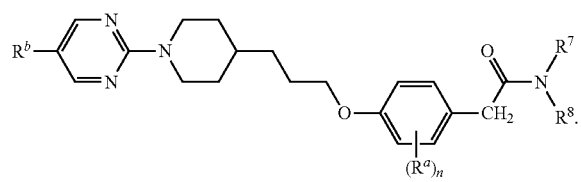

or a pharmaceutically acceptable salt, solvate, stereoisomer, or prodrug thereof.

Disclosed herein, in certain embodiments, are pharmaceutical compositions comprising a compound disclosed herein, or a pharmaceutically acceptable salt, solvate, stereoisomer, or prodrug thereof, and at least one pharmaceutically acceptable excipient.

Disclosed herein, in certain embodiments, are methods of treating a condition or disorder involving the gut-brain axis in a subject in need thereof, the method comprising administering to the subject a therapeutically effective amount of a compound disclosed herein, or a pharmaceutically acceptable salt, solvate, stereoisomer, or prodrug thereof. In some embodiments, the condition or disorder is associated with GPR119 activity. In some embodiments, the condition or disorder is a metabolic disorder. In some embodiments, the condition or disorder is type 2 diabetes, hyperglycemia, metabolic syndrome, obesity, hypercholesterolemia, nonalcoholic steatohepatitis, or hypertension. In some embodiments, the condition or disorder is a nutritional disorder. In some embodiments, the condition or disorder is short bowel syndrome, intestinal failure, or intestinal insufficiency. In some embodiments, the condition or disorder is chemotherapy-induced enteritis or radiation-induced enteritis. In some embodiments, the compound disclosed herein is gut-restricted. In some embodiments, the compound disclosed herein has low systemic exposure.

In some embodiments, the methods disclosed herein further comprise administering one or more additional therapeutic agents to the subject. In some embodiments, the one or more additional therapeutic agents are selected from a TGR5 agonist, a GPR40 agonist, an SSTR5 antagonist, an SSTR5 inverse agonist, a CCK1 agonist, a PDE4 inhibitor, a DPP-4 inhibitor, a GLP-1 receptor agonist, metformin, or a combination thereof. In some embodiments, the TGR5 agonist, GPR40 agonist, SSTR5 antagonist, SSTR5 inverse agonist, or CCK1 agonist is gut-restricted.

Also disclosed herein, in certain embodiments, is the use of a compound disclosed herein, or a pharmaceutically acceptable salt, solvate, stereoisomer, or prodrug thereof, for the preparation of a medicament for the treatment of a condition or disorder involving the gut-brain axis in a subject in need thereof.

Also disclosed herein, in certain embodiments, are methods of treating a condition or disorder involving the gut-brain axis in a subject in need thereof, the method comprising administering to the subject a therapeutically effective amount of a gut-restricted GPR119 modulator.

Also disclosed herein, in certain embodiments, is the use of a gut-restricted GPR119 modulator for the preparation of a medicament for the treatment of a condition or disorder involving the gut-brain axis in a subject in need thereof.

DETAILED DESCRIPTION OF THE INVENTION

This disclosure is directed, at least in part, to GPR119 agonists useful for the treatment of conditions or disorders involving the gut-brain axis. In some embodiments, the GPR119 agonists are gut-restricted compounds.

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulas, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range, in some instances, will vary between 1% and 15% of the stated number or numerical range.

The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below:

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e., groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

"Alkyl" refers to an optionally substituted straight-chain, or optionally substituted branched-chain saturated hydrocarbon monoradical having from one to about ten carbon atoms, or more preferably, from one to six carbon atoms, wherein an $sp^3$-hybridized carbon of the alkyl residue is attached to the rest of the molecule by a single bond. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted as described below by one or more of the following substituents: halo, cyano, nitro, oxo, thioxo, imino, oximo, trimethylsilanyl, —OR$^a$, —SR$^a$, —OC(O)R$^a$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^a$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R is independently alkyl, haloalkyl, cycloalkyl, aryl, aralkyl, heterocycloalkyl, heteroaryl or heteroarylalkyl.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein an $sp^2$-hybridized carbon or an $sp^3$-hybridized carbon of the alkenyl residue is attached to the rest of the molecule by a single bond. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl (—C(CH$_3$)=CH$_2$), butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. Unless stated otherwise specifically in the specification, an alkenyl group is optionally substituted as described below by one or more of the following substituents: halo, cyano, nitro, oxo, thioxo, imino, oximo, trimethylsilanyl, —OR$^a$, —SR$^a$, —OC(O)—R$^f$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR, —OC(O)—N(R$^a$)$_2$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms, wherein an sp-hybridized carbon or an $sp^3$-hybridized carbon of the alkynyl residue is attached to the rest of the molecule by a single bond. Examples include, but are not limited to ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted as described below by one or more of the following substituents: halo, cyano, nitro, oxo, thioxo, imino, oximo, trimethylsilanyl, —OR$^a$, —SR$^a$, —OC(O)R$^a$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. Unless stated otherwise specifically in the specification, an alkylene group is optionally substituted as described below by one or more of the following substituents: halo, cyano, nitro, oxo, thioxo, imino, oximo, trimethylsilanyl, —OR$^a$, —SR$^a$, —OC(O)R$^a$, —OC(O)—OR, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each f is independently alkyl, haloalkyl, cycloalkyl, aryl, aralkyl, heterocycloalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. Unless stated otherwise specifically in the specification, an alkenylene group is optionally substituted as described below by one or more of the following substituents: halo, cyano, nitro, oxo, thioxo, imino, oximo, trimethylsilanyl, —OR$^a$, —SR$^a$, —OC(O)—R$^E$, —OC(O)—OR, —N(R$^a$)$_2$, —N$^+$(R$^a$)$_3$, —C(O)R$^a$, —C(O)OR$^a$, —C(O)N(R$^a$)$_2$, —N(R$^a$)C(O)OR, —OC(O)—N(R$^a$)$_2$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each R is independently alkyl, haloalkyl, cycloalkyl, aryl, aralkyl, heterocycloalkyl, heteroaryl or heteroarylalkyl.

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. Unless stated otherwise specifically in the specification, an alkynylene group is optionally substituted as described below by one or more of the following substituents: halo, cyano, nitro, oxo, thioxo, imino, oximo, trimethylsilanyl, —OR$^a$, —SR$^a$, —OC(O)R$^a$, —OC(O)—OR$^f$, —N(R$^a$)$_2$, —N$^+$(R$^a$)$_3$, —C(O)R$^a$, —C(O)OR$^a$, —C(O)N(R$^a$)$_2$, —N(R$^a$)C(O)OR$^f$, —OC(O)—N(R$^a$)$_2$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl or heteroarylalkyl, and each f is independently alkyl, haloalkyl, cycloalkyl, aryl, aralkyl, heterocycloalkyl, heteroaryl or heteroarylalkyl.

"Alkoxy" or "alkoxyl" refers to a radical bonded through an oxygen atom of the formula —O-alkyl, where alkyl is an alkyl chain as defined above.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from 6 to 18 carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. In some embodiments, the aryl is a $C_6$-$C_{10}$ aryl. In some embodiments, the aryl is a phenyl. Unless stated otherwise specifically in the specification, the term "aryl" or the prefix "ar-" (such as in "aralkyl") is meant to include aryl radicals optionally substituted as described below by one or more substituents independently selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —R$^b$—OR$^a$, —R$^b$—SR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—N$^+$(R$^a$)$_3$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR, —R$^b$—N(R$^a$)C(O)R$^a$, —R$^b$—N(R$^a$)S(O)$_t$R$^f$ (where t is 1 or 2), —R$^b$—S(O)$_t$OR$^a$ (where t is 1 or 2), —R$^b$—S(O)$_t$R$^f$ (where t is 1 or 2) and —R$^b$—S(O)$_t$N(R$^a$)$_2$ (where t is 1 or 2), where each R$^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, f is independently alkyl, haloalkyl, cycloalkyl, cycloalkylalkyl, aryl (optionally substituted with one or more halo groups), aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

An "arylene" refers to a divalent radical derived from an "aryl" group as described above linking the rest of the molecule to a radical group. The arylene is attached to the rest of the molecule through a single bond and to the radical group through a single bond. In some embodiments, the arylene is a phenylene. Unless stated otherwise specifically in the specification, an arylene group is optionally substituted as described above for an aryl group.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0] nonane, cis-decalin, trans-decalin, bicyclo[2.1.1]hexane, bicyclo[2.2.1]heptane, bicyclo[2.2.2]octane, bicyclo[3.2.2]

nonane, and bicyclo[3.3.2]decane, 7,7-dimethyl-bicyclo [2.2.1]heptanyl, and the like. Unless otherwise stated specifically in the specification, the term "cycloalkyl" is meant to include cycloalkyl radicals optionally substituted as described below by one or more substituents independently selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$SR^a$, —$R^b$—OC(O)—$R^a$, —$R^b$—OC(O)—$OR^f$, —$R^b$—OC(O)—N($R^a$)$_2$, —$R^b$—N($R^a$)$_2$, —$R^b$—N($R^a$)$_3$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^f$, —$R^b$—N($R^a$)C(O)$R^a$, —$R^b$—N($R^a$)S(O)$_t R^f$ (where t is 1 or 2), —$R^b$—S(O)$_t OR^a$ (where t is 1 or 2), —$R^b$—S(O)$_t R^f$ (where t is 1 or 2) and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, $R^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

A "cycloalkylene" refers to a divalent radical derived from a "cycloalkyl" group as described above linking the rest of the molecule to a radical group. The cycloalkylene is attached to the rest of the molecule through a single bond and to the radical group through a single bond. Unless stated otherwise specifically in the specification, a cycloalkylene group is optionally substituted as described above for a cycloalkyl group.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more hydroxy radicals, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like.

"Haloalkoxy" or "haloalkoxyl" refers to an alkoxyl radical, as defined above, that is substituted by one or more halo radicals, as defined above.

"Fluoroalkoxy" or "fluoroalkoxyl" refers to an alkoxy radical, as defined above, that is substituted by one or more fluoro radicals, as defined above, for example, trifluoromethoxy, difluoromethoxy, fluoromethoxy, and the like.

"Hydroxyalkyl" refers to an alkyl radical, as defined above, that is substituted by one or more halo radicals, as defined above, e.g., hydroxymethyl, 1-hydroxyethyl, 2-hydroxyethyl, 2-hydroxypropyl, 3-hydroxypropyl, 1,2-dihydroxyethyl, 2,3-dihydroxypropyl, 2,3,4,5,6-pentahydroxyhexyl, and the like.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. In some embodiments, the heterocycloalkyl is a 3- to 8-membered heterocycloalkyl. In some embodiments, the heterocycloalkyl is a 3- to 6-membered heterocycloalkyl. In some embodiments, the heterocycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. More preferably, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e., skeletal atoms of the heterocycloalkyl ring). Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$SR^a$, —$R^b$—OC(O)—$R^a$, —$R^b$—OC(O)—$OR^f$, —$R^b$—OC(O)—N($R^a$)$_2$, —$R^b$—$N^+(R^a)_2$, —$R^b$—$N^+(R^a)_3$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^f$, —$R^b$—N($R^a$)C(O)$R^a$, —$R^b$—N($R^a$)S(O)$_t R^f$ (where t is 1 or 2), —$R^b$—S(O)$_t OR^a$ (where t is 1 or 2), —$R^b$—S(O)$_t R^f$ (where t is 1 or 2) and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, $R^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"N-heterocycloalkyl" refers to a heterocycloalkyl radical as defined above containing at least one nitrogen and where the point of attachment of the heterocycloalkyl radical to the rest of the molecule is through a nitrogen atom in the heterocycloalkyl radical. An N-heterocycloalkyl radical is optionally substituted as described above for heterocycloalkyl radicals.

"C-heterocycloalkyl" refers to a heterocycloalkyl radical as defined above and where the point of attachment of the heterocycloalkyl radical to the rest of the molecule is through a carbon atom in the heterocycloalkyl radical. A C-heterocycloalkyl radical is optionally substituted as described above for heterocycloalkyl radicals.

A "heterocycloalkylene" refers to a divalent radical derived from a "heterocycloalkyl" group as described above linking the rest of the molecule to a radical group. The heterocycloalkylene is attached to the rest of the molecule through a single bond and to the radical group through a single bond. Unless stated otherwise specifically in the specification, a heterocycloalkylene group is optionally substituted as described above for a heterocycloalkyl group.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. In some embodiments, the heteroaryl is a 5- to 10-membered heteroaryl. In some embodiments, the heteroaryl is a monocyclic heteroaryl, or a monocyclic 5- or 6-membered heteroaryl. In some embodiments, the heteroaryl is a 6,5-fused bicyclic heteroaryl. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-SR^a$, $-R^b-OC(O)-R^a$, $-R^b-OC(O)-OR^f$, $-R^b-OC(O)-N(R^a)_2$, $-R^b-N(R^a)_2$, $-R^b-N(R^a)_3$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^f$, $-R^b-N(R^a)C(O)R^a$, $-R^b-N(R^a)S(O)_tR^f$ (where t is 1 or 2), $-R^b-S(O)_tOR^a$ (where t is 1 or 2), $-R^b-S(O)_tR^f$ (where t is 1 or 2) and $-R^b-S(O)_tN(R^a)_2$ (where t is 1 or 2), where each $R^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, $R^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

A "heteroarylene" refers to a divalent radical derived from a "heteroaryl" group as described above linking the rest of the molecule to a radical group. The heteroarylene is attached to the rest of the molecule through a single bond and to the radical group through a single bond. Unless stated otherwise specifically in the specification, a heteroarylene group is optionally substituted as described above for a heteroaryl group.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be unsubstituted (e.g., $-CH_2CH_3$), fully substituted (e.g., $-CF_2CF_3$), mono-substituted (e.g., $-CH_2CH_2F$) or substituted at a level anywhere in-between fully substituted and mono-substituted (e.g., $-CH_2CHF_2$, $-CH_2CF_3$, $-CF_2CH_3$, $-CFHCHF_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible.

The term "modulate" or "modulating" or "modulation" refers to an increase or decrease in the amount, quality, or effect of a particular activity, function or molecule. By way of illustration and not limitation, agonists, partial agonists, inverse agonists, antagonists, and allosteric modulators of a G protein-coupled receptor are modulators of the receptor.

The term "agonism" as used herein refers to the activation of a receptor or enzyme by a modulator, or agonist, to produce a biological response.

The term "agonist" as used herein refers to a modulator that binds to a receptor or target enzyme and activates the receptor or enzyme to produce a biological response. By way of example, "GPR119 agonist" can be used to refer to a compound that exhibits an $EC_{50}$ with respect to GPR119 activity of no more than about 100 μM, as measured in the as measured in the inositol phosphate accumulation assay. In some embodiments, the term "agonist" includes full agonists or partial agonists.

The term "full agonist" refers to a modulator that binds to and activates a receptor or target enzyme with the maximum response that an agonist can elicit at the receptor or enzyme.

The term "partial agonist" refers to a modulator that binds to and activates a receptor or target enzyme, but has partial efficacy, that is, less than the maximal response, at the receptor or enzyme relative to a full agonist.

The term "positive allosteric modulator" refers to a modulator that binds to a site distinct from the orthosteric binding site and enhances or amplifies the effect of an agonist.

The term "antagonism" as used herein refers to the inactivation of a receptor or target enzyme by a modulator, or antagonist. Antagonism of a receptor, for example, is when a molecule binds to the receptor or target enzyme and does not allow activity to occur.

The term "antagonist" or "neutral antagonist" as used herein refers to a modulator that binds to a receptor or target enzyme and blocks a biological response. An antagonist has no activity in the absence of an agonist or inverse agonist but can block the activity of either, causing no change in the biological response.

The term "inverse agonist" refers to a modulator that binds to the same receptor or target enzyme as an agonist but induces a pharmacological response opposite to that agonist, i.e., a decrease in biological response.

The term "negative allosteric modulator" refers to a modulator that binds to a site distinct from the orthosteric binding site and reduces or dampens the effect of an agonist.

As used herein, "$EC_{50}$" is intended to refer to the concentration of a substance (e.g., a compound or a drug) that is required for 50% activation or enhancement of a biological process. In some instances, $EC_{50}$ refers to the concentration of agonist that provokes a response halfway between the baseline and maximum response in an in vitro assay. In some embodiments as used herein, $EC_{50}$ refers to the concentration of an agonist (e.g., a GPR119 agonist) that is required for 50% activation of GPR119.

As used herein, "$IC_{50}$" is intended to refer to the concentration of a substance (e.g., a compound or a drug) that is required for 50% inhibition of a biological process. For example, $IC_{50}$ refers to the half maximal (50%) inhibitory concentration (IC) of a substance as determined in a suitable assay. In some instances, an $IC_{50}$ is determined in an in vitro assay system. In some embodiments as used herein, $IC_{50}$ refers to the concentration of a modulator (e.g., an antagonist or inhibitor) that is required for 50% inhibition of a receptor or a target enzyme.

The terms "subject," "individual," and "patient" are used interchangeably. These terms encompass mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like.

The term "gut-restricted" as used herein refers to a compound, e.g., a GPR119 agonist, that is predominantly active in the gastrointestinal system. In some embodiments, the biological activity of the gut-restricted compound, e.g., a gut-restricted GPR119 agonist, is restricted to the gastrointestinal system. In some embodiments, gastrointestinal concentration of a gut-restricted modulator, e.g., a gut-restricted GPR119 agonist, is higher than the $IC_{50}$ value or the $EC_{50}$ value of the gut-restricted modulator against its receptor or target enzyme, e.g., GPR119, while the plasma levels of said gut-restricted modulator, e.g., gut-restricted GPR119 agonist, are lower than the $IC_{50}$ value or the $EC_{50}$ value of the gut-restricted modulator against its receptor or target enzyme, e.g., GPR119. In some embodiments, the gut-restricted compound, e.g., a gut-restricted GPR119 agonist, is non-systemic. In some embodiments, the gut-restricted compound, e.g., a gut-restricted GPR119 agonist, is a non-absorbed compound. In other embodiments, the gut-restricted compound, e.g., a gut-restricted GPR119 agonist, is absorbed, but is rapidly metabolized to metabolites that are significantly less active than the modulator itself toward the target receptor or enzyme, i.e., a "soft drug." In other embodiments, the gut-restricted compound, e.g., a gut-restricted GPR119 agonist, is minimally absorbed and rapidly metabolized to metabolites that are significantly less active than the modulator itself toward the target receptor or enzyme.

In some embodiments, the gut-restricted modulator, e.g., a gut-restricted GPR119 agonist, is non-systemic but is instead localized to the gastrointestinal system. For example, the modulator, e.g., a gut-restricted GPR119 agonist, may be present in high levels in the gut, but low levels in serum. In some embodiments, the systemic exposure of a gut-restricted modulator, e.g., a gut-restricted GPR119 agonist, is, for example, less than 100, less than 50, less than 20, less than 10, or less than 5 nM, bound or unbound, in blood serum. In some embodiments, the intestinal exposure of a gut-restricted modulator, e.g., a gut-restricted GPR119 agonist, is, for example, greater than 1000, 5000, 10000, 50000, 100000, or 500000 nM. In some embodiments, a modulator, e.g., a GPR119 agonist, is gut-restricted due to poor absorption of the modulator itself, or because of absorption of the modulator which is rapidly metabolized in serum resulting in low systemic circulation, or due to both poor absorption and rapid metabolism in the serum. In some embodiments, a modulator, e.g., a GPR119 agonist, is covalently bonded to a kinetophore, optionally through a linker, which changes the pharmacokinetic profile of the modulator.

In particular embodiments, the gut-restricted GPR119 agonist is a soft drug. The term "soft drug" as used herein refers to a compound that is biologically active but is rapidly metabolized to metabolites that are significantly less active than the compound itself toward the target receptor. In some embodiments, the gut-restricted GPR119 agonist is a soft drug that is rapidly metabolized in the blood to significantly less active metabolites. In some embodiments, the gut-restricted GPR119 agonist is a soft drug that is rapidly metabolized in the liver to significantly less active metabolites. In some embodiments, the gut-restricted GPR119 agonist is a soft drug that is rapidly metabolized in the blood and the liver to significantly less active metabolites. In some embodiments, the gut-restricted GPR119 agonist is a soft drug that has low systemic exposure. In some embodiments, the biological activity of the metabolite(s) is/are 10-fold, 20-fold, 50-fold, 100-fold, 500-fold, or 1000-fold lower than the biological activity of the soft drug gut-restricted GPR119 agonist.

The term "kinetophore" as used herein refers to a structural unit tethered to a small molecule modulator, e.g., a GPR119 agonist, optionally through a linker, which makes the whole molecule larger and increases the polar surface area while maintaining biological activity of the small molecule modulator. The kinetophore influences the pharmacokinetic properties, for example solubility, absorption, distribution, rate of elimination, and the like, of the small molecule modulator, e.g., a GPR119 agonist, and has minimal changes to the binding to or association with a receptor or target enzyme. The defining feature of a kinetophore is not its interaction with the target, for example a receptor, but rather its effect on specific physiochemical characteristics of the modulator to which it is attached, e.g., a GPR119 agonist. In some instances, kinetophores are used to restrict a modulator, e.g., a GPR119 agonist, to the gut.

The term "linked" as used herein refers to a covalent linkage between a modulator, e.g., a GPR119 agonist, and a kinetophore. The linkage can be through a covalent bond, or through a "linker." As used herein, "linker" refers to one or more bifunctional molecules which can be used to covalently bond to the modulator, e.g., a GPR119 agonist, and kinetophore. In some embodiments, the linker is attached to any part of the modulator, e.g., a GPR119 agonist, so long as the point of attachment does not interfere with the binding of the modulator to its receptor or target enzyme. In some embodiments, the linker is non-cleavable. In some embodiments, the linker is cleavable. In some embodiments, the linker is cleavable in the gut. In some embodiments, cleaving the linker releases the biologically active modulator, e.g., a GPR119 agonist, in the gut.

The term "gastrointestinal system" (GI system) or "gastrointestinal tract" (GI tract) as used herein, refers to the organs and systems involved in the process of digestion. The gastrointestinal tract includes the esophagus, stomach, small intestine, which includes the duodenum, jejunum, and ileum, and large intestine, which includes the cecum, colon, and rectum. In some embodiments herein, the GI system refers to the "gut," meaning the stomach, small intestines, and large intestines or to the small and large intestines, including, for example, the duodenum, jejunum, and/or colon.

Gut-Brain Axis

The gut-brain axis refers to the bidirectional biochemical signaling that connects the gastrointestinal tract (GI tract) with the central nervous system (CNS) through the peripheral nervous system (PNS) and endocrine, immune, and metabolic pathways.

In some instances, the gut-brain axis comprises the GI tract; the PNS including the dorsal root ganglia (DRG) and the sympathetic and parasympathetic arms of the autonomic nervous system including the enteric nervous system and the vagus nerve; the CNS; and the neuroendocrine and neuroimmune systems including the hypothalamic-pituitary-adrenal axis (HPA axis). The gut-brain axis is important for maintaining homeostasis of the body and is regulated and modulates physiology through the central and peripheral nervous systems and endocrine, immune, and metabolic pathways.

The gut-brain axis modulates several important aspects of physiology and behavior. Modulation by the gut-brain axis occurs via hormonal and neural circuits. Key components of these hormonal and neural circuits of the gut-brain axis include highly specialized, secretory intestinal cells that release hormones (enteroendocrine cells or EECs), the autonomic nervous system (including the vagus nerve and enteric nervous system), and the central nervous system. These systems work together in a highly coordinated fashion to modulate physiology and behavior.

Defects in the gut-brain axis are linked to a number of diseases, including those of high unmet need. Diseases and conditions affected by the gut-brain axis, include central nervous system (CNS) disorders including mood disorders, anxiety, depression, affective disorders, schizophrenia, malaise, cognition disorders, addiction, autism, epilepsy, neurodegenerative disorders, Alzheimer's disease, and Parkinson's disease, Lewy Body dementia, episodic cluster headache, migraine, pain; metabolic conditions including diabetes and its complications such as chronic kidney disease/diabetic nephropathy, diabetic retinopathy, diabetic neuropathy, and cardiovascular disease, metabolic syndrome, obesity, dyslipidemia, and nonalcoholic steatohepatitis (NASH); eating and nutritional disorders including hyperphagia, cachexia, anorexia nervosa, short bowel syndrome, intestinal failure, intestinal insufficiency and other eating disorders; inflammatory disorders and autoimmune diseases such as inflammatory bowel disease, ulcerative colitis, Crohn's disease, psoriasis, celiac disease, and enteritis, including chemotherapy-induced enteritis or radiation-induced enteritis; necrotizing enterocolitis; diseases/disorders of gastrointestinal barrier dysfunction including environmental enteric dysfunction, spontaneous bacterial peritonitis; functional gastrointestinal disorders such as irritable bowel syndrome, functional dyspepsia, functional abdominal bloating/distension, functional diarrhea, functional constipation, and opioid-induced constipation; gastroparesis; nausea and vomiting; disorders related to microbiome dysbiosis, and other conditions involving the gut-brain axis.

GPR119 in the Gut-Brain Axis

In some instances, GPR119 is expressed in the pancreas and in enteroendocrine cells of the gastrointestinal tract. In some instances, GPR119 is expressed in enteroendocrine cells. GPR119 is activated by oleoylethanolamide (OEA) and other oleic acid derivatives and N-acylethanolamides. GPR119 agonists may be useful in the treatment of metabolic diseases such as diabetes and obesity, and other diseases involving the gut-brain axis.

In some instances, modulators of GPR119, for example, GPR119 agonists, induce the production of intracellular cAMP. In some instances, modulators of GPR119, for example, GPR119 agonists, induce the secretion of GLP-1, GLP-2, GIP, PYY, CCK, or other hormones. In some instances, modulators of GPR119, for example, GPR119 agonists, induce the secretion of GLP-1, GIP, CCK or PYY. In some instances, modulators of GPR119, for example, GPR119 agonists, induce the secretion of GLP-1.

Described herein is a method of treating a condition or disorder involving the gut-brain axis in an individual in need thereof, the method comprising administering to the individual a GPR119 receptor modulator. In some embodiments, the GPR119 receptor modulator is a GPR119 agonist. In some embodiments, the GPR119 modulator is a gut-restricted GPR119 modulator.

In some embodiments, the condition or disorder involving the gut-brain axis is selected from the group consisting of: central nervous system (CNS) disorders including mood disorders, anxiety, depression, affective disorders, schizophrenia, malaise, cognition disorders, addiction, autism, epilepsy, neurodegenerative disorders, Alzheimer's disease, and Parkinson's disease, Lewy Body dementia, episodic cluster headache, migraine, pain; metabolic conditions including diabetes and its complications such as chronic kidney disease/diabetic nephropathy, diabetic retinopathy, diabetic neuropathy, and cardiovascular disease, metabolic syndrome, obesity, dyslipidemia, and nonalcoholic steatohepatitis (NASH); eating and nutritional disorders including hyperphagia, cachexia, anorexia nervosa, short bowel syndrome, intestinal failure, intestinal insufficiency and other eating disorders; inflammatory disorders and autoimmune diseases such as inflammatory bowel disease, ulcerative colitis, Crohn's disease, psoriasis, celiac disease, and enteritis, including chemotherapy-induced enteritis or radiation-induced enteritis; necrotizing enterocolitis; diseases/disorders of gastrointestinal barrier dysfunction including environmental enteric dysfunction, spontaneous bacterial peritonitis; functional gastrointestinal disorders such as irritable bowel syndrome, functional dyspepsia, functional abdominal bloating/distension, functional diarrhea, functional constipation, and opioid-induced constipation; gastroparesis; nausea and vomiting; disorders related to microbiome dysbiosis, other conditions involving the gut-brain axis. In some embodiments, the condition is a metabolic disorder. In some embodiments, the metabolic disorder is type 2 diabetes, hyperglycemia, metabolic syndrome, obesity, hypercholesterolemia, nonalcoholic steatohepatitis, or hypertension. In some embodiments, the metabolic disorder is diabetes. In other embodiments, the metabolic disorder is obesity. In other embodiments, the metabolic disorder is nonalcoholic steatohepatitis. In some embodiments, the condition involving the gut-brain axis is a nutritional disorder. In some embodiments, the nutritional disorder is short bowel syndrome, intestinal failure, or intestinal insufficiency. In some embodiments, the nutritional disorder is short bowel syndrome. In some embodiments, the condition involving the gut-brain axis is enteritis. In some embodiments, the condition involving the gut-brain axis is chemotherapy-induced enteritis or radiation-induced enteritis.

Gut-Restricted Modulators

Differentiation of undesirable systemic effects of a GPR119 agonist from beneficial, gut-driven effects would be critical for the development of a GPR119 agonist for the treatment of disease. For example, activation of GPR119 in alpha cells of pancreatic islets by systemic GPR119 agonists can lead to secretion of glucagon, causing undesired metabolic effects, e.g., increased plasma glucose levels. Furthermore, systemic GPR119 agonists are typically hydrophobic ligands that suffer from undesirable off-target activity, such as hERG channel and/or CYP enzyme inhibition.

In contrast, some embodiments provided herein describe a GPR119 modulator that is non-systemic. In some embodiments, the GPR119 modulator described herein is substantially non-systemic. In some embodiments, the GPR119 modulator described herein has low bioavailability. In some embodiments, the GPR119 modulator described herein is bound to a kinetophore and is non-systemic. In some embodiments, the GPR119 modulator described herein is bound to a kinetophore and is substantially non-systemic. In some embodiments, the GPR119 modulator described herein is bound to a kinetophore and has lower bioavailability than a corresponding compound without a kinetophore.

In some embodiments, the GPR119 agonist is gut-restricted. In some embodiments, the GPR119 agonist is substantially non-permeable or substantially non-bioavailable in the blood stream. In some embodiments, the GPR119 agonist activates GPR119 activity in the gut and is substantially non-systemic. In some embodiments, the GPR119 agonist has low systemic exposure. In some embodiments, the gut-restricted GPR119 agonists described herein provide fewer undesired side effects than systemic GPR119 agonists.

In some embodiments, a gut-restricted GPR119 agonist has low oral bioavailability. In some embodiments, a gut-restricted GPR119 agonist has <10% oral bioavailability, <8% oral bioavailability, <5% oral bioavailability, <3% oral bioavailability, or <2% oral bioavailability.

In some embodiments, the unbound plasma levels of a gut-restricted GPR119 agonist are lower than the $EC_{50}$ value of the GPR119 agonist against GPR119. In some embodiments, the unbound plasma levels of a gut-restricted GPR119 agonist are significantly lower than the $EC_{50}$ value of the gut-restricted GPR119 agonist against GPR119. In some embodiments, the unbound plasma levels of the GPR119 agonist are 2-fold, 10-fold, 20-fold, 30-fold, 40-fold, 50-fold, or 100-fold lower than the $EC_{50}$ value of the gut-restricted GPR119 agonist against GPR119.

In some embodiments, a gut-restricted GPR119 agonist has low systemic exposure. In some embodiments, the systemic exposure of a gut-restricted GPR119 agonist is, for example, less than 500, less than 200, less than 100, less than 50, less than 20, less than 10, or less than 5 nM, bound or unbound, in blood serum. In some embodiments, the systemic exposure of a gut-restricted GPR119 agonist is, for example, less than 500, less than 200, less than 100, less than 50, less than 20, less than 10, or less than 5 ng/mL, bound or unbound, in blood serum.

In some embodiments, a gut-restricted GPR119 agonist has low permeability. In some embodiments, a gut-restricted GPR119 agonist has low intestinal permeability. In some embodiments, the permeability of a gut-restricted GPR119 agonist is, for example, less than $5.0 \times 10^{-6}$ cm/s, less than $2.0 \times 10^{-6}$ cm/s, less than $1.5 \times 10^{-6}$ cm/s, less than $1.0 \times 10^{-6}$ cm/s, less than $0.75 \times 10^{-6}$ cm/s, less than $0.50 \times 10^{-6}$ cm/s, less than $0.25 \times 10^{-6}$ cm/s, less than $0.10 \times 10^{-6}$ cm/s, or less than $0.05 \times 10^{-6}$ cm/s.

In some embodiments, a gut-restricted GPR119 agonist has low absorption. In some embodiments, the absorption of a gut-restricted GPR119 agonist is less than less than 20%, or less than 10%, less than 5%, or less than 1%.

In some embodiments, a gut-restricted GPR119 agonist has high plasma clearance. In some embodiments, a gut-restricted GPR119 agonist is undetectable in plasma in less than 8 hours, less than 6 hours, less than 4 hours, less than 3 hours, less than 120 min, less than 90 min, less than 60 min, less than 45 min, less than 30 min, or less than 15 min.

In some embodiments, a gut-restricted GPR119 agonist is rapidly metabolized upon administration. In some embodiments, a gut-restricted GPR119 agonist has a short half-life. In some embodiments, the half-life of a gut-restricted GPR119 agonist (e.g., in plasma) is less than less than 8 hours, less than 6 hours, less than 4 hours, less than 3 hours, less than 120 min, less than 90 min, less than 60 min, less than 45 min, less than 30 min, or less than 15 min. In some embodiments, the metabolites of a gut-restricted GPR119 agonist have rapid clearance (e.g., systemic clearance). In some embodiments, the metabolites of a gut-restricted GPR119 agonist are undetectable (e.g., in plasma) in less than 8 hours, less than 6 hours, less than 4 hours, less than 3 hours, less than 120 min, less than 90 min, less than 60 min, less than 45 min, less than 30 min, or less than 15 min. In some embodiments, the metabolites of a gut-restricted GPR119 agonist have low bioactivity. In some embodiments, the $EC_{50}$ value of the metabolites of a gut-restricted GPR119 agonist is 10-fold, 20-fold, 30-fold, 40-fold, 50-fold, 100-fold, 500-fold, or 1000-fold higher than the $EC_{50}$ value of the gut-restricted GPR119 agonist against GPR119. In some embodiments, the metabolites of a gut-restricted GPR119 agonist have rapid clearance and low bioactivity.

In some embodiments of the methods described herein, the GPR119 modulator is gut-restricted. In some embodiments, the GPR119 modulator is a gut-restricted GPR119 agonist. In some embodiments, the GPR119 agonist is covalently bonded to a kinetophore. In some embodiments, the GPR119 agonist is covalently bonded to a kinetophore through a linker.

In some instances, known GPR119 agonists are systemic. In some instances, known systemic GPR119 agonists are not bonded to a kinetophore as described herein. In some instances, known GPR119 agonists have high oral bioavailability. In some embodiments, the GPR119 modulator described herein is bound to a kinetophore and is non-systemic. In some embodiments, the GPR119 modulator described herein is bound to a kinetophore and is substantially non-systemic. In some embodiments, the GPR119 modulator described herein is bound to a kinetophore and has lower bioavailability than a corresponding compound without a kinetophore.

Compounds

Disclosed herein, in certain embodiments, is a compound of Formula (A):

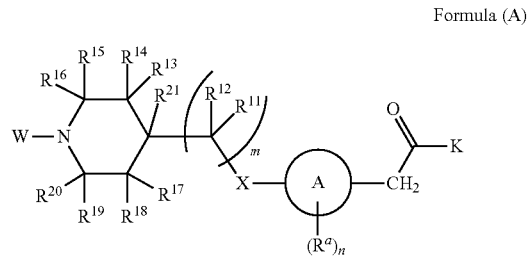

Formula (A)

or a pharmaceutically acceptable salt, solvate, stereoisomer, or prodrug thereof, wherein:

K is

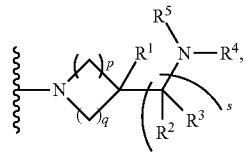

or

R$^1$ is hydrogen, —OH, C$_{1-8}$ alkyl, C$_{3-8}$ cycloalkyl, or 3- to 8-membered heterocycloalkyl, wherein the alkyl, cycloalkyl, and heterocycloalkyl are unsubstituted or substituted by 1-3 substituents independently selected from halogen, —OH, and —O(C$_{1-6}$ alkyl);
each R$^2$ and R$^3$ is independently hydrogen, C$_{1-6}$ alkyl, or C$_{1-6}$ fluoroalkyl;
or R$^2$ and R$^3$ on the same carbon atom are taken together to form =O;
R$^4$ is hydrogen, C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, 4- to 8-membered heterocycloalkyl, —[(CH$_2$)$_r$—O]$_t$—R$^6$, —[(CH$_2$)$_r$—NR$^d$]$_t$—R$^6$, —[(CH$_2$)$_r$—N$^+$(R$^d$)$_2$]$_t$—R$^6$, —[(CH$_2$)$_r$—NHC(=O)NH]$_t$—R$^6$, —[(CH$_2$)$_v$—C(=O)NH]$_t$—R$^6$, —[(C(R$^d$)$_2$)$_v$—C(=O)NH]$_t$—R$^6$, —[(CH$_2$)$_r$—S(=O)$_2$]$_t$—R$^6$, or —[(CH$_2$)$_r$—S(=O)]$_t$—R$^6$; wherein each alkyl, fluoroalkyl, alkenyl, alkynyl, cycloalkyl, cycloalkenyl, and 4- to 8-membered heterocycloalkyl is unsubstituted or substituted by 1-6 R$^c$ groups;
R$^5$ is C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, 4- to 8-membered heterocycloalkyl, —[(CH$_2$)$_r$—O]$_t$—R$^6$, —[(CH$_2$)$_r$—NR$^d$]$_t$—R$^6$, —[(CH$_2$)$_r$—N$^+$(R$^d$)$_2$]$_t$—R$^6$, —[(CH$_2$)$_r$—NHC(=O)NH]$_t$—R$^6$, —[(CH$_2$)$_v$—C(=O)NH]$_t$—R$^6$, —[(C(R$^d$)$_2$)$_v$—C(=O)NH]$_t$—R$^6$, —[(CH$_2$)$_r$—S(=O)$_2$]$_t$—R$^6$, or —[(CH$_2$)$_r$—S(=O)]$_t$—R$^6$; wherein each alkyl, fluoroalkyl, alkenyl, alkynyl, cycloalkyl, cycloalkenyl, and 4- to 8-membered heterocycloalkyl is substituted by 1-6 R$^c$ groups;
each r is independently 2-4;
each t is independently 1-6;
each v is independently 1-4;
R$^6$ is hydrogen, C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, or 4- to 8-membered heterocycloalkyl, wherein the alkyl, fluoroalkyl, alkenyl, alkynyl, cycloalkyl, cycloalkenyl, or 4- to 8-membered heterocycloalkyl is unsubstituted or substituted by 1-6 R$^c$ groups;
or R$^4$ and R$^5$ are taken together with the nitrogen to which they are attached to form a 4- to 8-membered heterocycloalkyl, which is unsubstituted or substituted by 1-6 R$^c$ groups;
R$^7$ is hydrogen, C$_{1-4}$ alkyl, or C$_{1-4}$ fluoroalkyl;
R$^8$ is C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, 4- to 8-membered heterocycloalkyl, —[(CH$_2$)$_r$—O]$_t$—R$^6$, —[(CH$_2$)$_r$—NR$^d$]$_t$—R$^6$, —[(CH$_2$)$_r$—N$^+$(R$^d$)$_2$]$_t$—R$^6$, —[(CH$_2$)$_r$—NHC(=O)NH]$_t$—R$^6$, —[(CH$_2$)$_v$—C(=O)NH]$_t$—R$^6$, —[(C(R$^d$)$_2$)$_v$—C(=O)NH]$_t$—R$^6$, —[(CH$_2$)$_r$—S(=O)$_2$]$_t$—R$^6$, or —[(CH$_2$)$_r$—S(=O)]$_t$—R$^6$; wherein each alkyl, fluoroalkyl, alkenyl, alkynyl, cycloalkyl, cycloalkenyl, and 4- to 8-membered heterocycloalkyl is substituted by 1-6 R$^e$ groups;
or R$^8$ is —(C$_{1-8}$ alkyl)-NH—R$^9$, —(C$_{1-8}$ alkyl)-C(=O)NH—R$^9$, —(C$_{1-8}$ alkyl)-C(=O)—N(R$^9$)$_2$, or —(C$_{1-8}$ alkyl)-NHC(=O)NH—R$^9$; wherein the alkyl is unsubstituted or substituted by 1-6 R$^c$ groups; each R$^9$ is independently C$_{1-8}$ alkyl, or C$_{1-8}$ fluoroalkyl which is substituted by 1-6 R$^c$ groups; or two R$^9$ are taken together with the nitrogen to which they are attached to form a 4- to 6-membered heterocycloalkyl, which is substituted by 1-6 R$^c$ groups;
each R$^c$ is independently —OH, —CH$_2$OH, —CH$_2$CH$_2$OH, —NH$_2$, —CH$_2$NH$_2$, —NH(R$^d$), —CH$_2$NH(R$^d$), —N(R$^d$)$_2$, —CH$_2$N(R$^d$)$_2$, —N(R$^d$)$_3$$^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), P(=O)(OH)(OR$^d$), —B(OH)$_2$, —B(OR$^d$)(OH), —NHCONHS(=O)$_2$(R$^d$), —N(R$^d$)CONHS(=O)$_2$(R$^d$), —NHCON(R$^d$)S(=O)$_2$(R$^d$), —C(=O)NHS(=O)$_2$(R$^d$), —S(=O)$_2$NHC(=O)R$^d$, —NHC(=NH)NH$_2$, —NHC(=NH)NHR$^d$, —NHC(=NH)N(R$^d$)$_2$, —N(R$^d$)C(=NH)NH$_2$, —N(R$^d$)C(=NH)NH(R$^d$), —N(R$^d$)C(=NH)N(R$^d$)$_2$, —NHC(=N(R$^d$))NH$_2$, —NHC(=N(R$^d$))NHR$^d$, —NHC(=N(R$^d$))N(R$^d$)$_2$, —N(R$^d$)C(=N(R$^d$))NH$_2$, —N(R$^d$)C(=N(R$^d$))NHR$^d$, —N(R$^d$)C(=N(R$^d$))N(R$^d$)$_2$, —NHC(=NH)NHC(=NH)NH$_2$, —N(R$^d$)C(=NH)NHC(=NH)NH$_2$,

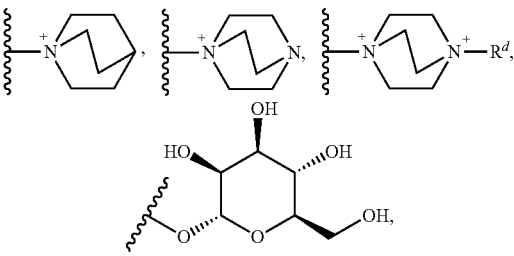

or a 4- to 6-membered heterocycle which is unsubstituted or substituted with 1, 2, 3, or 4 substituents selected from C$_{1-6}$ alkyl, —O—(C$_{1-6}$ alkyl), —OH, =O and =S;
each R$^d$ is independently C$_{1-6}$ alkyl, C$_{1-6}$ fluoroalkyl, or C$_{3-6}$ cycloalkyl;
each R$^e$ is independently —OH, —CH$_2$OH, —CH$_2$CH$_2$OH, —N(R$^d$)$_3$$^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), —P(=O)(OH)(OR$^d$), —B(OH)$_2$, —B(OR$^d$)(OH), —NHCONHS(=O)$_2$(R$^d$), —N(R$^d$)CONHS(=O)$_2$(R$^d$), —NHCON(R$^d$)S(=O)$_2$(R$^d$), —C(=O)NHS(=O)$_2$(R$^d$), —S(O)$_2$NHC(O)R$^d$, —NHC(=NH)NH$_2$, —NHC(=NH)NHR$^d$, —NHC(=NH)N(R$^d$)$_2$, —N(R$^d$)C(=NH)NH$_2$, N(R$^d$)C(=NH)NH(R$^d$), —N(R$^d$)C(=NH)N(R$^d$)$_2$, —NHC(=N(R$^d$))NH$_2$, —NHC(=N(R$^d$))NHR$^d$, —NHC(=N(R$^d$))N(R$^d$)$_2$, —N(R$^d$)C(=N(R$^d$))NH$_2$, —N(R$^d$)C(=N(R$^d$))NHR$^d$, —N(R$^d$)C(=N(R$^d$))N(R$^d$)$_2$, —NHC(=NH)NHC(=NH)NH$_2$, N(R$^d$)C(=NH)NHC(=NH)NH$_2$,

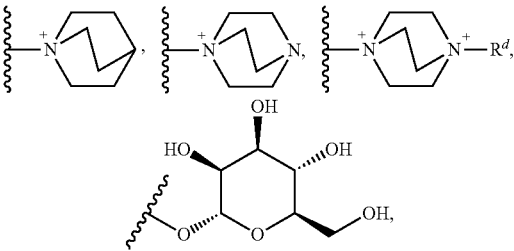

or a 4- to 6-membered heterocycle which is unsubstituted or substituted with 1, 2, 3, or 4 substituents selected from C$_{1-6}$ alkyl, —O—(C$_{1-6}$ alkyl), —OH, =O and =S;
Ring A is phenyl or 5-6 membered monocyclic heteroaryl;
each R$^a$ is independently halogen, —CN, C$_{1-6}$ alkyl, C$_{1-6}$ fluoroalkyl, or C$_{3-6}$ cycloalkyl;
X is —O—, —NR$^N$—, *—CH$_2$O—, *—CH$_2$NR$^N$—, *—C(=O)O—, *—C(=O)NR$^N$—, *—CH$_2$C(=O)O—,

*—CH$_2$C(=O)NR$^N$—, *—OC(=O)—, *—NR$^N$C(=O)—, *—CH$_2$OC(=O)—, or *—CH$_2$NR$^N$C(=O)—, where * represents the attachment point to Ring A;

R$^N$ is hydrogen or C$_{1-4}$ alkyl;

each R$^{11}$ is independently hydrogen, fluorine, —OH, C$_{1-6}$ alkyl, or C$_{1-6}$ alkoxy;

each R$^{12}$ is independently hydrogen, fluorine, or C$_{1-6}$ alkyl;

or two R$^{11}$ are taken together with the intervening atoms to which they are attached to form a C$_{3-6}$ cycloalkyl;

R$^{13}$, R$^{14}$, R$^{15}$, R$^{16}$, R$^{17}$, R$^{18}$, R$^{19}$, and R$^{20}$ are each independently hydrogen, C$_{1-6}$ alkyl, C$_{1-6}$ alkoxy, or C$_{1-6}$ fluoroalkyl;

or R$^{13}$ and R$^{17}$ or R$^{13}$ and R$^{19}$ or R$^{15}$ and R$^{19}$ are taken together with the intervening atoms to which they are attached to form a ring;

R$^{21}$ is hydrogen, C$_{1-6}$ alkyl, or C$_{1-6}$ fluoroalkyl;

or R$^{21}$ and one R$^{11}$ are taken together with the intervening atoms to which they are attached to form a C$_{3-6}$ cycloalkyl;

W is phenyl or 5-6 membered monocyclic heteroaryl, wherein the phenyl or heteroaryl is unsubstituted or substituted with 1, 2, or 3 substituents selected from R$^b$;

each R$^b$ is independently halogen, —OH, —CN, —C(O)OH, —C(O)O(C$_{1-6}$ alkyl), C$_{1-6}$ alkyl, C$_{1-6}$ alkoxy, C$_{3-6}$ cycloalkyl, phenyl, or 5- to 6-membered heteroaryl; wherein each alkyl, alkoxy, and cycloalkyl is unsubstituted or substituted with 1, 2, or 3 substituents selected from halogen, —OH, C$_{1-6}$ alkyl, and C$_{1-6}$ alkoxy;

or W is —C(=O)O—R$^{22}$;

R$^{22}$ is C$_{1-6}$ alkyl, C$_{3-6}$ cycloalkyl, or 3- to 6-membered heterocycloalkyl, wherein the alkyl, cycloalkyl, and heterocycloalkyl are unsubstituted or substituted by 1-3 substituents independently selected from fluorine, —OH, C$_{1-6}$ alkyl, C$_{1-6}$ haloalkyl or C$_{3-6}$ cycloalkyl;

m is 1-4;

n is 0-4;

p is 1 or 2;

q is 1 or 2; and s is 1 or 2.

In some embodiments, K is

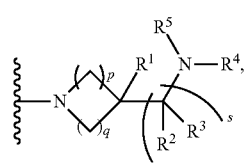

In some embodiments, when K is

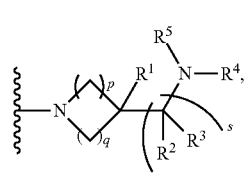

X is —O—, —NR$^N$—, *—CH$_2$O—, *—CH$_2$NR$^N$—, *—C(=O)O—, *—C(=O)NR$^N$—, *—CH$_2$C(=O)O—, *—CH$_2$C(=O)NR$^N$—, *—OC(=O)—, *—NR$^N$C(=O)—, *—CH$_2$OC(=O)—, or *—CH$_2$NR$^N$C(=O)—, where * represents the attachment point to Ring A. In some embodiments, when K is

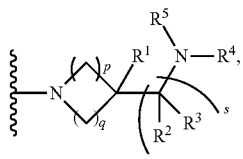

X is —O—, *—CH$_2$O—, *—C(=O)O—, or *—CH$_2$C(=O)O—, where * represents the attachment point to Ring A. In some embodiments, when K is

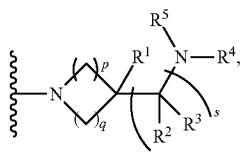

X is —O—. In some embodiments, when K is

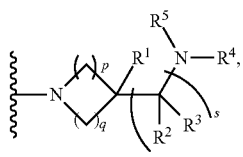

two R$^{11}$ are optionally taken together with the intervening atoms to which they are attached to form a C$_{3-6}$ cycloalkyl. In some embodiments, when K is

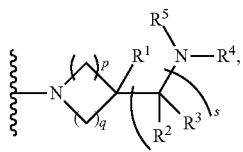

two R$^{11}$ are optionally taken together with the intervening atoms to which they are attached to form a cyclopropyl, cyclobutyl, cyclopentyl, or cyclohexyl. In some embodiments, when K is

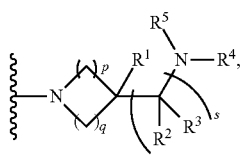

two R$^{11}$ are optionally taken together with the intervening atoms to which they are attached to form a cyclopropyl.

In some embodiments, K is

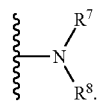

In some embodiments, when K is

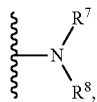

X is —O—, —NR$^N$—, *—CH$_2$O—, *—CH$_2$NR$^N$—, *—C(=O)O—, *—C(=O)NR$^N$—, *—CH$_2$C(=O)O—, *—CH$_2$C(=O)NR$^N$—, *—OC(=O)—, *—CH$_2$OC(=O)—, or *—CH$_2$NR$^N$C(=O)—, where * represents the attachment point to Ring A. In some embodiments, when K is

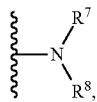

X is —O—, *—CH$_2$O—, *—C(=O)O—, or *—CH$_2$C(=O)O—, where * represents the attachment point to Ring A. In some embodiments, when K is

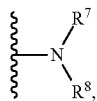

X is —O—. In some embodiments, when K is

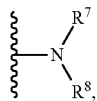

two R$^{11}$ are optionally taken together with the intervening atoms to which they are attached to form a C$_{4-6}$ cycloalkyl. In some embodiments, when K is

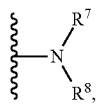

two R$^{11}$ are optionally taken together with the intervening atoms to which they are attached to form a cyclobutyl, cyclopentyl, or cyclohexyl.

In some embodiments, disclosed herein is a compound of Formula (I):

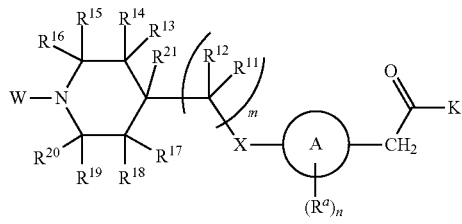

Formula (I)

or a pharmaceutically acceptable salt, solvate, stereoisomer, or prodrug thereof, wherein:

K is

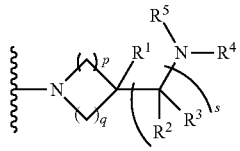

or

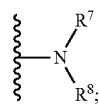

R$^1$ is hydrogen, —OH, C$_{1-8}$ alkyl, C$_{3-8}$ cycloalkyl, or 3- to 8-membered heterocycloalkyl, wherein the alkyl, cycloalkyl, and heterocycloalkyl are unsubstituted or substituted by 1-3 substituents independently selected from halogen, —OH, and —O(C$_{1-6}$ alkyl);

each R$^2$ and R$^3$ is independently hydrogen, C$_{1-6}$ alkyl, or C$_{1-6}$ fluoroalkyl;

or R$^2$ and R$^3$ on the same carbon atom are taken together to form =O;

R$^4$ is hydrogen, C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein each alkyl, fluoroalkyl, alkenyl, alkynyl, cycloalkyl, cycloalkenyl, and 4- to 8-membered heterocycloalkyl is unsubstituted or substituted by 1-6 R$^c$ groups;

R$^5$ is C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein each alkyl, fluoroalkyl, alkenyl, alkynyl, cycloalkyl, cycloalkenyl, and 4- to 8-membered heterocycloalkyl is substituted by 1-6 R$^c$ groups;

each Z is independently —CH$_2$O—, —CH$_2$NR$^d$—, —CH$_2$N$^+$(R$^d$)$_2$—, —NH—C(=O)—NH—, —C(=O)NH—, —CH$_2$S(=O)$_2$—, or —CH$_2$S(=O)—;

each r is independently 1-6;

each t is independently 1-6;

R$^6$ is hydrogen, C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, or 4- to 8-membered heterocycloalkyl, wherein the alkyl, fluoroalkyl, alkenyl, alkynyl, cycloalkyl, cycloalkenyl, or 4- to 8-membered heterocycloalkyl is unsubstituted or substituted by 1-6 R$^c$ groups;

or R$^4$ and R$^5$ are taken together with the nitrogen to which they are attached to form a 4- to 8-membered heterocycloalkyl, which is unsubstituted or substituted by 1-6 R$^c$ groups;

R$^7$ is hydrogen, C$_{1-4}$ alkyl, or C$_{1-4}$ fluoroalkyl;

R$^8$ is C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, 4- to 8-membered heterocycloalkyl, —[(CH$_2$)$_r$—Z]$_t$—R$^6$, —[(CHR$^d$)$_r$—Z]$_t$—R$^6$, or —[(CR$^d$)$_r$—Z]$_t$—R$^6$; wherein each alkyl, fluoroalkyl, alkenyl, alkynyl, cycloalkyl, cycloalkenyl, and 4- to 8-membered heterocycloalkyl is substituted by 1-6 R$^c$ groups;

or R$^8$ is —(C$_{1-8}$ alkyl)-NH—R$^9$, —(C$_{1-8}$ alkyl)-C(=O)NH—R$^9$, —(C$_{1-8}$ alkyl)-C(=O)—N(R$^9$)$_2$, or —(C$_{1-8}$ alkyl)-NHC(=O)NH—R$^9$; wherein the alkyl is unsubstituted or substituted by 1-6 R$^c$ groups;
each R$^9$ is independently C$_{1-8}$ alkyl, or C$_{1-8}$ fluoroalkyl which is substituted by 1-6 R$^c$ groups; or two R$^9$ are taken together with the nitrogen to which they are attached to form a 4- to 6-membered heterocycloalkyl, which is substituted by 1-6 R$^c$ groups;
each R$^c$ is independently —OH, —CH$_2$OH, —CH$_2$CH$_2$OH, —NH$_2$, —CH$_2$NH$_2$, —NH(R$^d$), —CH$_2$NH(R$^d$), —N(R$^d$)$_2$, —CH$_2$N(R$^d$)$_2$, —N(R$^d$)$_3^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), P(=O)(OH)(OR$^d$), —B(OH)$_2$, —B(OR$^d$)(OH), —NHCONHS(=O)$_2$(R$^d$), —N(R$^d$)CONHS(=O)$_2$(R$^d$), —NHCON(R$^d$)S(=O)$_2$(R$^d$), —C(=O)NHS(=O)$_2$(R$^d$), —S(=O)$_2$NHC(=O)R$^d$, —NHC(=NH)NH$_2$, —NHC(=NH)NHR$^d$, —NHC(=NH)N(R$^d$)$_2$, —N(R$^d$)C(=NH)NH$_2$, —N(R$^d$)C(=NH)NH(R$^d$), —N(R$^d$)C(=NH)N(R$^d$)$_2$, —NHC(=N(R$^d$))NH$_2$, —NHC(=N(R$^d$))NHR$^d$, —NHC(=N(R$^d$))N(R$^d$)$_2$, —N(R$^d$)C(=N(R$^d$))NH$_2$, —N(R$^d$)C(=N(R$^d$))NHR$^d$, —N(R$^d$)C(=N(R$^d$))N(R$^d$)$_2$, —NHC(=NH)NHC(=NH)NH$_2$, —N(R$^d$)C(=NH)NHC(=NH)NH$_2$,

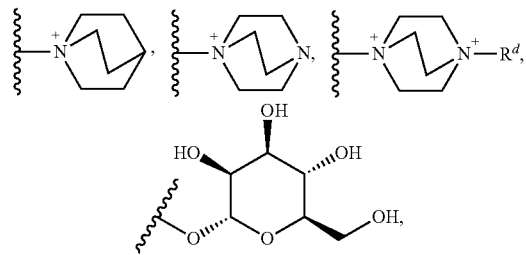

or a 4- to 6-membered heterocycle which is unsubstituted or substituted with 1, 2, 3, or 4 substituents selected from C$_{1-6}$ alkyl, —O—(C$_{1-6}$ alkyl), —OH, =O and =S;
each R$^d$ is independently C$_{1-6}$ alkyl, C$_{1-6}$ fluoroalkyl, or C$_{3-6}$ cycloalkyl;
each R$^e$ is independently —OH, —CH$_2$OH, —CH$_2$CH$_2$OH, —N(R$^d$)$_3^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), —P(=O)(OH)(OR$^d$), —B(OH)$_2$, —B(OR$^d$)(OH), —NHCONHS(=O)$_2$(R$^d$), —N(R$^d$)CONHS(=O)$_2$(R$^d$), —NHCON(R$^d$)S(=O)$_2$(R$^d$), —C(=O)NHS(=O)$_2$(R$^d$), —S(O)$_2$NHC(O)R$^d$, —NHC(=NH)NH$_2$, —NHC(=NH)NHR$^d$, —NHC(=NH)N(R$^d$)$_2$, —N(R$^d$)C(=NH)NH$_2$, N(R$^d$)C(=NH)NH(R$^d$), —N(R$^d$)C(=NH)N(R$^d$)$_2$, —NHC(=N(R$^d$))NH$_2$, —NHC(=N(R$^d$))NHR$^d$, —NHC(=N(R$^d$))N(R$^d$)$_2$, —N(R$^d$)C(=N(R$^d$))NH$_2$, —N(R$^d$)C(=N(R$^d$))NHR$^d$, —N(R$^d$)C(=N(R$^d$))N(R$^d$)$_2$, —NHC(=NH)NHC(=NH)NH$_2$, N(R$^d$)C(=NH)NHC(=NH)NH$_2$,

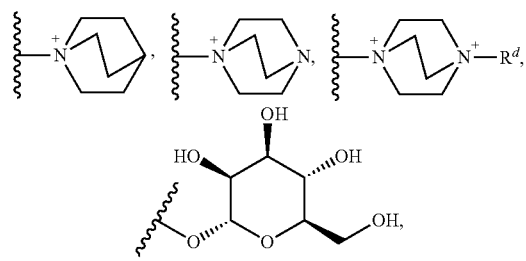

or a 4- to 6-membered heterocycle which is unsubstituted or substituted with 1, 2, 3, or 4 substituents selected from C$_{1-6}$ alkyl, —O—(C$_{1-6}$ alkyl), —OH, =O and =S;
Ring A is phenyl or 5-6 membered monocyclic heteroaryl;
each R$^a$ is independently halogen, —CN, C$_{1-6}$ alkyl, C$_{1-6}$ fluoroalkyl, or C$_{3-6}$ cycloalkyl;
X, when K is

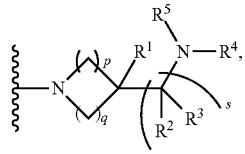

is —O—, —NR$^N$—, *—CH$_2$O—, *—CH$_2$NR$^N$—, *—C(=O)O—, *—C(=O)NR$^N$—, *—CH$_2$C(=O)O—, *—CH$_2$C(=O)NR$^N$—, *—OC(=O)—, *—NR$^N$C(=O)—, *—CH$_2$OC(=O)—, or *—CH$_2$NR$^N$C(=O)—, where * represents the attachment point to Ring A;
R$^N$ is hydrogen or C$_{1-4}$ alkyl;
or X, when K is

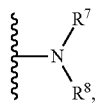

is —O—, —NR$^N$—, *—CH$_2$O—, *—CH$_2$NR$^N$—, *—C(=O)O—, *—C(=O)NR$^N$—, *—CH$_2$C(=O)O—, *—CH$_2$C(=O)NR$^N$—, *—OC(=O)—, *—CH$_2$OC(=O)—, or *—CH$_2$NR$^N$C(=O)—, where * represents the attachment point to Ring A;
R$^N$ is hydrogen or C$_{1-4}$ alkyl;
each R$^{11}$ is independently hydrogen, fluorine, —OH, C$_{1-6}$ alkyl, or C$_{1-6}$ alkoxy;
each R$^{12}$ is independently hydrogen, fluorine, or C$_{1-6}$ alkyl;
or, when K is

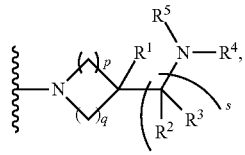

two R$^{11}$ are taken together with the intervening atoms to which they are attached to form a C$_{3-6}$ cycloalkyl;
or, when K is

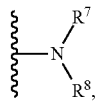

two R$^{11}$ are taken together with the intervening atoms to which they are attached to form a C$_{4-6}$ cycloalkyl;
R$^{13}$, R$^{14}$, R$^{15}$, R$^{16}$, R$^{17}$, R$^{18}$, R$^{19}$, and R$^{20}$ are each independently hydrogen, C$_{1-6}$ alkyl, C$_{1-6}$ alkoxy, or C$_{1-6}$ fluoroalkyl;
or R$^{13}$ and R$^{17}$ or R$^{13}$ and R$^{19}$ or R$^{15}$ and R$^{19}$ are taken together with the intervening atoms to which they are attached to form a ring;

$R^{21}$ is hydrogen, $C_{1-6}$ alkyl, or $C_{1-6}$ fluoroalkyl;
or $R^{21}$ and one $R^{11}$ are taken together with the intervening atoms to which they are attached to form a $C_{3-6}$ cycloalkyl;
W is phenyl or 5-6 membered monocyclic heteroaryl, wherein the phenyl or heteroaryl is unsubstituted or substituted with 1, 2, or 3 substituents selected from $R^b$;
each $R^b$ is independently halogen, —OH, —CN, —C(O)OH, —C(O)O($C_{1-6}$ alkyl), $C_{1-6}$ alkyl, $C_{1-6}$ alkoxy, $C_{3-6}$ cycloalkyl, phenyl, or 5- to 6-membered heteroaryl; wherein each alkyl, alkoxy, and cycloalkyl is unsubstituted or substituted with 1, 2, or 3 substituents selected from halogen, —OH, $C_{1-6}$ alkyl, and $C_{1-6}$ alkoxy;
or W is —C(=O)O—$R^{22}$;
$R^{22}$ is $C_{1-6}$ alkyl, $C_{3-6}$ cycloalkyl, or 3- to 6-membered heterocycloalkyl, wherein the alkyl, cycloalkyl, and heterocycloalkyl are unsubstituted or substituted by 1-3 substituents independently selected from fluorine, —OH, $C_{1-6}$ alkyl, $C_{1-6}$ haloalkyl or $C_{3-6}$ cycloalkyl;
m is 1-4;
n is 0-4;
p is 1 or 2;
q is 1 or 2; and
s is 1 or 2.

In some embodiments, disclosed herein is a compound of Formula (II):

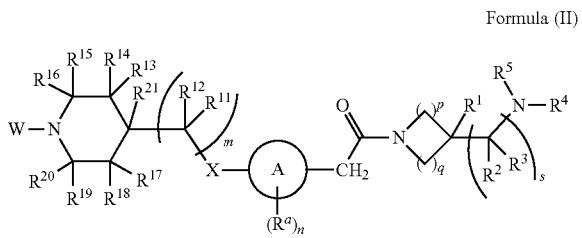

Formula (II)

or a pharmaceutically acceptable salt, solvate, stereoisomer, or prodrug thereof, wherein:
$R^1$ is hydrogen, —OH, $C_{1-8}$ alkyl, $C_{3-8}$ cycloalkyl, or 3- to 8-membered heterocycloalkyl, wherein the alkyl, cycloalkyl, and heterocycloalkyl are unsubstituted or substituted by 1-3 substituents independently selected from halogen, —OH, and —O($C_{1-6}$ alkyl);
each $R^2$ and $R^3$ is independently hydrogen, $C_{1-6}$ alkyl, or $C_{1-6}$ fluoroalkyl;
or $R^2$ and $R^3$ on the same carbon atom are taken together to form =O;
$R^4$ is hydrogen, $C_{1-8}$ alkyl, $C_{1-8}$ fluoroalkyl, $C_{2-8}$ alkenyl, $C_{2-8}$ alkynyl, $C_{3-8}$ cycloalkyl, $C_{5-8}$ cycloalkenyl, 4- to 8-membered heterocycloalkyl, —[(CH$_2$)$_r$—Z]$_t$—$R^6$, —[(CHR$^d$)$_r$—Z]$_t$—$R^6$, or —[(C(R$^d$)$_2$)$_r$—Z]$_t$—$R^6$; wherein each alkyl, fluoroalkyl, alkenyl, alkynyl, cycloalkyl, cycloalkenyl, and 4- to 8-membered heterocycloalkyl is unsubstituted or substituted by 1-6 $R^c$ groups;
$R^5$ is $C_{1-8}$ alkyl, $C_{1-8}$ fluoroalkyl, $C_{2-8}$ alkenyl, $C_{2-8}$ alkynyl, $C_{3-8}$ cycloalkyl, $C_{5-8}$ cycloalkenyl, 4- to 8-membered heterocycloalkyl, —[(CH$_2$)$_r$—Z]$_t$—$R^6$, —[(CHR$^d$)$_r$—Z]$_t$—$R^6$, or —[(C(R$^d$)$_2$)$_r$—Z]$_t$—$R^6$; wherein each alkyl, fluoroalkyl, alkenyl, alkynyl, cycloalkyl, cycloalkenyl, and 4- to 8-membered heterocycloalkyl is substituted by 1-6 $R^c$ groups;
each Z is independently —CH$_2$O—, —CH$_2$NR$^d$—, —CH$_2$N$^+$(R$^d$)$_2$—, —NH—C(=O)—NH—, —C(=O)NH—, —CH$_2$S(=O)$_2$—, or —CH$_2$S(=O)—;
each r is independently 1-6;
each t is independently 1-6;

$R^6$ is hydrogen, $C_{1-8}$ alkyl, $C_{1-8}$ fluoroalkyl, $C_{2-8}$ alkenyl, $C_{2-8}$ alkynyl, $C_{3-8}$ cycloalkyl, $C_{5-8}$ cycloalkenyl, or 4- to 8-membered heterocycloalkyl, wherein the alkyl, fluoroalkyl, alkenyl, alkynyl, cycloalkyl, cycloalkenyl, or 4- to 8-membered heterocycloalkyl is unsubstituted or substituted by 1-6 $R^c$ groups;
or $R^4$ and $R^5$ are taken together with the nitrogen to which they are attached to form a 4- to 8-membered heterocycloalkyl, which is unsubstituted or substituted by 1-6 $R^c$ groups;
each $R^c$ is independently —OH, —CH$_2$OH, —CH$_2$CH$_2$OH, —NH$_2$, —CH$_2$NH$_2$, —NH(R$^d$), —CH$_2$NH(R$^d$), —N(R$^d$)$_2$, —CH$_2$N(R$^d$)$_2$, —N(R$^d$)$_3$$^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), P(=O)(OH)(OR$^d$), —B(OH)$_2$, —B(OR$^d$)(OH), —NHCONHS(=O)$_2$(R$^d$), —N(R$^d$)CONHS(=O)$_2$(R$^d$), —NHCON(R$^d$)S(=O)$_2$(R$^d$), —C(=O)NHS(=O)$_2$(R$^d$), —S(=O)$_2$NHC(=O)R$^d$, —NHC(=NH)NH$_2$, —NHC(=NH)NHR$^d$, —NHC(=NH)N(R$^d$)$_2$, —N(R$^d$)C(=NH)NH$_2$, —N(R$^d$)C(=NH)NH(R$^d$), —N(R$^d$)C(=NH)N(R$^d$)$_2$, —NHC(=N(R$^d$))NH$_2$, —NHC(=N(R$^d$))NHR$^d$, —NHC(=N(R$^d$))N(R$^d$)$_2$, —N(R$^d$)C(=N(R$^d$))NH$_2$, —N(R$^d$)C(=N(R$^d$))NHR$^d$, —N(R$^d$)C(=N(R$^d$))N(R$^d$)$_2$, —NHC(=NH)NHC(=NH)NH$_2$, —N(R$^d$)C(=NH)NHC(=NH)NH$_2$,

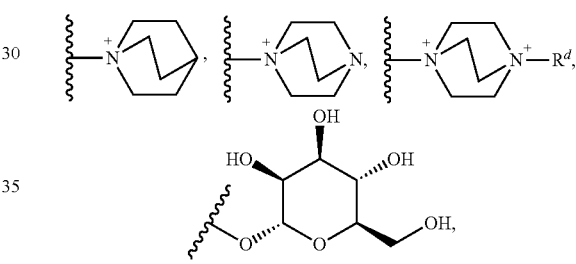

or a 4- to 6-membered heterocycle which is unsubstituted or substituted with 1, 2, 3, or 4 substituents selected from $C_{1-6}$ alkyl, —O—($C_{1-6}$ alkyl), —OH, =O and =S;
each $R^d$ is independently $C_{1-6}$ alkyl, $C_{1-6}$ fluoroalkyl, or $C_{3-6}$ cycloalkyl;
Ring A is phenyl or 5-6 membered monocyclic heteroaryl;
each $R^a$ is independently halogen, —CN, $C_{1-6}$ alkyl, $C_{1-6}$ fluoroalkyl, or $C_{3-6}$ cycloalkyl;
X is —O—, —NR$^N$—, *—CH$_2$O—, *—CH$_2$NR$^N$—, *—C(=O)O—, *—C(=O)NR$^N$—, *—CH$_2$C(=O)O—, *—CH$_2$C(=O)NR$^N$—, *—OC(=O)—, *—NR$^N$C(=O)—, *—CH$_2$OC(=O)—, or *—CH$_2$NR$^N$C(=O)—, where * represents the attachment point to Ring A;
$R^N$ is hydrogen or $C_{1-4}$ alkyl;
each $R^{11}$ is independently hydrogen, fluorine, —OH, $C_{1-6}$ alkyl, or $C_{1-6}$ alkoxy;
each $R^{12}$ is independently hydrogen, fluorine, or $C_{1-6}$ alkyl;
or two $R^{11}$ are taken together with the intervening atoms to which they are attached to form a $C_{3-6}$ cycloalkyl;
$R^{13}$, $R^{14}$, $R^{15}$, $R^{16}$, $R^{17}$, $R^{18}$, $R^{19}$, and $R^{20}$ are each independently hydrogen, $C_{1-6}$ alkyl, $C_{1-6}$ alkoxy, or $C_{1-6}$ fluoroalkyl;
or $R^{13}$ and $R^{17}$ or $R^{13}$ and $R^{19}$ or $R^{15}$ and $R^{19}$ are taken together with the intervening atoms to which they are attached to form a ring;
$R^{21}$ is hydrogen, $C_{1-6}$ alkyl, or $C_{1-6}$ fluoroalkyl;
or $R^{21}$ and one $R^{11}$ are taken together with the intervening atoms to which they are attached to form a $C_{3-6}$ cycloalkyl;

W is phenyl or 5-6 membered monocyclic heteroaryl, wherein the phenyl or heteroaryl is unsubstituted or substituted with 1, 2, or 3 substituents selected from $R^b$;
each $R^b$ is independently halogen, —OH, —CN, —C(O)OH, —C(O)O($C_{1-6}$ alkyl), $C_{1-6}$ alkyl, $C_{1-6}$ alkoxy, $C_{3-6}$ cycloalkyl, phenyl, or 5- to 6-membered heteroaryl; wherein each alkyl, alkoxy, and cycloalkyl is unsubstituted or substituted with 1, 2, or 3 substituents selected from halogen, —OH, $C_{1-6}$ alkyl, and $C_{1-6}$ alkoxy;
or W is —C(=O)O—$R^{22}$;
$R^{22}$ is $C_{1-6}$ alkyl, $C_{3-6}$ cycloalkyl, or 3- to 6-membered heterocycloalkyl, wherein the alkyl, cycloalkyl, and heterocycloalkyl are unsubstituted or substituted by 1-3 substituents independently selected from fluorine, —OH, $C_{1-6}$ alkyl, $C_{1-6}$ haloalkyl or $C_{3-6}$ cycloalkyl;
m is 1-4;
n is 0-4;
p is 1 or 2;
q is 1 or 2; and
s is 1 or 2.

In some embodiments, disclosed herein is a compound of Formula (III):

Formula (III)

or a pharmaceutically acceptable salt, solvate, stereoisomer, or prodrug thereof, wherein:
$R^7$ is hydrogen, $C_{1-4}$ alkyl, or $C_{1-4}$ fluoroalkyl;
$R^8$ is $C_{1-8}$ alkyl, $C_{1-8}$ fluoroalkyl, $C_{2-8}$ alkenyl, $C_{2-8}$ alkynyl, $C_{3-8}$ cycloalkyl, $C_{5-8}$ cycloalkenyl, 4- to 8-membered heterocycloalkyl, —[(CH$_2$)$_r$—Z]$_t$—$R^6$, —[(CHR$^d$)$_r$—Z]$_t$—$R^6$, or —[(CR$^d_2$)$_r$—Z]$_t$—$R^6$;
wherein each alkyl, fluoroalkyl, alkenyl, alkynyl, cycloalkyl, cycloalkenyl, and 4- to 8-membered heterocycloalkyl is substituted by 1-6 $R^c$ groups;
each r is independently 1-6;
each t is independently 1-6;
$R^6$ is hydrogen, $C_{1-8}$ alkyl, $C_{1-8}$ fluoroalkyl, $C_{2-8}$ alkenyl, $C_{2-8}$ alkynyl, $C_{3-8}$ cycloalkyl, $C_{5-8}$ cycloalkenyl, or 4- to 8-membered heterocycloalkyl, wherein the alkyl, fluoroalkyl, alkenyl, alkynyl, cycloalkyl, cycloalkenyl, or 4- to 8-membered heterocycloalkyl is unsubstituted or substituted by 1-6 $R^c$ groups;
or $R^8$ is —($C_{1-8}$ alkyl)-NH—$R^9$, —($C_{1-8}$ alkyl)-C(=O)NH—$R^9$, —($C_{1-8}$ alkyl)-C(=O)—N($R^9$)$_2$, or —($C_{1-8}$ alkyl)-NHC(=O)NH—$R^9$; wherein the alkyl is unsubstituted or substituted by 1-6 $R^c$ groups;
each $R^9$ is independently $C_{1-8}$ alkyl, or $C_{1-8}$ fluoroalkyl which is substituted by 1-6 $R^c$ groups; or two $R^9$ are taken together with the nitrogen to which they are attached to form a 4- to 6-membered heterocycloalkyl, which is substituted by 1-6 $R^c$ groups;
each $R^c$ is independently —OH, —CH$_2$OH, —CH$_2$CH$_2$OH, —NH$_2$, —CH$_2$NH$_2$, —NH($R^d$), —CH$_2$NH($R^d$), —N($R^d$)$_2$, —CH$_2$N($R^d$)$_2$, —N($R^d$)$_3^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)($R^d$), —P(=O)(OH)(H), P(=O)(OH)(O$R^d$), —B(OH)$_2$, —B(O$R^d$)(OH), —NHCONHS(=O)$_2$($R^d$), —N($R^d$)CONHS(=O)$_2$($R^d$), CONHS(=O)$_2$($R^d$), —NHCON($R^d$)S(=O)$_2$($R^d$), —C(=O)NHS(=O)$_2$($R^d$), —S(=O)$_2$NHC(=O)$R^d$, —NHC(=NH)NH$_2$, —NHC(=NH)NH$R^d$, —NHC(=NH)N($R^d$)$_2$, —N($R^d$)C(=NH)NH$_2$, —N($R^d$)C(=NH)NH($R^d$), —N($R^d$)C(=NH)N($R^d$)$_2$, —NHC(=N($R^d$))NH$_2$, —NHC(=N($R^d$))NH$R^d$, —NHC(=N($R^d$))N($R^d$)$_2$, —N($R^d$)C(=N($R^d$))NH$_2$, —N($R^d$)C(=N($R^d$))NH$R^d$, —N($R^d$)C(=N($R^d$))N($R^d$)$_2$, —NHC(=NH)NHC(=NH)NH$_2$, —N($R^d$)C(=NH)NHC(=NH)NH$_2$, or a 4- to 6-membered heterocycle which is unsubstituted or substituted with 1, 2, 3, or 4 substituents selected from $C_{1-6}$ alkyl, —O—($C_{1-6}$ alkyl), —OH, =O and =S;
each $R^d$ is independently $C_{1-6}$ alkyl, $C_{1-6}$ fluoroalkyl, or $C_{3-6}$ cycloalkyl;
each $R^e$ is independently —OH, —CH$_2$OH, —CH$_2$CH$_2$OH, —N($R^d$)$_3^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)($R^d$), —P(=O)(OH)(H), —P(=O)(OH)(O$R^d$), —B(OH)$_2$, —B(O$R^d$)(OH), —NHCONHS(=O)$_2$($R^d$), —N($R^d$)CONHS(=O)$_2$($R^d$), —NHCON($R^d$)S(=O)$_2$($R^d$), —C(=O)NHS(=O)$_2$($R^d$), —S(O)$_2$NHC(O)$R^d$, —NHC(=NH)NH$_2$, —NHC(=NH)NH$R^d$, —NHC(=NH)N($R^d$)$_2$, —N($R^d$)C(=NH)NH$_2$, N($R^d$)C(=NH)NH($R^d$), —N($R^d$)C(=NH)N($R^d$)$_2$, —NHC(=N($R^d$))NH$_2$, —NHC(=N($R^d$))NH$R^d$, —NHC(=N($R^d$))N($R^d$)$_2$, —N($R^d$)C(=N($R^d$))NH$_2$, —N($R^d$)C(=N($R^d$))NH$R^d$, —N($R^d$)C(=N($R^d$))N($R^d$)$_2$, —NHC(=NH)NHC(=NH)NH$_2$, N($R^d$)C(=NH)NHC(=NH)NH$_2$, or a 4- to 6-membered heterocycle which is unsubstituted or substituted with 1, 2, 3, or 4 substituents selected from $C_{1-6}$ alkyl, —O—($C_{1-6}$ alkyl), —OH, =O and =S;
Ring A is phenyl or 5-6 membered monocyclic heteroaryl;
each $R^a$ is independently halogen, —CN, $C_{1-6}$ alkyl, $C_{1-6}$ fluoroalkyl, or $C_{3-6}$ cycloalkyl;
X is —O—, —NR$^N$—, *—CH$_2$O—, *—CH$_2$NR$^N$—, *—C(=O)O—, *—C(=O)NR$^N$—, *—CH$_2$C(=O)O—, *—CH$_2$C(=O)NR$^N$—, *—OC(=O)—, *—CH$_2$OC(=O)—, or *—CH$_2$NR$^N$C(=O)—, where * represents the attachment point to Ring A;

$R^N$ is hydrogen or $C_{1-4}$ alkyl;
each $R^{11}$ is independently hydrogen, fluorine, —OH, $C_{1-6}$ alkyl, or $C_{1-6}$ alkoxy;
each $R^{12}$ is independently hydrogen, fluorine, or $C_{1-6}$ alkyl;
or two $R^{11}$ are taken together with the intervening atoms to which they are attached to form a $C_{4-6}$ cycloalkyl;
$R^{13}$, $R^{14}$, $R^{15}$, $R^{16}$, $R^{17}$, $R^{18}$, $R^{19}$, and $R^{20}$ are each independently hydrogen, $C_{1-6}$ alkyl, $C_{1-6}$ alkoxy, or $C_{1-6}$ fluoroalkyl;
or $R^{13}$ and $R^{17}$ or $R^{13}$ and $R^{19}$ or $R^{15}$ and $R^{19}$ are taken together with the intervening atoms to which they are attached to form a ring;
$R^{21}$ is hydrogen, $C_{1-6}$ alkyl, or $C_{1-6}$ fluoroalkyl;
or $R^{21}$ and one $R^{11}$ are taken together with the intervening atoms to which they are attached to form a $C_{3-6}$ cycloalkyl;
W is phenyl or 5-6 membered monocyclic heteroaryl, wherein the phenyl or heteroaryl is unsubstituted or substituted with 1, 2, or 3 substituents selected from $R^b$;
each $R^b$ is independently halogen, —OH, —CN, —C(O)OH, —C(O)O($C_{1-6}$ alkyl), $C_{1-6}$ alkyl, $C_{1-6}$ alkoxy, $C_{3-6}$ cycloalkyl, phenyl, or 5- to 6-membered heteroaryl; wherein each alkyl, alkoxy, and cycloalkyl is unsubstituted or substituted with 1, 2, or 3 substituents selected from halogen, —OH, $C_{1-6}$ alkyl, and $C_{1-6}$ alkoxy;
or W is —C(=O)O—$R^{22}$;
$R^{22}$ is $C_{1-6}$ alkyl, $C_{3-6}$ cycloalkyl, or 3- to 6-membered heterocycloalkyl, wherein the alkyl, cycloalkyl, and heterocycloalkyl are unsubstituted or substituted by 1-3 substituents independently selected from fluorine, —OH, $C_{1-6}$ alkyl, $C_{1-6}$ haloalkyl or $C_{3-6}$ cycloalkyl;
m is 1-4;
n is 0-4;
p is 1 or 2;
q is 1 or 2; and
s is 1 or 2.

In some embodiments, X is —O—, —NR$^N$—, *—CH$_2$O—, *—CH$_2$NR$^N$—, *—C(=O)O—, *—C(=O)NR$^N$—, *—CH$_2$C(=O)O—, *—CH$_2$C(=O)NR$^N$—, *—OC(=O)—, *—NR$^N$C(=O)—, *—CH$_2$OC(=O)—, or *—CH$_2$NR$^N$C(=O)—, where * represents the attachment point to Ring A. In some embodiments, X is —O—, —NR$^N$—, *—CH$_2$O—, *—CH$_2$NR$^N$—, *—C(=O)O—, *—C(=O)NR$^N$—, *—CH$_2$C(=O)O—, *—CH$_2$C(=O)NR$^N$—, *—OC(=O)—, *—CH$_2$OC(=O)—, or *—CH$_2$NR$^N$C(=O)—, where * represents the attachment point to Ring A. In some embodiments, X is —O—, —NR$^N$—, *—CH$_2$O—, or *—CH$_2$NR$^N$—, where * represents the attachment point to Ring A. In some embodiments, X is —O— or —NR$^N$—. In some embodiments, X is —O—, *—CH$_2$O—, *—C(=O)O—, or *—CH$_2$C(=O)O—, where * represents the attachment point to Ring A. In some embodiments, X is —O— or *—CH$_2$O—, where * represents the attachment point to Ring A. In some embodiments, X is —O—. In some embodiments, X is —NR$^N$—.

In some embodiments, $R^N$ is hydrogen, methyl, ethyl, n-propyl, i-propyl, n-butyl, i-butyl, s-butyl, or t-butyl. In some embodiments, $R^N$ is hydrogen, methyl, or ethyl. In some embodiments, $R^N$ is hydrogen or methyl. In some embodiments, $R^N$ is hydrogen. In some embodiments, $R^N$ is methyl.

In some embodiments, each $R^{11}$ is independently hydrogen, fluorine, $C_{1-6}$ alkyl, or $C_{1-6}$ alkoxy. In some embodiments, each $R^{11}$ is independently hydrogen, fluorine, or $C_{1-6}$ alkyl. In some embodiments, each $R^{11}$ is independently hydrogen or $C_{1-6}$ alkyl. In some embodiments, each $R^{11}$ is independently hydrogen, fluorine, or $C_{1-4}$ alkyl. In some embodiments, each $R^{11}$ is independently hydrogen or $C_{1-4}$ alkyl. In some embodiments, each $R^{11}$ is independently hydrogen, methyl, ethyl, n-propyl, i-propyl, n-butyl, i-butyl, s-butyl, or t-butyl. In some embodiments, each $R^{11}$ is hydrogen.

In some embodiments, each $R^{12}$ is independently hydrogen, fluorine, or $C_{1-4}$ alkyl. In some embodiments, each $R^{12}$ is independently hydrogen or $C_{1-4}$ alkyl. In some embodiments, each $R^{12}$ is independently hydrogen, methyl, ethyl, n-propyl, i-propyl, n-butyl, i-butyl, s-butyl, or t-butyl. In some embodiments, each $R^{12}$ is hydrogen.

In some embodiments, two $R^{11}$ are taken together with the intervening atoms to which they are attached to form a $C_{3-6}$ cycloalkyl. In some embodiments, two $R^{11}$ are taken together with the intervening atoms to which they are attached to form a $C_{4-6}$ cycloalkyl. In some embodiments, two $R^{11}$ are taken together with the intervening atoms to which they are attached to form a $C_{3-4}$ cycloalkyl. In some embodiments, two $R^{11}$ are taken together with the intervening atoms to which they are attached to form a cyclopropyl, cyclobutyl, cyclopentyl, or cyclohexyl. In some embodiments, two $R^{11}$ are taken together with the intervening atoms to which they are attached to form a cyclobutyl, cyclopentyl, or cyclohexyl. In some embodiments, two $R^{11}$ are taken together with the intervening atoms to which they are attached to form a cyclopropyl or cyclobutyl. In some embodiments, two $R^{11}$ are taken together with the intervening atoms to which they are attached to form a cyclopropyl. In some embodiments, two $R^{11}$ are taken together with the intervening atoms to which they are attached to form a cyclobutyl.

In some embodiments, $R^{13}$, $R^{14}$, $R^5$, $R^{16}$, $R^7$, $R^{18}$, $R^{19}$, and $R^{20}$ are each independently hydrogen, $C_{1-6}$ alkyl, $C_{1-6}$ alkoxy, or $C_{1-6}$ fluoroalkyl. In some embodiments, $R^{13}$, $R^{14}$, $R^5$, $R^{16}$, $R^{17}$, $R^{18}$, $R^{19}$, and $R^{20}$ are each independently hydrogen, $C_{1-6}$ alkyl, or $C_{1-6}$ fluoroalkyl. In some embodiments, $R^{13}$, $R^{14}$, $R^{15}$, $R^{16}$, $R^{17}$, $R^{18}$, $R^{19}$, and $R^{20}$ are each independently hydrogen or $C_{1-6}$ alkyl. In some embodiments, $R^{13}$, $R^{14}$, $R^5$, $R^{16}$, $R^7$, $R^{18}$, $R^{19}$, and $R^{20}$ are each independently hydrogen, $C_{1-4}$ alkyl, or $C_{1-4}$ fluoroalkyl. In some embodiments, $R^{13}$, $R^{14}$, $R^{15}$, $R^{16}$, $R^{17}$, $R^1$, $R^{19}$, and $R^{20}$ are each independently hydrogen or $C_{1-4}$ alkyl. In some embodiments, $R^{13}$, $R^{14}$, $R^5$, $R^{16}$, $R^{17}$, $R^{18}$, $R^{19}$, and $R^{20}$ are each independently hydrogen, methyl, ethyl, n-propyl, i-propyl, n-butyl, i-butyl, s-butyl, t-butyl, —CF$_3$, CHF$_2$, or CH$_2$F. In some embodiments, $R^{13}$, $R^{14}$, $R^5$, $R^{16}$, $R^{17}$, $R^{18}$, $R^{19}$, and $R^{20}$ are each independently hydrogen, methyl, ethyl, n-propyl, i-propyl, n-butyl, i-butyl, s-butyl, or t-butyl. In some embodiments, $R^{13}$, $R^{14}$, $R^5$, $R^{16}$, $R^{17}$, $R^{18}$, $R^{19}$, and $R^{20}$ are each hydrogen.

In some embodiments, $R^{13}$ and $R^{17}$ or $R^{13}$ and $R^{19}$ or $R^{15}$ and $R^{19}$ are taken together with the intervening atoms to which they are attached to form a ring. In some embodiments, $R^{13}$ and $R^7$ or $R^{13}$ and $R^{19}$ or $R^{15}$ and $R^{19}$ are taken together with the intervening atoms to which they are attached to form a 4- to 6-membered ring. In some embodiments, $R^{13}$ and $R^{17}$ or $R^{13}$ and $R^{19}$ or $R^{15}$ and $R^{19}$ are taken together to form a bond, —CH$_2$—, or —CH$_2$CH$_2$—. In some embodiments, $R^{13}$ and $R^{17}$ or $R^{13}$ and $R^{19}$ or $R^{15}$ and $R^{19}$ are taken together to form a bond. In some embodiments, $R^{13}$ and $R^{17}$ are taken together with the intervening atoms to which they are attached to form a ring. In some embodiments, or $R^{13}$ and $R^{19}$ are taken together with the intervening atoms to which they are attached to form a ring. In some embodiments, $R^{15}$ and $R^{19}$ are taken together with the intervening atoms to which they are attached to form a ring. In some embodiments, $R^{13}$ and $R^{17}$ are taken together to form a bond. In some embodiments, or $R^{13}$ and $R^{19}$ are taken together to form a bond. In some embodiments, $R^{15}$ and $R^{19}$ are taken together to form a bond.

In some embodiments, $R^{21}$ is hydrogen, $C_{1-6}$ alkyl, or $C_{1-6}$ fluoroalkyl. In some embodiments, $R^{21}$ is hydrogen or $C_{1-6}$ alkyl. In some embodiments, $R^{21}$ is hydrogen, $C_{1-4}$ alkyl, or $C_{1-4}$ fluoroalkyl. In some embodiments, $R^{21}$ is hydrogen or $C_{1-4}$ alkyl. In some embodiments, $R^{21}$ is hydrogen, methyl, ethyl, n-propyl, i-propyl, n-butyl, i-butyl, s-butyl, t-butyl, —$CF_3$, $CHF_2$, or $CH_2F$. In some embodiments, $R^{21}$ is hydrogen, methyl, ethyl, n-propyl, i-propyl, n-butyl, i-butyl, s-butyl, or t-butyl. In some embodiments, $R^{21}$ is hydrogen.

In some embodiments, $R^{21}$ and one $R^{11}$ are taken together with the intervening atoms to which they are attached to form a $C_{3-6}$ cycloalkyl. In some embodiments, $R^{21}$ and one $R^{11}$ are taken together with the intervening atoms to which they are attached to form a $C_{3-4}$ cycloalkyl. In some embodiments, $R^{21}$ and one $R^{11}$ are taken together with the intervening atoms to which they are attached to form a cyclopropyl, cyclobutyl, cyclopentyl, or cyclohexyl. In some embodiments, $R^{21}$ and one $R^{11}$ are taken together with the intervening atoms to which they are attached to form a cyclopropyl or cyclobutyl. In some embodiments, $R^{21}$ and one $R^{11}$ are taken together with the intervening atoms to which they are attached to form a cyclopropyl. In some embodiments, $R^{21}$ and one $R^{11}$ are taken together with the intervening atoms to which they are attached to form a cyclobutyl.

In some embodiments,

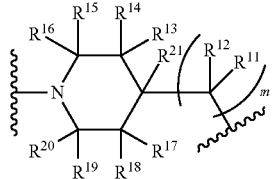

is

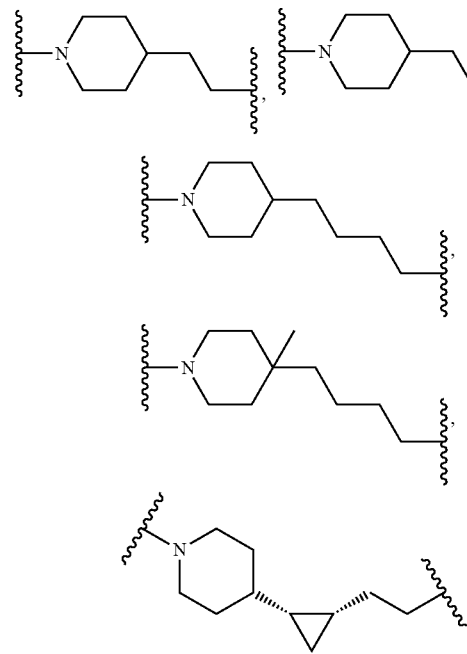

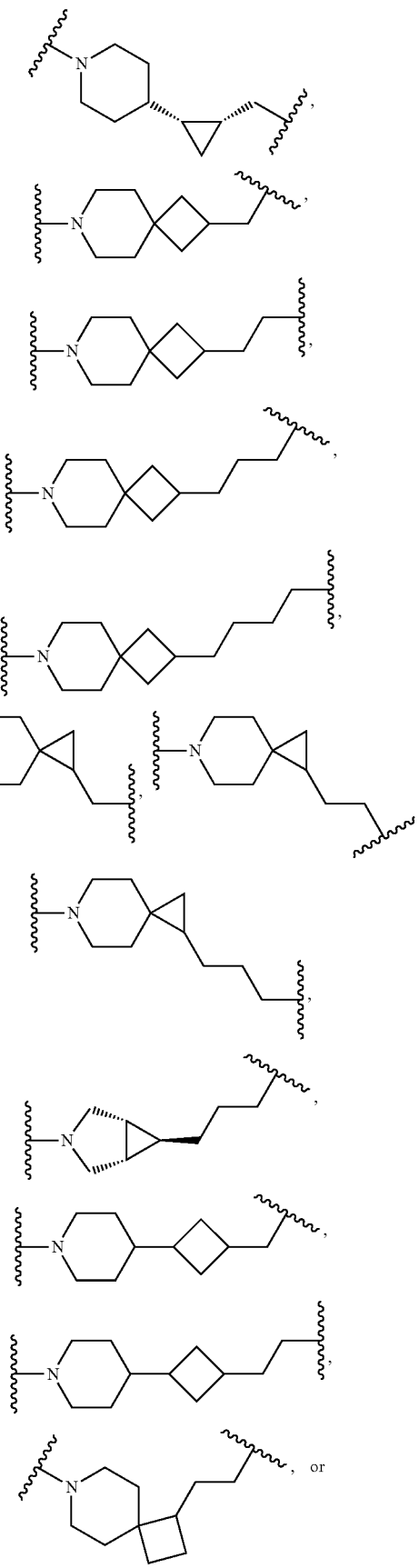

, or

-continued
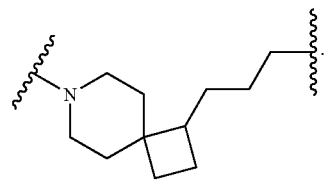
In some embodiments,
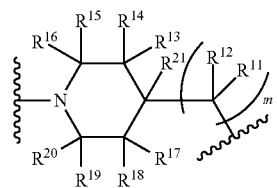
is
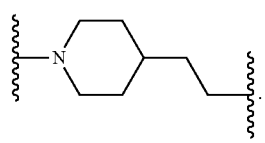 [SMILES: *CCC1CCN(*)CC1]
In some embodiments,
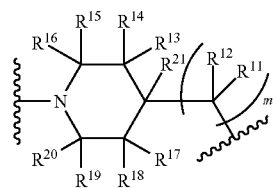
is
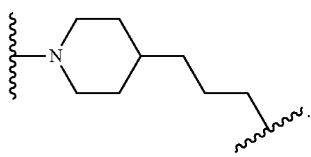 [SMILES: *CCCC1CCN(*)CC1]
In some embodiments,
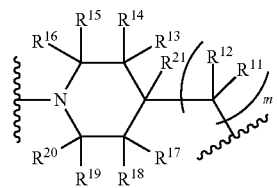
is
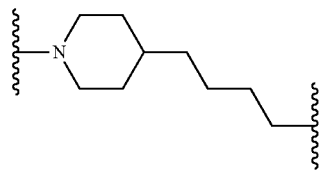
In some embodiments,
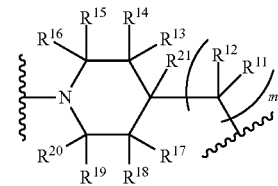
is
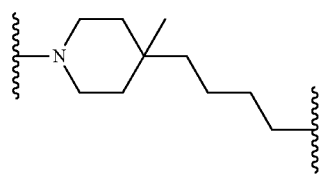
In some embodiments,
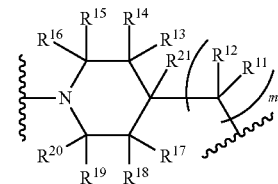
is
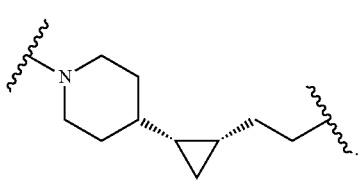 [SMILES: *CC[C@@H]1C[C@@H]1C1CCN(*)CC1]
In some embodiments,
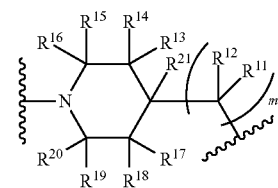

is
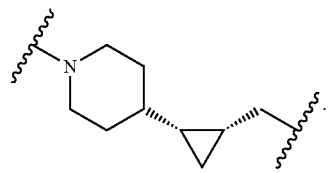 [SMILES: *C[C@@H]1C[C@@H]1C1CCN(*)CC1]
In some embodiments,
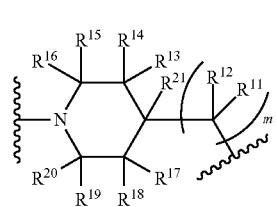
is
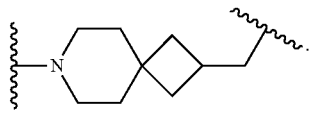 [SMILES: *CC1CC2(CCN(*)CC2)C1]
In some embodiments,
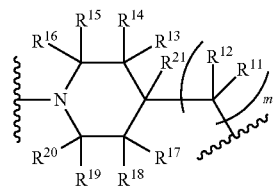
is
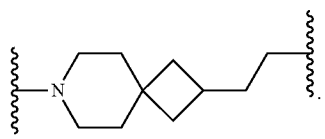 [SMILES: *CCC1CC2(CCN(*)CC2)C1]
In some embodiments,
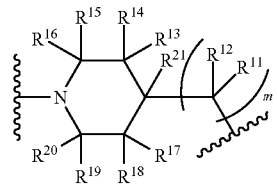
is
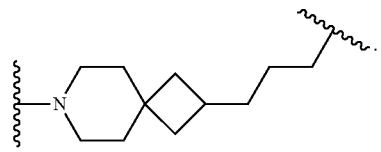 [SMILES: *CCCC1CC2(CCN(*)CC2)C1]
In some embodiments,
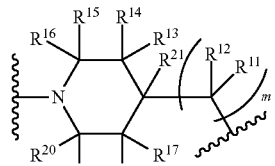
is
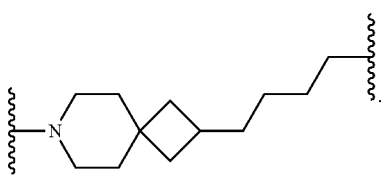 [SMILES: *CCCCC1CC2(CCN(*)CC2)C1]
In some embodiments,
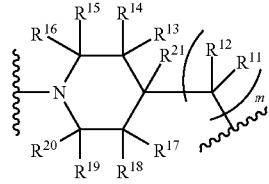
is
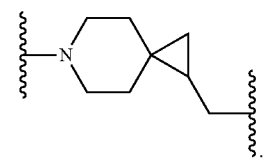 [SMILES: *CC1CC12CCN(*)CC2]
In some embodiments,
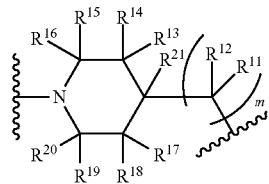

is
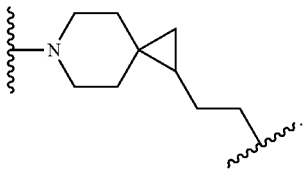 [SMILES: *CCC1CC12CCN(*)CC2]
In some embodiments,
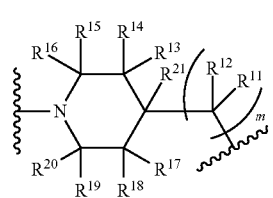
is
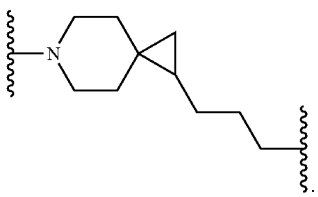 [SMILES: *CCCC1CC12CCN(*)CC2]
In some embodiments,
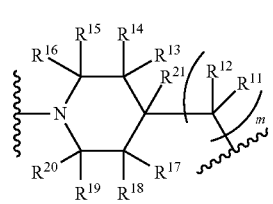
is
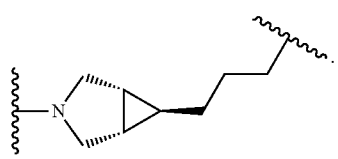 [SMILES: *CCC[C@@H]1[C@H]2CN(*)C[C@@H]12]
In some embodiments,
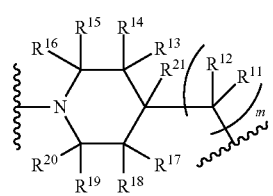
is
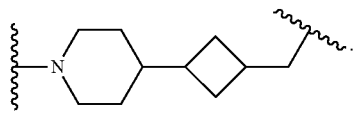 [SMILES: *CC1CC(C2CCN(*)CC2)C1]
In some embodiments,
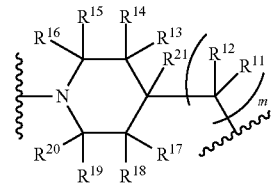
is
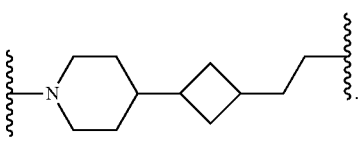
In some embodiments,
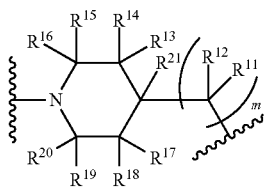
is
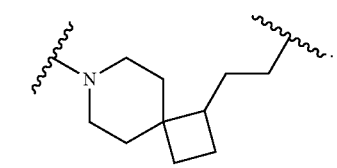 [SMILES: *CCC1CCC12CCN(*)CC2]
In some embodiments,
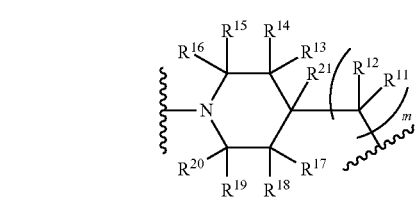

is

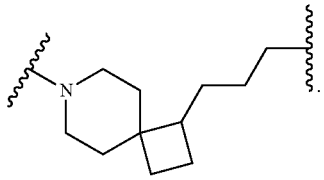 [SMILES: *CCCC1CCC12CCN(*)CC2]

In some embodiments, X is —O—, *—CH₂O—, *—C(=O)O—, or *—CH₂C(=O)O—, where * represents the attachment point to Ring A; each $R^{11}$ is independently hydrogen, fluorine, —OH, $C_{1-6}$ alkyl, or $C_{1-6}$ alkoxy; or, when K is

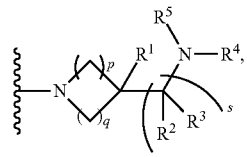

two $R^{11}$ on adjacent carbon atoms are taken together with the intervening atoms to which they are attached to form a cyclopropyl; $R^{21}$ is hydrogen or $C_{1-6}$ alkyl; and $R^{13}$, $R^{14}$, $R^{15}$, $R^{16}$, $R^{17}$, $R^{18}$, $R^{19}$, and $R^{20}$ are each independently hydrogen or $C_{1-6}$ alkyl. In some embodiments, X is —O—; each $R^{11}$ is hydrogen; each $R^{12}$ is hydrogen; $R^{21}$ is hydrogen; and $R^{13}$, $R^{14}$, $R^{15}$, $R^{16}$, $R^{17}$, $R^{18}$, $R^{19}$, and $R^{20}$ are each hydrogen.

In some embodiments, Ring A is 5-6 membered monocyclic heteroaryl. In some embodiments, Ring A is 5-membered monocyclic heteroaryl. In some embodiments, Ring A is pyrrolyl, furanyl, thiophenyl, pyrazolyl, imidazolyl, oxazolyl, isoxazolyl, thiazolyl, isothiazolyl, triazolyl, oxadiazolyl, or thiadiazolyl. In some embodiments, Ring A is 6-membered monocyclic heteroaryl. In some embodiments, Ring A is pyridyl, pyridazinyl, pyrimidinyl, pyrazinyl, or triazinyl. In some embodiments, Ring A is pyridyl.

In some embodiments, Ring A is phenyl.

In some embodiments, Ring A is phenyl or 6-membered monocyclic heteroaryl. In some embodiments, Ring A is phenyl or pyridyl.

In some embodiments, each $R^a$ is independently halogen, —CN, $C_{1-6}$ alkyl, $C_{1-6}$ fluoroalkyl. In some embodiments, each $R^a$ is independently halogen, $C_{1-6}$ alkyl, $C_{1-6}$ fluoroalkyl, or $C_{3-6}$ cycloalkyl. In some embodiments, each $R^a$ is independently halogen, $C_{1-6}$ alkyl, or $C_{1-6}$ fluoroalkyl. In some embodiments, each $R^a$ is independently halogen or $C_{1-6}$ alkyl. In some embodiments, each $R^a$ is independently halogen. In some embodiments, each $R^a$ is independently —F, —Cl, —Br, $C_{1-4}$ alkyl, or $C_{1-4}$ fluoroalkyl. In some embodiments, each $R^a$ is independently —F, —Cl, $C_{1-4}$ alkyl, or $C_{1-4}$ fluoroalkyl. In some embodiments, each $R^a$ is —F.

In some embodiments, n is 0-4. In some embodiments, n is 1-4. In some embodiments, n is 1-3. In some embodiments, n is 1-2. In some embodiments, n is 0, 1, 2, 3, or 4. In some embodiments, n is 1. In some embodiments, n is 2.

In some embodiments, Ring A is phenyl; each $R^a$ is independently halogen or $C_{1-6}$ alkyl; and n is 1-3. In some embodiments, Ring A is phenyl; each $R^a$ is independently halogen; and n is 1-2. In some embodiments, Ring A is phenyl; each $R^a$ is independently —F; and n is 1. In some embodiments, Ring A is phenyl; each $R^a$ is independently —F; and n is 2.

In some embodiments, disclosed herein is a compound of Formula (Ia):

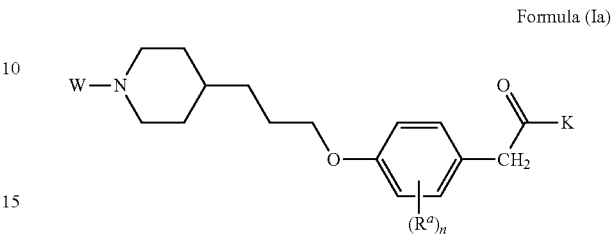

Formula (Ia)

or a pharmaceutically acceptable salt, solvate, stereoisomer, or prodrug thereof.

In some embodiments, disclosed herein is a compound of Formula (IIa):

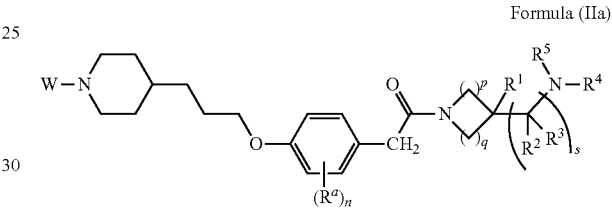

Formula (IIa)

or a pharmaceutically acceptable salt, solvate, stereoisomer, or prodrug thereof.

In some embodiments, disclosed herein is a compound of Formula (IIIa):

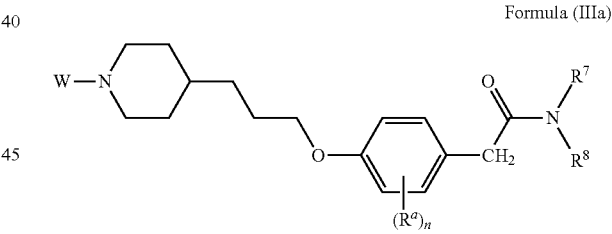

Formula (IIIa)

or a pharmaceutically acceptable salt, solvate, stereoisomer, or prodrug thereof.

In some embodiments, W is phenyl or 5-6 membered monocyclic heteroaryl. In some embodiments, W is optionally substituted phenyl or optionally substituted 5-6 membered monocyclic heteroaryl. In some embodiments, W is phenyl or 5-6 membered monocyclic heteroaryl, wherein the phenyl or heteroaryl is unsubstituted or substituted. In some embodiments, W is phenyl or 5-6 membered monocyclic heteroaryl, wherein the phenyl or heteroaryl is unsubstituted or substituted with 1, 2, or 3 substituents selected from $R^b$. In some embodiments, W is phenyl or 5-6 membered monocyclic heteroaryl, wherein the phenyl or heteroaryl is unsubstituted or substituted with 1 or 2 substituents selected from $R^b$. In some embodiments, W is phenyl or 5-6 membered monocyclic heteroaryl, wherein the phenyl or heteroaryl is unsubstituted or substituted with 1 substituent selected from $R^b$.

In some embodiments, W is 5-6 membered monocyclic heteroaryl. In some embodiments, W is 5-6 membered monocyclic heteroaryl which is unsubstituted or substituted with 1, 2, or 3 substituents selected from $R^b$.

In some embodiments, W is 5-membered monocyclic heteroaryl. In some embodiments, W is 5-membered monocyclic heteroaryl. In some embodiments, W is 5-membered monocyclic heteroaryl which is unsubstituted or substituted with 1, 2, or 3 substituents selected from $R^b$. In some embodiments, W is pyrrolyl, furanyl, thiophenyl, pyrazolyl, imidazolyl, oxazolyl, isoxazolyl, thiazolyl, isothiazolyl, triazolyl, oxadiazolyl, or thiadiazolyl. In some embodiments, W is pyrrolyl, furanyl, thiophenyl, pyrazolyl, imidazolyl, oxazolyl, isoxazolyl, thiazolyl, isothiazolyl, triazolyl, oxadiazolyl, or thiadiazolyl which is unsubstituted or substituted with 1, 2, or 3 substituents selected from $R^b$. In some embodiments, W is 6-membered monocyclic heteroaryl. In some embodiments, W is 6-membered monocyclic heteroaryl which is unsubstituted or substituted with 1, 2, or 3 substituents selected from $R^b$. In some embodiments, W is 6-membered monocyclic heteroaryl which is unsubstituted or substituted with 1 or 2 substituents selected from $R^b$. In some embodiments, W is pyridyl, pyridazinyl, pyrimidinyl, pyrazinyl, or triazinyl. In some embodiments, W is pyridyl, pyridazinyl, pyrimidinyl, pyrazinyl, or triazinyl which is unsubstituted or substituted with 1, 2, or 3 substituents selected from $R^b$.

In some embodiments, W is phenyl. In some embodiments, W is phenyl which is unsubstituted or substituted with 1, 2, or 3 substituents selected from $R^b$.

In some embodiments, W is phenyl or 6-membered monocyclic heteroaryl. In some embodiments, W is phenyl or pyrimidinyl. In some embodiments, W is phenyl or 6-membered monocyclic heteroaryl which is unsubstituted or substituted with 1, 2, or 3 substituents selected from $R^b$. In some embodiments, W is phenyl or pyrimidinyl which is unsubstituted or substituted with 1, 2, or 3 substituents selected from $R^b$.

In some embodiments, W is pyrimidinyl. In some embodiments, W is pyrimidinyl which is unsubstituted or substituted with 1, 2, or 3 substituents selected from $R^b$. In some embodiments, W is pyrimidinyl which is unsubstituted or substituted with 1 or 2 substituents selected from $R^b$. In some embodiments, W is pyrimidinyl which is unsubstituted or substituted with 1 substituent selected from $R^b$.

In some embodiments, W is unsubstituted or substituted with 1, 2, or 3 substituents selected from $R^b$. In some embodiments, W is unsubstituted or substituted with 1 or 2 substituents selected from $R^b$. In some embodiments, W is unsubstituted or substituted with 1 substituent selected from $R^b$. In some embodiments, W is unsubstituted. In some embodiments, W is substituted with 1 substituent selected from $R^b$.

In some embodiments, each $R^b$ is independently halogen, —OH, —CN, —C(O)OH, —C(O)O($C_{1-6}$ alkyl), $C_{1-6}$ alkyl, $C_{1-6}$ alkoxy, $C_{3-6}$ cycloalkyl, phenyl, or 5- to 6-membered heteroaryl. In some embodiments, each $R^b$ is independently halogen, —OH, —CN, —C(O)OH, —C(O)O($C_{1-6}$ alkyl), $C_{1-6}$ alkyl, $C_{1-6}$ alkoxy, $C_{3-6}$ cycloalkyl, phenyl, or 5- to 6-membered heteroaryl; wherein each alkyl, alkoxy, and cycloalkyl is unsubstituted or substituted with 1, 2, or 3 substituents selected from halogen, —OH, $C_{1-6}$ alkyl, and $C_{1-6}$ alkoxy. In some embodiments, each $R^b$ is independently halogen, —C(O)OH, —C(O)O($C_{1-6}$ alkyl), $C_{1-6}$ alkyl, $C_{1-6}$ alkoxy, or $C_{3-6}$ cycloalkyl; wherein each alkyl, alkoxy, and cycloalkyl is unsubstituted or substituted with 1, 2, or 3 substituents selected from halogen, —OH, $C_{1-6}$ alkyl, and $C_{1-6}$ alkoxy. In some embodiments, each $R^b$ is independently halogen, —C(O)O($C_{1-6}$ alkyl), $C_{1-6}$ alkyl, or $C_{1-6}$ alkoxy; wherein each alkyl and alkoxy is unsubstituted or substituted with 1, 2, or 3 substituents selected from —OH, and $C_{1-6}$ alkoxy. In some embodiments, each $R^b$ is independently —F, —Cl, —Br, —C(O)O($C_{1-4}$ alkyl), $C_{1-4}$ alkyl, or $C_{1-4}$ alkoxy; wherein each alkyl and alkoxy is unsubstituted or substituted with —OH or $C_{1-4}$ alkoxy. In some embodiments, each $R^b$ is independently —F, —Cl, —C(O)O(Me), —C(O)O(Et), methyl, ethyl, n-propyl, i-propyl, n-butyl, i-butyl, s-butyl, t-butyl, —OCH3, —$CH_2OCH_3$, or —$CH_2OH$.

In some embodiments, W is 6-membered monocyclic heteroaryl, wherein the heteroaryl is unsubstituted or substituted with 1 or 2 substituents selected from $R^b$; and each $R^b$ is independently halogen, —C(O)OH, —C(O)O($C_{1-6}$ alkyl), $C_{1-6}$ alkyl, $C_{1-6}$ alkoxy, or $C_{3-6}$ cycloalkyl; wherein each alkyl, alkoxy, and cycloalkyl is unsubstituted or substituted with 1, 2, or 3 substituents selected from halogen, —OH, $C_{1-6}$ alkyl, and $C_{1-6}$ alkoxy. In some embodiments, W is 6-membered monocyclic heteroaryl, wherein the heteroaryl is unsubstituted or substituted with 1 or 2 substituents selected from $R^b$; and each $R^b$ is independently halogen, —C(O)OH, —C(O)O($C_{1-6}$ alkyl), $C_{1-6}$ alkyl, or $C_{1-6}$ alkoxy; wherein each alkyl is unsubstituted or substituted with 1 —OH or $C_{1-6}$ alkoxy substituent. In some embodiments, W is 6-membered monocyclic heteroaryl, wherein the heteroaryl is unsubstituted or substituted with 1 or 2 substituents $R^b$; and each $R^b$ is independently —F, —Cl, —$CH_3$, —$CH_2CH_3$, —$CH_2CH_2CH_3$, —$CH_2OH$, —$CH_2OCH_3$, —$OCH_3$, —$OCH_2CH_3$, —C(O)OH, or —C(O)$OCH_3$.

In some embodiments, W is pyridinyl, wherein the pyridinyl is unsubstituted or substituted with 1 or 2 substituents selected from $R^b$; and each $R^b$ is independently halogen, —C(O)OH, —C(O)O($C_{1-6}$ alkyl), $C_{1-6}$ alkyl, $C_{1-6}$ alkoxy, or $C_{3-6}$ cycloalkyl; wherein each alkyl, alkoxy, and cycloalkyl is unsubstituted or substituted with 1, 2, or 3 substituents selected from halogen, —OH, $C_{1-6}$ alkyl, and $C_{1-6}$ alkoxy. In some embodiments, W is pyridinyl, wherein the pyridinyl is unsubstituted or substituted with 1 or 2 substituents selected from $R^b$; and each $R^b$ is independently —F, —Cl, —$CH_3$, —$CH_2CH_3$, —$CH_2CH_2CH_3$, —$CH_2OH$, —$CH_2OCH_3$, —$OCH_3$, —$OCH_2CH_3$, —C(O)OH, or —C(O)$OCH_3$.

In some embodiments, W is pyrimidinyl, wherein the pyrimidinyl is unsubstituted or substituted with 1 or 2 substituents selected from $R^b$; and each $R^b$ is independently halogen, —C(O)OH, —C(O)O($C_{1-6}$ alkyl), $C_{1-6}$ alkyl, $C_{1-6}$ alkoxy, or $C_{3-6}$ cycloalkyl; wherein each alkyl, alkoxy, and cycloalkyl is unsubstituted or substituted with 1, 2, or 3 substituents selected from halogen, —OH, $C_{1-6}$ alkyl, and $C_{1-6}$ alkoxy. In some embodiments, W is pyrimidinyl, wherein the pyrimidinyl is unsubstituted or substituted with 1 or 2 substituents selected from $R^b$; and each $R^b$ is independently —F, —Cl, —$CH_3$, —$CH_2CH_3$, —$CH_2CH_2CH_3$, —$CH_2OH$, —$CH_2OCH_3$, —$OCH_3$, —$OCH_2CH_3$, —C(O)OH, or —C(O)$OCH_3$.

In some embodiments, W is pyrazinyl, wherein the pyrazinyl is unsubstituted or substituted with 1 or 2 substituents selected from $R^b$; and each $R^b$ is independently halogen, —C(O)OH, —C(O)O($C_{1-6}$ alkyl), $C_{1-6}$ alkyl, $C_{1-6}$ alkoxy, or $C_{3-6}$ cycloalkyl; wherein each alkyl, alkoxy, and cycloalkyl is unsubstituted or substituted with 1, 2, or 3 substituents selected from halogen, —OH, $C_{1-6}$ alkyl, and $C_{1-6}$ alkoxy. In some embodiments, W is pyrazinyl, wherein the pyrazinyl is unsubstituted or substituted with 1 or 2 substituents selected from $R^b$; and each $R^b$ is independently —F, —Cl, —CH$_3$, —CH$_2$CH$_3$, —CH$_2$CH$_2$CH$_3$, —CH$_2$OH, —CH$_2$OCH$_3$, —OCH$_3$, —OCH$_2$CH$_3$, —C(O)OH, or —C(O)OCH$_3$.

In some embodiments, W is pyridazinyl, wherein the pyridazinyl is unsubstituted or substituted with 1 or 2 substituents selected from R$^b$; and each R$^b$ is independently halogen, —C(O)OH, —C(O)O(C$_{1-6}$ alkyl), C$_{1-6}$ alkyl, C$_{1-6}$ alkoxy, or C$_{3-6}$ cycloalkyl; wherein each alkyl, alkoxy, and cycloalkyl is unsubstituted or substituted with 1, 2, or 3 substituents selected from halogen, —OH, C$_{1-6}$ alkyl, and C$_{1-6}$ alkoxy. In some embodiments, W is pyridazinyl, wherein the pyridazinyl is unsubstituted or substituted with 1 or 2 substituents selected from R$^b$; and each R$^b$ is independently —F, —Cl, —CH$_3$, —CH$_2$CH$_3$, —CH$_2$CH$_2$CH$_3$, —CH$_2$OH, —CH$_2$OCH$_3$, —OCH$_3$, —OCH$_2$CH$_3$, —C(O)OH, or —C(O)OCH$_3$.

In some embodiments, disclosed herein is a compound of Formula (Ib):

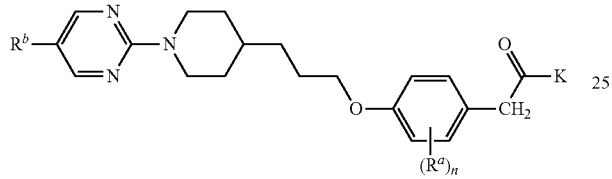

Formula (Ib)

or a pharmaceutically acceptable salt, solvate, stereoisomer, or prodrug thereof.

In some embodiments, disclosed herein is a compound of Formula (IIb):

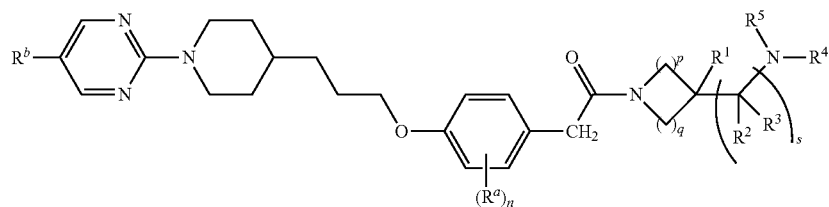

Formula (IIb)

or a pharmaceutically acceptable salt, solvate, stereoisomer, or prodrug thereof.

In some embodiments, disclosed herein is a compound of Formula (IIIb):

Formula (IIIb)

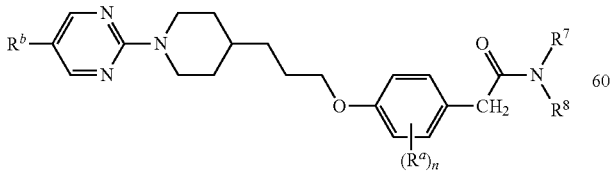

or a pharmaceutically acceptable salt, solvate, stereoisomer, or prodrug thereof.

In some embodiments, W is —C(=O)O—R$^{22}$. In some embodiments, W is —C(=O)O—R$^{22}$; and R$^{22}$ is C$_{1-6}$ alkyl, C$_{3-6}$ cycloalkyl, or 3- to 6-membered heterocycloalkyl. In some embodiments, W is —C(=O)O—R$^{22}$; and R$^{22}$ is C$_{1-6}$ alkyl, C$_{3-6}$ cycloalkyl, or 3- to 6-membered heterocycloalkyl, wherein the alkyl, cycloalkyl, and heterocycloalkyl are unsubstituted or substituted by 1-3 substituents independently selected from fluorine, —OH, C$_{1-6}$ alkyl, C$_{1-6}$ haloalkyl, and C$_{3-6}$ cycloalkyl. In some embodiments, W is —C(=O)O—R$^{22}$; and R$^{22}$ is C$_{1-6}$ alkyl or C$_{3-6}$ cycloalkyl, wherein the alkyl and cycloalkyl are unsubstituted or substituted by 1-3 substituents independently selected from fluorine, —OH, C$_{1-6}$ alkyl, C$_{1-6}$ haloalkyl, and C$_{3-6}$ cycloalkyl. In some embodiments, W is —C(=O)O—R$^{22}$; and R$^{22}$ is C$_{1-4}$ alkyl or C$_{3-6}$ cycloalkyl, wherein the alkyl and cycloalkyl are unsubstituted or substituted by 1-3 substituents independently selected from fluorine and —OH. In some embodiments, W is —C(=O)O—R$^{22}$; and R$^{22}$ is C$_{1-6}$ alkyl or C$_{3-6}$ cycloalkyl, wherein the alkyl and cycloalkyl are unsubstituted or substituted by 1-3 substituents independently selected from C$_{1-6}$ alkyl and C$_{1-6}$ haloalkyl.

In some embodiments, K is

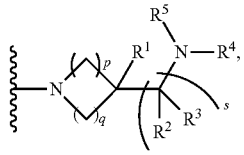

In some embodiments, when K is

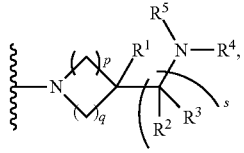

p is 1 and q is 1. In some embodiments, p is 1 and q is 2. In some embodiments, p is 2 and q is 1. In some embodiments, p is 2 and q is 2.

In some embodiments, when K is

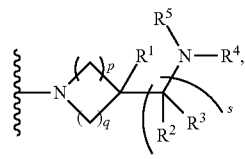

$R^1$ is hydrogen, —OH, $C_{1-8}$ alkyl, $C_{3-8}$ cycloalkyl, or 3- to 8-membered heterocycloalkyl. In some embodiments, $R^1$ is hydrogen, —OH, $C_{1-8}$ alkyl, $C_{3-8}$ cycloalkyl, or 3- to 8-membered heterocycloalkyl, wherein the alkyl, cycloalkyl, or heterocycloalkyl are unsubstituted or substituted by 1-3 substituents independently selected from halogen, —OH, and —O($C_{1-6}$ alkyl). In some embodiments, $R^1$ is hydrogen, —OH, or $C_{1-8}$ alkyl, wherein the alkyl is unsubstituted or substituted by —OH or —O($C_{1-6}$ alkyl). In some embodiments, R is hydrogen or $C_{1-8}$ alkyl, wherein the alkyl is unsubstituted or substituted by —OH or —O($C_{1-6}$ alkyl). In some embodiments, $R^1$ is hydrogen, —OH, or $C_{1-4}$ alkyl. In some embodiments, R is hydrogen or $C_{1-4}$ alkyl. In some embodiments, R is hydrogen, —OH, methyl, ethyl, n-propyl, i-propyl, n-butyl, i-butyl, s-butyl, t-butyl. In some embodiments, R is hydrogen, —OH, or methyl. In some embodiments, R is hydrogen or methyl. In some embodiments, R is hydrogen. In some embodiments, R is —OH. In some embodiments, R is methyl.

In some embodiments, when K is

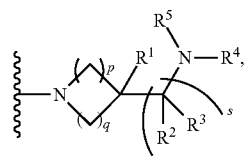

each $R^2$ and $R^3$ is independently hydrogen, $C_{1-6}$ alkyl, or $C_{1-6}$ fluoroalkyl. In some embodiments, each $R^2$ and $R^3$ is independently hydrogen or $C_{1-6}$ alkyl. In some embodiments, each $R^2$ and $R^3$ is independently hydrogen or $C_{1-4}$ alkyl. In some embodiments, each $R^2$ and $R^3$ is independently hydrogen, methyl, ethyl, n-propyl, i-propyl, n-butyl, i-butyl, s-butyl, t-butyl. In some embodiments, each $R^2$ and $R^3$ is independently hydrogen or methyl. In some embodiments, each $R^2$ and $R^3$ is hydrogen. In some embodiments, s is 1. In some embodiments, s is 2. In some embodiments, each $R^2$ and $R^3$ is hydrogen; and s is 1. In some embodiments, each $R^2$ and $R^3$ is hydrogen; and s is 2.

In some embodiments, when K is

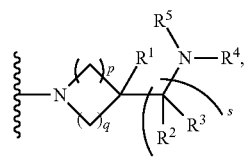

$R^2$ and $R^3$ on the same carbon atom are taken together to form =O. In some embodiments, s is 1; and $R^2$ and $R^3$ are taken together to form =O.

In some embodiments, when K is

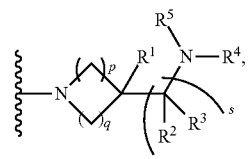

$R^1$ is hydrogen, —OH, or $C_{1-8}$ alkyl, wherein the alkyl is unsubstituted or substituted by —OH or —O($C_{1-6}$ alkyl); each $R^2$ and $R^3$ is hydrogen; or $R^2$ and $R^3$ on the same carbon atom are taken together to form =O; p is 1; and q is 1.

In some embodiments, disclosed herein is a compound of Formula (IIc):

Formula (IIc)

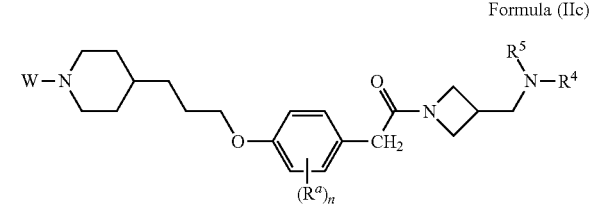

or a pharmaceutically acceptable salt, solvate, stereoisomer, or prodrug thereof.

In some embodiments, disclosed herein is a compound of Formula (IId):

Formula (IId)

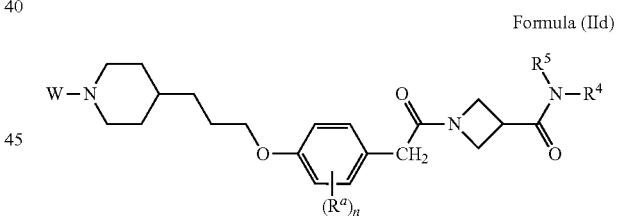

or a pharmaceutically acceptable salt, solvate, stereoisomer, or prodrug thereof.

In some embodiments, disclosed herein is a compound of Formula (IIe):

Formula (IIe)

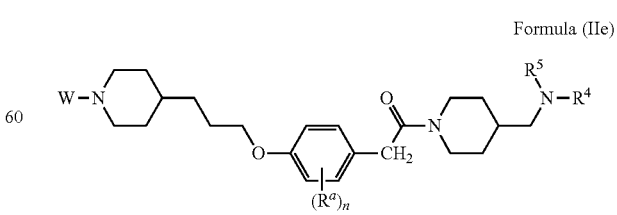

or a pharmaceutically acceptable salt, solvate, stereoisomer, or prodrug thereof.

In some embodiments, disclosed herein is a compound of Formula (IIf):

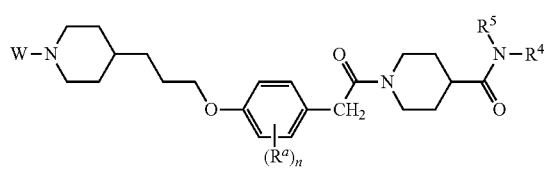

Formula (IIf)

or a pharmaceutically acceptable salt, solvate, stereoisomer, or prodrug thereof.

In some embodiments, disclosed herein is a compound of Formula (IIg):

Formula (IIg)

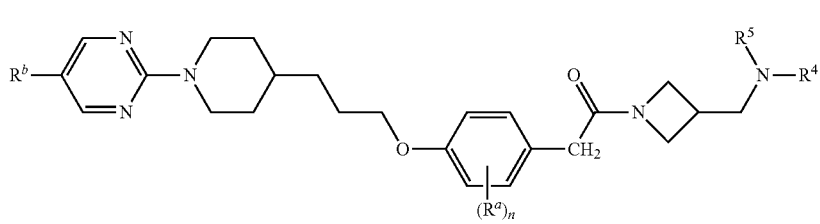

or a pharmaceutically acceptable salt, solvate, stereoisomer, or prodrug thereof.

In some embodiments, disclosed herein is a compound of Formula (IIh):

Formula (IIh)

or a pharmaceutically acceptable salt, solvate, stereoisomer, or prodrug thereof.

In some embodiments, disclosed herein is a compound of Formula (IIi):

or a pharmaceutically acceptable salt, solvate, stereoisomer, or prodrug thereof.

In some embodiments, when K is

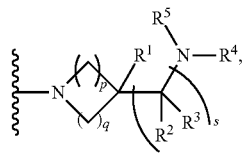

$R^4$ is hydrogen, $C_{1-8}$ alkyl, $C_{1-8}$ fluoroalkyl, $C_{2-8}$ alkenyl, $C_{2-8}$ alkynyl, $C_{3-8}$ cycloalkyl, $C_{5-8}$ cycloalkenyl, 4- to 8-membered heterocycloalkyl, $—[(CH_2)_r—Z]_t—R^6$, $—[(CHR^d)_r—Z]_t—R^6$, or $—[(C(R^d)_2)_r—Z]_t—R^6$. In some embodiments, $R^4$ is hydrogen, $C_{1-8}$ alkyl, $C_{1-8}$ fluoroalkyl, $C_{2-8}$ alkenyl, $C_{2-8}$ alkynyl, $C_{3-8}$ cycloalkyl, $C_{5-8}$ cycloalkenyl, 4- to 8-membered heterocycloalkyl, $—[(CH_2)_r—Z]_t—R^6$, $—[(CHR^d)_r—Z]_t—R^6$, or $—[(C(R^d)_2)_r—Z]_t—R^6$;

wherein each alkyl, fluoroalkyl, alkenyl, alkynyl, cycloalkyl, cycloalkenyl, and 4- to 8-membered heterocycloalkyl is unsubstituted or substituted by 1-6 $R^c$ groups. In some embodiments, $R^4$ is hydrogen, $C_{1-8}$ alkyl, $C_{1-8}$ fluoroalkyl, Formula (IIi)

$C_{3-8}$ cycloalkyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$;

wherein each alkyl, fluoroalkyl, cycloalkyl, and 4- to 8-membered heterocycloalkyl is unsubstituted or substituted by 1-6 R$^c$ groups; and each Z is independently —CH$_2$O—, —CH$_2$NR$^d$—, —CH$_2$N$^+$(R$^d$)$_2$—, or —NH—C(=O)—NH—. In some embodiments, R$^4$ is hydrogen, C$_{1-8}$ alkyl, C$_{1-8}$ fluoroalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein each alkyl, or fluoroalkyl is unsubstituted or substituted by 1-6 R$^c$ groups; and each Z is independently —CH$_2$O—, —CH$_2$NR$^d$—, —CH$_2$N$^+$(R$^d$)$_2$—, or —NH—C(=O)—NH—. In some embodiments, R$^4$ is hydrogen, C$_{1-8}$ alkyl, C$_{1-8}$ fluoroalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein each Z is independently —CH$_2$O—, —CH$_2$NR$^d$—, —CH$_2$N$^+$(R$^d$)$_2$—, or —NH—C(=O)—NH—. In some embodiments, R$^4$ is hydrogen, C$_{1-8}$ alkyl, C$_{1-8}$ fluoroalkyl, —[(CH$_2$)$_r$—Z]$_t$—R$^6$; wherein each Z is independently —CH$_2$O—, —CH$_2$NR$^d$—, —CH$_2$N$^+$(R$^d$)$_2$—, or —NH—C(=O)—NH—. In some embodiments, R$^4$ is hydrogen, C$_{1-8}$ alkyl, or C$_{1-8}$ fluoroalkyl. In some embodiments, R$^4$ is hydrogen or C$_{1-8}$ alkyl. In some embodiments, R$^4$ is hydrogen or C$_{1-6}$ alkyl. In some embodiments, R$^4$ is hydrogen or C$_{1-4}$ alkyl. In some embodiments, R$^4$ is hydrogen, methyl, ethyl, n-propyl, i-propyl, n-butyl, i-butyl, s-butyl, or t-butyl. In some embodiments, R$^4$ is hydrogen or methyl. In some embodiments, R$^4$ is hydrogen.

In some embodiments, when K is

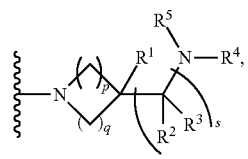

R$^5$ is C$_{1-8}$ alkyl, C$_{1-8}$ fluoroalkyl, C$_{2-8}$ alkenyl, O$_{2-8}$ alkynyl, C$_{3-8}$ cycloalkyl, C$_{5-8}$ cycloalkenyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$. In some embodiments, R$^5$ is C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein each alkyl, fluoroalkyl, alkenyl, alkynyl, cycloalkyl, cycloalkenyl, and 4- to 8-membered heterocycloalkyl is substituted by 1-6 R$^c$ groups. In some embodiments, R$^5$ is C$_{1-8}$ alkyl, C$_{1-8}$ fluoroalkyl, C$_{3-8}$ cycloalkyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein each alkyl, fluoroalkyl, cycloalkyl, and 4- to 8-membered heterocycloalkyl is substituted by 1-6 R$^c$ groups; and each Z is independently —CH$_2$O—, —CH$_2$NR$^d$—, —CH$_2$N$^+$(R$^d$)$_2$—, or —NH—C(=O)—NH—. In some embodiments, R$^5$ is C$_{1-8}$ alkyl, C$_{3-8}$ cycloalkyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein each alkyl, cycloalkyl, and 4- to 8-membered heterocycloalkyl is substituted by 1-6 R$^c$ groups; and each Z is independently —CH$_2$O—, —CH$_2$NR$^d$—, —CH$_2$N$^+$(R$^d$)$_2$—, or —NH—C(=O)—NH—. In some embodiments, R$^5$ is C$_{1-8}$ alkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein the alkyl is substituted by 1-6 R$^c$ groups; and each Z is independently —CH$_2$O—, —CH$_2$NR$^d$—, —CH$_2$N$^+$(R$^d$)$_2$—, or —NH—C(=O)—NH—. In some embodiments, R$^5$ is C$_{1-8}$ alkyl or —[(CH$_2$)$_r$—Z]$_t$—R$^6$; wherein the alkyl is substituted by 1-6 R$^c$ groups; and each Z is independently —CH$_2$O—, —CH$_2$NR$^d$—, —CH$_2$N$^+$(R$^d$)$_2$—, or —NH—C(=O)—NH—. In some embodiments, R$^5$ is C$_{1-8}$ alkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein the alkyl is substituted by 1-6 R$^c$ groups; and each Z is independently —CH$_2$O—, —CH$_2$NR$^d$—, or —NH—C(=O)—NH—. In some embodiments, R$^5$ is C$_{1-8}$ alkyl or —[(CH$_2$)$_r$—Z]$_t$—R$^6$; wherein the alkyl is substituted by 1-6 R$^c$ groups; and each Z is independently —CH$_2$O—, —CH$_2$NR$^d$—, or —NH—C(=O)—NH—. In some embodiments, R$^5$ is C$_{1-8}$ alkyl which is substituted by 1-6 R$^c$ groups. In some embodiments, R$^5$ is C$_{1-8}$ alkyl which is substituted by 1-6 —OH groups.

In some embodiments, when K is

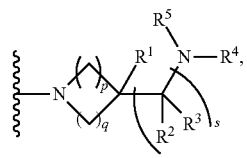

R$^4$ and R$^5$ are taken together with the nitrogen to which they are attached to form a 4- to 8-membered heterocycloalkyl, which is unsubstituted or substituted by 1-6 R$^c$ groups. In some embodiments, R$^4$ and R$^5$ are taken together with the nitrogen to which they are attached to form a 5- or 6-membered heterocycloalkyl, which is unsubstituted or substituted by 1-3 —OH groups.

In some embodiments, K is

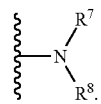

In some embodiments, when K is

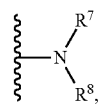

R$^7$ is hydrogen, C$_{1-4}$ alkyl, or C$_{1-4}$ fluoroalkyl. In some embodiments, R$^7$ is hydrogen or C$_{1-4}$ alkyl. In some embodiments, R$^7$ is hydrogen, methyl, ethyl, n-propyl, i-propyl, n-butyl, i-butyl, s-butyl, or t-butyl. In some embodiments, R$^7$ is hydrogen or methyl. In some embodiments, R$^7$ is hydrogen.

In some embodiments, when K is

R$^8$ is C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, 4- to 8-membered heterocycloalkyl, —[(CH$_2$)$_r$—Z]$_t$—R$^6$, —[(CHR$^d$)$_r$—Z]$_t$—R$^6$, or —[(CR$^d_2$)$_r$—Z]$_t$—R$^6$. In some embodiments, R$^8$ is C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, 4- to 8-membered heterocycloalkyl, —[(CH$_2$)$_r$—Z]$_t$—R$^6$, —[(CHR$^d$)$_r$—Z]$_t$—R$^6$, or —[(CR$^d_2$)$_r$—Z]$_t$—R$^6$; wherein each alkyl, fluoroalkyl, alkenyl, alkynyl, cycloalkyl, cycloalkenyl, and 4- to 8-membered heterocycloalkyl is substituted by 1-6 R$^c$ groups. In some embodiments, R$^8$ is C$_{1-8}$ alkyl, C$_{3-8}$ cycloalkyl, —[(CH$_2$)$_r$—Z]$_t$—R$^6$, —[(CHR$^d$)$_r$—Z]$_t$—R$^6$, or —[(CR$^d_2$)$_r$—Z]$_t$—R$^6$; wherein the alkyl and cycloalkyl is substituted by 1-6 R$^c$ groups. In some embodiments, R$^8$ is C$_{1-8}$ alkyl, C$_{3-8}$ cycloalkyl, —[(CH$_2$)$_r$—Z]$_t$—R$^6$, —[(CHR$^d$)$_r$—Z]$_t$—R$^6$, or —[(CR$^d_2$)$_r$—Z]$_t$—R$^6$; wherein the alkyl and cycloalkyl is substituted by 1-6 R$^c$ groups; and each Z is independently —CH$_2$O—, —CH$_2$NR$^d$—, —CH$_2$N$^+$(R$^d$)$_2$—, or —NH—C(=O)—NH—. In some embodiments, R$^8$ is C$_{1-8}$ alkyl, C$_{3-8}$ cycloalkyl, or —[(CH$_2$)$_r$—Z]$_t$—R$^6$; wherein the alkyl and cycloalkyl is substituted by 1-6 R$^c$ groups; and each Z is independently —CH$_2$O—, —CH$_2$NR$^d$—, —CH$_2$N$^+$(R$^d$)$_2$—, or —NH—C(=O)—NH—. In some embodiments, R$^8$ is C$_{1-8}$ alkyl, —[(CH$_2$)$_r$—Z]$_t$—R$^6$, —[(CHR$^d$)$_r$—Z]$_t$—R$^6$, or —[(CR$^d_2$)$_r$—Z]$_t$—R$^6$; wherein the alkyl is substituted by 1-6 R$^c$ groups. In some embodiments, R$^8$ is C$_{1-8}$ alkyl, —[(CH$_2$)$_r$—Z]$_t$—R$^6$, —[(CHR$^d$)$_r$—Z]$_t$—R$^6$, or —[(CR$^d_2$)$_r$—Z]$_t$—R$^6$; wherein the alkyl is substituted by 1-6 R$^c$ groups; and each Z is independently —CH$_2$O—, —CH$_2$NR$^d$—, —CH$_2$N$^+$(R$^d$)$_2$—, or —NH—C(=O)—NH—. In some embodiments, R$^8$ is C$_{1-8}$ alkyl or —[(CH$_2$)$_r$—Z]$_t$—R$^6$; wherein the alkyl is substituted by 1-6 R$^c$ groups; and each Z is independently —CH$_2$O—, —CH$_2$NR$^d$—, —CH$_2$N$^+$(R$^d$)$_2$—, or —NH—C(=O)—NH—. In some embodiments, R$^8$ is C$_{1-8}$ alkyl; wherein the alkyl is substituted by 1-6 R$^c$ groups.

In some embodiments, when K is

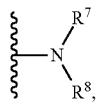

R$^8$ is —(C$_{1-8}$ alkyl)-NH—R$^9$, —(C$_{1-8}$ alkyl)-C(=O)NH—R$^9$, —(C$_{1-8}$ alkyl)-C(=O)—N(R$^9$)$_2$, or —(C$_{1-8}$ alkyl)-NHC(=O)NH—R$^9$.

In some embodiments, R$^8$ is —(C$_{1-8}$ alkyl)-NH—R$^9$, —(C$_{1-8}$ alkyl)-C(=O)NH—R$^9$, —(C$_{1-8}$ alkyl)-C(=O)—N(R$^9$)$_2$, or —(C$_{1-8}$ alkyl)-NHC(=O)NH—R$^9$; wherein the alkyl is unsubstituted or substituted by 1-6 R$^c$ groups; and each R$^9$ is independently C$_{1-8}$ alkyl, or C$_{1-8}$ fluoroalkyl which is substituted by 1-6 R$^c$ groups; or two R$^9$ are taken together with the nitrogen to which they are attached to form a 4- to 6-membered heterocycloalkyl, which is substituted by 1-6 R$^c$ groups. In some embodiments, R$^8$ is —(C$_{1-8}$ alkyl)-NH—R$^9$, —(C$_{1-8}$ alkyl)-C(=O)NH—R$^9$, —(C$_{1-8}$ alkyl)-C(=O)—N(R$^9$)$_2$, or —(C$_{1-8}$ alkyl)-NHC(=O)NH—R$^9$; wherein the alkyl is unsubstituted or substituted by 1-6 R$^c$ groups; and each R$^9$ is independently C$_{1-8}$ alkyl which is substituted by 1-6 R$^c$ groups; or two R$^9$ are taken together with the nitrogen to which they are attached to form a 4- to 6-membered heterocycloalkyl, which is substituted by 1-6 R$^c$ groups. In some embodiments, R$^8$ is —(C$_{1-8}$ alkyl)-NH—R$^9$, —(C$_{1-8}$ alkyl)-C(=O)NH—R$^9$, —(C$_{1-8}$ alkyl)-C(=O)—N(R$^9$)$_2$, or —(C$_{1-8}$ alkyl)-NHC(=O)NH—R$^9$; wherein the alkyl is unsubstituted.

In some embodiments, R$^6$ is hydrogen, C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, or 4- to 8-membered heterocycloalkyl. In some embodiments, R$^6$ is hydrogen, C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, or 4- to 8-membered heterocycloalkyl, wherein the alkyl, fluoroalkyl, alkenyl, alkynyl, cycloalkyl, cycloalkenyl, or 4- to 8-membered heterocycloalkyl is unsubstituted or substituted by 1-6 R$^c$ groups. In some embodiments, R$^6$ is hydrogen, C$_{1-8}$ alkyl, C$_{3-8}$ cycloalkyl, or 4- to 8-membered heterocycloalkyl, wherein the alkyl, cycloalkyl, or 4- to 8-membered heterocycloalkyl is unsubstituted or substituted by 1-6 R$^c$ groups. In some embodiments, R$^6$ is hydrogen or C$_{1-8}$ alkyl, wherein the alkyl is substituted by 1-6 R$^c$ groups.

In some embodiments, each Z is independently —CH$_2$O—, —CH$_2$NR$^d$—, —CH$_2$N$^+$(R$^d$)$_2$—, —NH—C(=O)—NH—, —C(=O)NH—, —CH$_2$S(=O)$_2$—, or —CH$_2$S(=O)—. In some embodiments, each Z is independently —CH$_2$O—, —CH$_2$NR$^d$—, —CH$_2$N$^+$(R$^d$)$_2$—, —NH—C(=O)—NH—, or —CH$_2$S(=O)$_2$—. In some embodiments, each Z is independently —CH$_2$O—, —CH$_2$NR$^d$—, —CH$_2$N$^+$(R$^d$)$_2$—, or —NH—C(=O)—NH—. In some embodiments, each Z is independently —CH$_2$O—, —CH$_2$NR$^d$—, or —NH—C(=O)—NH—. In some embodiments, each Z is independently —CH$_2$O— or —CH$_2$NR$^d$—. In some embodiments, each Z is —CH$_2$O—.

In some embodiments, each r is independently 1-6. In some embodiments, each r is 1-4. In some embodiments, each r is 1-3. In some embodiments, each r is 1-2. In some embodiments, each r is 1. In some embodiments, each r is 2. In some embodiments, each r is 3.

In some embodiments, each t is independently 1-6. In some embodiments, each t is independently 1-5. In some embodiments, each t is independently 1-4. In some embodiments, each t is independently 1-3. In some embodiments, each t is independently 1-2. In some embodiments, each t is 1. In some embodiments, each t is 2. In some embodiments, each t is 3.

In some embodiments, each r is independently 1-6; each t is independently 1-6; and R$^6$ is hydrogen, C$_{1-8}$ alkyl, C$_{1-8}$ fluoroalkyl, C$_{2-8}$ alkenyl, C$_{2-8}$ alkynyl, C$_{3-8}$ cycloalkyl, C$_{5-8}$ cycloalkenyl, or 4- to 8-membered heterocycloalkyl, wherein the alkyl, fluoroalkyl, alkenyl, alkynyl, cycloalkyl, cycloalkenyl, or 4- to 8-membered heterocycloalkyl is unsubstituted or substituted by 1-6 R$^c$ groups.

In some embodiments, each R$^c$ is independently —OH, —CH$_2$OH, —CH$_2$CH$_2$OH, —NH$_2$, —CH$_2$NH$_2$, —NH(R$^d$), —CH$_2$NH(R$^d$), —N(R$^d$)$_2$, —CH$_2$N(R$^d$)$_2$, —N(R$^d$)$_3^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), P(=O)(OH)(OR$^d$), —B(OH)$_2$, —B(OR$^d$)(OH), —NHCONHS(=O)$_2$(R$^d$), —N(R$^d$)CONHS(=O)$_2$(R$^d$), —NHCON(R$^d$)S(=O)$_2$(R$^d$), —C(=O)NHS(=O)$_2$(R$^d$), —S(=O)$_2$NHC(=O)R$^d$, —NHC(=NH)NH$_2$, —NHC(=NH)NHR$^d$, —NHC(=NH)N(R$^d$)$_2$, —N(R$^d$)C(=NH)NH$_2$, —N(R$^d$)C(=NH)NH(R$^d$), —N(R$^d$)C(=NH)N(R$^d$)$_2$, —NHC(=N(R$^d$))NH$_2$, —NHC(=N(R$^d$))NHR$^d$, —NHC(=N(R$^d$))N(R$^d$)$_2$, —N(R$^d$)C(=N(R$^d$))NH$_2$, —N(R$^d$)C(=N(R$^d$))NHR$^d$, —N(R$^d$)C(=N(R$^d$))N(R$^d$)$_2$, —NHC(=NH)NHC(=NH)NH$_2$, —N(R$^d$)C(=NH)NHC(=NH)NH$_2$,

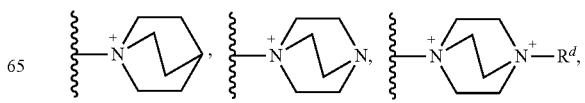

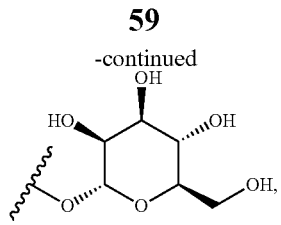

or a 4- to 6-membered heterocycle which is unsubstituted or substituted with 1, 2, 3, or 4 substituents selected from $C_{1-6}$ alkyl, —O—($C_{1-6}$ alkyl), —OH, =O and =S. In some embodiments, each $R^c$ is independently —OH, —CH$_2$OH, —CH$_2$CH$_2$OH, —NH$_2$, —CH$_2$NH$_2$, —NH($R^d$), —CH$_2$NH($R^d$), —N($R^d$)$_2$, —CH$_2$N($R^d$)$_2$, —N($R^d$)$_3^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)($R^d$), —P(=O)(OH)(H), P(=O)(OH)(O$R^d$), —B(OH)$_2$, —B(O$R^d$)(OH), —NHCONHS(=O)$_2$($R^d$), —N($R^d$)CONHS(=O)$_2$($R^d$), —NHCON($R^d$)S(=O)$_2$($R^d$), —C(=O)NHS(=O)$_2$($R^d$), —S(=O)$_2$NHC(=O)$R^d$, —NHC(=NH)NH$_2$, —NHC(=NH)NH$R^d$, —NHC(=NH)N($R^d$)$_2$, —N($R^d$)C(=NH)NH$_2$, —N($R^d$)C(=NH)NH($R^d$), —N($R^d$)C(=NH)N($R^d$)$_2$, —NHC(=N($R^d$))NH$_2$, —NHC(=N($R^d$))NH$R^d$, —NHC(=N($R^d$))N($R^d$)$_2$, —N($R^d$)C(=N($R^d$))NH$_2$, —N($R^d$)C(=N($R^d$))NH$R^d$, —N($R^d$)C(=N($R^d$))N($R^d$)$_2$, —NHC(=NH)NHC(=NH)NH$_2$, —N($R^d$)C(=NH)NHC(=NH)NH$_2$,

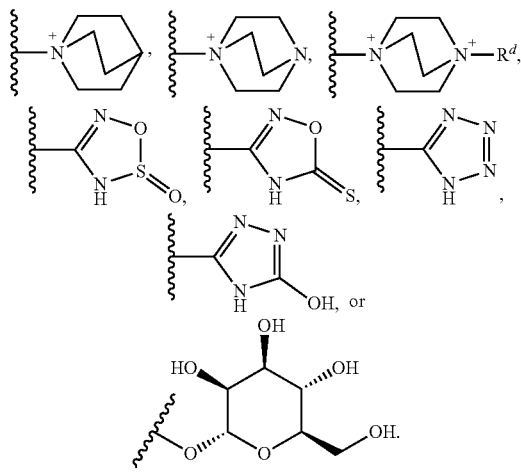

In some embodiments, each $R^c$ is independently —OH, —CH$_2$OH, —CH$_2$CH$_2$OH, —NH$_2$, —CH$_2$NH$_2$, —NH($R^d$), —CH$_2$NH($R^d$), —N($R^d$)$_2$, —CH$_2$N($R^d$)$_2$, —N($R^d$)$_3^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)($R^d$), —P(=O)(OH)(H), —P(=O)(OH)(O$R^d$), —B(OH)$_2$, —B(O$R^d$)(OH), —N($R^d$)CONHS(=O)$_2$($R^d$), —C(=O)NHS(=O)$_2$($R^d$), —NHC(=NH)NH$_2$, —N($R^d$)C(=NH)NH$_2$, —NHC(=NH)NHC(=NH)NH$_2$,

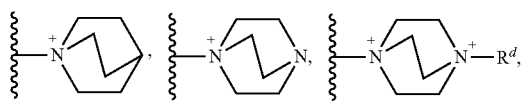

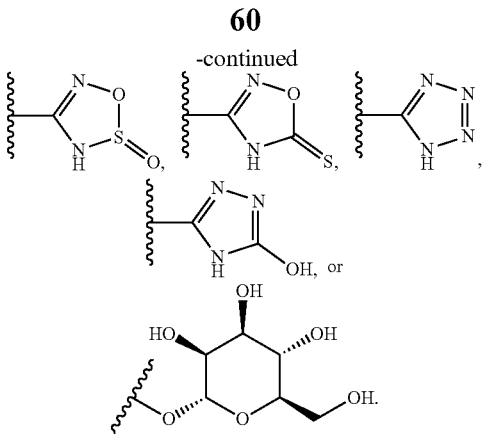

In some embodiments, each $R^c$ is independently —OH, —CH$_2$OH, —NH$_2$, —CH$_2$NH$_2$, —N($R^d$)$_3^+$, —C(=O)OH, —S(=O)$_2$OH, —S(=O)OH, —S(=O)$_2$NH$_2$, —P(=O)(OH)$_2$, —P(=O)(OH)($R^d$), —P(=O)(OH)(H), —P(=O)(OH)(O$R^d$), —B(OH)$_2$, —B(O$R^d$)(OH), —N($R^d$)CONHS(=O)$_2$($R^d$), —C(=O)NHS(=O)$_2$($R^d$), —NHC(=NH)NH$_2$, —N($R^d$)C(=NH)NH$_2$, —NHC(=NH)NHC(=NH)NH$_2$,

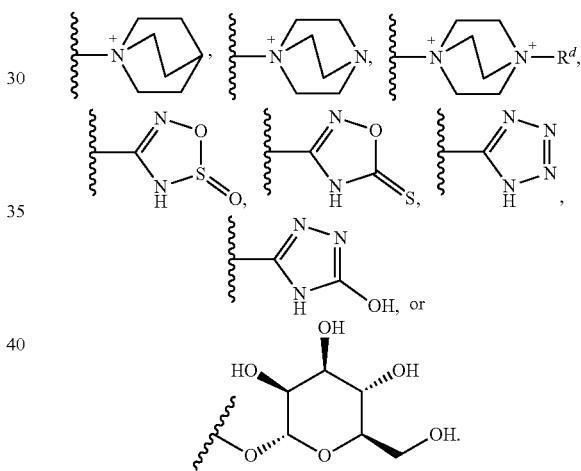

In some embodiments, each $R^c$ is independently —OH, —CH$_2$OH, —NH$_2$, —N($R^d$)$_3^+$, —C(=O)OH, —S(=O)$_2$OH, —S(=O)$_2$NH$_2$, —P(=O)(OH)$_2$, —P(=O)(OH)($R^d$), —P(=O)(OH)(O$R^d$),

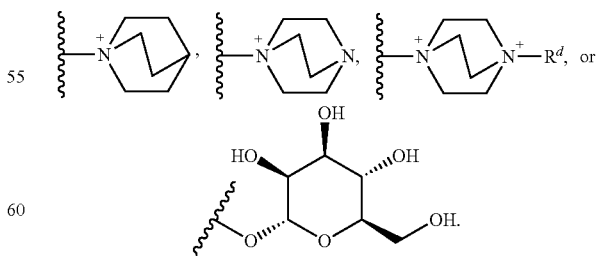

In some embodiments, each $R^c$ is independently —OH, —NH$_2$, —N($R^d$)$_3^+$, —C(=O)OH, —S(=O)$_2$OH, —S(=O)$_2$NH$_2$, —P(=O)(OH)$_2$, —P(=O)(OH)($R^d$), —P(=O)(OH)(O$R^d$)

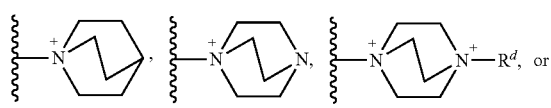

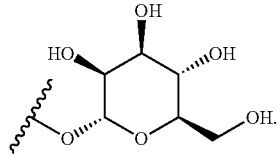

In some embodiments, each $R^c$ is independently —OH, —CH$_2$OH, —NH$_2$, —N(R$^d$)$_3{}^+$, —C(=O)OH, or

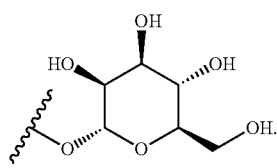 [SMILES: *O[C@H]1O[C@H](CO)[C@@H](O)[C@H](O)[C@@H]1O]

In some embodiments, each $R^c$ is independently —OH, —NH$_2$, —N(R$^d$)$_3{}^+$, —C(=O)OH, or

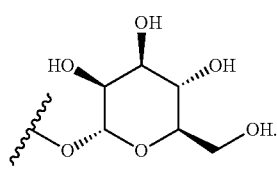 [SMILES: *O[C@H]1O[C@H](CO)[C@@H](O)[C@H](O)[C@@H]1O]

In some embodiments, each $R^c$ is independently —OH, —CH$_2$OH, —N(R$^d$)$_3{}^+$, —C(=O)OH, or

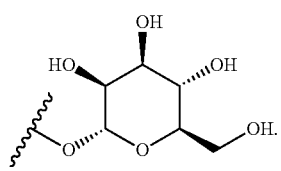 [SMILES: *O[C@H]1O[C@H](CO)[C@@H](O)[C@H](O)[C@@H]1O]

In some embodiments, each $R^c$ is independently —OH, —N(R$^d$)$_3{}^+$, —C(=O)OH, or

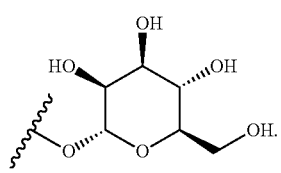 [SMILES: *O[C@H]1O[C@H](CO)[C@@H](O)[C@H](O)[C@@H]1O]

In some embodiments, each $R^c$ is independently —OH, —CH$_2$OH, or —N(R$^d$)$_3{}^+$. In some embodiments, each $R^c$ is —OH or —C(O)OH. In some embodiments, each $R^c$ is —OH.

In some embodiments, each $R^d$ is independently C$_{1-6}$ alkyl, C$_{1-6}$ fluoroalkyl, or C$_{3-6}$ cycloalkyl. In some embodiments, each $R^d$ is independently C$_{1-6}$ alkyl or C$_{3-6}$ cycloalkyl. In some embodiments, each $R^d$ is independently C$_{1-6}$ alkyl or C$_{1-6}$ fluoroalkyl. In some embodiments, each $R^d$ is independently C$_{1-6}$ alkyl. In some embodiments, each $R^d$ is independently C$_{1-4}$ alkyl. In some embodiments, each $R^d$ is independently methyl, ethyl, n-propyl, i-propyl, n-butyl, i-butyl, s-butyl, or t-butyl. In some embodiments, each $R^d$ is methyl.

In some embodiments, each $R^e$ is independently —OH, —CH$_2$OH, —CH$_2$CH$_2$OH, —N(R$^d$)$_3{}^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), —P(=O)(OH)(OR$^d$), —B(OH)$_2$, —B(OR$^d$)(OH), —NHCONHS(=O)$_2$(R$^d$), —N(R$^d$)CONHS(=O)$_2$(R$^d$), —NHCON(R$^d$)S(=O)$_2$(R$^d$), —C(=O)NHS(=O)$_2$(R$^d$), —S(O)$_2$NHC(O)R$^d$, —NHC(=NH)NH$_2$, —NHC(=NH)NHR$^d$, —NHC(=NH)N(R$^d$)$_2$, —N(R$^d$)C(=NH)NH$_2$, N(R$^d$)C(=NH)NH(R$^d$), —N(R$^d$)C(=NH)N(R$^d$)$_2$, —NHC(=N(R$^d$))NH$_2$, —NHC(=N(R$^d$))NHR$^d$, —NHC(=N(R$^d$))N(R$^d$)$_2$, —N(R$^d$)C(=N(R$^d$))NH$_2$, —N(R$^d$)C(=N(R$^d$))NHR$^d$, —N(R$^d$)C(=N(R$^d$))N(R$^d$)$_2$, —NHC(=NH)NHC(=NH)NH$_2$, N(R$^d$)C(=NH)NHC(=NH)NH$_2$,

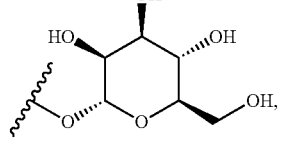

or a 4- to 6-membered heterocycle which is unsubstituted or substituted with 1, 2, 3, or 4 substituents selected from C$_{1-6}$ alkyl, —O—(C$_{1-6}$ alkyl), —OH, =O and =S. In some embodiments, each $R^e$ is independently —OH, —CH$_2$OH, —CH$_2$CH$_2$OH, —N(R$^d$)$_3{}^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), —P(=O)(OH)(OR$^d$), —B(OH)$_2$, —B(OR$^d$)(OH), —NHCONHS(=O)$_2$(R$^d$), —N(R$^d$)CONHS(=O)$_2$(R$^d$), —NHCON(R$^d$)S(=O)$_2$(R$^d$), —C(=O)NHS(=O)$_2$(R$^d$), —S(O)$_2$NHC(O)R$^d$, —NHC(=NH)NH$_2$, —NHC(=NH)NHR$^d$, —NHC(=NH)N(R$^d$)$_2$, —N(R$^d$)C(=NH)NH$_2$, N(R$^d$)C(=NH)NH(R$^d$), —N(R$^d$)C(=NH)N(R$^d$)$_2$, —NHC(=N(R$^d$))NH$_2$, —NHC(=N(R$^d$))NHR$^d$, —NHC(=N(R$^d$))N(R$^d$)$_2$, —N(R$^d$)C(=N(R$^d$))NH$_2$, —N(R$^d$)C(=N(R$^d$))NHR$^d$, —N(R$^d$)C(=N(R$^d$))N(R$^d$)$_2$, —NHC(=NH)NHC(=NH)NH$_2$, N(R$^d$)C(=NH)NHC(=NH)NH$_2$,

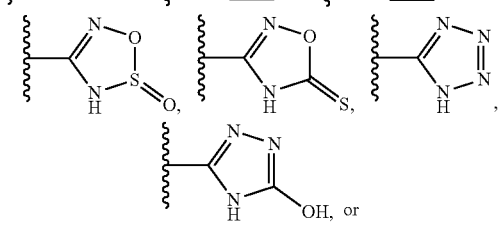

-continued

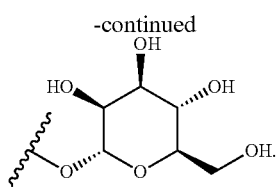

In some embodiments, each $R^c$ is independently —OH, —CH$_2$OH, —CH$_2$CH$_2$OH, —N(R$^d$)$_3^+$, —C(=O)OH, —CH$_2$C(=O)OH, —CH$_2$CH$_2$C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), —P(=O)(OH)(OR$^d$), —B(OH)$_2$, —B(OR$^d$)(OH), —N(R$^d$)CONHS(=O)$_2$(R$^d$), —C(=O)NHS(=O)$_2$(R$^d$), —NHC(=NH)NH$_2$, —N(R$^d$)C(=NH)NH$_2$, —NHC(=NH)NHC(=NH)NH$_2$,

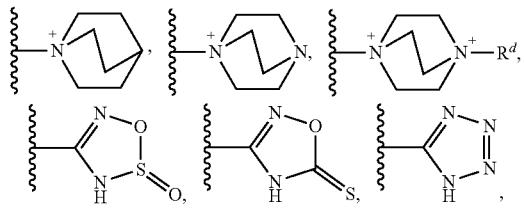

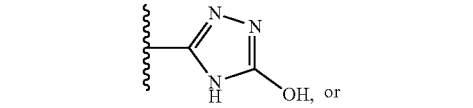

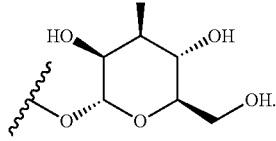

In some embodiments, each $R^c$ is independently —OH, —CH$_2$OH, —N(R$^d$)$_3^+$, —C(=O)OH, —S(=O)$_2$OH, —S(=O)OH, —S(=O)$_2$NH$_2$, —P(=O)(OH)$_2$, —P(=O)(OH)(R$^d$), —P(=O)(OH)(H), —P(=O)(OH)(OR$^d$), —B(OH)$_2$, —B(OR$^d$)(OH), —N(R$^d$)CONHS(=O)$_2$(R$^d$), —C(=O)NHS(=O)$_2$(R$^d$), —NHC(=NH)NH$_2$, —N(R$^d$)C(=NH)NH$_2$, —NHC(=NH)NHC(=NH)NH$_2$,

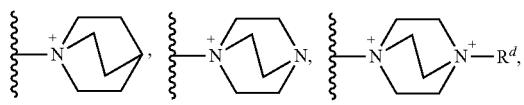

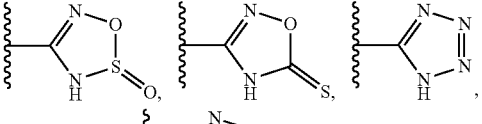

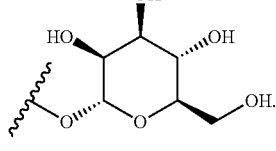

In some embodiments, each $R^c$ is independently —OH, —CH$_2$OH, —N(R$^d$)$_3^+$, —C(=O)OH, —S(=O)$_2$OH, —S(=O)$_2$NH$_2$, —P(=O)(OH)$_2$, —P(=O)(OH)(R$^d$), —P(=O)(OH)(OR$^d$),

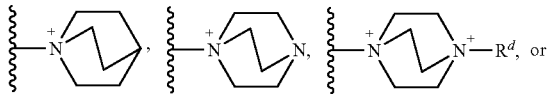

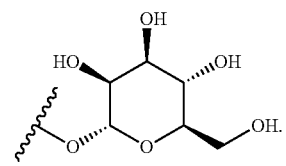

In some embodiments, each $R^c$ is independently —OH, —N(R$^d$)$_3^+$, —C(=O)OH, —S(=O)$_2$OH, —S(=O)$_2$NH$_2$, —P(=O)(OH)$_2$, —P(=O)(OH)(R$^d$), —P(=O)(OH)(OR$^d$),

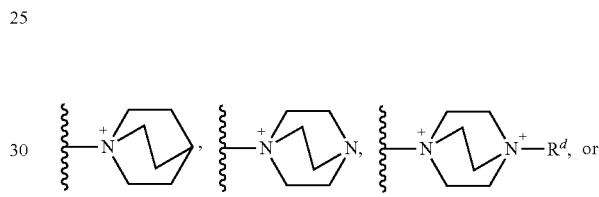

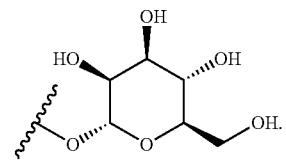 [SMILES: *O[C@H]1O[C@H](CO)[C@@H](O)[C@H](O)[C@@H]1O]

In some embodiments, each $R^e$ is independently —OH, —CH$_2$OH, —N(R$^d$)$_3^+$, —S(=O)$_2$OH, —S(=O)$_2$NH$_2$, or

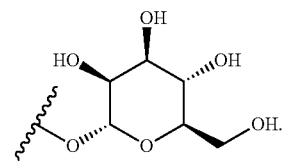 [SMILES: *O[C@H]1O[C@H](CO)[C@@H](O)[C@H](O)[C@@H]1O]

In some embodiments, each $R^e$ is independently —OH, —CH$_2$OH, —N(R$^d$)$_3^+$, —C(=O)OH, or

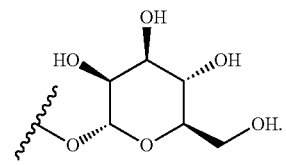

In some embodiments, each $R^e$ is independently —OH or —C(O)OH. In some embodiments, each R is —OH.

In some embodiments, when K is

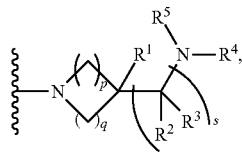

each $R^c$ is independently —OH, —CH$_2$OH, —NH$_2$, —N(R$^d$)$_3^+$, —C(=O)OH, —S(=O)$_2$OH, —S(=O)$_2$NH$_2$, —P(=O)(OH)$_2$, —P(=O)(OH)(R$^d$), —P(=O)(OH)(OR$^d$),

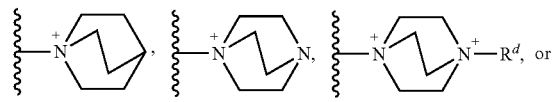

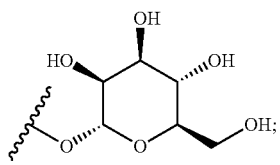

and each $R^d$ is independently C$_{1-6}$ alkyl.

In some embodiments, when K is

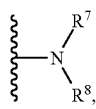

each $R^c$ is independently —OH, —CH$_2$OH, —NH$_2$, —N(R$^d$)$_3^+$, —C(=O)OH, —S(=O)$_2$OH, —S(=O)$_2$NH$_2$, —P(=O)(OH)$_2$, —P(=O)(OH)(R$^d$), —P(=O)(OH)(OR$^d$),

each $R^d$ is independently C$_{1-6}$ alkyl; and each $R^e$ is independently —OH, —CH$_2$OH, —N(R$^d$)$_3^+$, —C(=O)OH, —S(=O)$_2$OH, —S(=O)$_2$NH$_2$, —P(=O)(OH)$_2$, —P(=O)(OH)(R$^d$), —P(=O)(OH)(OR$^d$),

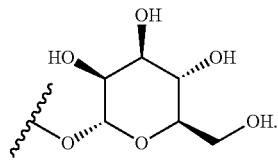 [SMILES: *O[C@H]1O[C@H](CO)[C@@H](O)[C@H](O)[C@@H]1O]

In some embodiments, each $R^c$ is independently —OH, —CH$_2$OH, —N(R$^d$)$_3^+$; and each $R^e$ is independently —OH, —CH$_2$OH, —N(R$^d$)$_3^+$, —S(=O)$_2$OH, —S(=O)$_2$NH$_2$, or

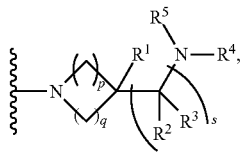

In some embodiments, each $R^c$ is —OH; and each $R^e$ is independently —OH or —C(=O)OH. In some embodiments, each $R^c$ is —OH; and each $R^e$ is independently —OH.

In some embodiments, when K is

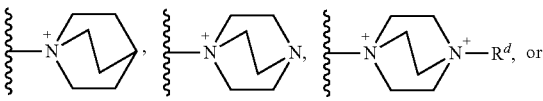

$R^4$ is hydrogen or C$_{1-8}$ alkyl; and $R^5$ is C$_{1-8}$ alkyl, C$_{2-8}$ alkenyl, C$_{2-8}$ alkynyl, C$_{3-8}$ cycloalkyl, C$_{5-8}$ cycloalkenyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein each alkyl, alkenyl, alkynyl, cycloalkyl, cycloalkenyl, and 4- to 8-membered heterocycloalkyl is substituted by 1-6 R$^c$ groups. In some embodiments, $R^4$ is hydrogen or C$_{1-6}$ alkyl; $R^5$ is C$_{1-8}$ alkyl, C$_{3-8}$ cycloalkyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein each alkyl, cycloalkyl, and 4- to 8-membered heterocycloalkyl is substituted by 1-6 R$^c$ groups; each Z is independently —CH$_2$O—, —CH$_2$NR$^d$—, —CH$_2$N$^+$(R$^d$)$_2$—, or —NH—C(=O)—NH—; R$^6$ is hydrogen, C$_{1-8}$ alkyl, C$_{3-8}$ cycloalkyl, or 4- to 8-membered heterocycloalkyl, wherein the alkyl, cycloalkyl, or 4- to 8-membered heterocycloalkyl is unsubstituted or substituted by 1-6 R$^c$ groups; each R$^c$ is independently —OH, —CH$_2$OH, —NH$_2$, —N(R$^d$)$_3^+$, —C(=O)OH, —S(=O)$_2$OH, —S(=O)$_2$NH$_2$, —P(=O)(OH)$_2$, —P(=O)(OH)(R$^d$), —P(=O)(OH)(OR$^d$),

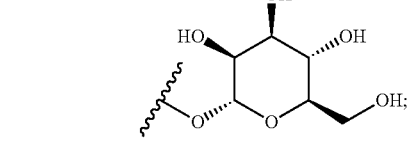

and each $R^d$ is independently $C_{1-6}$ alkyl. In some embodiments, $R^4$ is hydrogen or $C_{1-4}$ alkyl; $R^5$ is $C_{1-8}$ alkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein the alkyl is substituted by 1-6 $R^c$ groups; each Z is independently —CH$_2$O—, —CH$_2$NR$^d$—, or —NH—C(=O)—NH—; r is 1-3; t is 1-3; and $R^6$ is hydrogen or $C_{1-8}$ alkyl, wherein the alkyl is substituted by 1-6 $R^c$ groups. In some embodiments, each $R^c$ is independently —OH, —CH$_2$OH, —NH$_2$, —N(R$^d$)$_3^+$, —C(=O)OH, or

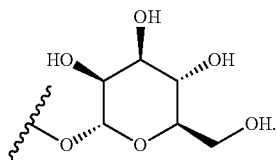 [SMILES: *O[C@H]1O[C@H](CO)[C@@H](O)[C@H](O)[C@@H]1O]

In some embodiments, $R^5$ is $C_{1-8}$ alkyl which is substituted by 1-6 $R^c$ groups; and each $R^c$ is independently —OH, —CH$_2$OH, —N(R$^d$)$_3^+$, —C(=O)OH, or

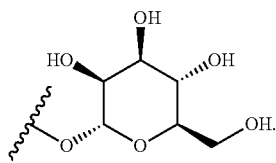 [SMILES: *O[C@H]1O[C@H](CO)[C@@H](O)[C@H](O)[C@@H]1O]

In some embodiments, $R^4$ is hydrogen; and $R^5$ is $C_{1-8}$ alkyl which is substituted by 1-6 —OH groups.

In some embodiments, when K is

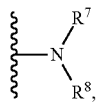

$R^7$ is hydrogen or $C_{1-4}$ alkyl; $R^8$ is $C_{1-8}$ alkyl, $C_{3-8}$ cycloalkyl, —[(CH$_2$)$_r$—Z]$_t$—R$^6$, —[(CHR$^d$)$_r$—Z]$_t$—R$^6$, or —[(CR$^d_2$)$_r$—Z]$_t$—R$^6$; wherein the alkyl and cycloalkyl is substituted by 1-6 $R^c$ groups; each Z is independently —CH$_2$O—, —CH$_2$NR$^d$—, —CH$_2$N$^+$(R$^d$)$_2$—, or —NH—C(=O)—NH—; $R^6$ is hydrogen, $C_{1-8}$ alkyl, $C_{3-8}$ cycloalkyl, or 4- to 8-membered heterocycloalkyl, wherein the alkyl, cycloalkyl, or 4- to 8-membered heterocycloalkyl is unsubstituted or substituted by 1-6 $R^c$ groups; or $R^8$ is —(C$_{1-8}$ alkyl)-NH—R$^9$, —(C$_{1-8}$ alkyl)-C(=O)NH—R$^9$, —(C$_{1-8}$ alkyl)-C(=O)—N(R$^9$)$_2$, or —(C$_{1-8}$ alkyl)-NHC(=O)NH—R$^9$; wherein the alkyl is unsubstituted or substituted by 1-6 $R^c$ groups; each $R^9$ is independently $C_{1-8}$ alkyl which is substituted by 1-6 $R^c$ groups; or two $R^9$ are taken together with the nitrogen to which they are attached to form a 4- to 6-membered heterocycloalkyl, which is substituted by 1-6 $R^c$ groups; each $R^c$ is independently —OH, —CH$_2$OH, —NH$_2$, —N(R$^d$)$_3^+$, —C(=O)OH, —S(=O)$_2$OH, —S(=O)$_2$NH$_2$, —P(=O)(OH)$_2$, —P(=O)(OH)(R$^d$), —P(=O)(OH)(OR$^d$),

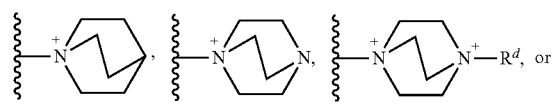

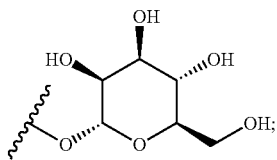

each $R^d$ is independently $C_{1-6}$ alkyl; and each $R^e$ is independently —OH, —CH$_2$OH, —N(R$^d$)$_3^+$, —C(=O)OH, —S(=O)$_2$OH, —S(=O)$_2$NH$_2$, —P(=O)(OH)$_2$, —P(=O)(OH)(R$^d$), —P(=O)(OH)(OR$^d$),

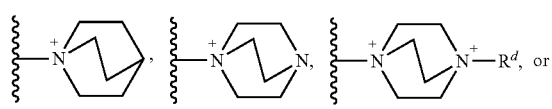

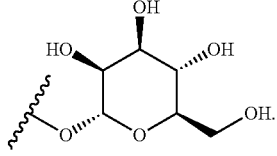

In some embodiments, $R^8$ is $C_{1-8}$ alkyl; wherein the alkyl is substituted by 1-6 $R^e$ groups; or $R^8$ is —(C$_{1-8}$ alkyl)-NH—R$^9$, —(C$_{1-8}$ alkyl)-C(=O)NH—R$^9$, —(C$_{1-8}$ alkyl)-C(=O)—N(R$^9$)$_2$, or —(C$_{1-8}$ alkyl)-NHC(=O)NH—R$^9$; wherein the alkyl is unsubstituted. In some embodiments, each $R^c$ is independently —OH, —CH$_2$OH, —N(R$^d$)$_3^+$; and each R is independently —OH, —CH$_2$OH, —N(R$^d$)$_3^+$, —S(=O)$_2$OH, —S(=O)$_2$NH$_2$, or

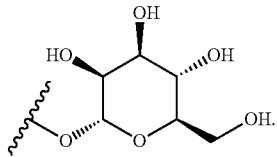

In some embodiments, $R^7$ is hydrogen; each $R^c$ is —OH; and each $R^e$ is independently —OH or —C(=O)OH. In some embodiments, $R^7$ is hydrogen; each $R^c$ is —OH; and each $R^e$ is independently —OH.

In some embodiments, when K is

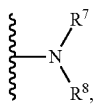

$R^7$ and $R^8$ are taken together with the nitrogen to which they are attached to form a 4- to 6-membered heterocycloalkyl, which is substituted by 1-5 $R^f$ groups; and each $R^f$ is independently —CH$_2$OH, —CH$_2$CH$_2$OH, —N(R$^d$)$_3^+$, —CH$_2$N(R$^d$)$_2^+$—R$^9$, —C(=O)OH, —CH$_2$C(=O)OH, —CH$_2$CH$_2$C(=O)OH, —S(=O)$_2$OH, —S(=O)$_2$NH$_2$, —P(=O)(OH)$_2$, —P(=O)(OH)(R$^d$), —P(=O)(OH)(OR$^d$),

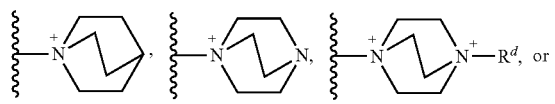
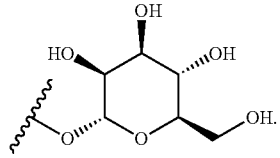 [SMILES: *O[C@H]1O[C@H](CO)[C@@H](O)[C@H](O)[C@@H]1O]
In some embodiments, $R^7$ and $R^8$ are taken together with the nitrogen to which they are attached to form an azetidine, which is substituted by 1-2 $R^f$ groups; and each $R^f$ is independently —$CH_2OH$, —$CH_2CH_2OH$, —$CH_2N(R^d)_2{}^+$—$R^9$, —$C(=O)OH$, —$CH_2C(=O)OH$, or —$CH_2CH_2C(=O)OH$.
In some embodiments, the compound described herein has a structure provided in Table 1.

TABLE 1

| Ex. # | Structure | Name |
|---|---|---|
| 1 | 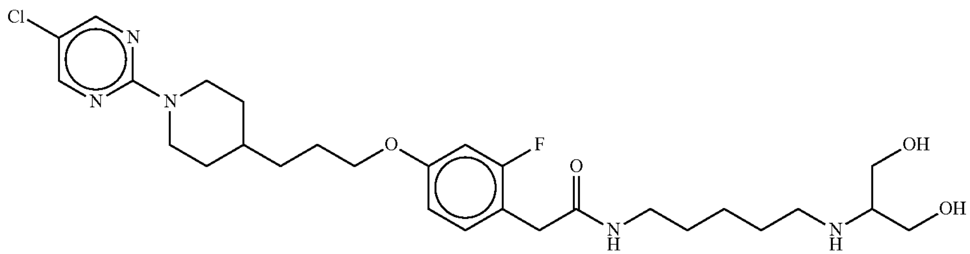 | 2-[4-[3-[1-(5-chloropyrimidin-2-yl)-4-piperidyl]propoxy]-2-fluoro-phenyl]-N-[5-[[2-hydroxy-1-(hydroxymethyl)ethyl]amino]pentyl]-acetamide |
| 2 | 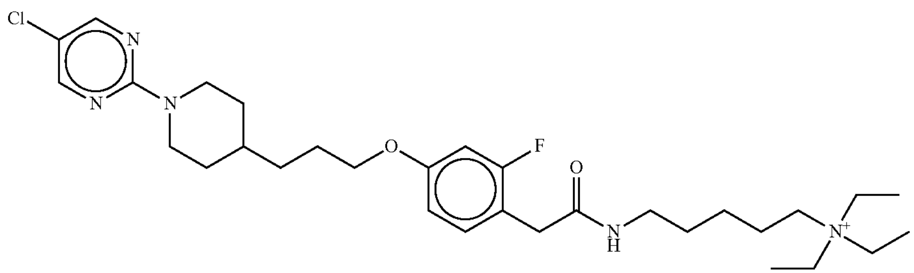 | 5-[[2-[4-[3-[1-(5-chloropyrimidin-2-yl)-4-piperidyl]propoxy]-2-fluoro-phenyl]acetyl]amino]pentyl-triethyl-ammonium |
| 3 | 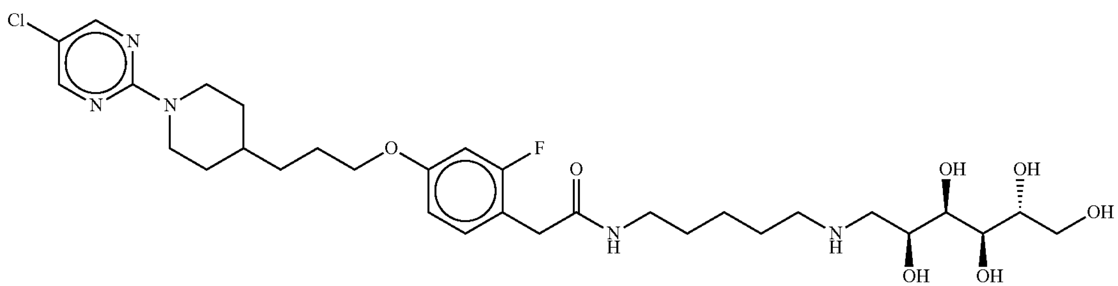 | 2-[4-[3-[1-(5-chloropyrimidin-2-yl)-4-piperidyl]propoxy]-2-fluoro-phenyl]-N-[5-[[(2S,3R,4R,5R)-2,3,4,5,6-pentahydroxyhexyl]amino]pentyl]-acetamide |

TABLE 1-continued

| Ex. # | Structure | Name |
|---|---|---|
| 4 | 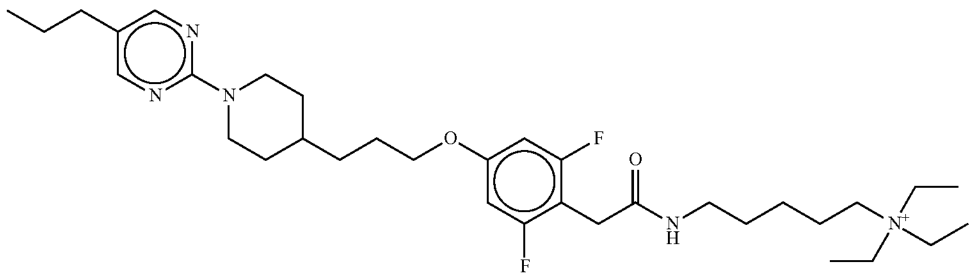 | 5-[[2-[2,6-difluoro-4-[3-[1-(5-propylpyrimidin-2-yl)-4-piperidyl]propoxy]phenyl]acetyl]amino]pentyl-triethyl-ammonium |
| 5 | 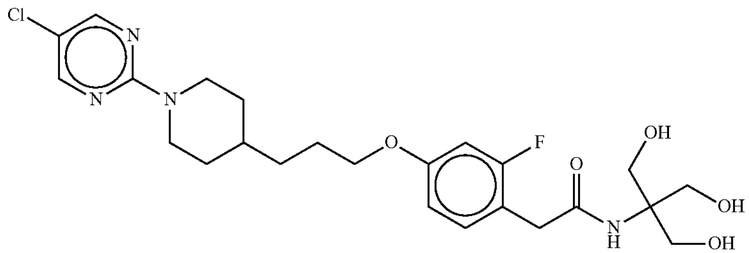 | 2-[4-[3-[1-(5-chloropyrimidin-2-yl)-4-piperidyl]propoxy]-2-fluoro-phenyl]-N-[2-hydroxy-1,1-bis(hydroxymethyl)ethyl]acetamide |
| 6 | 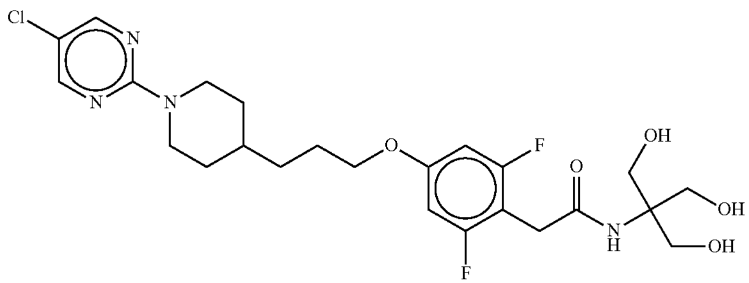 | 2-[4-[3-[1-(5-chloropyrimidin-2-yl)-4-piperidyl]propoxy-2,6-difluoro-phenyl]-N-[2-hydroxy-1,1-bis(hydroxymethyl)ethyl]acetamide |

TABLE 1-continued

| Ex. # | Structure | Name |
|---|---|---|
| 7 | 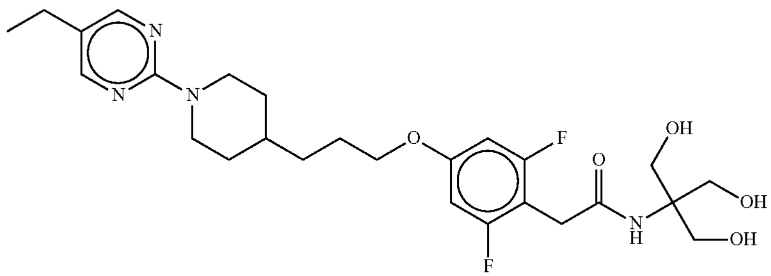 | 2-[4-[3-[1-(5-ethylpyrimidin-2-yl)-4-piperidyl]propoxy]-2,6-difluoro-phenyl]-N-[2-hydroxy-1,1-bis(hydroxymethyl)ethyl]acetamide |
| 8 | 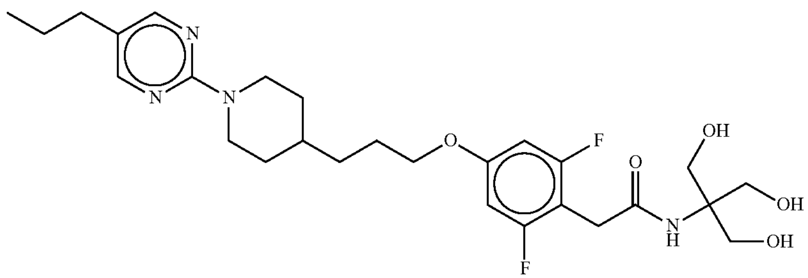 | 2-[2,6-difluoro-4-[3-[1-(5-propylpyrimidin-2-yl)-4-piperidyl]propoxy]phenyl]-N-[2-hydroxy-1,1-bis(hydroxymethyl)ethyl]acetamide |
| 9 | 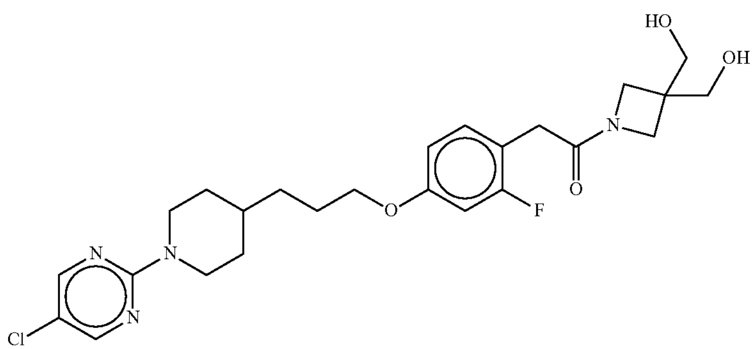 | 1-[3,3-bis(hydroxymethyl)azetidin-1-yl]-2-[4-[3-[1-(5-chloropyrimidin-2-yl)-4-piperidyl]propoxy]-2-fluoro-phenyl]ethanone |

TABLE 1-continued

| Ex. # | Structure | Name |
|---|---|---|
| 10 | 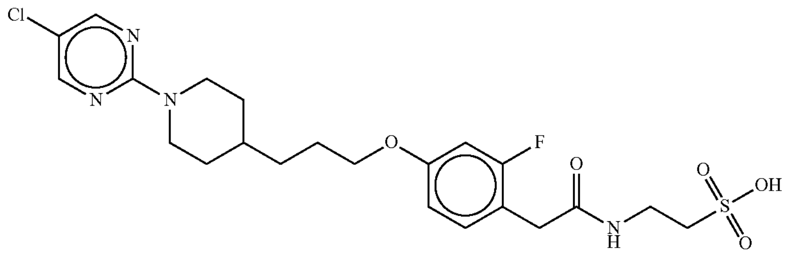 | 2-[[2-[4-[3-[1-(5-chloropyrimidin-2-yl)-4-piperidyl]propoxy]-2-fluorophenyl]acetyl]amino]ethanesulfonic acid |
| 11 | 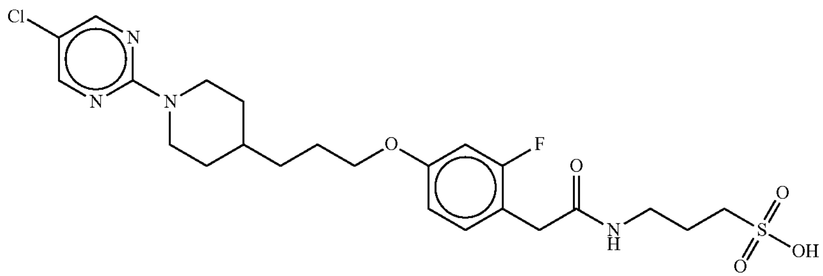 | 3-[[2-[4-[3-[1-(5-chloropyrimidin-2-yl)-4-piperidyl]propoxy]-2-fluorophenyl]acetyl]amino]propane-1-sulfonic acid |
| 12 | 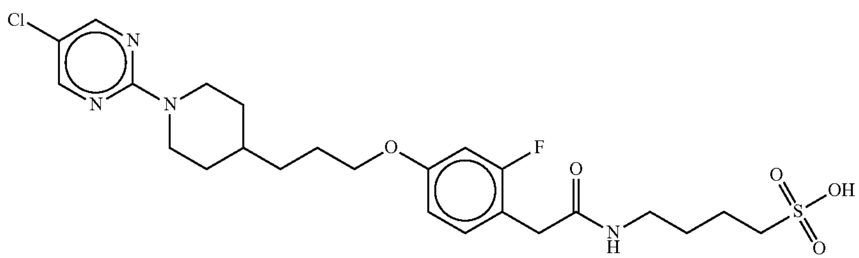 | 4-[[2-[4-[3-[1-(5-chloropyrimidin-2-yl)-4-piperidyl]propoxy]-2-fluorophenyl]acetyl]amino]butane-1-sulfonic acid |

TABLE 1-continued

| Ex. # | Structure | Name |
|---|---|---|
| 13 | 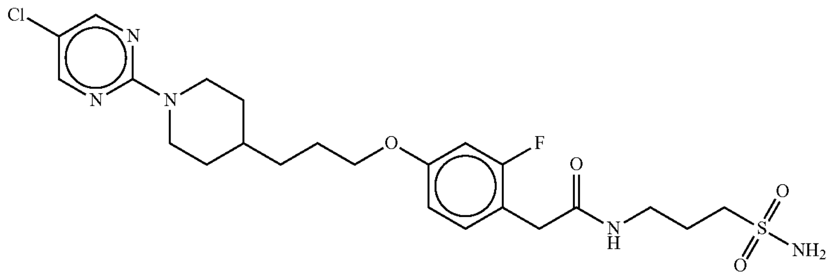 | 2-[4-[3-[1-(5-chloropyrimidin-2-yl)-4-piperidyl]propoxy]-2-fluoro-phenyl]-N-(3-sulfamoylpropyl)acetamide |
| 14 | 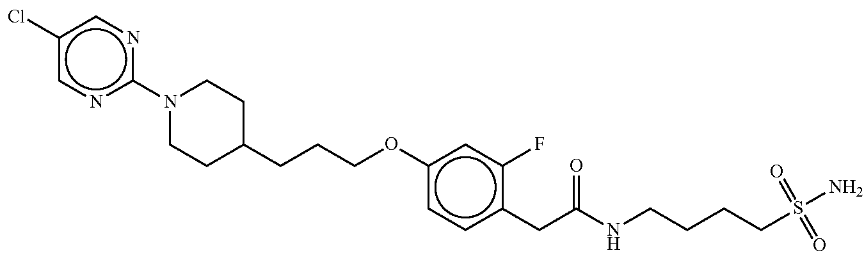 | 2-[4-[3-[1-(5-chloropyrimidin-2-yl)-4-piperidyl]propoxy]-2-fluoro-phenyl]-N-(4-sulfamoylbutyl)acetamide |
| 15 | 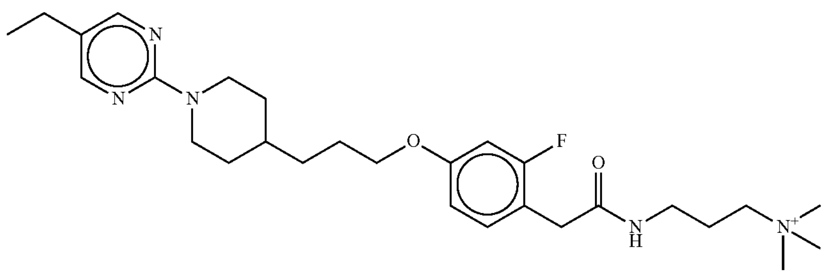 | 3-[[2-[4-[3-[1-(5-ethylpyrimidin-2-yl)-4-piperidyl]propoxy]-2-fluoro-phenyl]acetyl]amino]propyl-trimethyl-ammonium |

TABLE 1-continued

| Ex. # | Structure | Name |
|---|---|---|
| 16 | 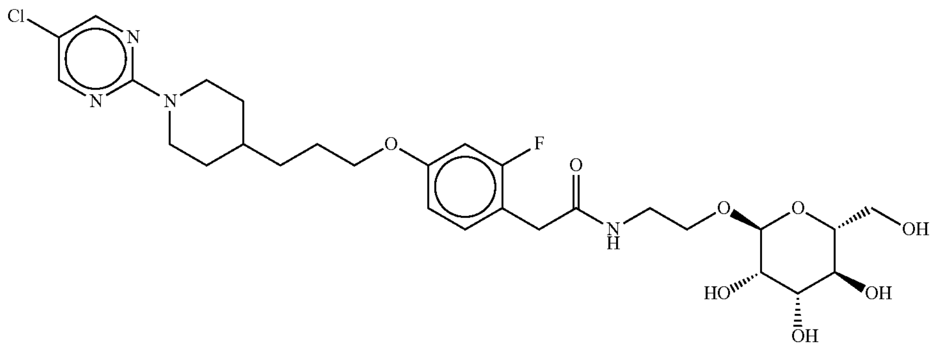 | 2-[4-[3-[1-(5-chloropyrimidin-2-yl)-4-piperidyl]propoxy]-2-fluoro-phenyl]-N-[2-[rac-(2S,3S,4S,5S,6R)-3,4,5-trihydroxy-6-(hydroxymethyl)tetrahydropyran-2-yl]oxyethyl]acetamide |
| 17 | 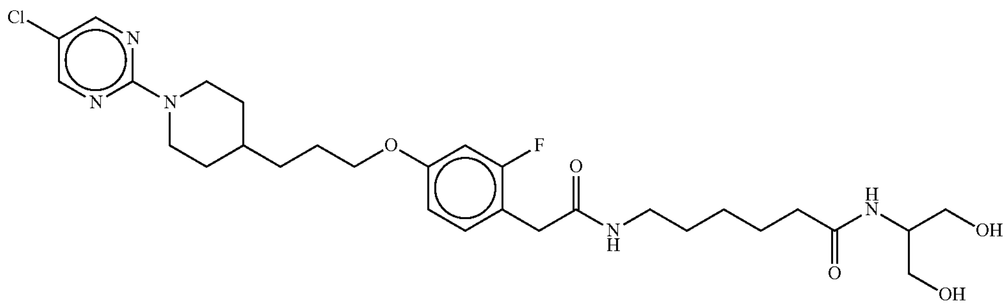 | 6-[[2-[4-[3-[1-(5-chloropyrimidin-2-yl)-4-piperidyl]propoxy]-2-fluoro-phenyl]acetyl]amino]-N-[2-hydroxy-1-(hydroxymethyl)ethyl]hexanamide |
| 18 | 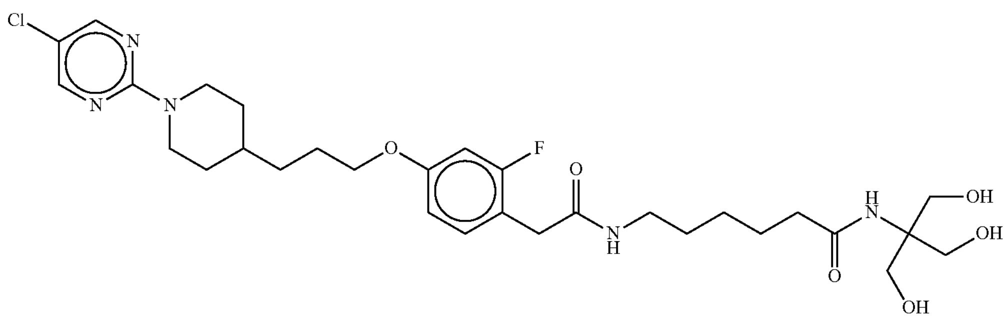 | 6-[[2-[4-[3-[1-(5-chloropyrimidin-2-yl)-4-piperidyl]propoxy]-2-fluoro-phenyl]acetyl]amino]-N-[2-hydroxy-1,1-bis(hydroxymethyl)ethyl]hexanamide |

TABLE 1-continued

| Ex. # | Structure | Name |
|---|---|---|
| 19 | 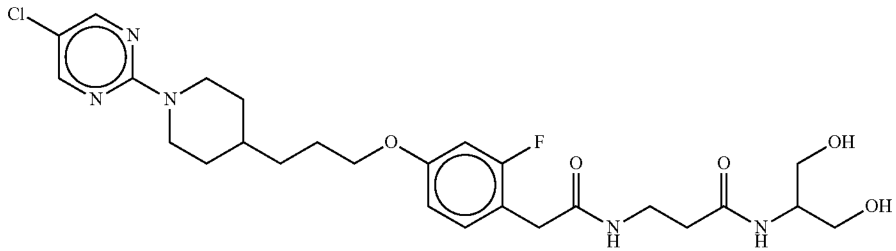 | 3-[[2-[4-[3-[1-(5-chloropyrimidin-2-yl)-4-piperidyl]propoxy]-2-fluoro-phenyl]acetyl]amino]-N-[2-hydroxy-1-(hydroxymethyl)ethyl]propanamide |
| 20 | 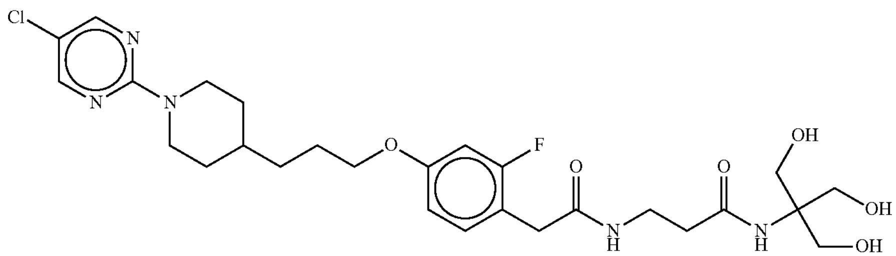 | 3-[[2-[4-[3-[1-(5-chloropyrimidin-2-yl)-4-piperidyl]propoxy]-2-fluoro-phenyl]acetyl]amino]-N-[2-hydroxy-1,1-bis(hydroxymethyl)ethyl]propanamide |
| 21 | 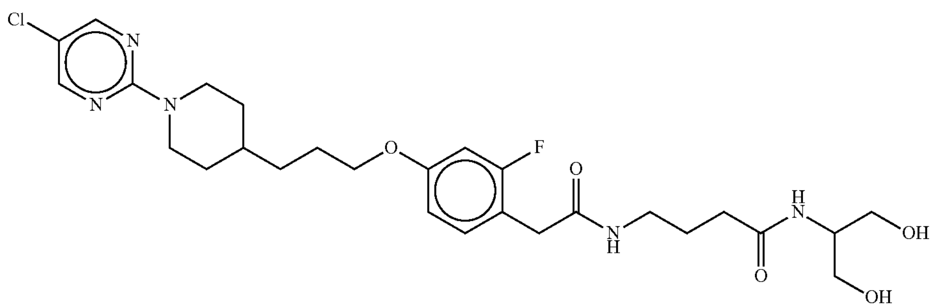 | 4-[[2-[4-[3-[1-(5-chloropyrimidin-2-yl)-4-piperidyl]propoxy]-2-fluoro-phenyl]acetyl]amino]-N-[2-hydroxy-1-(hydroxymethyl)ethyl]butanamide |

TABLE 1-continued

| Ex. # | Structure | Name |
|---|---|---|
| 22 | 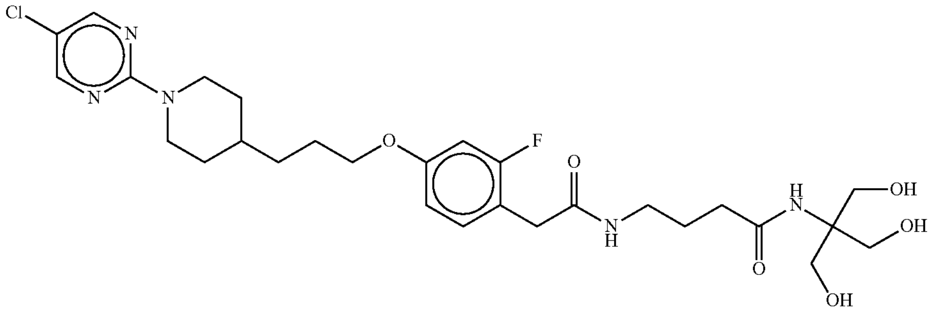 | 4-[[2-[4-[3-[1-(5-chloropyrimidin-2-yl)-4-piperidyl]propoxy]-2-fluoro-phenyl]acetyl]amino]-N-[2-hydroxy-1,1-bis(hydroxymethyl)ethyl]butanamide |
| 23 | 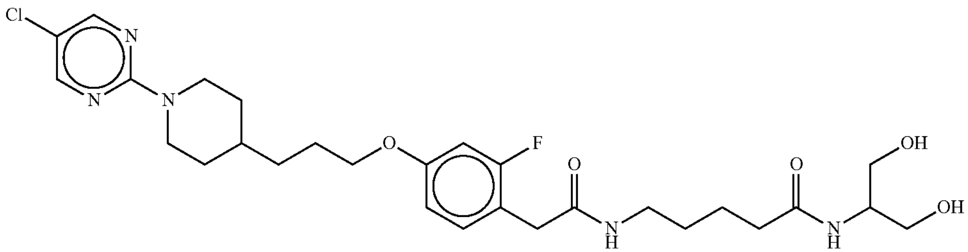 | 5-[[2-[4-[3-[1-(5-chloropyrimidin-2-yl)-4-piperidyl]propoxy]-2-fluoro-phenyl]acetyl]amino]-N-[2-hydroxy-1-(hydroxymethyl)ethyl]pentanamide |
| 24 | 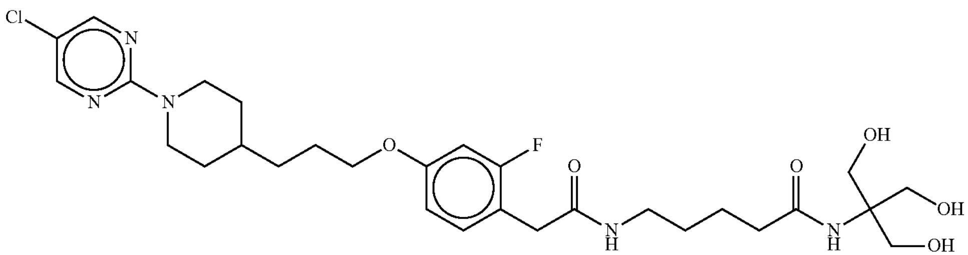 | 5-[[2-[4-[3-[1-(5-chloropyrimidin-2-yl)-4-piperidyl]propoxy]-2-fluoro-phenyl]acetyl]amino]-N-[2-hydroxy-1,1-bis(hydroxymethyl)ethyl]pentanamide |

TABLE 1-continued

| Ex. # | Structure | Name |
|---|---|---|
| 25 | 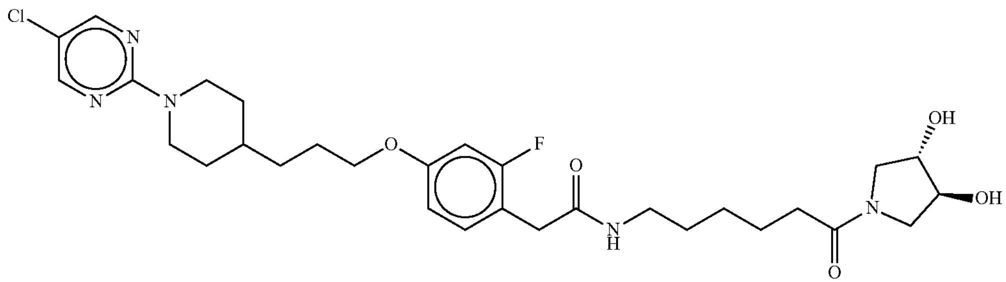 | 2-[4-[3-[1-(5-chloropyrimidin-2-yl)-4-piperidyl]propoxy]-2-fluoro-phenyl]-N-[6-[(3S,4S)-3,4-dihydroxypyrrolidin-1-yl]-6-oxo-hexyl]acetamide |
| 26 | 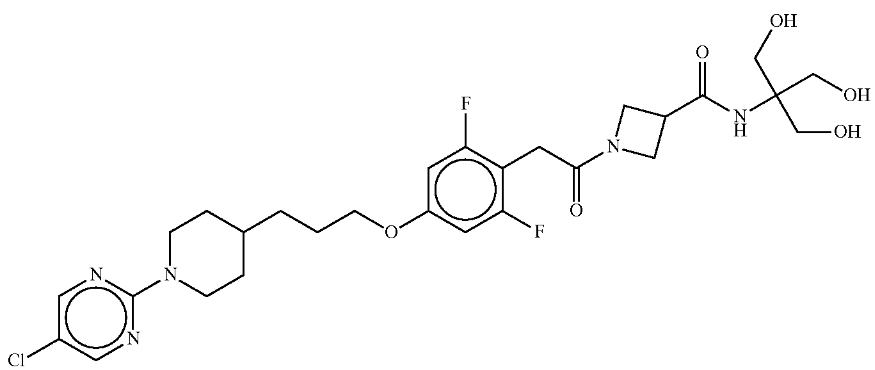 | 1-[2-[4-[3-[1-(5-chloropyrimidin-2-yl)-4-piperidyl]propoxy]-2,6-difluoro-phenyl]acetyl]-N-[2-hydroxy-1,1-bis(hydroxymethyl)ethyl]azetidine-3-carboxamide |
| 27 | 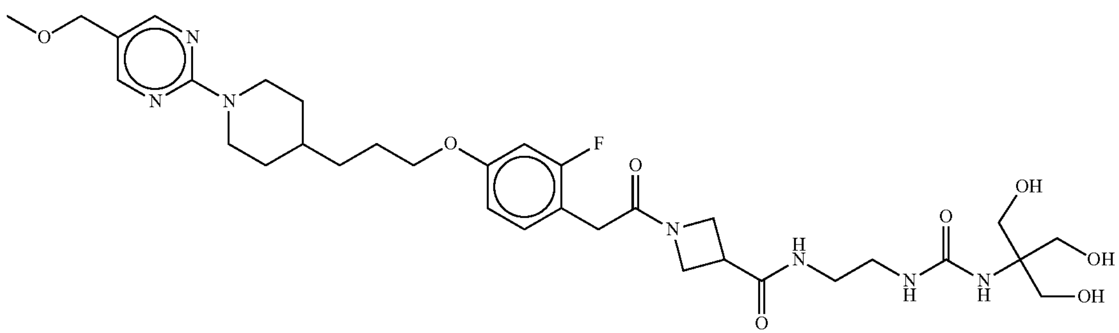 | 1-[2-[2-fluoro-4-[3-[1-[5-(methoxymethyl)pyrimidin-2-yl]-4-piperidyl]propoxy]phenyl]acetyl]-N-[2-[[2-hydroxy-1,1-bis(hydroxymethyl)ethyl]carbamoyl-amino]ethyl]azetidine-3-carboxamide |

TABLE 1-continued

| Ex. # | Structure | Name |
|---|---|---|
| 28 | 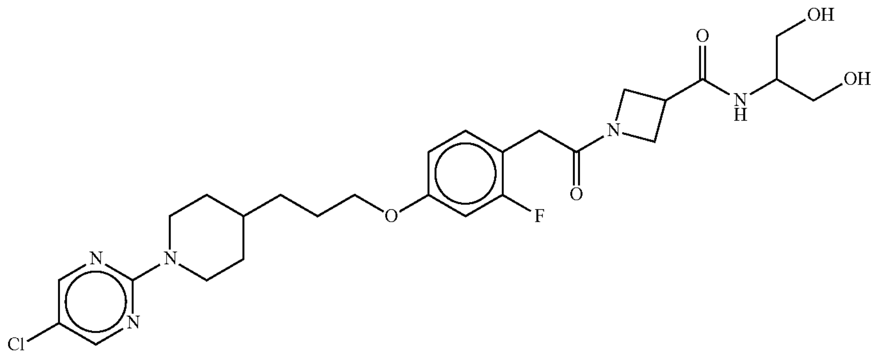 | 1-[2-[4-[3-[1-(5-chloropyrimidin-2-yl)-4-piperidyl]propoxy]-2-fluoro-phenyl]acetyl]-N-[2-hydroxy-1-(hydroxymethyl)ethyl]azetidine-3-carboxamide |
| 29 | 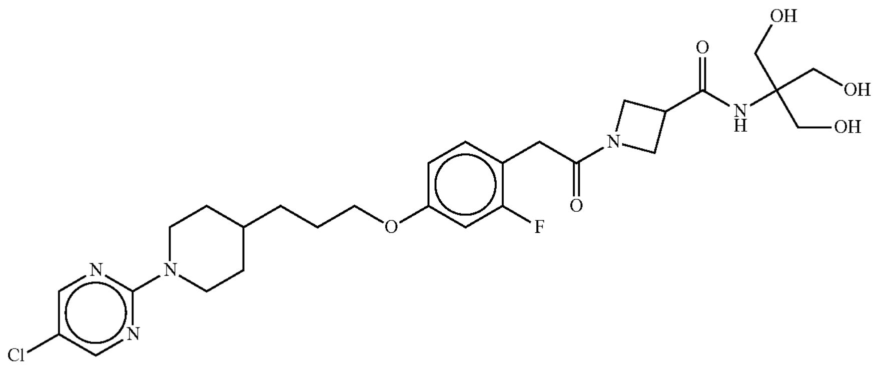 | 1-[2-[4-[3-[1-(5-chloropyrimidin-2-yl)-4-piperidyl]propoxy]-2-fluoro-phenyl]acetyl]-N-[2-hydroxy-1,1-bis(hydroxymethyl)ethyl]azetidine-3-carboxamide |
| 30 | 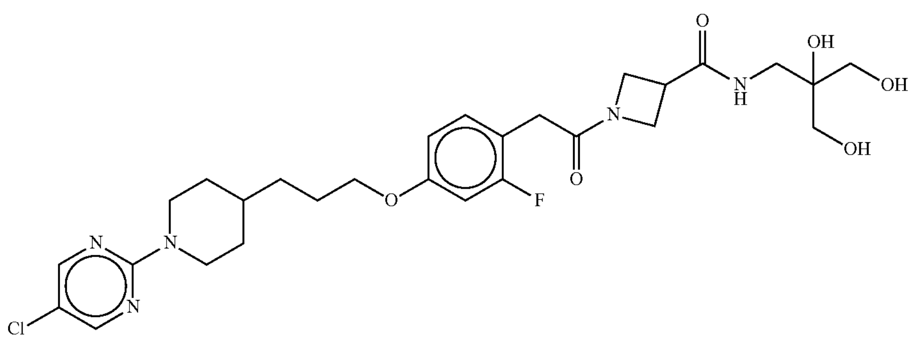 | 1-[2-[4-[3-[1-(5-chloropyrimidin-2-yl)-4-piperidyl]propoxy]-2-fluoro-phenyl]acetyl]-N-[2,3-dihydroxy-2-(hydroxymethyl)propyl]azetidine-3-carboxamide |

TABLE 1-continued

| Ex. # | Structure | Name |
|---|---|---|
| 31 | 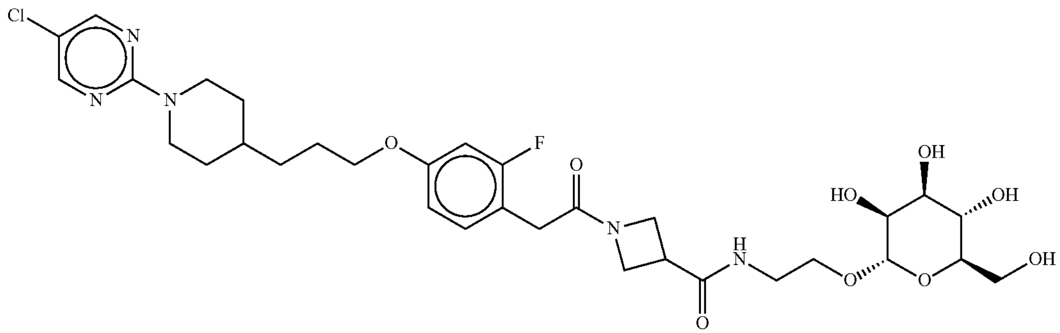 | 1-[2-[4-[3-[1-(5-chloropyrimidin-2-yl)-4-piperidyl]propoxy]-2-fluoro-phenyl]acetyl]-N-[2-[rac-(2S,3S,4S,5S,6R)-3,4,5-trihydroxy-6-(hydroxymethyl)tetrahydropyran-2-yl]oxyethyl]azetidine-3-carboxamide |
| 32 | 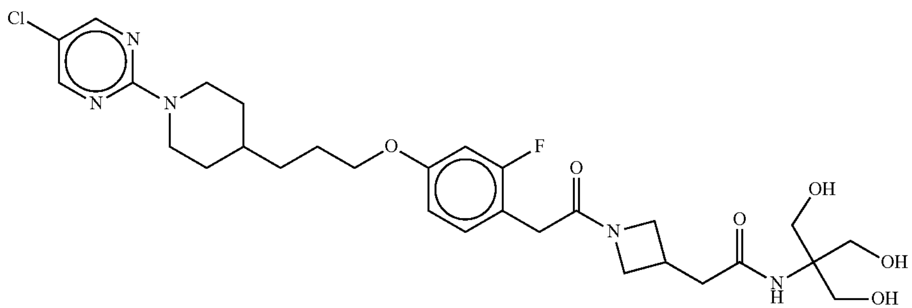 | 2-[1-[2-[4-[3-[1-(5-chloropyrimidin-2-yl)-4-piperidyl]propoxy]-2-fluoro-phenyl]acetyl]azetidin-3-yl]-N-[2-hydroxy-1,1-bis(hydroxymethyl)ethyl]acetamide |
| 33 | 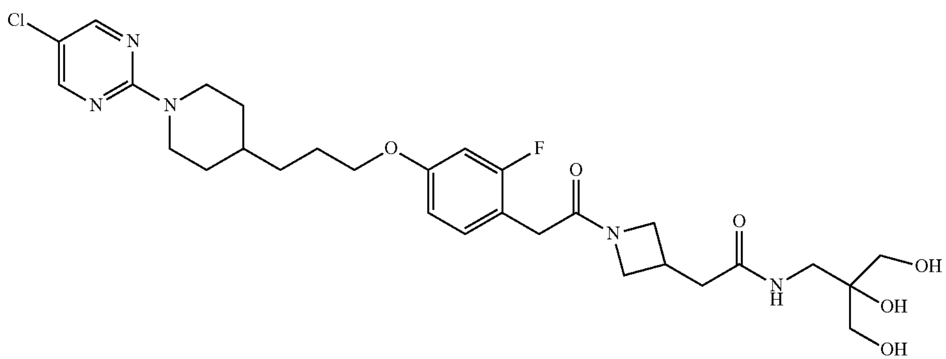 [SMILES: O=C(CC1CN(C(=O)Cc2ccc(OCCCC3CCN(c4ncc(Cl)cn4)CC3)cc2F)C1)NCC(O)(CO)CO] | 2-[1-[2-[4-[3-[1-(5-chloropyrimidin-2-yl)-4-piperidyl]propoxy]-2-fluoro-phenyl]acetyl]azetidin-3-yl]-N-[2,3-dihydroxy-2-(hydroxymethyl)propyl]acetamide |

TABLE 1-continued

| Ex. # | Structure | Name |
|---|---|---|
| 34 | 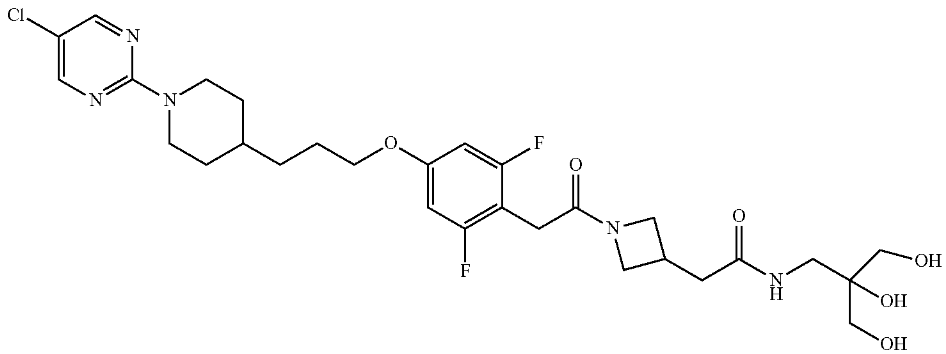 [SMILES: O=C(CC1CN(C(=O)Cc2c(F)cc(OCCCC3CCN(c4ncc(Cl)cn4)CC3)cc2F)C1)NCC(O)(CO)CO] | 2-[1-[2-[4-[3-[1-(5-chloropyrimidin-2-yl)-4-piperidyl]propoxy]-2,6-difluorophenyl]acetyl]azetidin-3-yl]-N-[2,3-dihydroxy-2-(hydroxymethyl)propyl]acetamide |
| 35 | 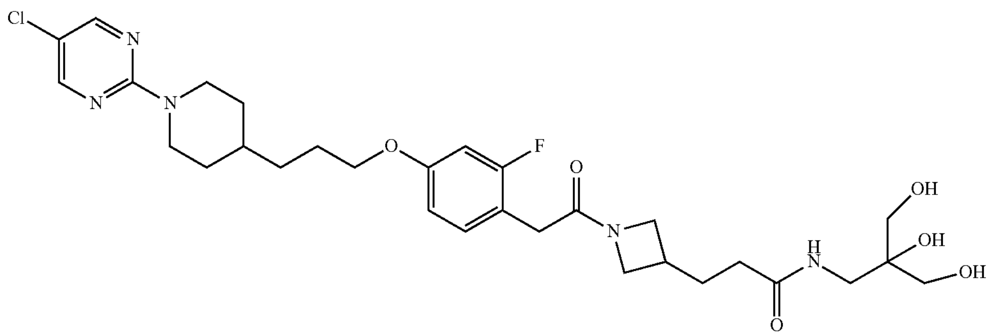 [SMILES: O=C(CCC1CN(C(=O)Cc2ccc(OCCCC3CCN(c4ncc(Cl)cn4)CC3)cc2F)C1)NCC(O)(CO)CO] | 3-[1-[2-[4-[3-[1-(5-chloropyrimidin-2-yl)-4-piperidyl]propoxy]-2-fluorophenyl]acetyl]azetidin-3-yl]-N-[2,3-dihydroxy-2-(hydroxymethyl)propyl]propanamide |
| 36 | 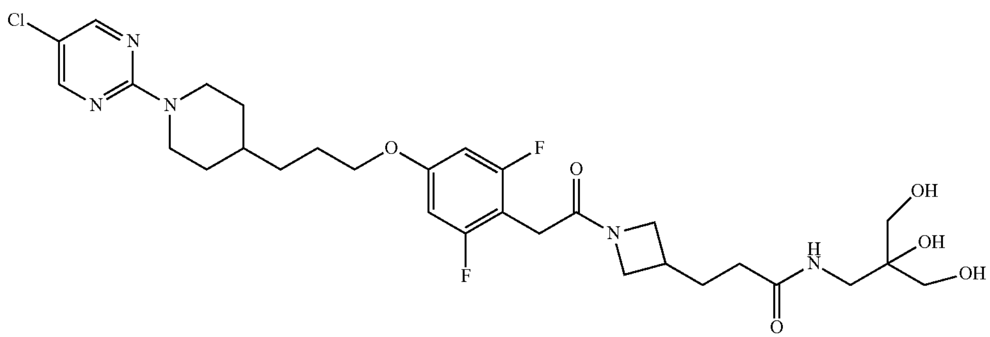 [SMILES: O=C(CCC1CN(C(=O)Cc2c(F)cc(OCCCC3CCN(c4ncc(Cl)cn4)CC3)cc2F)C1)NCC(O)(CO)CO] | 3-[1-[2-[4-[3-[1-(5-chloropyrimidin-2-yl)-4-piperidyl]propoxy]-2,6-difluorophenyl]acetyl]azetidin-3-yl]-N--2,3-dihydroxy-2-(hydroxymethyl)propyl]propanamide |

TABLE 1-continued

| Ex. # | Structure | Name |
|---|---|---|
| 37 | 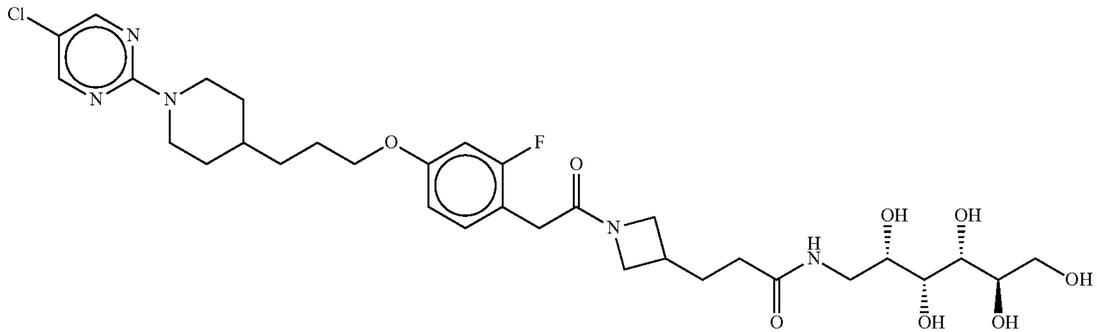 | 1-[2-[4-[3-[1-(5-chloropyrimidin-2-yl)-4-piperidyl]propoxy]-2-fluorophenyl]acetyl]-N-[rac-(2S,3R,4R,5R)-2,3,4,5,6-pentahydroxyhexyl]azetidine-3-carboxamide |
| 38 | 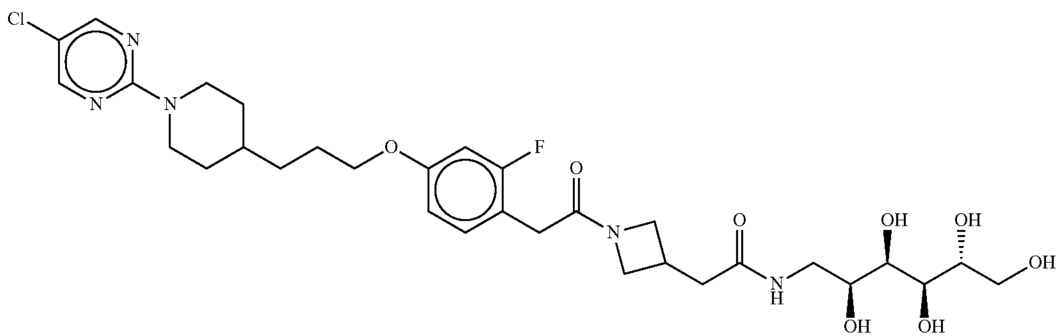 | 2-[1-[2-[4-[3-[1-(5-chloropyrimidin-2-yl)-4-piperidyl]propoxy]-2-fluorophenyl]acetyl]azetidin-3-yl]-N-[rac-(2S,3R,4R,5R)-2,3,4,5,6-pentahydroxyhexyl]acetamide |
| 39 | 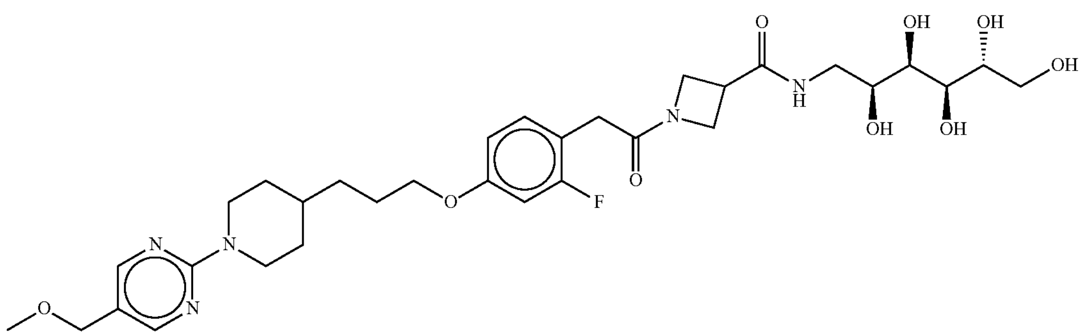 | 1-[2-[2-fluoro-4-[3-[1-[5-(methoxymethyl)pyrimidin-2-yl]-4-piperidyl]propoxy]phenyl]acetyl]-N-[rac-(2S,3R,4R,5R)-2,3,4,5,6-pentahydroxyhexyl]azetidine-3-carboxamide |

TABLE 1-continued

| Ex. # | Structure | Name |
|---|---|---|
| 40 | 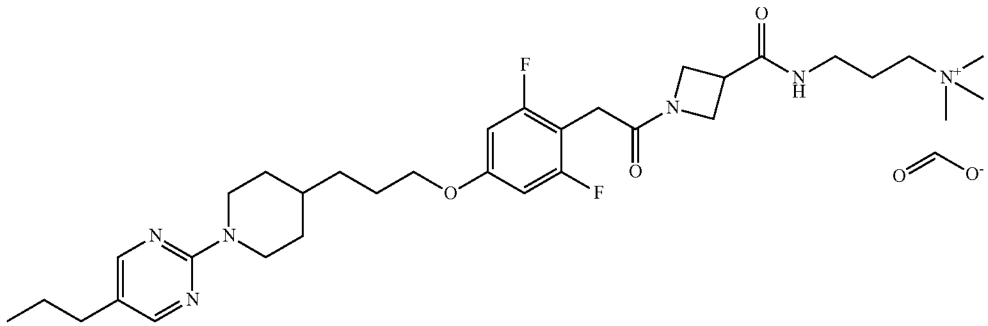 | 3-[[1-[2-[2,6-difluoro-4-[3-[1-(5-propylpyrimidin-2-yl)-4-piperidyl]propoxy]phenyl]acetyl]azetidine-3-carbonyl]amino]propyl]-trimethyl-ammonium formate |
| 41 | 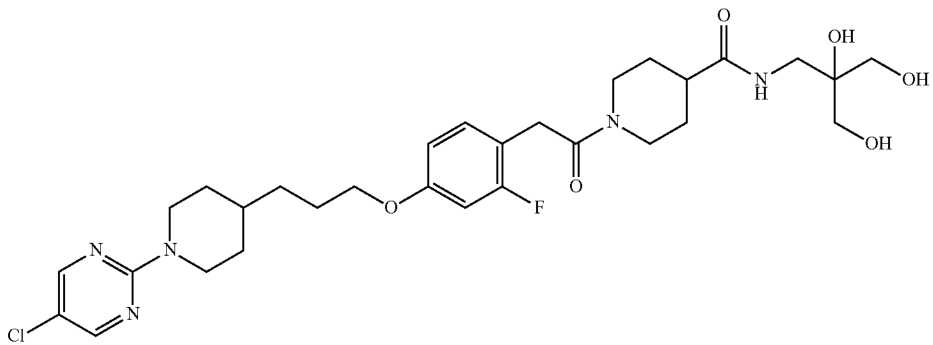 [SMILES: O=C(NCC(O)(CO)CO)C1CCN(C(=O)Cc2ccc(OCCCC3CCN(c4ncc(Cl)cn4)CC3)cc2F)CC1] | 1-[2-[4-(3-[1-(5-chloropyrimidin-2-yl)-4-piperidyl]propoxy]-2-fluoro-phenyl]acetyl]-N-[2,3-dihydroxy-2-(hydroxymethyl)propyl]piperidine-4-carboxamide |
| 42 | 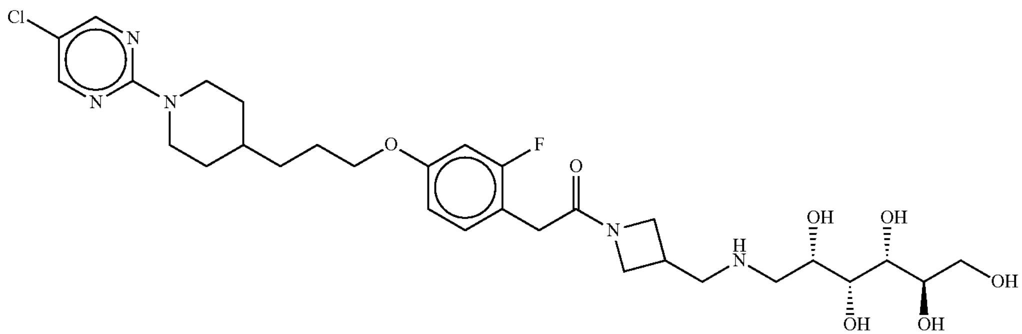 | 2-[4-[3-[1-(5-chloropyrimidin-2-yl)-4-piperidyl]propoxy]-2-fluoro-phenyl]-1-[3-[[(2S,3R,4R,5R)-2,3,4,5,6-pentahydroxyhexyl]amino]methyl]azetidin-1-yl]ethanone |

TABLE 1-continued

| Ex. # | Structure | Name |
|---|---|---|
| 43 | 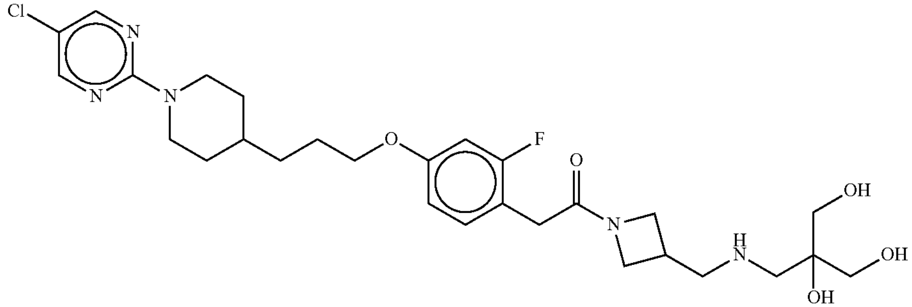 | 2-[4-[3-[1-(5-chloropyrimidin-2-yl)-4-piperidyl]propoxy]-2-fluoro-phenyl]-1-[3-[[[2,3-dihydroxy-2-(hydroxymethyl)propyl]amino]methyl]-azetidin-1-yl]ethanone |
| 44 | 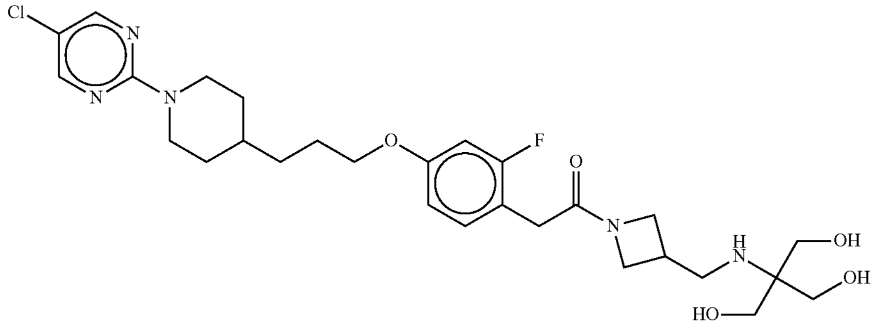 | 2-[4-[3-[1-(5-chloropyrimidin-2-yl)-4-piperidyl]propoxy]-2-fluoro-phenyl]-1-[3-[[[2-hydroxy-1,1-bis(hydroxymethyl)ethyl]amino]methyl]azetidin-1-yl]ethanone |
| 45 | 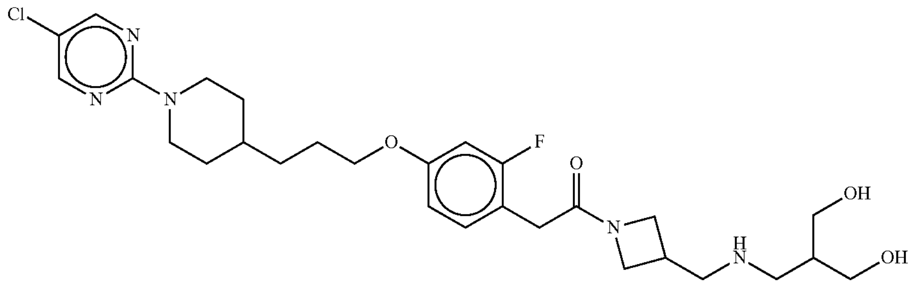 | 2-[4-[3-[1-(5-chloropyrimidin-2-yl)-4-piperidyl]propoxy]-2-fluoro-phenyl]-1-[3-[[[3-hydroxy-2-(hydroxymethyl)propyl]amino]methyl]-azetidin-1-yl]ethanone |

TABLE 1-continued

| Ex. # | Structure | Name |
|---|---|---|
| 46 | 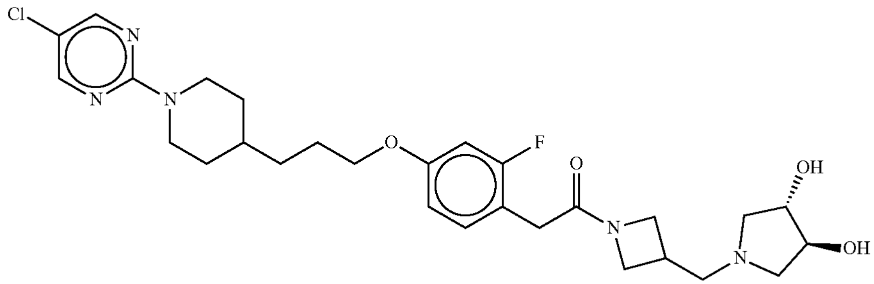 | 2-[4-[3-[1-(5-chloropyrimidin-2-yl)-4-piperidyl]propoxy]-2-fluoro-phenyl]-1-[3-[[rac-(3S,4S)-3,4-dihydroxypyrrolidin-1-yl]methyl]azetidin-1-yl]ethanone |
| 47 | 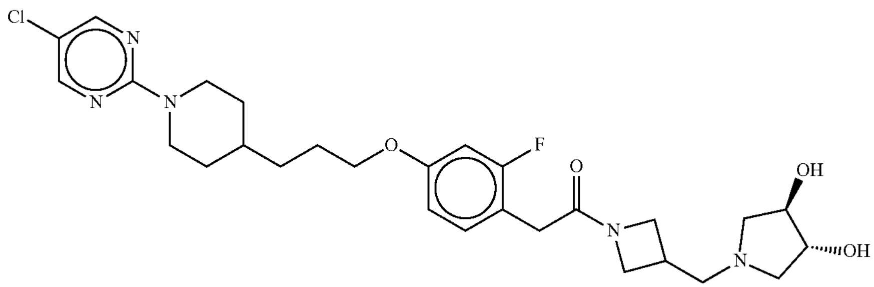 | 2-[4-[3-[1-(5-chloropyrimidin-2-yl)-4-piperidyl]propoxy]-2-fluoro-phenyl]-1-[3-[[rac-(3R,4R)-3,4-dihydroxypyrrolidin-1-yl]methyl]azetidin-1-yl]ethanone |
| 48 | 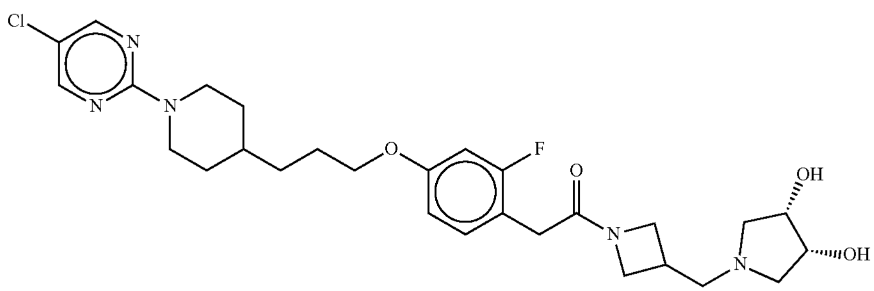 | 2-[4-[3-[1-(5-chloropyrimidin-2-yl)-4-piperidyl]propoxy]-2-fluoro-phenyl]-1-[3-[[rac-(3S,4R)-3,4-dihydroxypyrrolidin-1-yl]methyl]azetidin-1-yl]ethanone |

TABLE 1-continued

| Ex. # | Structure | Name |
|---|---|---|
| 49 | 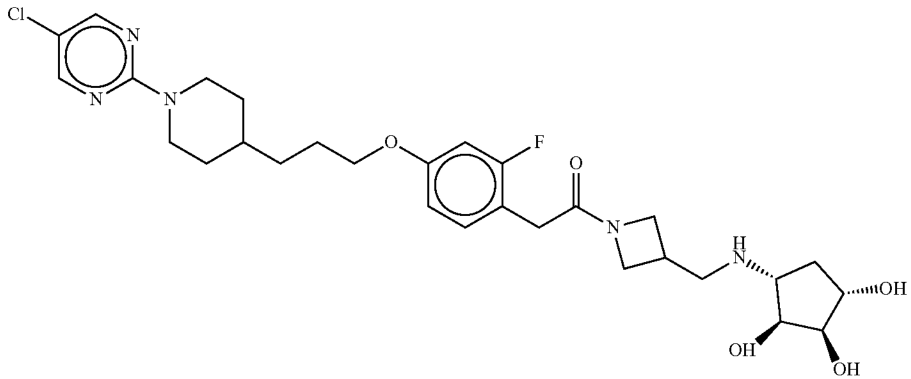 | 2-[4-[3-[1-(5-chloropyrimidin-2-yl)-4-piperidyl]propoxy]-2-fluoro-phenyl]-1-[3-[[[rac-(1R,2S,3R,4S)-2,3,4-trihydroxycyclopentyl]amino]methyl]-azetidin-1-yl]ethanone |
| 50 | 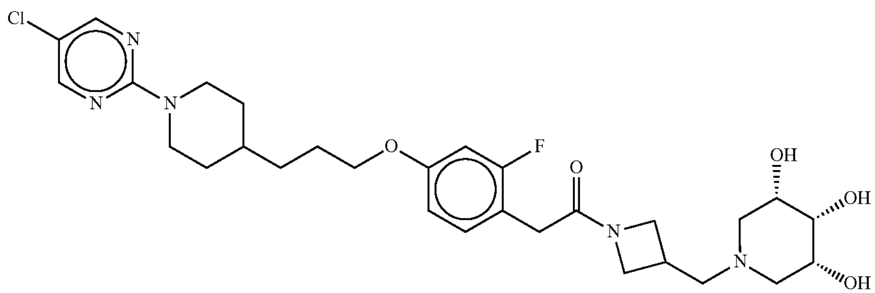 | 2-[4-[3-[1-(5-chloropyrimidin-2-yl)-4-piperidyl]propoxy]-2-fluoro-phenyl]-1-[3-[rac-(3R,5S)-3,4,5-trihydroxy-1-piperidyl]methylazetidin-1-yl]ethanone |
| 51 | 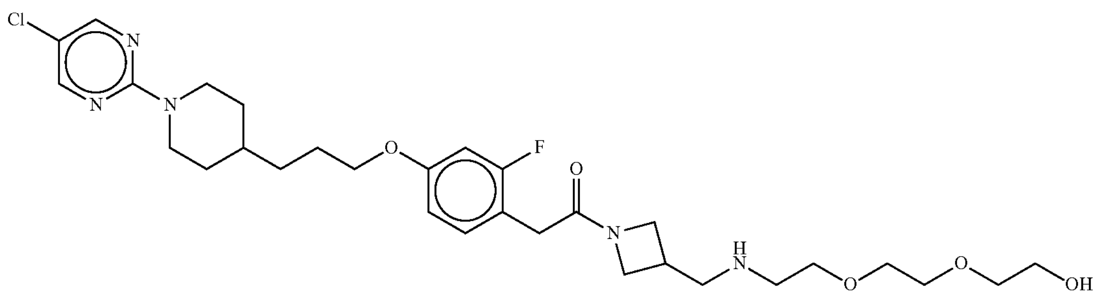 | 2-[4-[3-[1-(5-chloropyrimidin-2-yl)-4-piperidyl]propoxy]-2-fluoro-phenyl]-1-[3-[[2-[2-(2-hydroxyethoxy)ethoxy]ethylamino]-methyl]azetidin-1-yl]ethanone |

TABLE 1-continued

| Ex. # | Structure | Name |
|---|---|---|
| 52 | 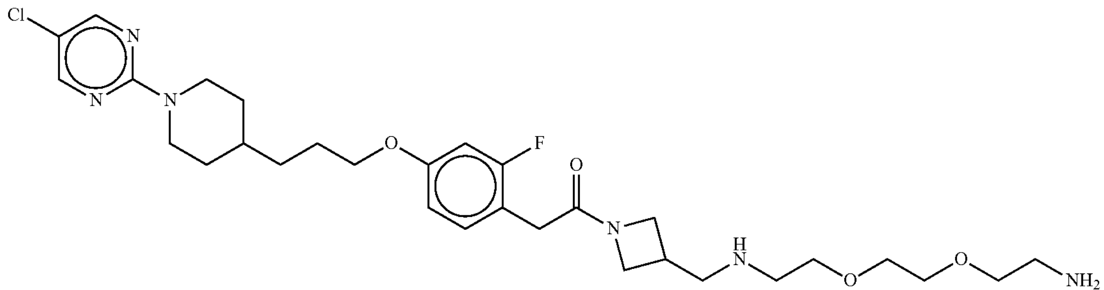 | 1-[3-[[2-[2-(2-aminoethoxy)ethoxy]ethylamino]methyl]azetidin-1-yl]-2-[4-[3-[1-(5-chloropyrimidin-2-yl)-4-piperidyl]propoxy]-2-fluoro-phenyl]ethanone |
| 53 | 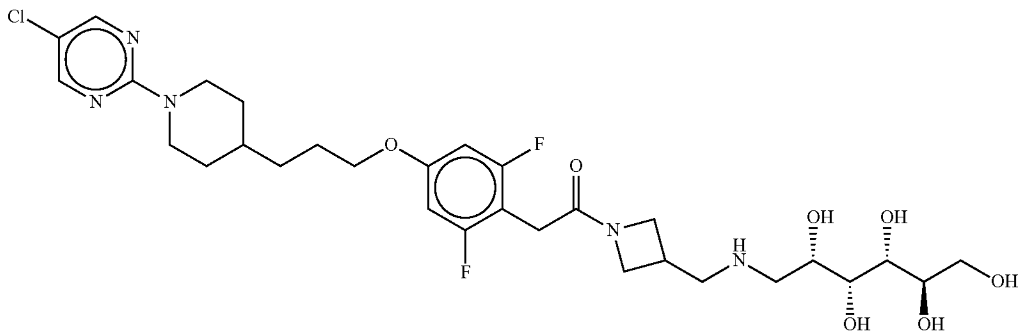 | 2-[4-[3-[1-(5-chloropyrimidin-2-yl)-4-piperidyl]propoxy]-2,6-difluoro-phenyl]-1-[3-[[[(2S,3R,4R,5R)-2,3,4,5,6-pentahydroxyhexyl]amino]methyl]-azetidin-1-yl]ethanone |
| 54 | 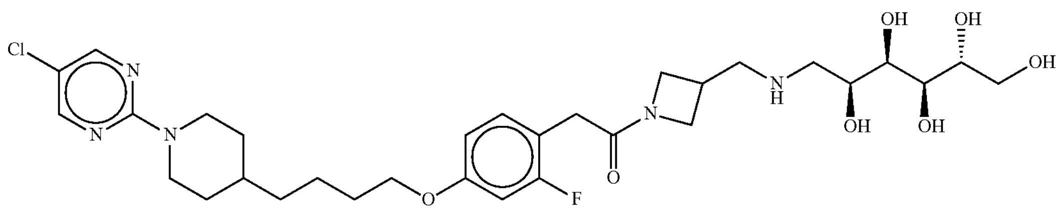 | 2-[4-[4-[1-(5-chloropyrimidin-2-yl)-4-piperidyl]butoxy]-2-fluoro-phenyl]-1-[3-[[[(2S,3R,4R,5R)-2,3,4,5,6-pentahydroxyhexyl]amino]methyl]-azetidin-1-yl]ethanone |
| 55 | 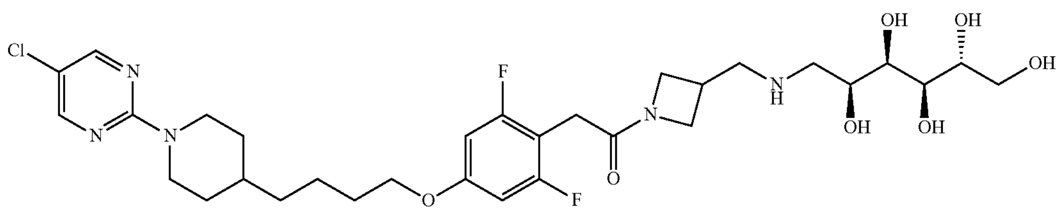 [SMILES: O=C(Cc1c(F)cc(OCCCCC2CCN(c3ncc(Cl)cn3)CC2)cc1F)N1CC(CNC[C@H](O)[C@@H](O)[C@H](O)[C@H](O)CO)C1] | 2-(4-(4-(1-(5-chloropyrimidin-2-yl)piperidin-4-yl)butoxy)-2,6-difluorophenyl)-1-(3-((((2S,3R,4R,5R)-2,3,4,5,6-pentahydroxyhexyl)amino)methyl)-azetidin-1-yl)ethan-1-one |

TABLE 1-continued

| Ex. # | Structure | Name |
|---|---|---|
| 56 | 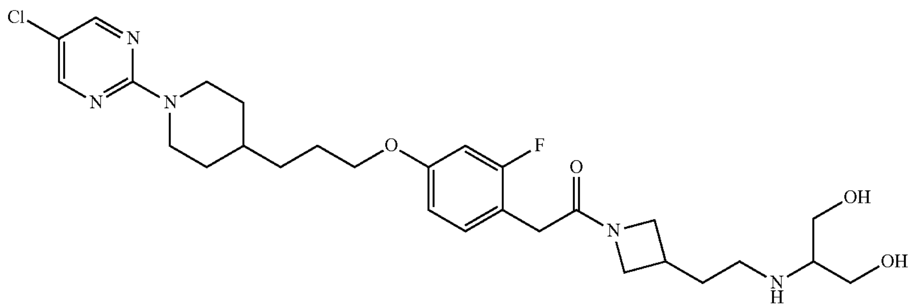 [SMILES: O=C(Cc1ccc(OCCCC2CCN(c3ncc(Cl)cn3)CC2)cc1F)N1CC(CCNC(CO)CO)C1] | 2-(4-(3-(1-(5-chloropyrimidin-2-yl)piperidin-4-yl)propoxy)-2-fluorophenyl)-1-(3-(2-((1,3-dihydroxypropan-2-yl)amino)ethyl)azetidin-1-yl)ethan-1-one |
| 57 | 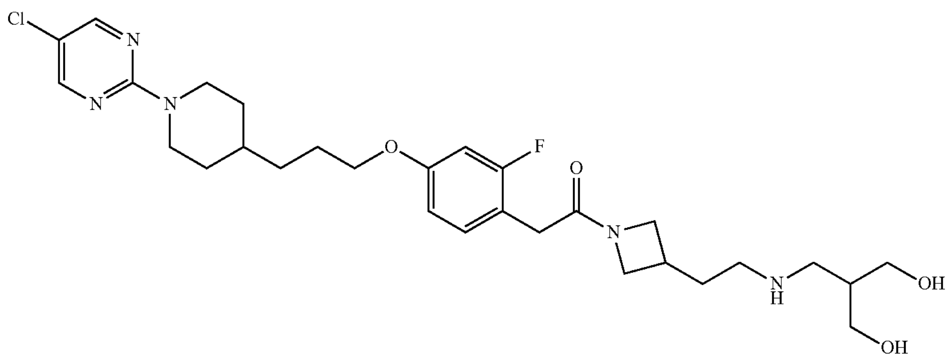 [SMILES: O=C(Cc1ccc(OCCCC2CCN(c3ncc(Cl)cn3)CC2)cc1F)N1CC(CCNCC(CO)CO)C1] | 2-(4-(3-(1-(5-chloropyrimidin-2-yl)piperidin-4-yl)propoxy)-2-fluorophenyl)-1-(3-(2-((3-hydroxy-2-(hydroxymethyl)propyl)amino)ethyl)-azetidin-1-yl)ethan-1-one |
| 58 | 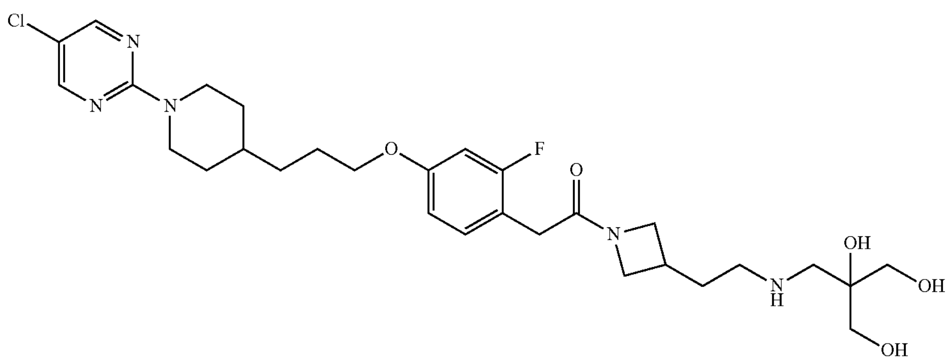 [SMILES: O=C(Cc1ccc(OCCCC2CCN(c3ncc(Cl)cn3)CC2)cc1F)N1CC(CCNCC(O)(CO)CO)C1] | 2-(4-(3-(1-(5-chloropyrimidin-2-yl)piperidin-4-yl)propoxy)-2-fluorophenyl)-1-(3-(2-((2,3-dihydroxy-2-(hydroxymethyl)propyl)amino)ethyl)-azetidin-1-yl)ethan-1-one |

TABLE 1-continued

| Ex. # | Structure | Name |
|---|---|---|
| 59 | 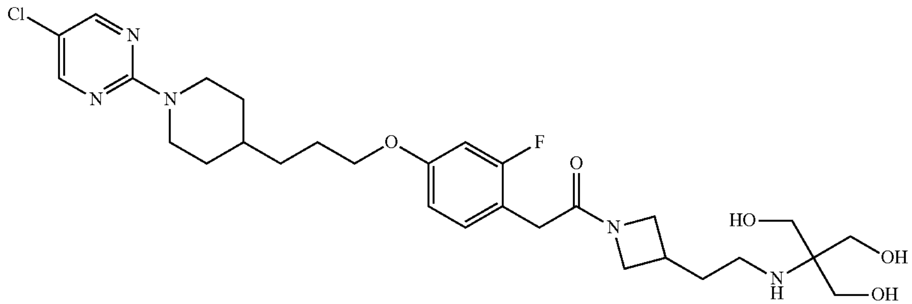 [SMILES: O=C(Cc1ccc(OCCCC2CCN(c3ncc(Cl)cn3)CC2)cc1F)N1CC(CCNC(CO)(CO)CO)C1] | 2-(4-(3-(1-(5-chloropyrimidin-2-yl)piperidin-4-yl)propoxy)-2-fluorophenyl)-1-(3-(2-((1,3-dihydroxy-2-(hydroxymethyl)propan-2-yl)amino)ethyl)azetidin-1-yl)ethan-1-one |
| 60 | 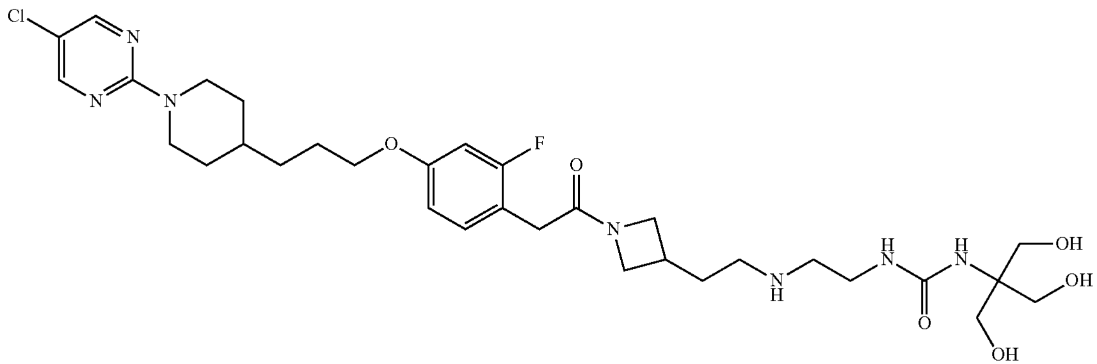 [SMILES: O=C(NCCNCCC1CN(C(=O)Cc2ccc(OCCCC3CCN(c4ncc(Cl)cn4)CC3)cc2F)C1)NC(CO)(CO)CO] | 1-(2-((2-(1-(2-(4-(3-(1-(5-chloropyrimidin-2-yl)piperidin-4-yl)propoxy)-2-fluorophenyl)acetyl)azetidin-3-yl)ethyl)amino)ethyl)-3-(1,3-dihydroxy-2-(hydroxymethyl)propan-2-yl)urea |
| 61 | 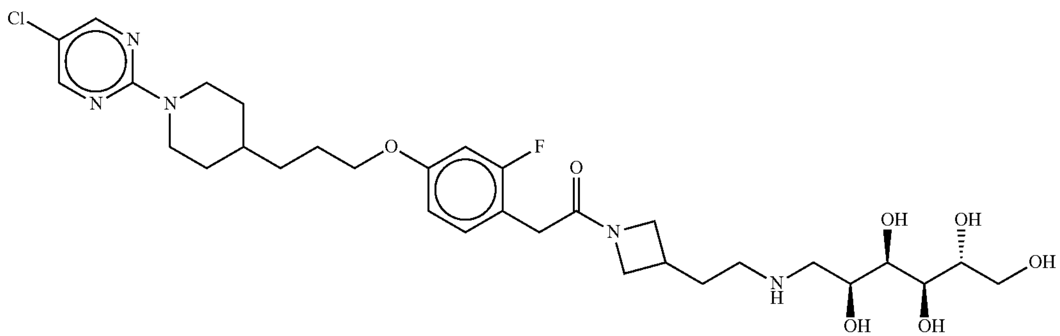 | 2-[4-[3-[1-(5-chloropyrimidin-2-yl)-4-piperidyl]propoxy]-2-fluoro-phenyl]-1-[3-[2-[[(2S,3R,4R,5R)-2,3,4,5,6-pentahydroxyhexyl]amino]ethyl]azetidin-1-yl]ethanone |

TABLE 1-continued

| Ex. # | Structure | Name |
|---|---|---|
| 62 | 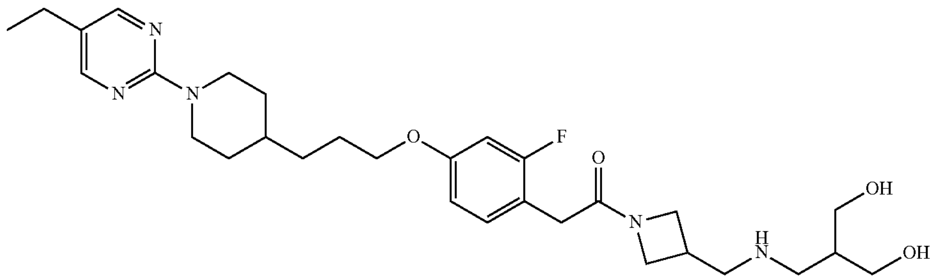 [SMILES: CCc1cnc(N2CCC(CCCOc3ccc(CC(=O)N4CC(CNCC(CO)CO)C4)c(F)c3)CC2)nc1] | 2-(4-(3-(1-(5-ethylpyrimidin-2-yl)piperidin-4-yl)propoxy)-2-fluorophenyl)-1-(3-(((3-hydroxy-2-(hydroxymethyl)propyl)amino)methyl)-azetidin-1-yl)ethan-1-one |
| 63 | 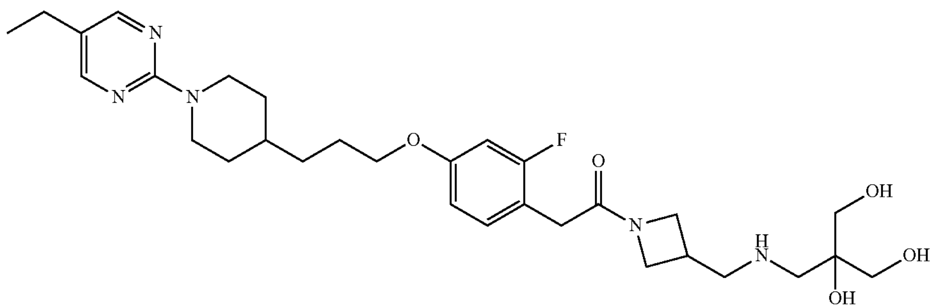 [SMILES: CCc1cnc(N2CCC(CCCOc3ccc(CC(=O)N4CC(CNCC(O)(CO)CO)C4)c(F)c3)CC2)nc1] | 1-(3-(((2,3-dihydroxypropyl)amino)methyl)-azetidin-1-yl)-2-(4-(3-(1-(5-ethylpyrimidin-2-yl)piperidin-4-yl)propoxy)-2-fluorophenyl)ethan-1-one |
| 64 | 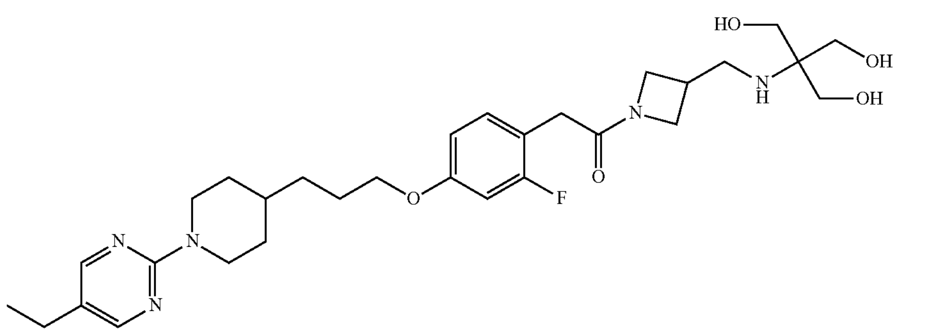 [SMILES: CCc1cnc(N2CCC(CCCOc3ccc(CC(=O)N4CC(CNC(CO)(CO)CO)C4)c(F)c3)CC2)nc1] | 1-(3-((((1,3-dihydroxy-2-(hydroxymethyl)propan-2-yl)amino)methyl)azetidin-1-yl)-2-(4-(3-(1-(5-ethylpyrimidin-2-yl)piperidin-4-yl)propoxy)-2-fluorophenyl)ethan-1-one |

TABLE 1-continued

| Ex. # | Structure | Name |
|---|---|---|
| 65 | 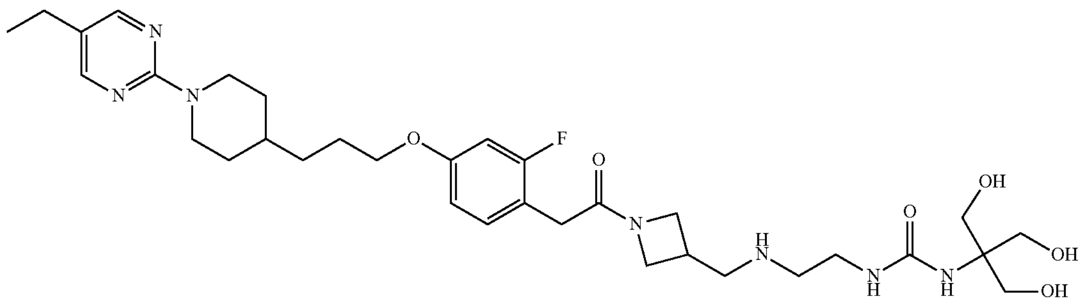 [SMILES: CCc1cnc(N2CCC(CCCOc3ccc(CC(=O)N4CC(CNCCNC(=O)NC(CO)(CO)CO)C4)c(F)c3)CC2)nc1] | 1-(1,3-dihydroxy-2-(hydroxymethyl)propan-2-yl)-3-(2-(((1-(2-(4-(3-(1-(5-ethylpyrimidin-2-yl)piperidin-4-yl)propoxy)-2-fluorophenyl)acetyl)azetidin-3-yl)methyl)amino)ethyl)urea |
| 66 | 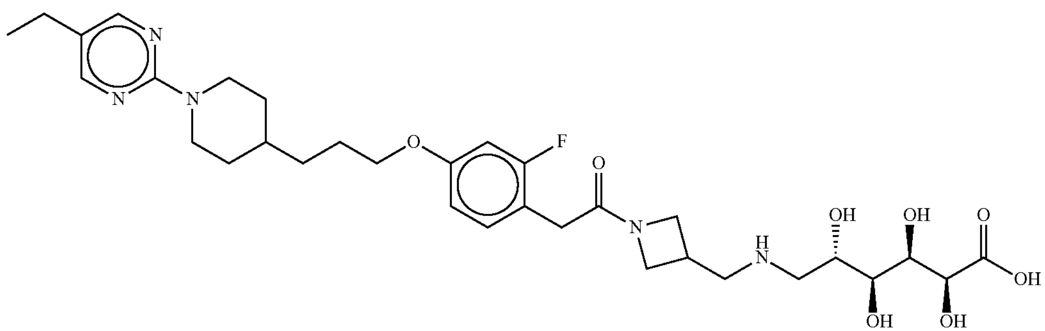 | (2S,3R,4S,5S)-6-[[1-[2-[4-(3-[1-(5-ethylpyrimidin-2-yl)-4-piperidyl]propoxy]-2-fluoro-phenyl]acetyl]azetidin-3-yl]methylamino]-2,3,4,5-tetrahydroxy-hexanoic acid |
| 67 | 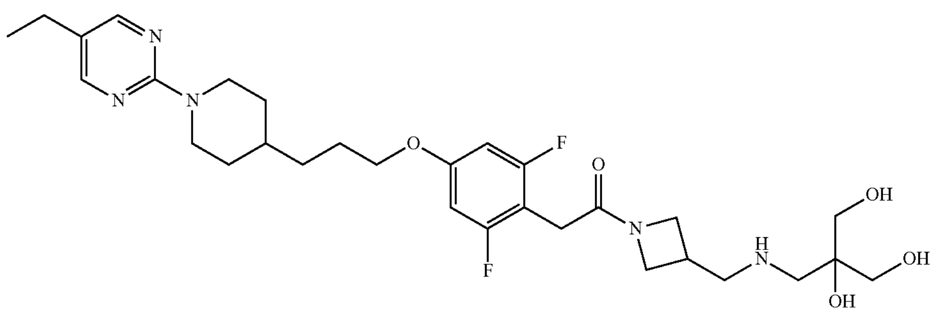 [SMILES: CCc1cnc(N2CCC(CCCOc3cc(F)c(CC(=O)N4CC(CNCC(O)(CO)CO)C4)c(F)c3)CC2)nc1] | 1-(3-(((2,3-dihydroxy-2-(hydroxymethyl)propyl)amino)methyl)-azetidin-1-yl)-2-(4-(3-(1-(5-ethylpyrimidin-2-yl)piperidin-4-yl)propoxy)-2,6-difluorophenyl)ethan-1-one |

TABLE 1-continued

| Ex. # | Structure | Name |
|---|---|---|
| 68 | 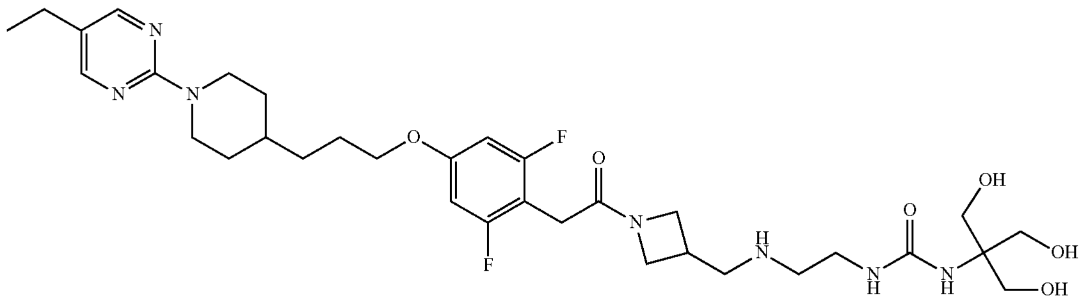 [SMILES: CCc1cnc(N2CCC(CCCOc3cc(F)c(CC(=O)N4CC(CNCCNC(=O)NC(CO)(CO)CO)C4)c(F)c3)CC2)nc1] | 1-(1,3-dihydroxy-2-(hydroxymethyl)propan-2-yl)-3-(2-(((1-(2-(4-(3-(1-(5-ethylpyrimidin-2-yl)piperidin-4-yl)propoxy)-2,6-difluorophenyl)acetyl)azetidin-3-yl)methyl)amino)ethyl)urea |
| 69 | 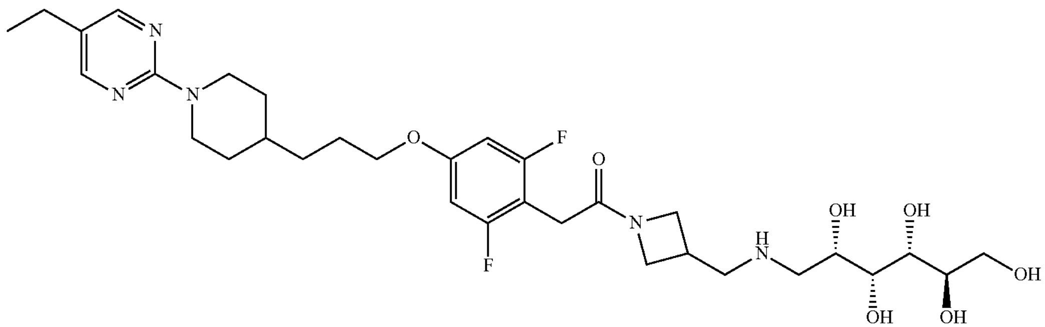 [SMILES: CCc1cnc(N2CCC(CCCOc3cc(F)c(CC(=O)N4CC(CNC[C@H](O)[C@@H](O)[C@H](O)[C@H](O)CO)C4)c(F)c3)CC2)nc1] | 2-(4-(3-(1-(5-ethylpyrimidin-2-yl)piperidin-4-yl)propoxy)-2,6-difluorophenyl)-1-(3-((((2S,3R,4R,5R)-2,3,4,5,6-pentahydroxyhexyl)amino)methyl)azetidin-1-yl)ethan-1-one |
| 70 | 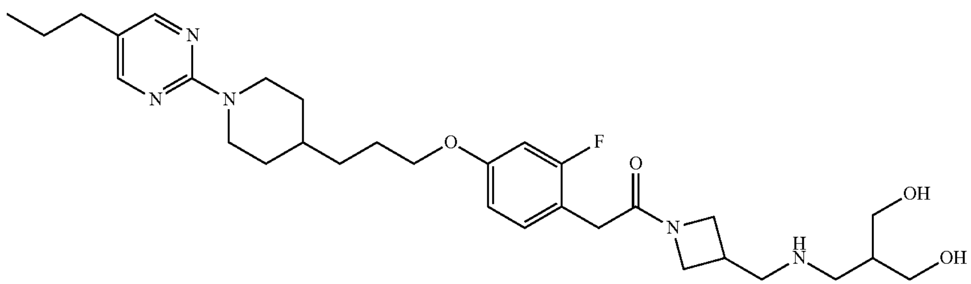 [SMILES: CCCc1cnc(N2CCC(CCCOc3ccc(CC(=O)N4CC(CNCC(CO)CO)C4)c(F)c3)CC2)nc1] | 2-(2-fluoro-4-(3-(1-(5-propylpyrimidin-2-yl)piperidin-4-yl)propoxy)phenyl)-1-(3-(((3-hydroxy-2-(hydroxymethyl)propyl)amino)methyl)azetidin-1-yl)ethan-1-one |

TABLE 1-continued

| Ex. # | Structure | Name |
|---|---|---|
| 71 | 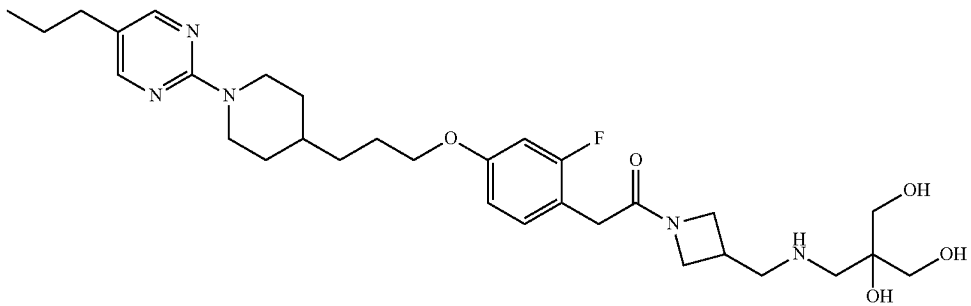 [SMILES: CCCc1cnc(N2CCC(CCCOc3ccc(CC(=O)N4CC(CNCC(O)(CO)CO)C4)c(F)c3)CC2)nc1] | 1-(3-(((2,3-dihydroxy-2-(hydroxymethyl)propyl)amino)methyl)-azetidin-1-yl)-2-(2-fluoro-4-(3-(1-(5-propylpyrimidin-2-yl)piperidin-4-yl)propoxy)phenyl)ethan-1-one |
| 72 | 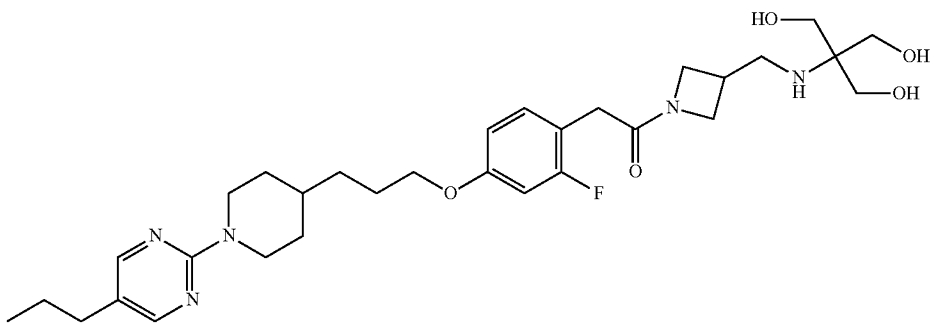 [SMILES: CCCc1cnc(N2CCC(CCCOc3ccc(CC(=O)N4CC(CNC(CO)(CO)CO)C4)c(F)c3)CC2)nc1] | 1-(3-(((1,3-dihydroxy-2-(hydroxymethyl)propan-2-yl)amino)methyl)azetidin-1-yl)-2-(2-fluoro-4-(3-(1-(5-propylpyrimidin-2-yl)piperidin-4-yl)propoxy)phenyl)ethan-1-one |
| 73 | 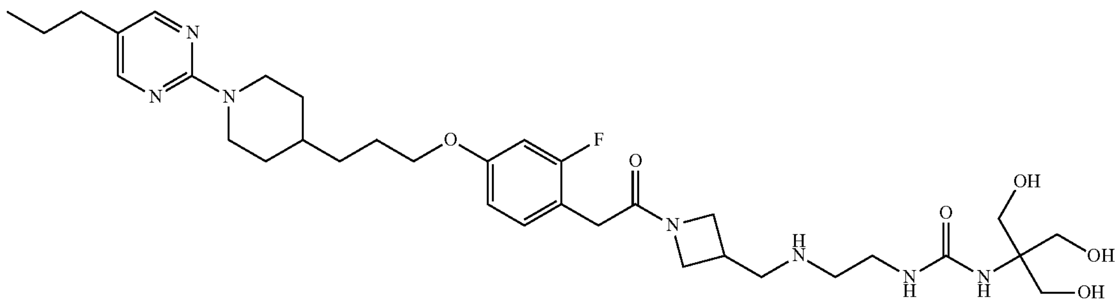 [SMILES: CCCc1cnc(N2CCC(CCCOc3ccc(CC(=O)N4CC(CNCCNC(=O)NC(CO)(CO)CO)C4)c(F)c3)CC2)nc1] | 1-(1,3-dihydroxy-2-(hydroxymethyl)propan-2-yl)-3-(2-(((1-(2-(2-fluoro-4-(3-(1-(5-propylpyrimidin-2-yl)piperidin-4-yl)propoxy)phenyl)acetyl)azetidin-3-yl)methyl)amino)ethyl)urea |

TABLE 1-continued

| Ex. # | Structure | Name |
|---|---|---|
| 74 | 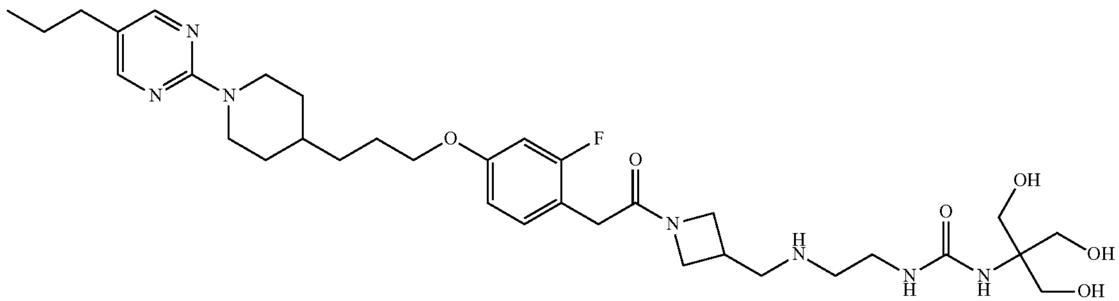 [SMILES: CCCc1cnc(N2CCC(CCCOc3ccc(CC(=O)N4CC(CNCCNC(=O)NC(CO)(CO)CO)C4)c(F)c3)CC2)nc1] | 2-(2-fluoro-4-(3-(1-(5-propyl)pyrimidin-2-yl)piperidin-4-yl)propoxy)phenyl)-1-(3-(((2S,3R,4R,5R)-2,3,4,5,6-pentahydroxyhexyl)amino)methyl)azetidin-1-yl)ethan-1-one |
| 75 | 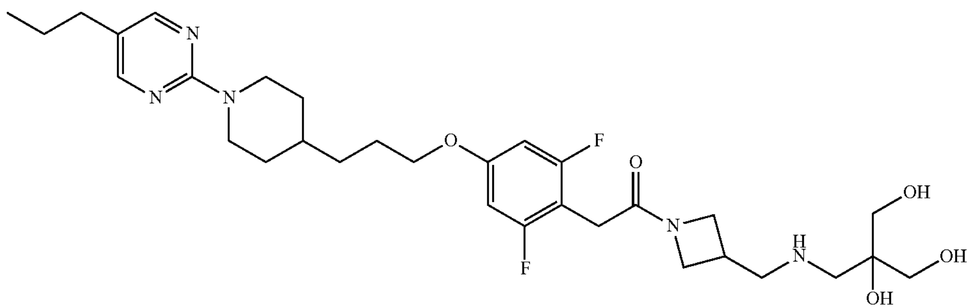 [SMILES: CCCc1cnc(N2CCC(CCCOc3cc(F)c(CC(=O)N4CC(CNCC(O)(CO)CO)C4)c(F)c3)CC2)nc1] | 2-(2,6-difluoro-4-(3-(1-(5-propyl)pyrimidin-2-yl)piperidin-4-yl)propoxy)phenyl)-1-(3-(((2,3-dihydroxy-2-(hydroxymethyl)propyl)amino)methyl)azetidin-1-yl)ethan-1-one |
| 76 | 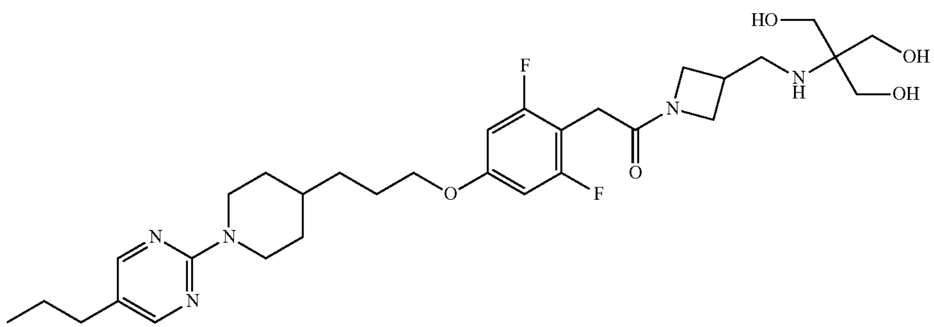 [SMILES: CCCc1cnc(N2CCC(CCCOc3cc(F)c(CC(=O)N4CC(CNC(CO)(CO)CO)C4)c(F)c3)CC2)nc1] | 2-(2,6-difluoro-4-(3-(1-(5-propyl)pyrimidin-2-yl)piperidin-4-yl)propoxy)phenyl)-1-(3-(((1,3-dihydroxy-2-(hydroxymethyl)propan-2-yl)amino)methyl)azetidin-1-yl)ethan-1-one |

TABLE 1-continued

| Ex. # | Structure | Name |
|---|---|---|
| 77 | 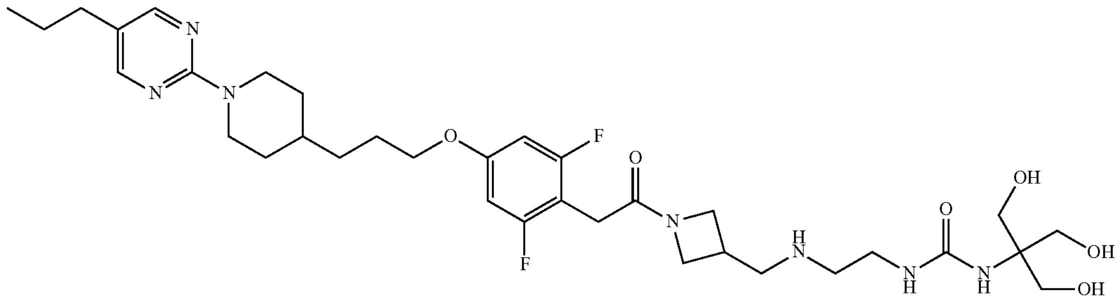 [SMILES: CCCc1cnc(N2CCC(CCCOc3cc(F)c(CC(=O)N4CC(CNCCNC(=O)NC(CO)(CO)CO)C4)c(F)c3)CC2)nc1] | 1-(2-(((1-(2-(2,6-difluoro-4-(3-(1-(5-propylpyrimidin-2-yl)piperidin-4-yl)propoxy)phenyl)acetyl)azetidin-3-yl)methyl)amino)ethyl)-3-(1,3-dihydroxy-2-(hydroxymethyl)propan-2-yl)urea |
| 78 | 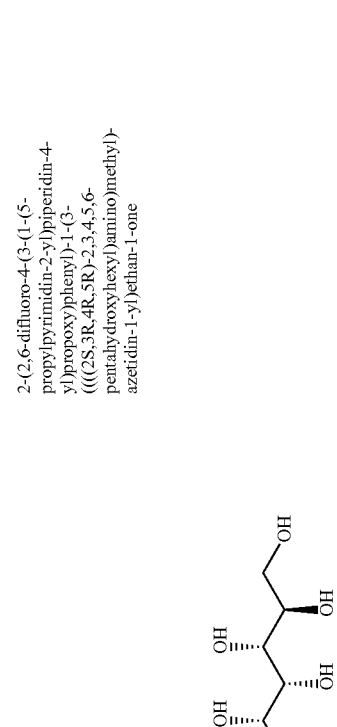 | 2-(2,6-difluoro-4-(3-(1-(5-propylpyrimidin-2-yl)piperidin-4-yl)propoxy)phenyl)-1-(3-((((2S,3R,4R,5R)-2,3,4,5,6-pentahydroxyhexyl)amino)methyl)-azetidin-1-yl)ethan-1-one |
| 79 | 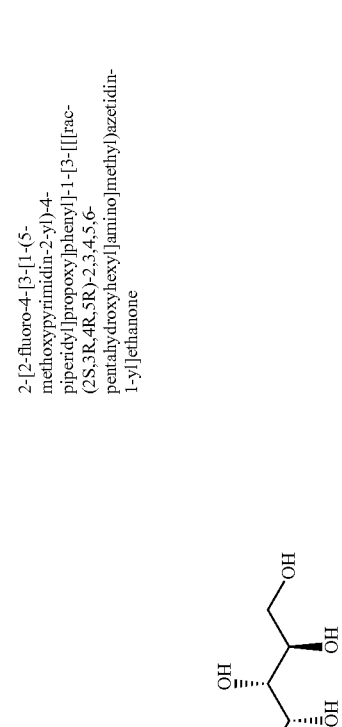 | 2-[2-fluoro-4-[3-[1-(5-methoxypyrimidin-2-yl)-4-piperidyl]propoxy]phenyl]-1-[3-[[[rac-(2S,3R,4R,5R)-2,3,4,5,6-pentahydroxyhexyl]amino]methyl]azetidin-1-yl]ethanone |

TABLE 1-continued

| Ex. # | Structure | Name |
|---|---|---|
| 80 | 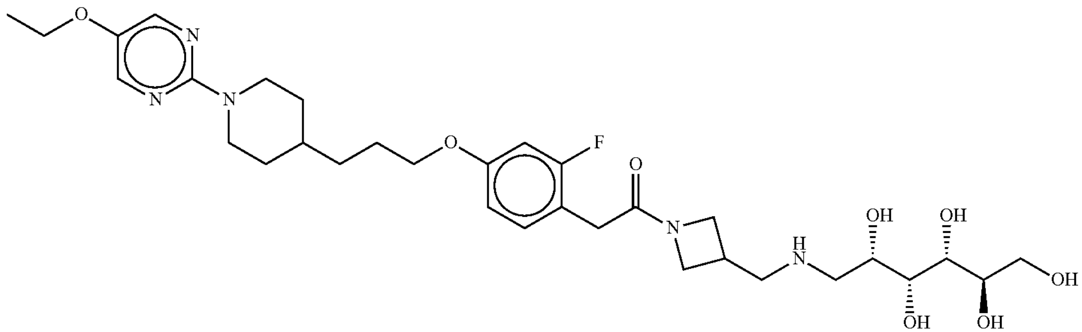 | 2-[4-[3-[1-(5-ethoxypyrimidin-2-yl)-4-piperidyl]propoxy]-2-fluoro-phenyl]-1-[3-[[[rac-(2S,3R,4R,5R)-2,3,4,5,6-pentahydroxyhexyl]amino]methyl]azetidin-1-yl]ethanone |
| 81 | 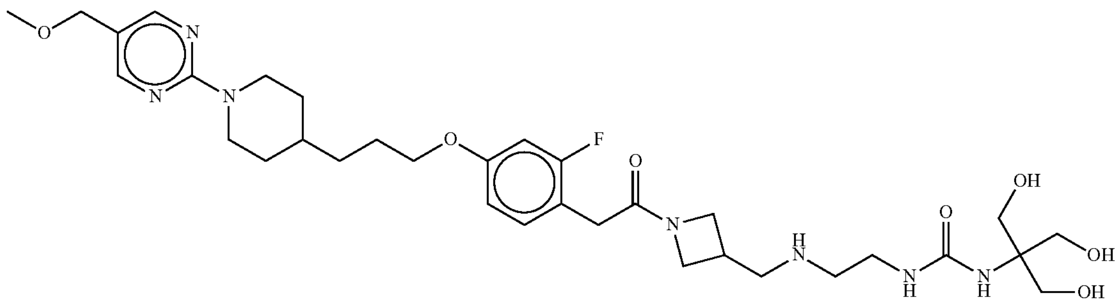 | 1-[2-[[1-[2-[2-fluoro-4-[3-[1-[5-(methoxymethyl)pyrimidin-2-yl]-4-piperidyl]propoxy]phenyl]acetyl]azetidin-3-yl]methylamino]ethyl]-3-(2-hydroxy-1,1-bis(hydroxymethyl)ethyl]urea |
| 82 | 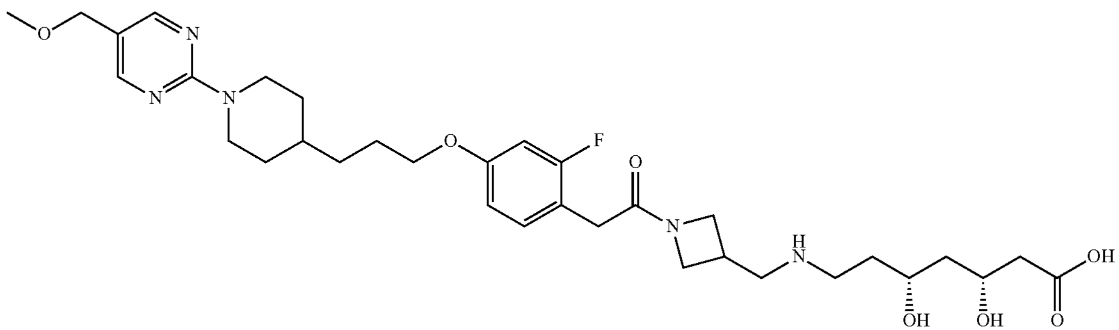 [SMILES: COCc1cnc(N2CCC(CCCOc3ccc(CC(=O)N4CC(CNCC[C@@H](O)C[C@@H](O)CC(=O)O)C4)c(F)c3)CC2)nc1] | (3R,5R)-7-[[1-[2-[2-fluoro-4-[3-[1-[5-(methoxymethyl)pyrimidin-2-yl]-4-piperidyl]propoxy]phenyl]acetyl]azetidin-3-yl]methylamino]-3,5-dihydroxy-heptanoic acid |

TABLE 1-continued

| Ex. # | Structure | Name |
|---|---|---|
| 83 | 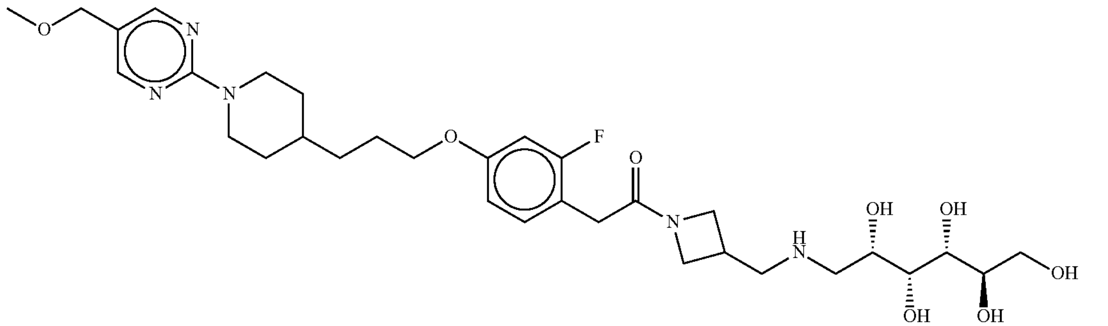 | 2-[2-fluoro-4-[3-[1-[5-(methoxymethyl)pyrimidin-2-yl]-4-piperidyl]propoxy]phenyl]-1-[3-[[[(2S,3R,4R,5R)-2,3,4,5,6-pentahydroxyhexyl]amino]methyl]azetidin-1-yl]ethanone |
| 84 | 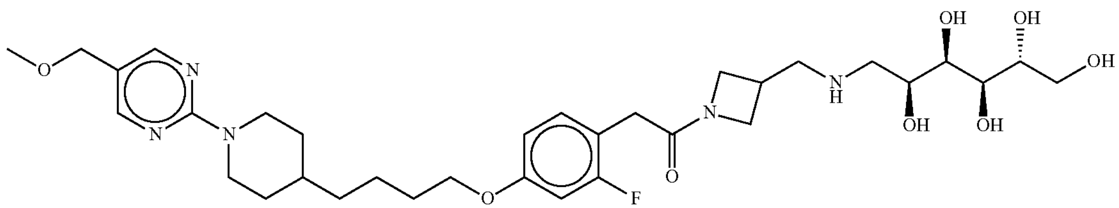 | 2-[2-fluoro-4-[4-[1-[5-(methoxymethyl)pyrimidin-2-yl]-4-piperidyl]butoxy]phenyl]-1-[3-[[[(2S,3R,4R,5R)-2,3,4,5,6-pentahydroxyhexyl]amino]methyl]azetidin-1-yl]ethanone |
| 85 | 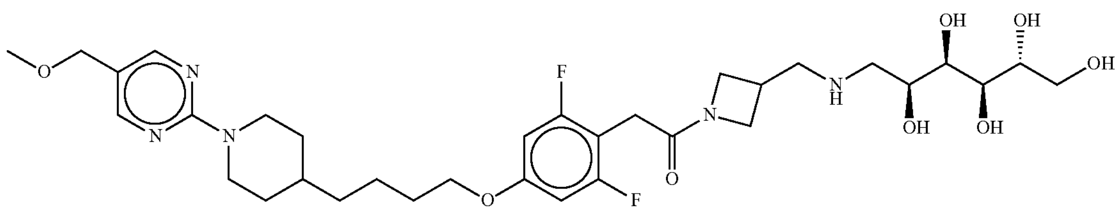 | 2-[2,6-difluoro-4-[1-[5-(methoxymethyl)pyrimidin-2-yl]-4-piperidyl]butoxy]phenyl]-1-[3-[[[rac-(2S,3R,4R,5R)-2,3,4,5,6-pentahydroxyhexyl]amino]methyl]azetidin-1-yl]ethanone |

TABLE 1-continued

| Ex. # | Structure | Name |
|---|---|---|
| 86 | 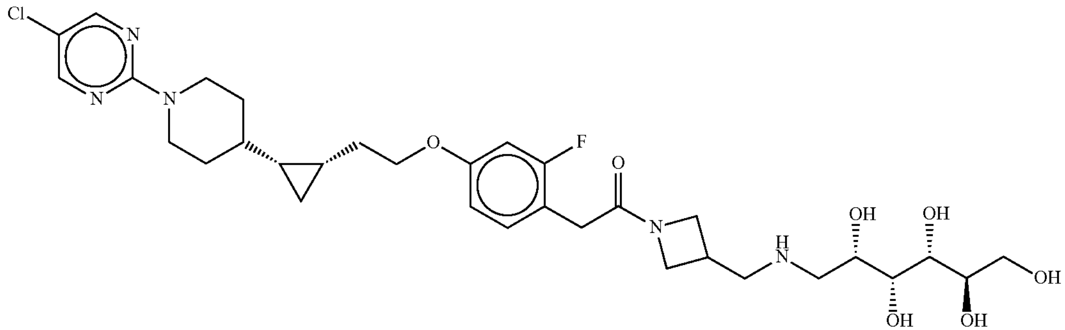 | 2-[4-[2-[(1S,2R)-2-[1-(5-chloropyrimidin-2-yl)-4-piperidyl]cyclopropyl]ethoxy]-2-fluorophenyl]-1-[3-[[[(2S,3R,4R,5R)-2,3,4,5,6-pentahydroxyhexyl]amino]methyl]azetidin-1-yl]ethanone |
| 87 | 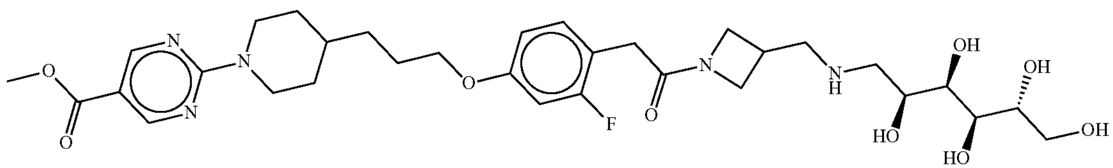 | methyl 2-[4-[3-[3-fluoro-4-[2-oxo-2-[3-[[[(2S,3R,4R,5R)-2,3,4,5,6-pentahydroxyhexyl]amino]methyl]azetidin-1-yl]ethyl]phenoxy]propyl]-1-piperidyl]pyrimidine-5-carboxylate |
| 88 | 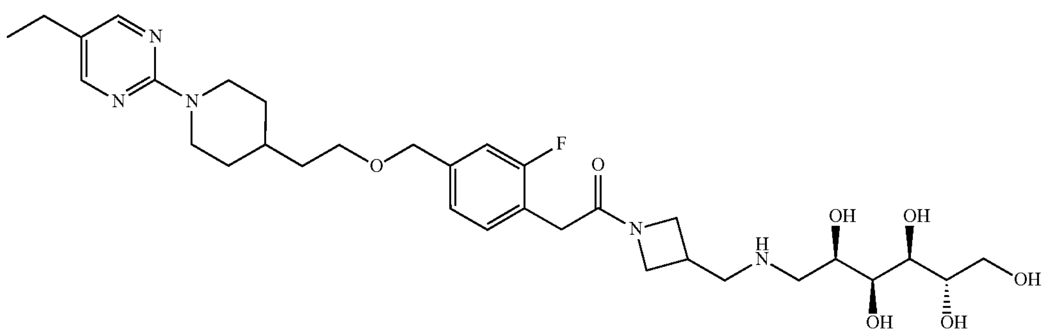 [SMILES: CCc1cnc(N2CCC(CCOCc3ccc(CC(=O)N4CC(CNC[C@@H](O)[C@H](O)[C@@H](O)[C@@H](O)CO)C4)c(F)c3)CC2)nc1] | 2-[4-[2-[1-(5-ethylpyrimidin-2-yl)-4-piperidyl]ethoxymethyl]-2-fluorophenyl]-1-[3-[[[(2S,3R,4R,5R)-2,3,4,5,6-pentahydroxyhexyl]amino]methyl]-cyclobutyl]ethanone |
| 89 | 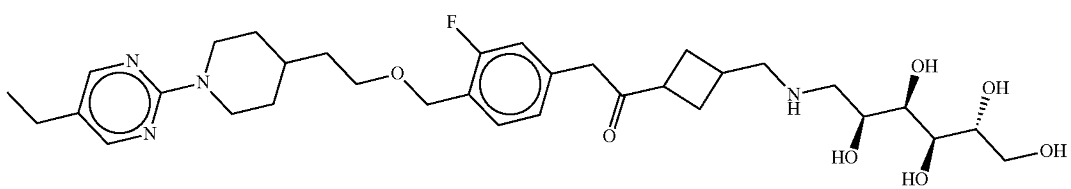 | 2-[4-[2-[1-(5-ethylpyrimidin-2-yl)-4-piperidyl]ethoxymethyl]-3-fluorophenyl]-1-[3-[[[(2S,3R,4R,5R)-2,3,4,5,6-pentahydroxyhexyl]amino]methyl]-cyclobutyl]ethanone |

TABLE 1-continued

| Ex. # | Structure | Name |
|---|---|---|
| 90 | 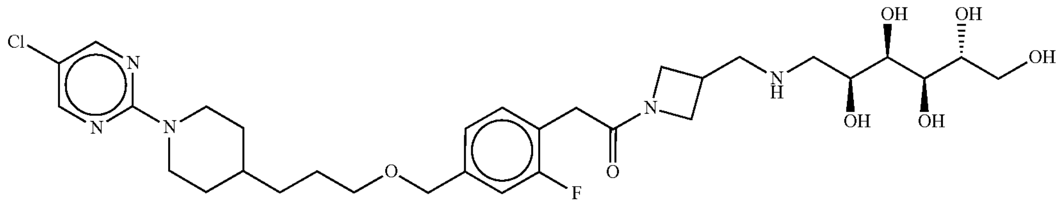 | 2-[4-[3-[1-(5-chloropyrimidin-2-yl)-4-piperidyl]propoxymethyl]-2-fluoro-phenyl]-1-[3-[[[(2S,3R,4R,5R)-2,3,4,5,6-pentahydroxyhexyl]amino]methyl]azetidin-1-yl]ethanone |
| 91 | 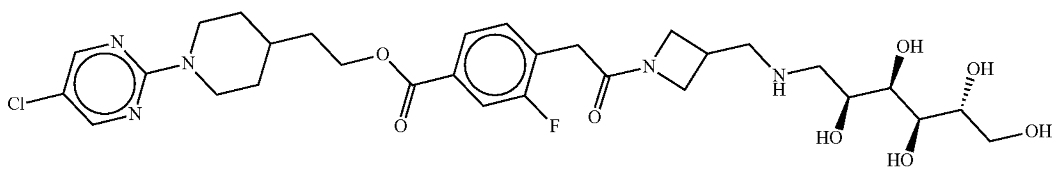 | 2-[1-(5-chloropyrimidin-2-yl)-4-piperidyl][ethyl 3-fluoro-4-[2-oxo-2-[3-[[[rac-(2S,3R,4R,5R)-2,3,4,5,6-pentahydroxyhexyl]amino]methyl]azetidin-1-yl]ethyl]benzoate |
| 92 | 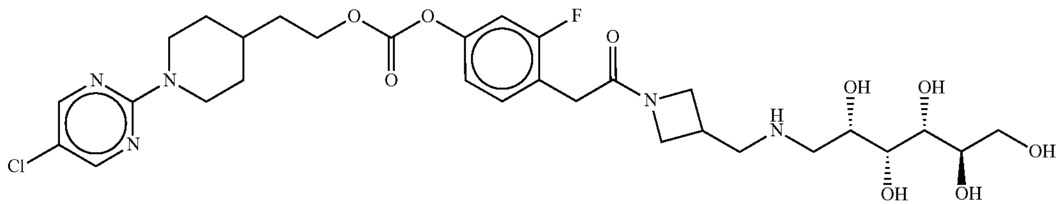 | 2-[1-(5-chloropyrimidin-2-yl)-4-piperidyl]ethyl 2-[3-fluoro-4-[2-oxo-2-[3-[[[rac-(2S,3R,4R,5R)-2,3,4,5,6-pentahydroxyhexyl]amino]methyl]azetidin-1-yl]ethyl]phenyl]acetate |
| 93 | 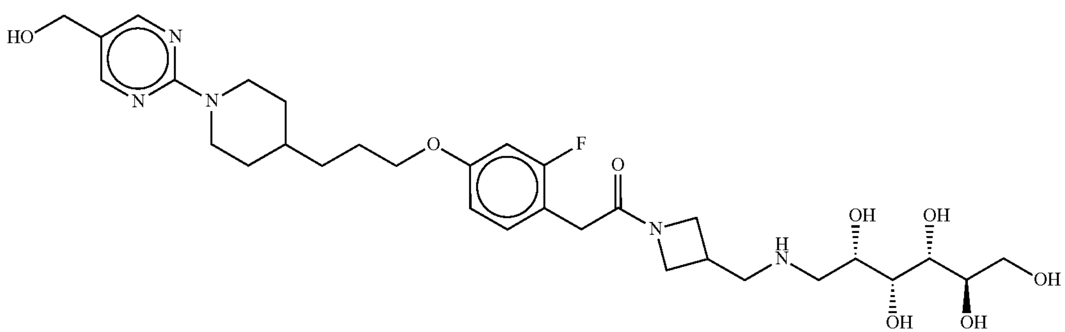 | 2-[2-fluoro-4-[3-[1-[5-(hydroxymethyl)pyrimidin-2-yl]-4-piperidyl]propoxy]phenyl]-1-[3-[[[(2S,3R,4R,5R)-2,3,4,5,6-pentahydroxyhexyl]amino]methyl]azetidin-1-yl]ethanone |

TABLE 1-continued

| Ex. # | Structure | Name |
|---|---|---|
| 94 | 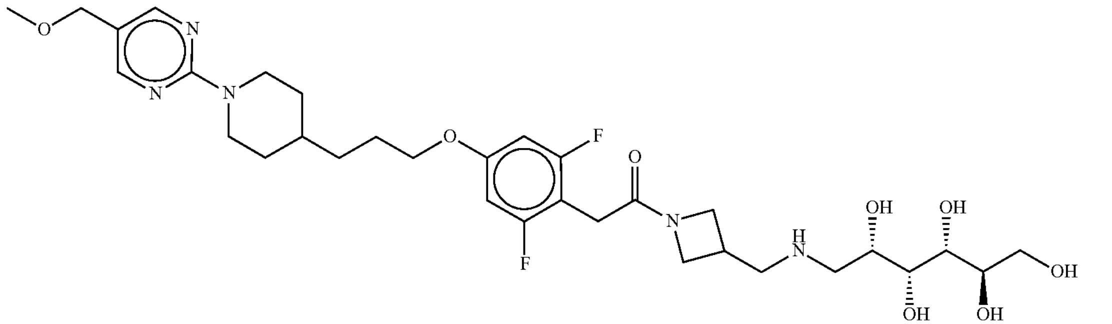 | 2-[2,6-difluoro-4-[3-[1-[5-(methoxymethyl)pyrimidin-2-yl]-4-piperidyl]propoxy]phenyl]-1-[3-[[[(2S,3R,4R,5R)-2,3,4,5,6-pentahydroxyhexyl]amino]methyl]azetidin-1-yl]ethanone |
| 95 | 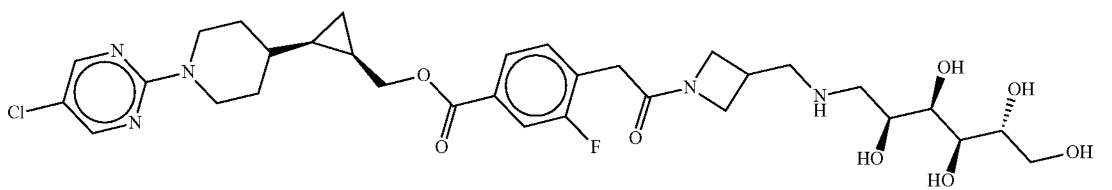 | [rac-(1R,2R)-2-[1-(5-chloropyrimidin-2-yl)-4-piperidyl]cyclopropyl]methyl 3-fluoro-4-[2-oxo-2-[3-[[[rac-(2S,3R,4R,5R)-2,3,4,5,6-pentahydroxyhexyl]amino]methyl]azetidin-1-yl]ethyl]benzoate |
| 96 | 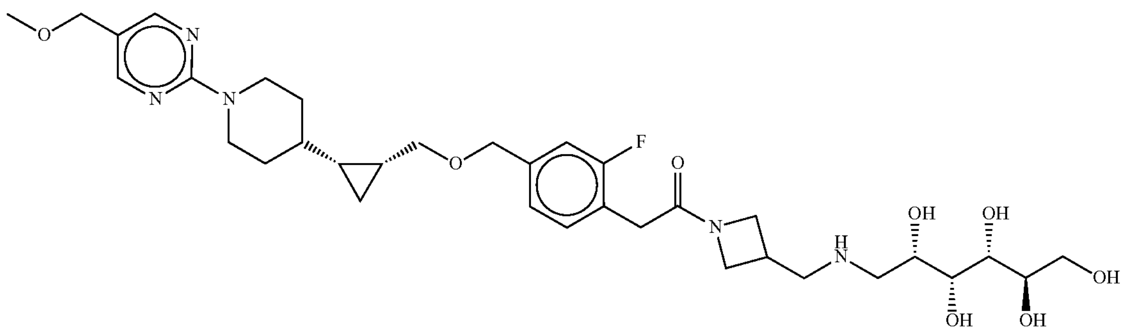 | 2-[2-fluoro-4-[[(1R,2R)-2-[1-[5-(methoxymethyl)pyrimidin-2-yl]-4-piperidyl]cyclopropyl]methoxymethyl]phenyl]-1-[3-[[[(2S,3R,4R,5R)-2,3,4,5,6-pentahydroxyhexyl]amino]methyl]azetidin-1-yl]ethanone |

TABLE 1-continued

| Ex. # | Structure | Name |
|---|---|---|
| 97 | 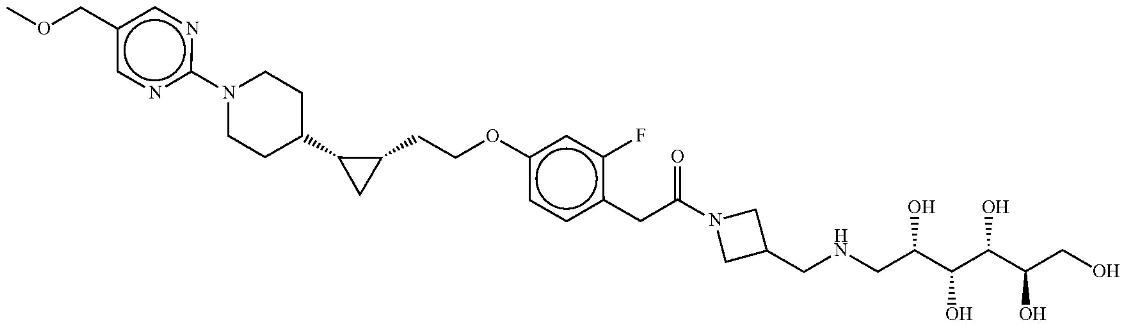 | 2-[2-fluoro-4-[2-[rac-(1S,2R)-2-[1-[5-(methoxymethyl)pyrimidin-2-yl]-4-piperidyl]cyclopropyl]ethoxy]phenyl]-1-[3-[[[rac-(2S,3R,4R,5R)-2,3,4,5,6-pentahydroxyhexyl]amino]methyl]azetidin-1-yl]ethanone |
| 98 | 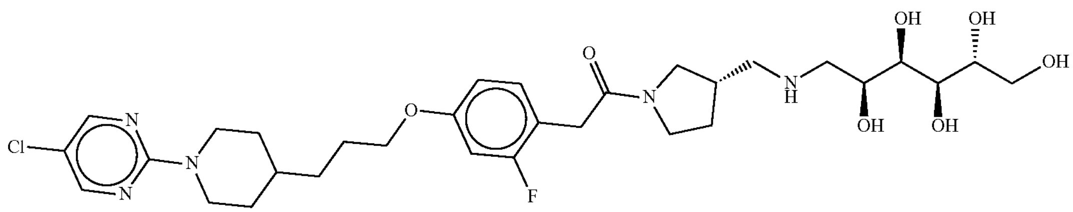 | 2-[4-[3-[1-(5-chloropyrimidin-2-yl)-4-piperidyl]propoxy]-2-fluoro-phenyl]-1-[(3S)-3-[[[(2S,3R,4R,5R)-2,3,4,5,6-pentahydroxyhexyl]amino]methyl]-pyrrolidin-1-yl]ethanone |
| 99 | 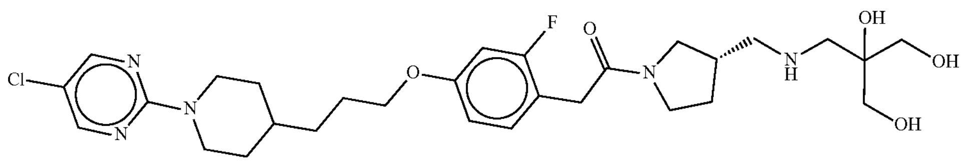 | 2-[4-[3-[1-(5-chloropyrimidin-2-yl)-4-piperidyl]propoxy]-2-fluoro-phenyl]-1-[(3S)-3-[[[2,3-dihydroxy-2-(hydroxymethyl)propyl]amino]methyl]-pyrrolidin-1-yl]ethanone |
| 100 | 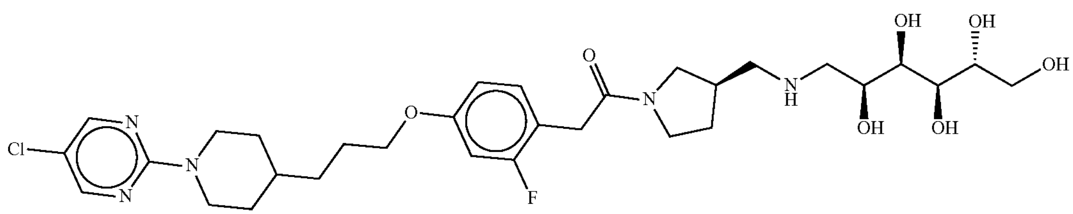 | 2-[4-[3-[1-(5-chloropyrimidin-2-yl)-4-piperidyl]propoxy]-2-fluoro-phenyl]-1-[(3R)-3-[[[(2S,3R,4R,5R)-2,3,4,5,6-pentahydroxyhexyl]amino]methyl]-pyrrolidin-1-yl]ethanone |

TABLE 1-continued

| Ex. # | Structure | Name |
|---|---|---|
| 101 | 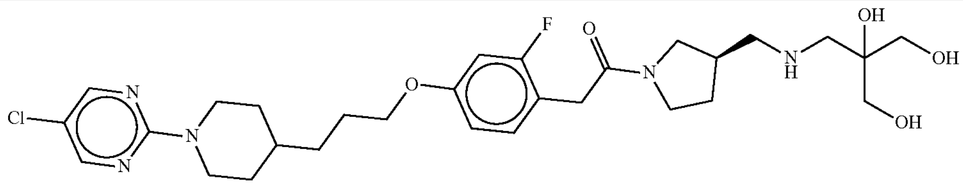 | 2-[4-[3-[1-(5-chloropyrimidin-2-yl)-4-piperidyl]propoxy]-2-fluoro-phenyl]-1-[(3R)-3-[[[2,3-dihydroxy-2-(hydroxymethyl)propyl]amino]methyl]-pyrrolidin-1-yl]ethanone |
| 102 | 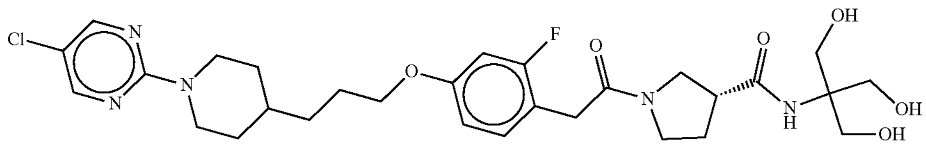 | (3R)-1-[2-[4-[3-[1-(5-chloropyrimidin-2-yl)-4-piperidyl]propoxy]-2-fluoro-phenyl]acetyl]-N-[2-hydroxy-1,1-bis(hydroxymethyl)ethyl]pyrrolidine-3-carboxamide |
| 103 | 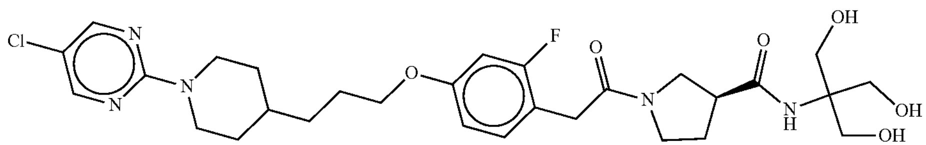 | (3S)-1-[2-[4-[3-[1-(5-chloropyrimidin-2-yl)-4-piperidyl]propoxy]-2-fluoro-phenyl]acetyl]-N-[2-hydroxy-1,1-bis(hydroxymethyl)ethyl]pyrrolidine-3-carboxamide |
| 104 | 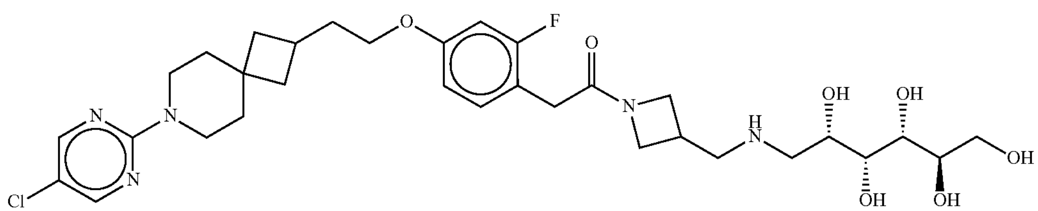 | 2-[4-[2-[7-(5-chloropyrimidin-2-yl)-7-azaspiro[3.5]nonan-2-yl]ethoxy]-2-fluoro-phenyl]-1-[3-[[[(2S,3R,4R,5R)-2,3,4,5,6-pentahydroxyhexyl]amino]methyl]-azetidin-1-yl]ethanone |
| 105 | 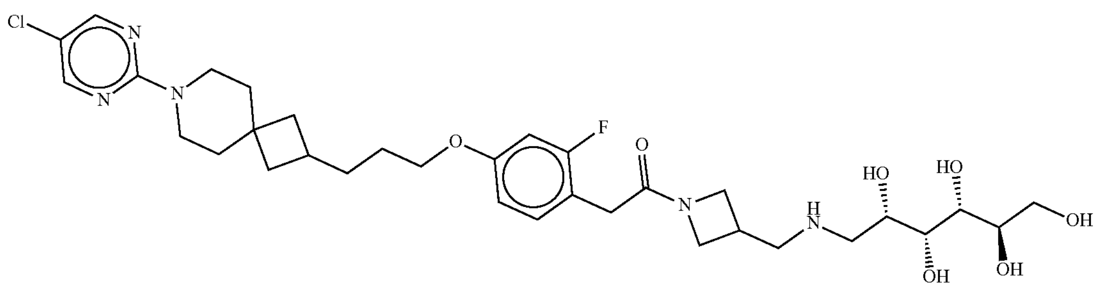 | 2-[4-[3-[7-(5-chloropyrimidin-2-yl)-7-azaspiro[3.5]nonan-2-yl]propoxy]-2-fluoro-phenyl]-1-[3-[[[(2S,3R,4R,5R)-2,3,4,5,6-pentahydroxyhexyl]amino]methyl]-azetidin-1-yl]ethanone |

TABLE 1-continued

| Ex. # | Structure | Name |
|---|---|---|
| 106 | 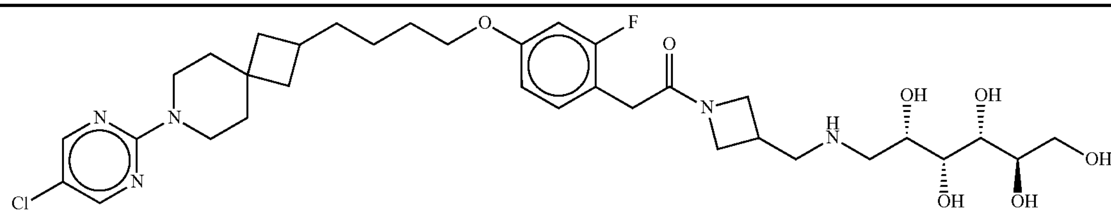 | 2-[4-[4-[7-(5-chloropyrimidin-2-yl)-7-azaspiro[3.5]nonan-2-yl]butoxy]-2-fluoro-phenyl]-1-[3-[[[(2S,3R,4R,5R)-2,3,4,5,6-pentahydroxyhexyl]amino]methyl]-azetidin-1-yl]ethanone |
| 107 | 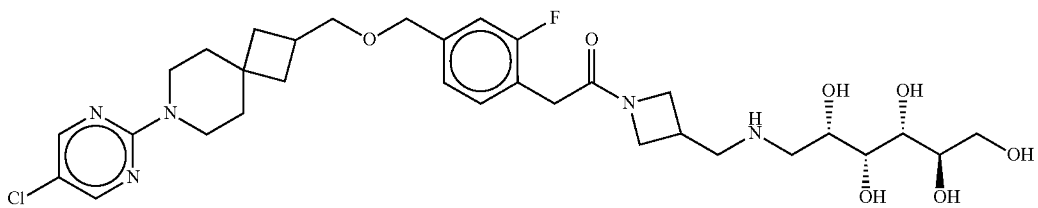 | 2-[4-[[7-(5-chloropyrimidin-2-yl)-7-azaspiro[3.5]nonan-2-yl]methoxymethyl]-2-fluoro-phenyl]-1-[3-[[[(2S,3R,4R,5R)-2,3,4,5,6-pentahydroxyhexyl]amino]methyl]-azetidin-1-yl]ethanone |
| 108 | 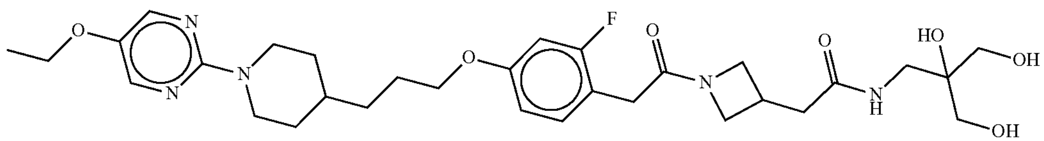 | N-[2,3-dihydroxy-2-(hydroxymethyl)propyl]-2-[1-[2-[4-[3-[1-(5-ethoxypyrimidin-2-yl)-4-piperidyl]propoxy]-2-fluoro-phenyl]acetyl]azetidin-3-yl]acetamide |
| 109 | 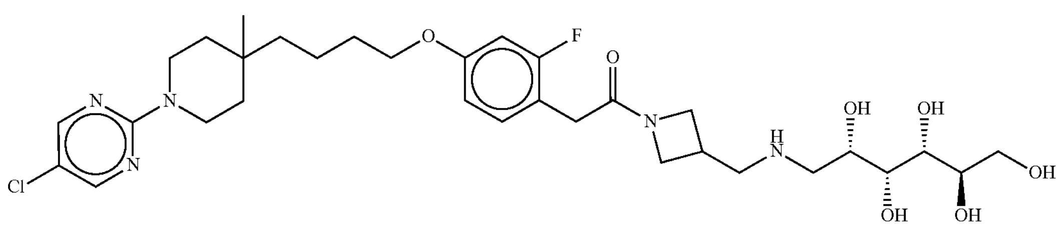 | 2-[4-[4-[1-(5-chloropyrimidin-2-yl)-4-methyl-4-piperidyl]butoxy]-2-fluoro-phenyl]-1-[3-[[[(2S,3R,4R,5R)-2,3,4,5,6-pentahydroxyhexyl]amino]methyl]-azetidin-1-yl]ethanone |
| 110 | 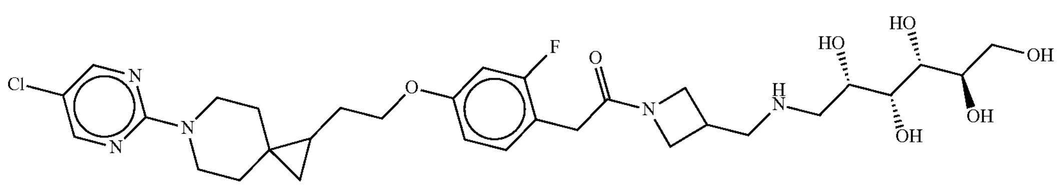 | 2-[4-[2-[6-(5-chloropyrimidin-2-yl)-6-azaspiro[2.5]octan-2-yl]ethoxy]-2-fluoro-phenyl]-1-[3-[[[(2S,3R,4R,5R)-2,3,4,5,6-pentahydroxyhexyl]amino]methyl]-azetidin-1-yl]ethanone |

TABLE 1-continued

| Ex. # | Structure | Name |
|---|---|---|
| 111 | 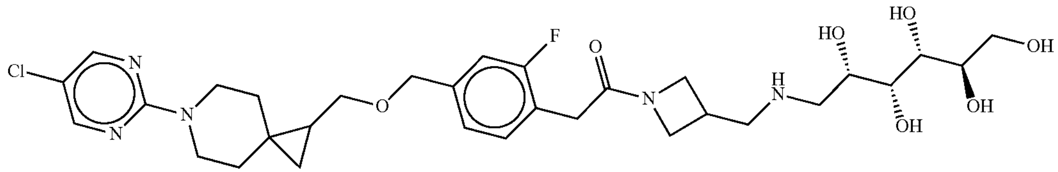 | 2-[4-[[6-(5-chloropyrimidin-2-yl)-6-azaspiro[2.5]octan-2-yl]methoxymethyl]-2-fluoro-phenyl]-1-[3-[[[(2S,3R,4R,5R)-2,3,4,5,6-pentahydroxyhexyl]amino]methyl]-azetidin-1-yl]ethanone |
| 112 | 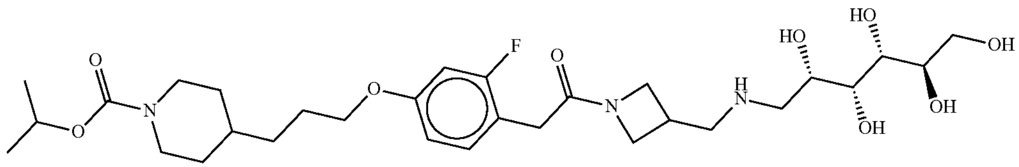 | isopropyl 4-[3-fluoro-4-[2-oxo-2-[3-[[[(2S,3R,4R,5R)-2,3,4,5,6-pentahydroxyhexyl]amino]methyl]azetidin-1-yl]ethyl]phenoxy]propyl]piperidine-1-carboxylate |
| 113 | 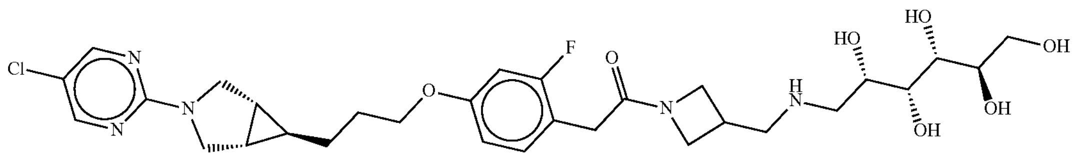 | 2-[4-[3-[(1R,5S)-3-(5-chloropyrimidin-2-yl)-3-azabicyclo[3.1.0]hexan-6-yl]propoxy]-2-fluoro-phenyl]-1-[3-[[[(2S,3R,4R,5R)-2,3,4,5,6-pentahydroxyhexyl]amino]methyl]-azetidin-1-yl]ethanone |
| 114 | 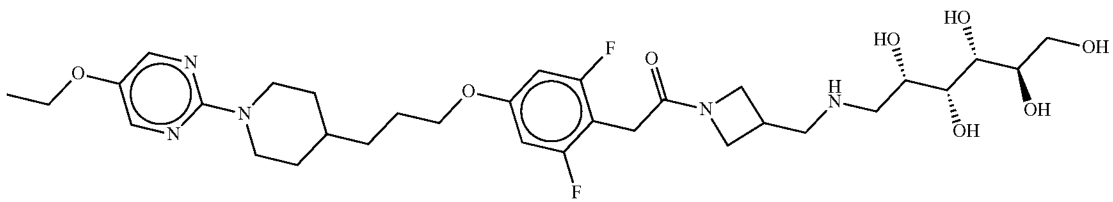 | 2-[4-[3-[1-(5-ethoxypyrimidin-2-yl)-4-piperidyl]propoxy]-2,6-difluoro-phenyl]-1-[3-[[[(2S,3R,4R,5R)-2,3,4,5,6-pentahydroxyhexyl]amino]methyl]-azetidin-1-yl]ethanone |
| 115 | 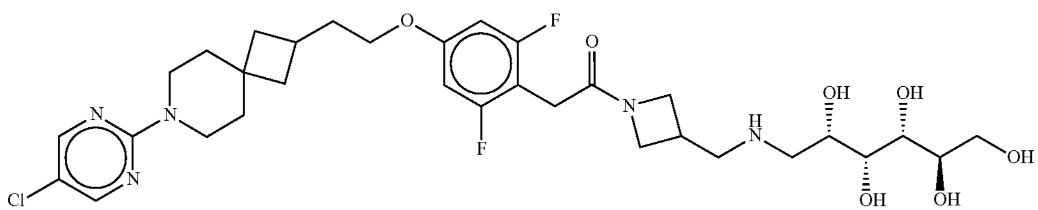 | 2-[4-[2-[7-(5-chloropyrimidin-2-yl)-7-azaspiro[3.5]nonan-2-yl]ethoxy]-2,6-difluoro-phenyl]-1-[3-[[[(2S,3R,4R,5R)-2,3,4,5,6-pentahydroxyhexyl]amino]methyl]-azetidin-1-yl]ethanone |

TABLE 1-continued

| Ex. # | Structure | Name |
|---|---|---|
| 116 | 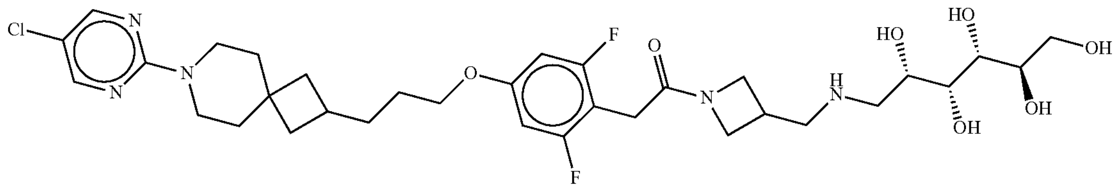 | 2-[4-[3-[7-(5-chloropyrimidin-2-yl)-7-azaspiro[3.5]nonan-2-yl]propoxy]-2,6-difluoro-phenyl]-1-[3-[[[(2S,3R,4R,5R)-2,3,4,5,6-pentahydroxyhexyl]amino]methyl]-azetidin-1-yl]ethanone |
| 117 | 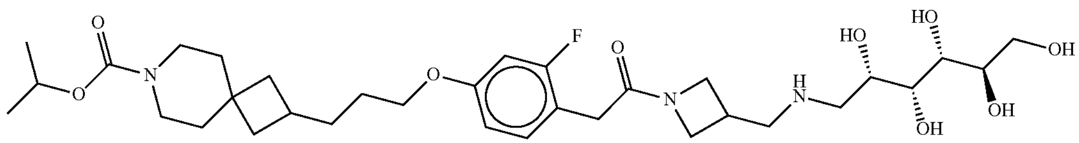 | isopropyl 2-[3-[3-fluoro-4-[2-oxo-2-[3-[[[(2S,3R,4R,5R)-2,3,4,5,6-pentahydroxyhexyl]amino]methyl]azetidin-1-yl]ethyl]phenoxy]propyl]-7-azaspiro[3.5]nonane-7-carboxylate |
| 118 | 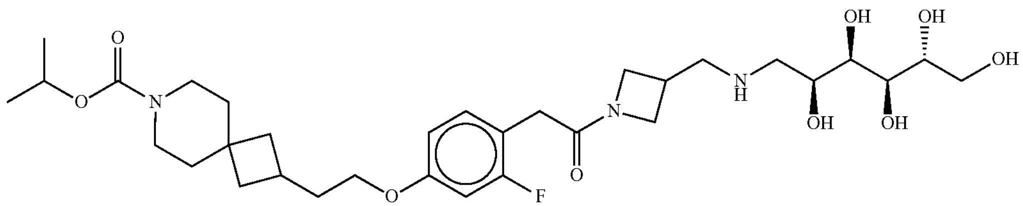 | isopropyl 2-[2-[3-fluoro-4-[2-oxo-2-[3-[[[(2S,3R,4R,5R)-2,3,4,5,6-pentahydroxyhexyl]amino]methyl]azetidin-1-yl]ethyl]phenoxy]ethyl]-7-azaspiro[3.5]nonane-7-carboxylate |
| 119 | 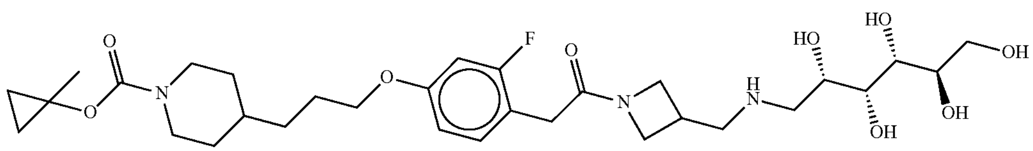 | (1-methylcyclopropyl) 4-[3-[3-fluoro-4-[2-oxo-2-[3-[[[rac-(2S,3R,4R,5R)-2,3,4,5,6-pentahydroxyhexyl]amino]methyl]azetidin-1-yl]ethyl]phenoxy]propyl]piperidine-1-carboxylate |
| 120 | 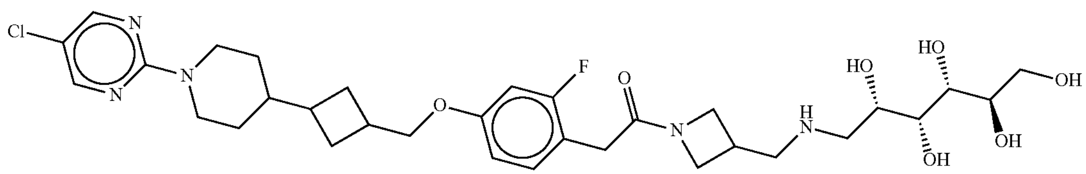 | 2-[4-[3-[1-(5-chloropyrimidin-2-yl)-4-piperidyl]cyclobutyl]methoxy]-2-fluoro-phenyl]-1-[3-[[[(2S,3R,4R,5R)-2,3,4,5,6-pentahydroxyhexyl]amino]methyl]-azetidin-1-yl]ethanone |
| 121 | | 2-[4-[3-[1-(5-chloropyrimidin-2-yl)-4-piperidyl]propoxy]-2-fluoro-phenyl]-1-[3-(methoxymethyl)-3-[[[r(2S,3R,4R,5R)-2,3,4,5,6-pentahydroxyhexyl]amino]methyl]-pyrrolidin-1-yl]ethanone |

| Ex. # | Structure | Name |
|---|---|---|
| 122 | 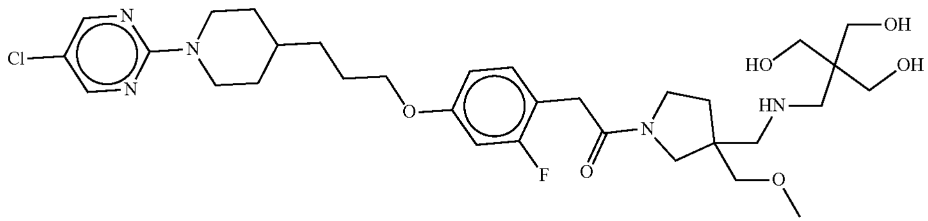 | 2-[4-[3-[1-(5-chloropyrimidin-2-yl)-4-piperidyl]propoxy]-2-fluoro-phenyl]-1-[3-[[[3-hydroxy-2,2-bis(hydroxymethyl)propyl]amino]methyl]-3-(methoxymethyl)pyrrolidin-1-yl]ethanone |
| 123 | 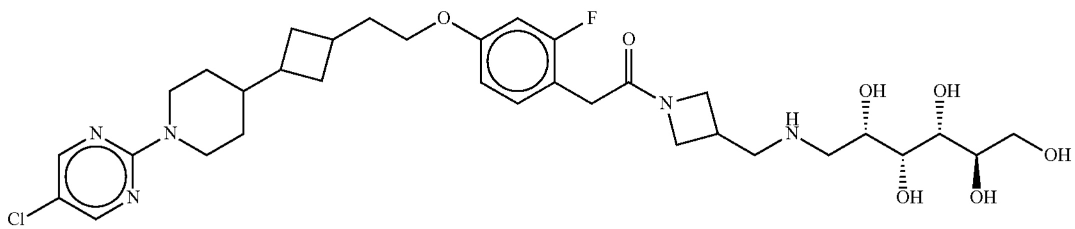 | 2-[4-[2-[3-[1-(5-chloropyrimidin-2-yl)-4-piperidyl]cyclobutyl]ethoxy]-2-(fluoro-phenyl]-[3-[[[(2S,3R,4R,5R)-2,3,4,5,6-pentahydroxyhexyl]amino]methyl]-azetidin-1-yl]ethanone |
| 124 | 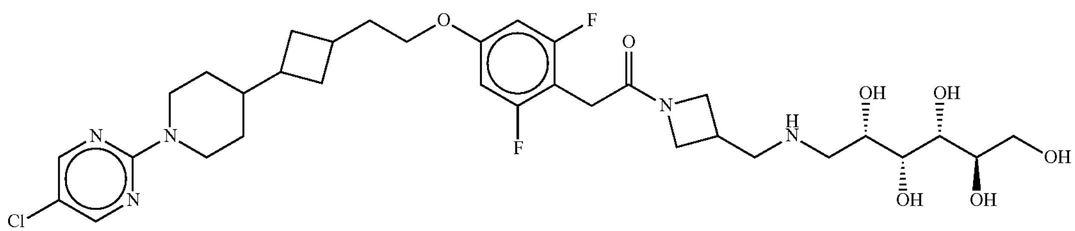 | 2-[4-[2-[3-[1-(5-chloropyrimidin-2-yl)-4-piperidyl]cyclobutyl]ethoxy]-2,6-difluoro-phenyl]-1-[3-[[[(2S,3R,4R,5R)-2,3,4,5,6-pentahydroxyhexyl]amino]methyl]-azeyidin-1-yl]ethanone |
| 125 | 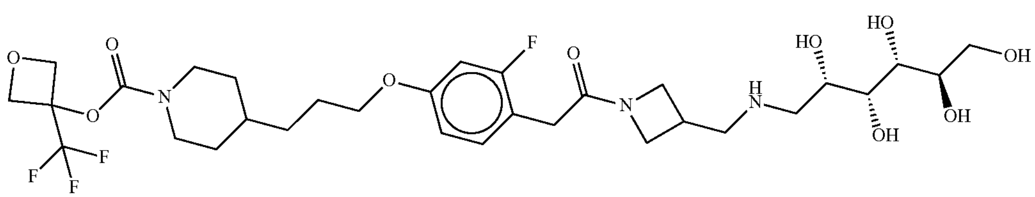 | [3-(trifluoromethyl)oxetan-3-yl] 4-[3-[3-fluoro-4-[2-oxo-2-[3-[[[(2S,3R,4R,5R)-2,3,4,5,6-pentahydroxyhexyl]amino]methyl]azetidin-1-yl]ethyl]phenoxy]propyl]piperidine-1-carboxylate |

TABLE 1-continued

| Ex. # | Structure | Name |
|---|---|---|
| 126 | 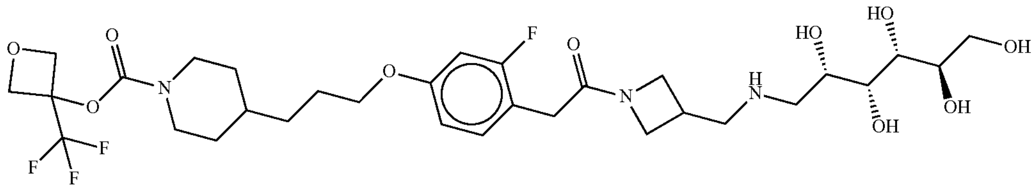 | [3-(trifluoromethyl)oxetan-3-yl] 4-[3-[3,5-difluoro-4-[2-oxo-2-[3-[[[(2S,3R,4R,5R)-2,3,4,5,6-pentahydroxyhexyl]amino]methyl]azetidin-1-yl]ethyl]phenoxy]propyl]piperidine-1-carboxylate |
| 127 | 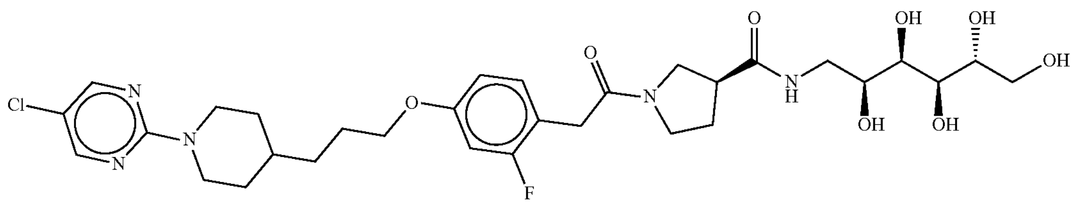 | (3S)-1-[2-[4-[3-[1-(5-chloropyrimidin-2-yl)-4-piperidyl]propoxy]-2-fluoro-phenyl]acetyl]-N-[(2S,3R,4R,5R)-2,3,4,5,6-pentahydroxyhexyl]pyrrolidine-3-carboxamide |
| 128 | 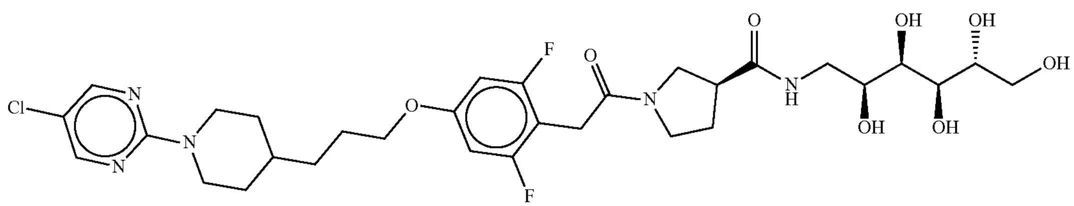 | (3S)-1-[2-[4-[3-[1-(5-chloropyrimidin-2-yl)-4-piperidyl]propoxy]-2,6-difluoro-phenyl]acetyl]-N-[(2S,3R,4R,5R)-2,3,4,5,6-pentahydroxyhexyl]pyrrolidine-3-carboxamide |
| 129 | 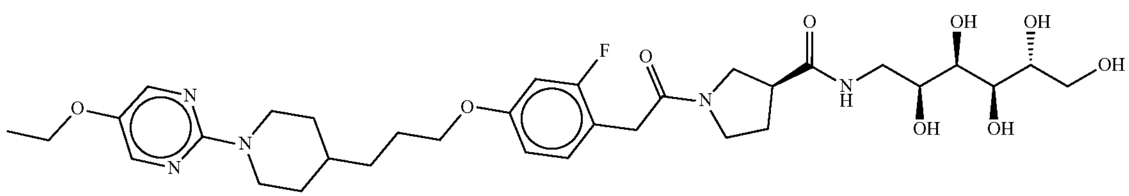 | (3S)-1-[2-[4-[3-[1-(5-ethoxypyrimidin-2-yl)-4-piperidyl]propoxy]-2-fluoro-phenyl]acetyl]-N-[(2S,3R,4R,5R)-2,3,4,5,6-pentahydroxyhexyl]pyrrolidine-3-carboxamide |
| 130 | 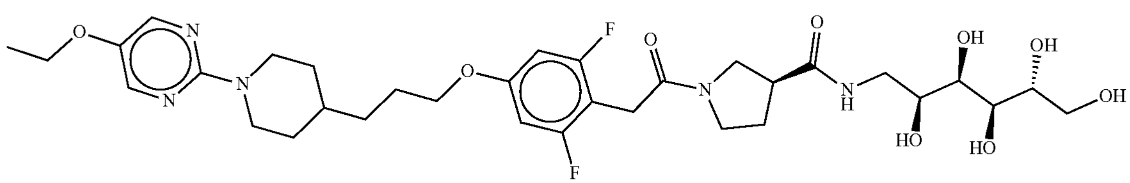 | (3S)-1-[2-[4-[3-[1-(5-ethoxypyrimidin-2-yl)-4-piperidyl]propoxy]-2,6-difluoro-phenyl]acetyl]-N-[(2S,3R,4R,5R)-2,3,4,5,6-pentahydroxyhexyl]pyrrolidine-3-carboxamide |

TABLE 1-continued

| Ex. # | Structure | Name |
|---|---|---|
| 131 | 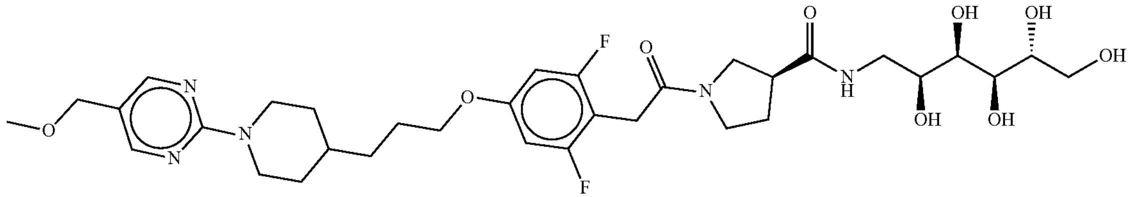 | (3S)-1-[2-[2,6-difluoro-4-[3-[1-[5-(methoxymethyl)pyrimidin-2-yl]-4-piperidyl]propoxy]phenyl]acetyl]-N-[(2S,3R,4R,5R)-2,3,4,5,6-pentahydroxyhexyl]pyrrolidine-3-carboxamide |
| 132 | 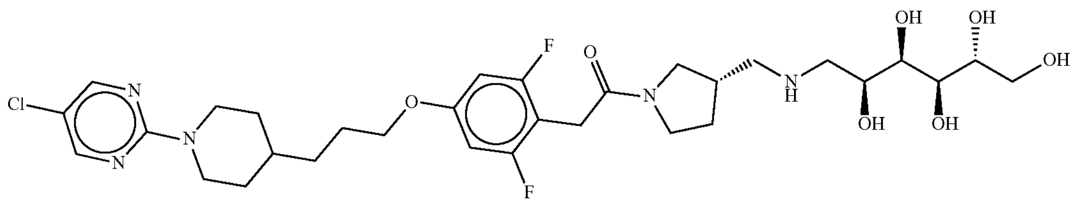 | 2-[4-[1-(5-chloropyrimidin-2-yl)-4-piperidyl]propoxy]-2,6-difluoro-phenyl]-1-[(3S)-3-[[[(2S,3R,4R,5R)-2,3,4,5,6-pentahydroxyhexyl]amino]methyl]pyrrolidin-1-yl]ethanone |
| 133 | 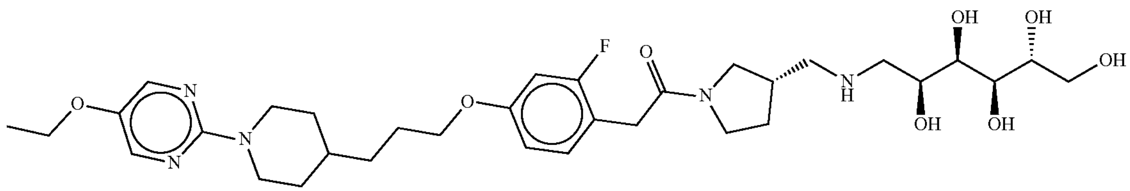 | 2-[4-[3-[1-(5-ethoxypyrimidin-2-yl)-4-piperidyl]propoxy]-2-fluoro-phenyl]-1-[(3S)-3-[[[(2S,3R,4R,5R)-2,3,4,5,6-pentahydroxyhexyl]amino]methyl]pyrrolidin-1-yl]ethanone |
| 134 | 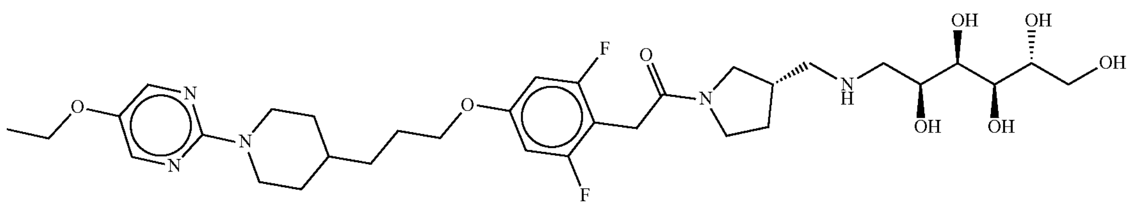 | 2-[4-[3-[1-(5-ethoxypyrimidin-2-yl)-4-piperidyl]propoxy]-2,6-difluoro-phenyl]-1-[(3S)-3-[[[(2S,3R,4R,5R)-2,3,4,5,6-pentahydroxyhexyl]amino]methyl]pyrrolidin-1-yl]ethanone |
| 135 | 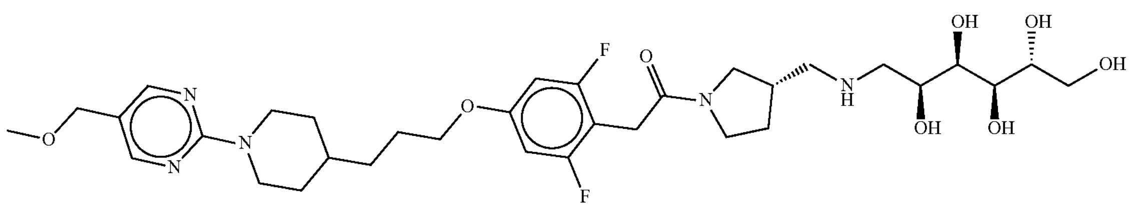 | 2-[2,6-difluoro-4-[3-[1-[5-(methoxymethyl)pyrimidin-2-yl]-4-piperidyl]propoxy]phenyl]-1-(3S)-3-[[[(2S,3R,4R,5R)-2,3,4,5,6-pentahydroxyhexyl]amino]methyl]pyrrolidin-1-yl]ethanone |

TABLE 1-continued

| Ex. # | Structure | Name |
|---|---|---|
| 136 | 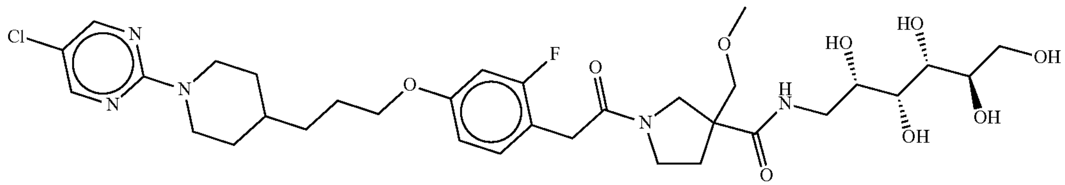 | 1-[2-[4-[3-[1-(5-chloropyrimidin-2-yl)-4-piperidyl]propoxy]-2-fluoro-phenyl]acetyl]-3-(methoxymethyl)-N-[(2S,3R,4R,5R)-2,3,4,5,6-pentahydroxyhexyl]pyrrolidine-3-carboxamide |
| 137 | 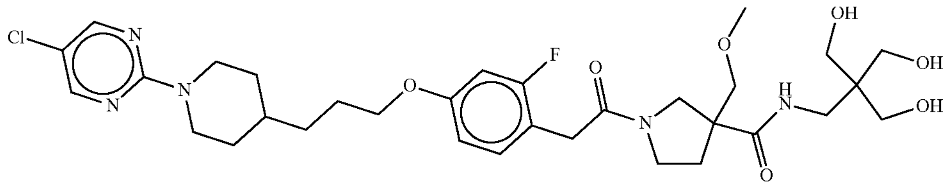 | 1-[2-[4-[3-[1-(5-chloropyrimidin-2-yl)-4-piperidyl]propoxy]-2-fluoro-phenyl]acetyl]-N-[3-hydroxy-2,2-bis(hydroxymethyl)propyl]-3-(methoxymethyl)pyrrolidine-3-carboxamide |
| 138 | 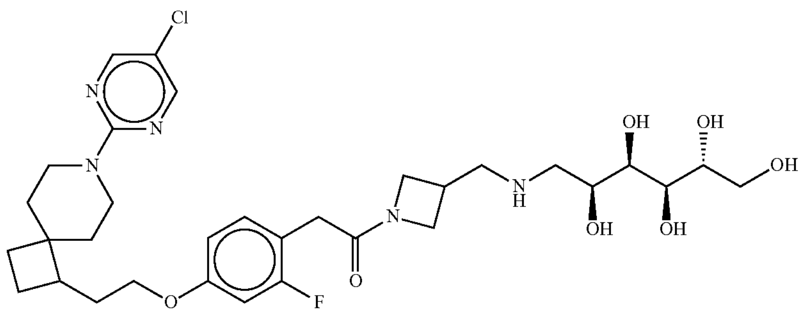 | 2-[4-[2-[7-(5-chloropyrimidin-2-yl)-7-azaspiro[3.5]nonan-3-yl]ethoxy]-2-fluoro-phenyl]-1-[3-[[[(2S,3R,4R,5R)-2,3,4,5,6-pentahydroxyhexyl]amino]methyl]-azetidin-1-yl]ethanone |
| 139 | 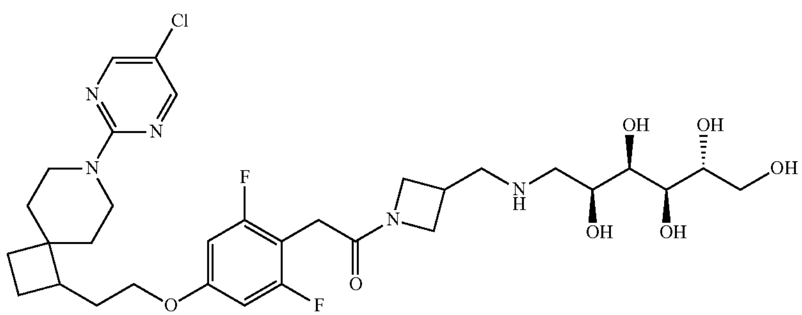 [SMILES: O=C(Cc1c(F)cc(OCCC2CCC23CCN(c2ncc(Cl)cn2)CC3)cc1F)N1CC(CNC[C@H](O)[C@@H](O)[C@H](O)[C@H](O)CO)C1] | 2-[4-[2-[7-(5-chloropyrimidin-2-yl)-7-azaspiro[3.5]nonan-3-yl]ethoxy]-2,6-difluoro-phenyl]-1-[3-[[[(2S,3R,4R,5R)-2,3,4,5,6-pentahydroxyhexyl]amino]methyl]-azetidin-1-yl]ethanone |

TABLE 1-continued

| Ex. # | Structure | Name |
|---|---|---|
| 140 | 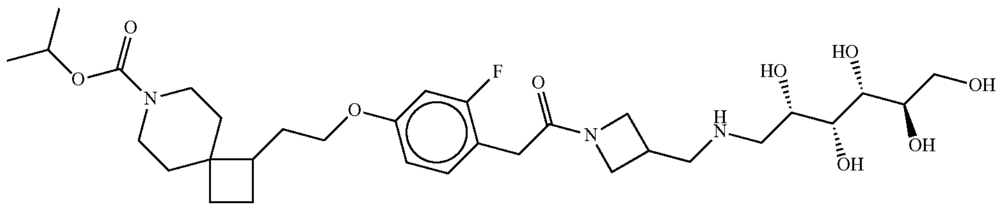 | isopropyl 3-[2-[3-fluoro-4-[2-oxo-2-[3-[[[(2S,3R,4R,5R)-2,3,4,5,6-pentahydroxyhexyl]amino]methyl]azetidin-1-yl]ethyl]phenoxy]ethyl]-7-azaspiro[3.5]nonane-7-carboxylate |
| 141 | 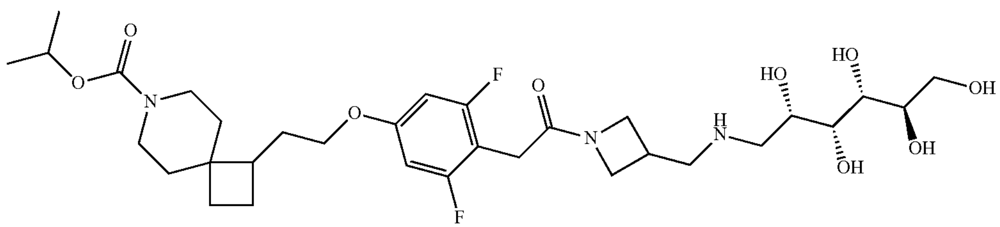 [SMILES: CC(C)OC(=O)N1CCC2(CCC2CCOc2cc(F)c(CC(=O)N3CC(CNC[C@H](O)[C@@H](O)[C@H](O)[C@H](O)CO)C3)c(F)c2)CC1] | isopropyl 3-[2-[3,5-difluoro-4-[2-oxo-2-[3-[[[(2S,3R,4R,5R)-2,3,4,5,6-pentahydroxyhexyl]amino]methyl]azetidin-1-yl]ethyl]phenoxy]ethyl]-7-azaspiro[3.5]nonane-7-carboxylate |
| 142 | 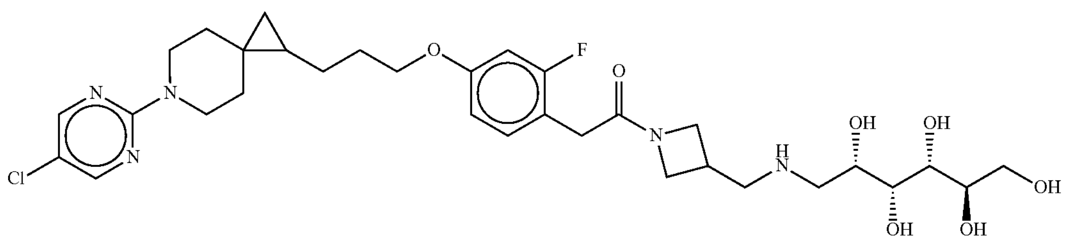 | 2-[4-[3-[6-(5-chloropyrimidin-2-yl)-6-azaspiro[2.5]octan-2-yl]propoxy]-2-fluoro-phenyl]-1-[3-[[[(2S,3R,4R,5R)-2,3,4,5,6-pentahydroxyhexyl]amino]methyl]azetidin-1-yl]ethanone |
| 143 | 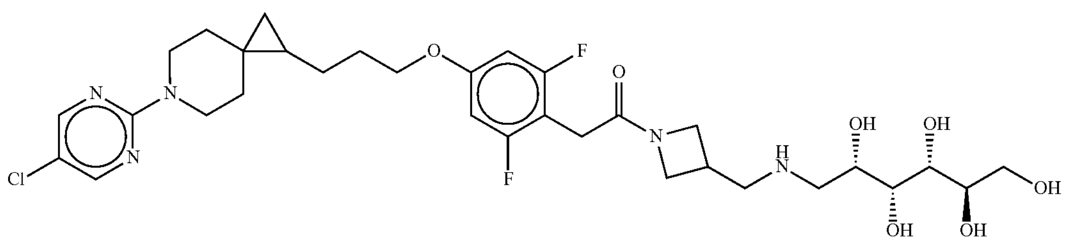 | 2-[4-[3-[6-(5-chloropyrimidin-2-yl)-6-azaspiro[2.5]octan-2-yl]propoxy]-2,6-difluoro-phenyl]-1-[3-[[[(2S,3R,4R,5R)-2,3,4,5,6-pentahydroxyhexyl]amino]methyl]azetidin-1-yl]ethanone |

TABLE 1-continued

| Ex. # | Structure | Name |
|---|---|---|
| 144 | 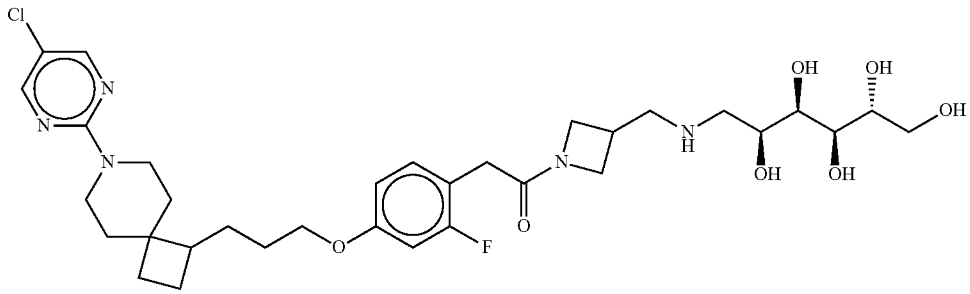 | 2-[4-[3-[7-(5-chloropyrimidin-2-yl)-7-azaspiro[3.5]nonan-3-yl]propoxy]-2-fluoro-phenyl]-1-[3-[[[(2S,3R,4R,5R)-2,3,4,5,6-pentahydroxyhexyl]amino]methyl]-azetidin-1-yl]ethanone |
| 145 | 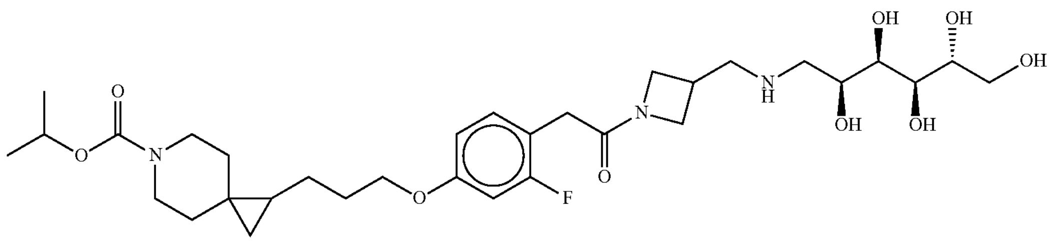 | isopropyl 2-[3-[3-fluoro-4-[2-oxo-2-[3-[[[(2S,3R,4R,5R)-2,3,4,5,6-pentahydroxyhexyl]amino]methyl]-azetidin-1-yl]ethyl]phenoxy]propyl]-6-azaspiro[2.5]octane-6-carboxylate |
| 146 | 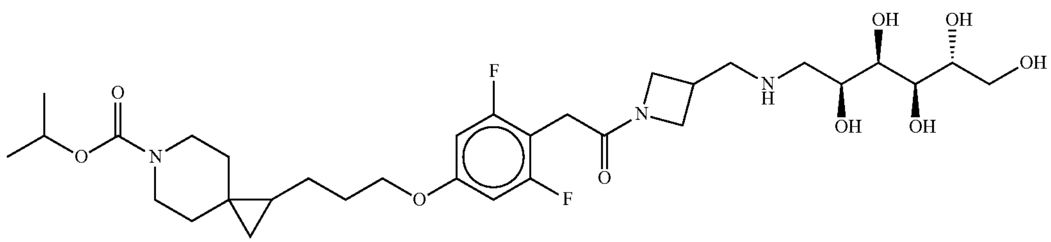 | isopropyl 2-[3-[3,5-difluoro-4-[2-oxo-2-[3-[[[(2S,3R,4R,5R)-2,3,4,5,6-pentahydroxyhexyl]amino]methyl]-azetidin-1-yl]ethyl]phenoxy]propyl]-6-azaspiro[2.5]octane-6-carboxylate |
| 147 | 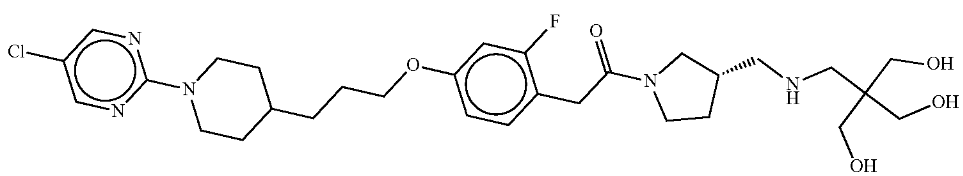 | 2-[4-[3-[1-(5-chloropyrimidin-2-yl)-4-piperidyl]propoxy]-2-fluoro-phenyl]-1-[(3S)-3-[[[3-hydroxy-2,2-bis(hydroxymethyl)propyl]amino]methyl]pyrrolidin-1-yl]ethanone |

TABLE 1-continued

| Ex. # | Structure | Name |
|---|---|---|
| 148 | | 2[4-[3-[1-(5-chloropyrimidin-2-yl)-4-piperidyl]propoxy]-2-fluoro-phenyl]-1-[(3S)-3-[[[2-hydroxy-1,1-bis(hydroxymethyl)ethyl]amino]methyl]pyrrolidin-1-yl]ethanone |
| 149 | 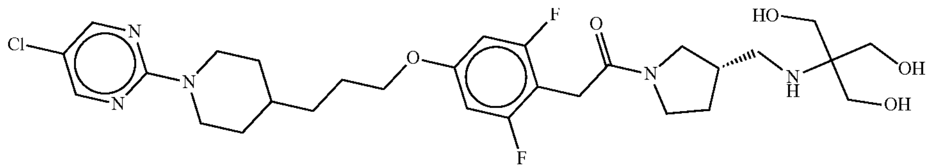 | 2-[4-[3-[1-(5-chloropyrimidin-2-yl)-4-piperidyl]propoxy]-2,6-difluoro-phenyl]-1-(3S)-3-[[[2-hydroxy-1,1-bis(hydroxymethyl)ethyl]amino]methyl]pyrrolidin-1-yl]ethanone |
| 150 | 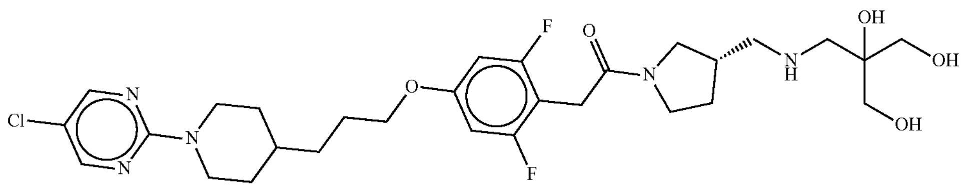 | 2-[4-[3-[1-(5-chloropyrimidin-2-yl)-4-piperidyl]propoxy]-2,6-difluoro-phenyl]-1-(3S)-3-[[[2,3-dihydroxy-2-(hydroxymethyl)propyl]amino]methyl]pyrrolidin-1-yl]ethanone |
| 151 | 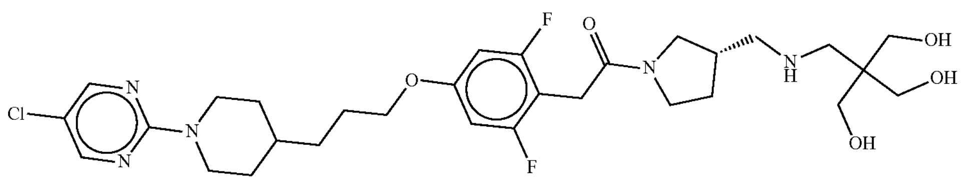 | 2-[4-[3-[1-(5-chloropyrimidin-2-yl)-4-piperidyl]propoxy]-2,6-difluoro-phenyl]-1-(3S)-3-[[[3-hydroxy-2,2-bis(hydroxymethyl)propyl]amino]methyl]pyrrolidin-1-yl]ethanone |
| 152 | 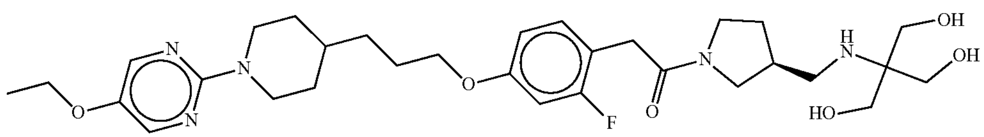 | 2-[4-[3-[1-(5-ethoxypyrimidin-2-yl)-4-piperidyl]propoxy]-2-fluoro-phenyl]-1-[(3S)-3-[[[2-hydroxy-1,1-bis(hydroxymethyl)ethyl]amino]methyl]pyrrolidin-1-yl]ethanone |
| 153 | 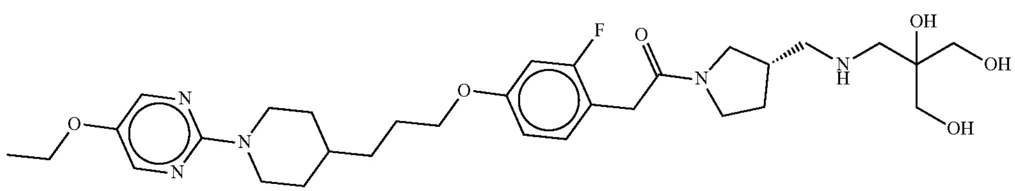 | 2-[4-[3-[1-(5-ethoxypyrimidin-2-yl)-4-piperidyl]propoxy]-2-fluoro-phenyl]-1-[(3S)-3-[[[2,3-dihydroxy-2-(hydroxymethyl)propyl]amino]methyl]pyrrolidin-1-yl]ethanone |

TABLE 1-continued

| Ex. # | Structure | Name |
|---|---|---|
| 154 | 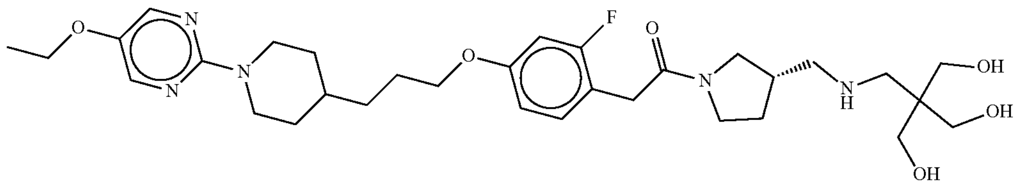 | 2-[4-[3-[1-(5-ethoxypyrimidin-2-yl)-4-piperidyl]propoxy]-2-fluoro-phenyl]-1-[(3S)-3-[[[3-hydroxy-2,2-bis(hydroxymethyl)propyl]amino]methyl]pyrrolidin-1-yl]ethanone |
| 155 | 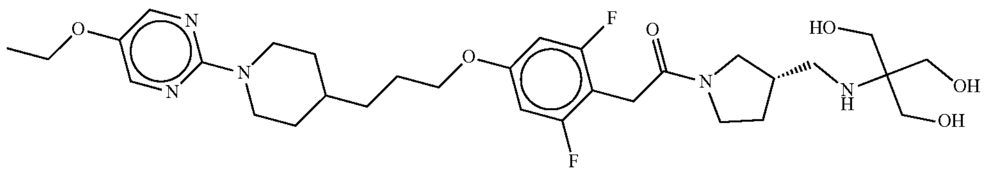 | 2-[4-[3-[1-(5-ethoxypyrimidin-2-yl)-4-piperidyl]propoxy]-2,6-difluoro-phenyl)-1-[(3S)-3-[[[2-hydroxy-1,1-bis(hydroxymethyl)ethyl]amino]methyl]pyrrolidin-1-yl]ethanone |
| 156 | 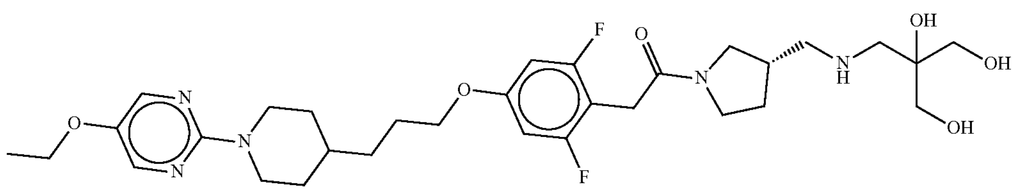 | 2-[4-[3-[1-(5-ethoxypyrimidin-2-yl)-4-piperidyl]propoxy]-2,6-difluoro-phenyl]-1-[(3S)-3-[[[2,3-dihydroxy-2-(hydroxymethyl)propyl]amino]methyl]-pyrrolidin-1-yl]ethanone |
| 157 | 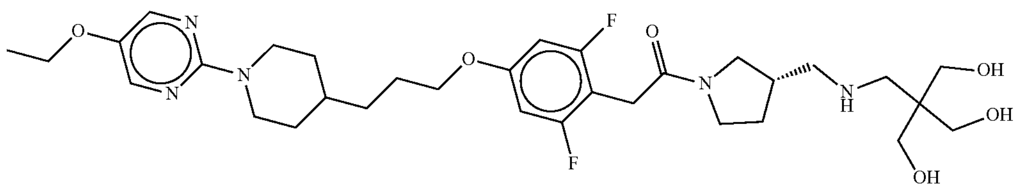 | 2-[4-[3-[1-(5-ethoxypyrimidin-2-yl)-4-piperidyl]propoxy]-2,6-difluoro-phenyl]-1-[(3S)-3-[[[3-hydroxy-2,2-bis(hydroxymethyl)propyl]amino]methyl]pyrrolidin-1-yl]ethanone |
| 158 | 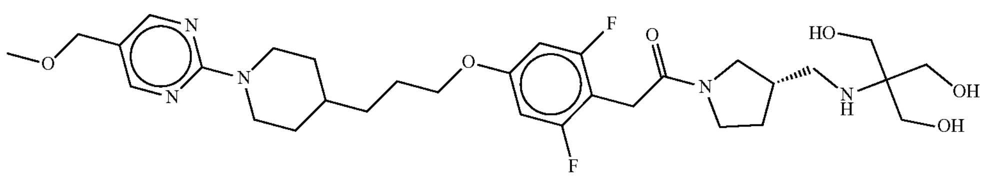 | 2-[2,6-difluoro-4-[3-[1-[5-(methoxymethyl)pyrimidin-2-yl]-4-piperidyl]propoxy]phenyl]-1-[(3S)-3-[[[2-hydroxy-1,1-bis(hydroxymethyl)ethyl]amino]methyl]pyrrolidin-1-yl]ethanone |

TABLE 1-continued

| Ex. # | Structure | Name |
|---|---|---|
| 159 | 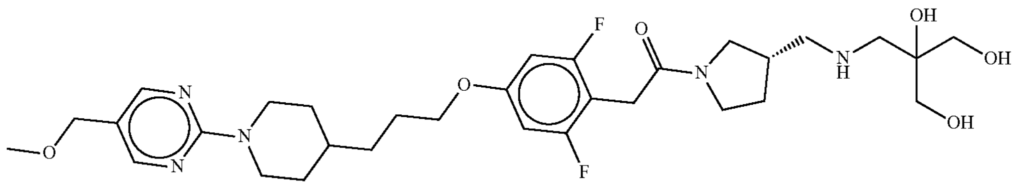 | 2-[2,6-difluoro-4-[3-[1-[5-(methoxymethyl)pyrimidin-2-yl]-4-piperidyl]propoxy]phenyl]-1-[(3S)-3-[[[2,3-dihydroxy-2-(hydroxymethyl)propyl]amino]methyl]pyrrolidin-1-yl]ethanone |
| 160 | 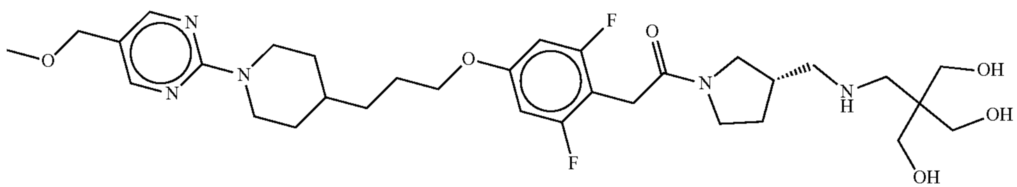 | 2-[2,6-difluoro-4-[3-[1-[5-(methoxymethyl)pyrimidin-2-yl]-4-piperidyl]propoxy]phenyl]-1-[(3S)-3-[[[3-hydroxy-2,2-bis(hydroxymethyl)propyl]amino]methyl]pyrrolidin-1-yl]ethanone |
| 161 | 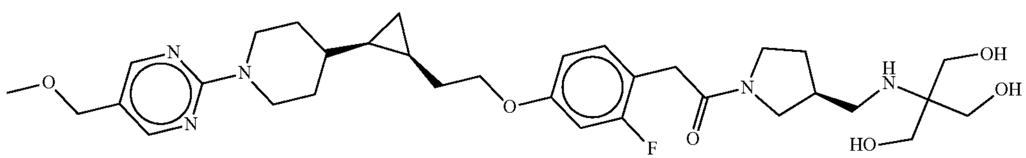 | 2-[2-fluoro-4-[2-[(1S,2R)-2-[1-[5-(methoxymethyl)pyrimidin-2-yl]-4-piperidyl]cyclopropyl]ethoxy]phenyl]-1-[(3S)-3-[[2-hydroxy-1,1-bis(hydroxymethyl)ethyl]amino]methyl]pyrrolidin-1-yl]ethanone |
| 162 | 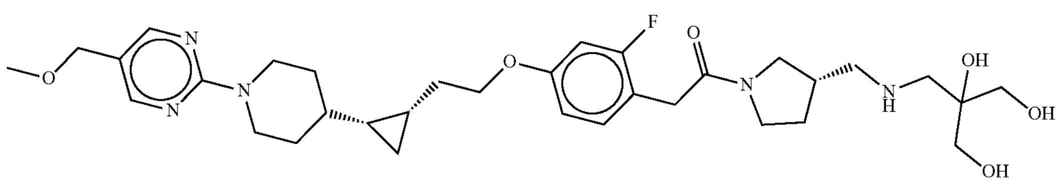 | 2-[2-fluoro-4-[2-[(1S,2R)-2-[1-[5-(methoxymethyl)pyrimidin-2-yl]-4-piperidyl]cyclopropyl]ethoxy]phenyl]-1-[(3S)-3-[[[2,3-dihydroxy-2-(hydroxymethyl)propyl]amino]methyl]pyrrolidin-1-yl]ethanone |
| 163 | 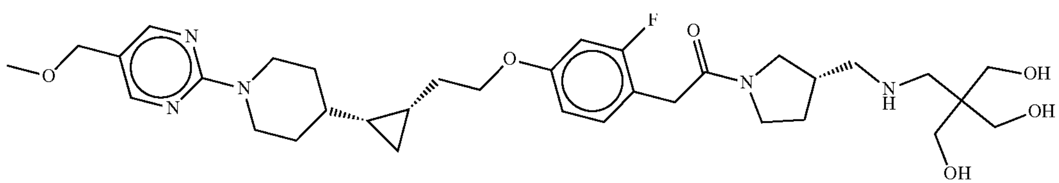 | 2-[2-fluoro-4-[2-[(1S,2R)-2-[1-[5-(methoxymethyl)pyrimidin-2-yl]-4-piperidyl]cyclopropyl]ethoxy]phenyl]-1-[(3S)-3-[[[3-hydroxy-2,2-bis(hydroxymethyl)propyl]amino]methyl]pyrrolidin-1-yl]ethanone |
| 164 | 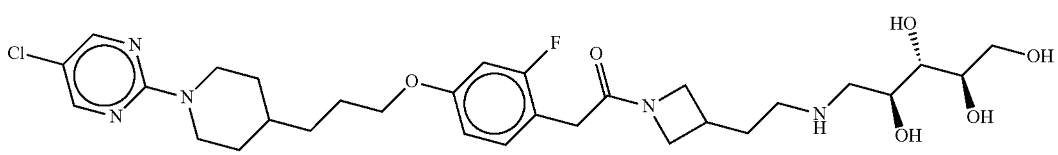 | 2-[4-[3-[1-(5-chloropyrimidin-2-yl)-4-piperidyl]propoxy]-2-fluoro-phenyl]-1-[3-[2-[[(2S,3S,4R)-2,3,4,5-tetrahydroxypentyl]amino]ethyl]azetidin-1-yl]ethanone |

TABLE 1-continued

| Ex. # | Structure | Name |
|---|---|---|
| 165 | 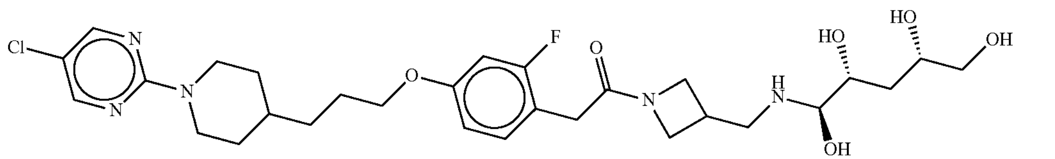 | 2-[4-[3-[1-(5-chloropyrimidin-2-yl)-4-piperidyl]propoxy]-2-fluoro-phenyl]-1-[3-[[[(2S,3S,4R)-2,3,4,5-tetrahydroxypentyl]amino]methl]-azetidin-1-yl]ethanone |
| 166 | 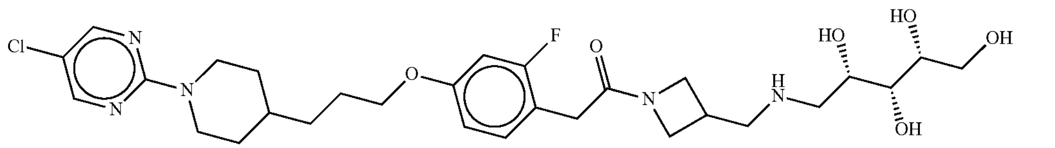 | 2-[4-[3-[1-(5-chloropyrimidin-2-yl)-4-piperidyl]propoxy]-2-fluoro-phenyl]-1-[3-[[[(2S,3R,4R)-2,3,4,5-tetrahydroxypentyl]amino]methyl]-azetidin-1-yl]ethanone |
| 167 | 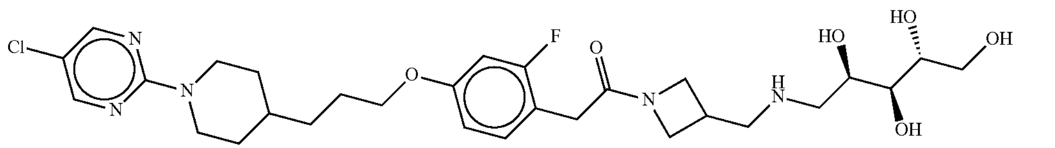 | 2-[4-[3-[1-(5-chloropyrimidin-2-yl)-4-piperidyl]propoxy]-2-fluoro-phenyl]-1-[3-[[[(2R,3S,4R)-2,3,4,5-tetrahydroxypentyl]amino]methyl]azetidin-1-yl]ethanone |
| 168 | 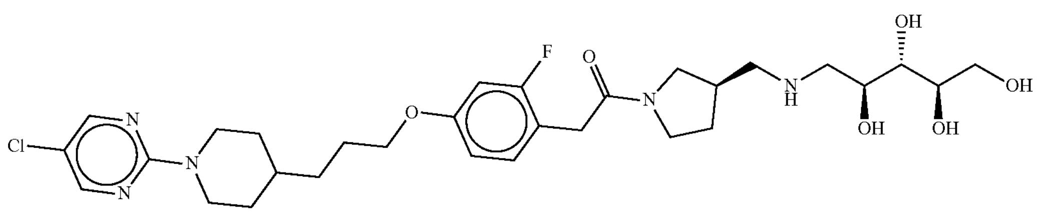 | 2-[4-[3-[1-(5-chloropyrimidin-2-yl)-4-piperidyl]propoxy]-2-fluoro-phenyl]-1-[(3R)-3-[[[(2S,3S,4R)-2,3,4,5-tetrahydroxypentyl]amino]methyl]pyrrolidin-1-yl]ethanone |
| 169 | 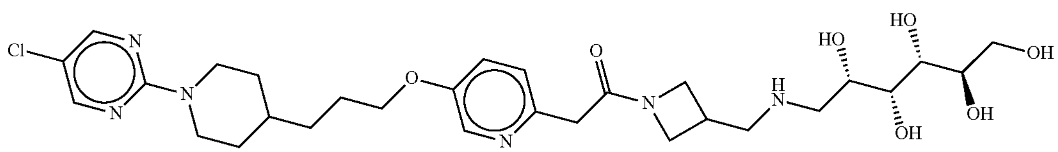 | 2-[5-[3-[1-(5-chloropyrimidin-2-yl)-4-piperidyl]propoxy]-2-pyridyl]-1-[3-[[[(2S,3R,4R,5R)-2,3,4,5,6-pentahydroxyhexyl]amino]methyl]-azetidin-1-yl]ethanone |
| 170 | 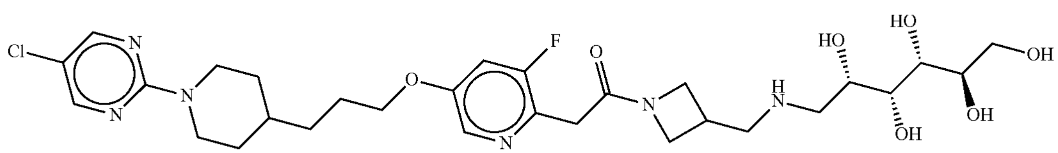 | 2-[5-[3-[1-(5-chloropyrimidin-2-yl)propoxy]-3-fluoro-2-pyridyl]-1-[3-[[[(2S,3R,4R,5R)-2,3,4,5,6-pentahydroxyhexyl]amino]methyl]-azetidin-1-yl]ethanone |

TABLE 1-continued

| Ex. # | Structure | Name |
|---|---|---|
| 171 | 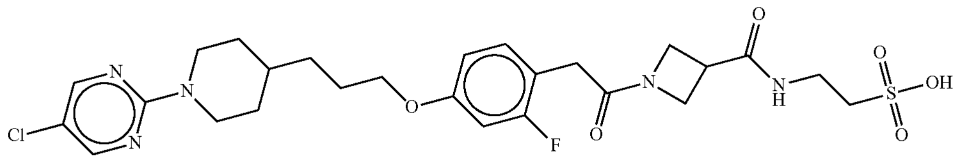 | 2-[[1-[2-[4-[3-[1-(5-chloropyrimidin-2-yl)-4-piperidyl]propoxy]-2-fluorophenyl]acetyl]azetidine-3-carbonyl]amino]ethanesulfonic acid |
| 172 | 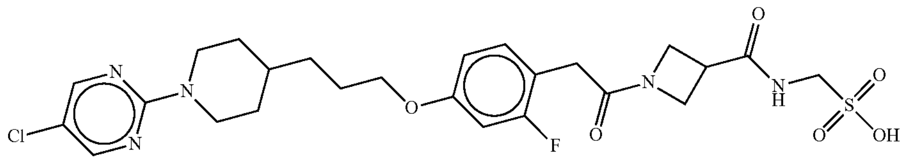 | 3-[[1-[2-[4-[3-[1-(5-chloropyrimidin-2-yl)-4-piperidyl]propoxy]-2-fluorophenyl]acetyl]azetidine-3-carbonyl]amino]propane-1-sulfonic acid |
| 173 | 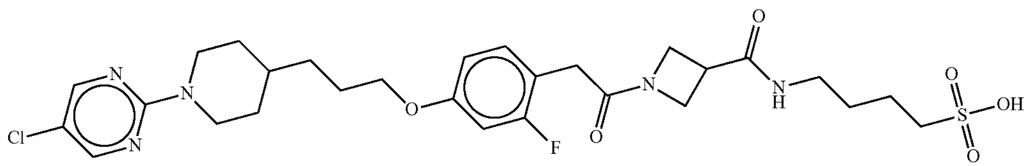 | 4-[[1-[2-[4-[3-[1-(5-chloropyrimidin-2-yl)-4-piperidyl]propoxy]-2-fluorophenyl]acetyl]azetidine-3-carbonyl]amino]butane-1-sulfonic acid |
| 174 | 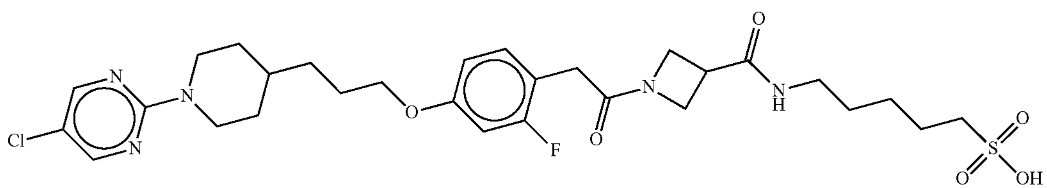 | 5-[[1-[2-[4-[3-[1-(5-chloropyrimidin-2-yl)-4-piperidyl]propoxy]-2-fluorophenyl]acetyl]azetidine-3-carbonyl]amino]pentane-1-sulfonic acid |
| 175 | 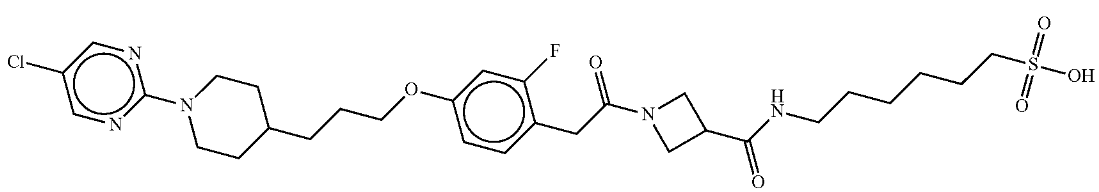 | 6-[[1-[2-[4-[3-[1-(5-chloropyrimidin-2-yl)-4-piperidyl]propoxy]-2-fluorophenyl]acetyl]azetidine-3-carbonyl]amino]hexane-1-sulfonic acid |
| 176 | 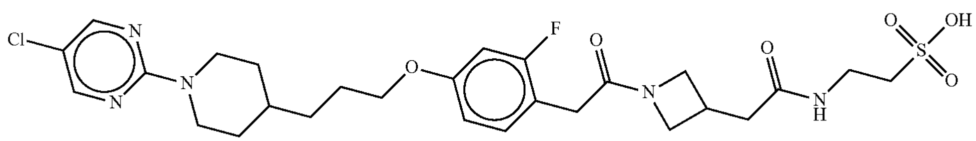 | 2-[[2-[1-[2-[4-[3-[1-(5-chloropyrimidin-2-yl)-4-piperidyl]propoxy]-2-fluorophenyl]acetyl]azetidin-3-yl]acetyl]amino]ethanesulfonic acid |

TABLE 1-continued

| Ex. # | Structure | Name |
|---|---|---|
| 177 | 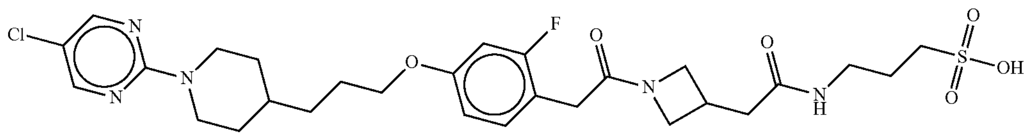 | 3-[[2-[1-[2-[4-[[3-[1-(5-chloropyrimidin-2-yl)-4-piperidyl]propoxy]-2-fluoro-phenyl]acetyl]azetidin-3-yl]acetyl]amino]propane-1-sulfonic acid |
| 178 | 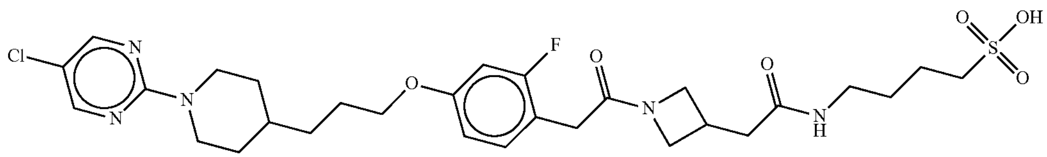 | 4-[[2-[1-[2-[4-[3-[1-(5-chloropyrimidin-2-yl)-4-piperidyl]propoxy]-2-fluoro-phenyl]acetyl]azetidin-3-yl]acetyl]amino]butane-1-sulfonic acid |
| 179 | 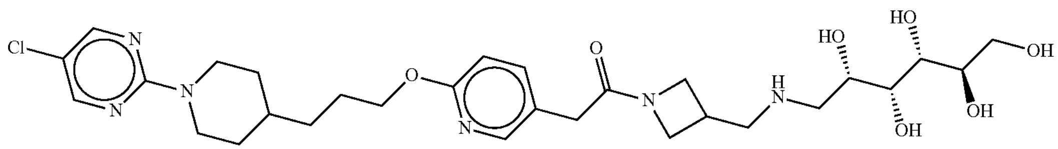 | 2-[6-[3-[1-(5-chloropyrimidin-2-yl)-4-piperidyl]propoxy]-3-pyridyl]-1-[3-[[[(2S,3R,4R,5R)-2,3,4,5,6-pentahydroxyhexyl]amino]methyl]-azetidin-1-yl]ethanone |
| 180 | 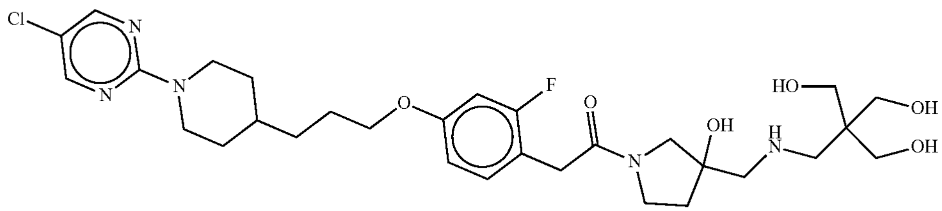 | 2-[4-[3-[1-(5-chloropyrimidin-2-yl)-4-piperidyl]propoxy]-2-fluoro-phenyl]-1-[3-hydroxy-3-[[[3-hydroxy-2,2-bis(hydroxymethyl)propyl]amino]methyl]pyrrolidin-1-yl]ethanone |
| 181 | 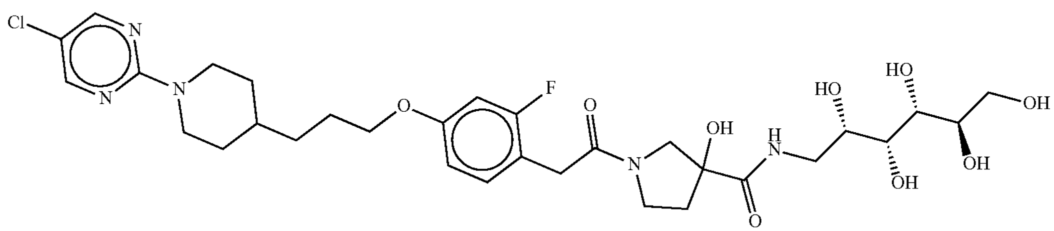 | 1-[2-[4-[3-[1-(5-chloropyrimidin-2-yl)-4-piperidyl]acetyl]-3-fluoro-phenyl]acetyl]-3-hydroxy-N-[(2S,3R,4R,5R)-2,3,4,5,6-pentahydroxyhexyl]pyrrolidine-3-carboxamide |

TABLE 1-continued

| Ex. # | Structure | Name |
|---|---|---|
| 182 | 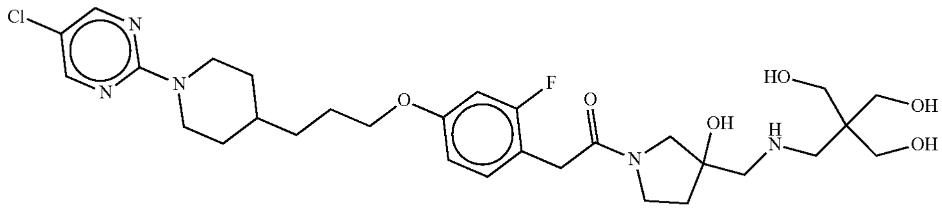 | 1-[2-[4-[3-[1-(5-chloropyrimidin-2-yl)-4-piperidyl]propoxy]-2-fluoro-phenyl]acetyl]-3-hydroxy-N-[3-hydroxy-2,2-bis(hydroxymethyl)propyl]pyrrolidine-3-carboxamide |
| 183 | 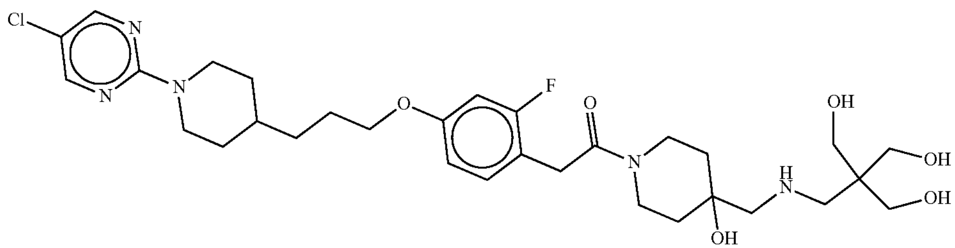 | 2-[4-[3-[1-(5-chloropyrimidin-2-yl)-4-piperidyl]propoxy]-2-fluoro-phenyl]-1-[4-hydroxy-4-[[[3-hydroxy-2,2-bis(hydroxymethyl)propyl]amino]methyl]-1-piperidyl]ethanone |
| 184 | 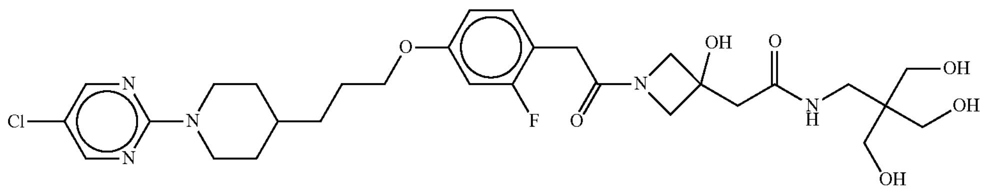 | 2-[1-[2-[4-[3-[1-(5-chloropyrimidin-2-yl)-4-piperidyl]propoxy]-2-fluoro-phenyl]acetyl]-3-hydroxy-azetidin-3-yl]-N-[3-hydroxy-2,2-bis(hydroxymethyl)propyl]acetamide |
| 185 | 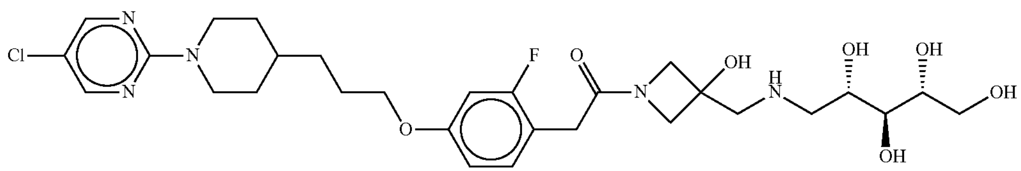 | 2-[4-[3-[1-(5-chloropyrimidin-2-yl)-4-piperidyl]propoxy]-2-fluoro-phenyl]-1-[3-hydroxy-3-[[[(2S,3S,4R)-2,3,4,5-tetrahydroxypentyl]amino]methyl]azetidin-1-yl]ethanone |
| 186 | 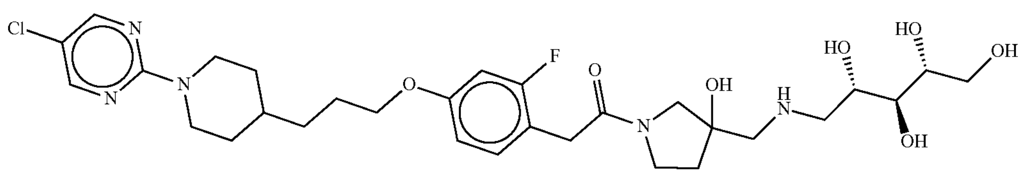 | 2-[4-[3-[1-(5-chloropyrimidin-2-yl)-4-piperidyl]propoxy]-2-fluoro-phenyl]-1-[3-hydroxy-3-[[[(2S,3S,4R)-2,3,4,5-tetrahydroxypentyl]amino]methyl]pyrrolidin-1-yl]ethanone |

TABLE 1-continued

| Ex. # | Structure | Name |
|---|---|---|
| 187 | 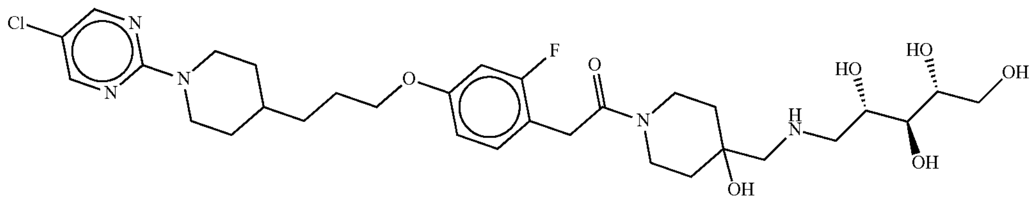 | 2-[4-[3-[1-(5-chloropyrimidin-2-yl)-4-piperidyl]propoxy]-2-fluoro-phenyl]-1-[4-hydroxy-4-[[[(2S,3S,4R)-2,3,4,5-tetrahydroxypentyl]amino]methyl]-1-piperidyl]ethanone |
| 188 | 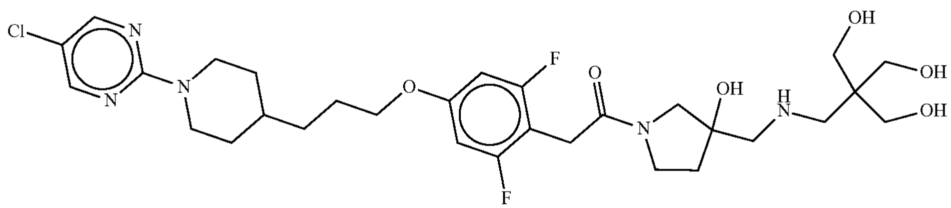 | 2-[4-[3-[1-(5-chloropyrimidin-2-yl)-4-piperidyl]propoxy]-2,6-difluoro-phenyl]-1-[3-hydroxy-3-[[[3-hydroxy-2,2-bis(hydroxymethyl)propyl]amino]methyl]pyrrolidin-1-yl]ethanone |
| 189 | 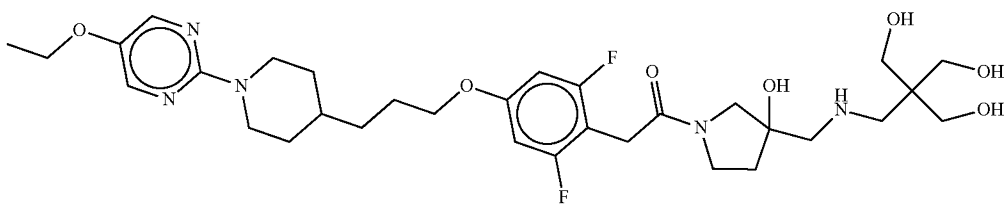 | 2-[4-[3-[1-(5-ethoxypyrimidin-2-yl)-4-piperidyl]propoxy]-2,6-difluoro-phenyl]-1-[3-hydroxy-3-[[[3-hydroxy-2,2-bis(hydroxymethyl)propyl]amino]methyl]pyrrolidin-1-yl]ethanone |
| 190 | 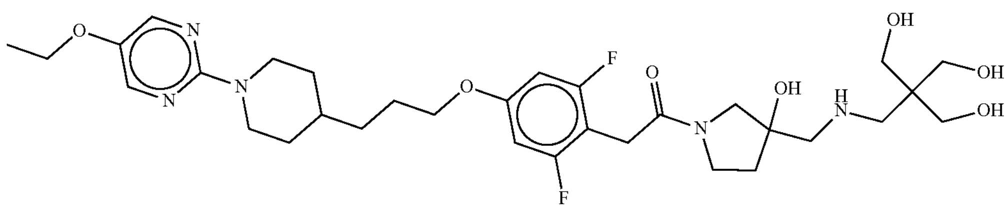 | 2-[2,6-difluoro-4-[3-[1-[5-(methoxymethyl)pyrimidin-2-yl]-4-piperidyl]propoxy]phenyl]-1-[3-hydroxy-3-[[[3-hydroxy-2,2-bis(hydroxymethyl)propyl]amino]methyl]pyrrolidin-1-yl]ethanone |

Further Forms of Compounds

Furthermore, in some embodiments, the compounds described herein exist as "geometric isomers." In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

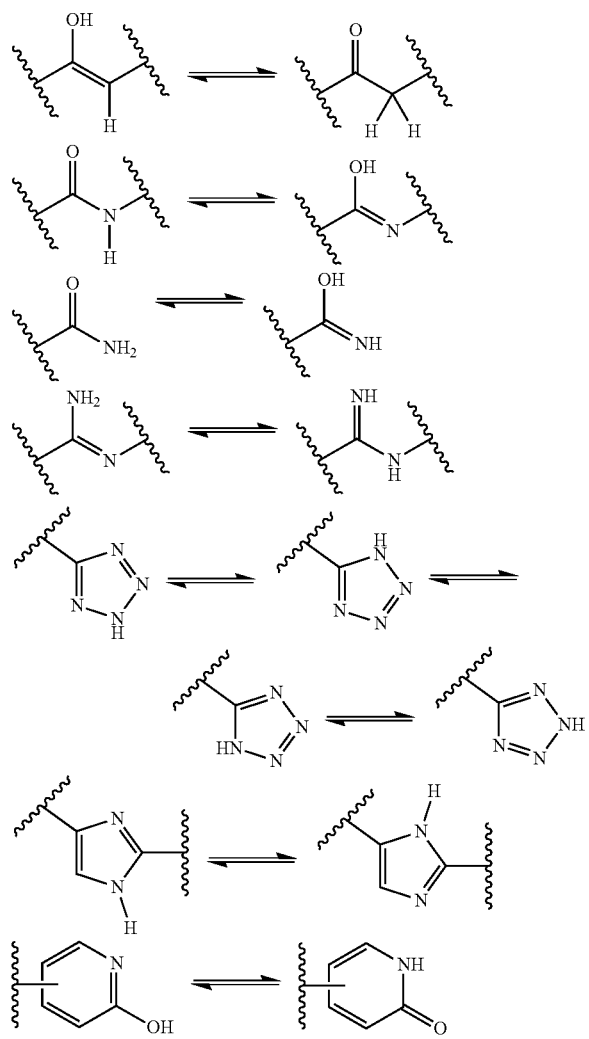

In some situations, the compounds described herein possess one or more chiral centers and each center exists in the (R)-configuration or (S)-configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

The term "positional isomer" refers to structural isomers around a central ring, such as ortho-, meta-, and para-isomers around a benzene ring.

The methods and formulations described herein include the use of N-oxides (if appropriate), crystalline forms (also known as polymorphs), or pharmaceutically acceptable salts of compounds described herein, as well as active metabolites of these compounds having the same type of activity.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of*

*Pharmaceutical Science*, 66:1-19 (1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that is, in some embodiments, converted under physiological conditions or by solvolysis to an active compound described herein. Thus, the term prodrug refers to a precursor of an active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino, carboxy, or mercapto group is bonded to any group that, when the prodrug of the active compound is administered to a mammalian subject, cleaves to form a free hydroxy, free amino, free carboxy, or free mercapto group, respectively. Examples of prodrugs include, but are not limited to, acetate, formate and benzoate derivatives of alcohol or amine functional groups in the active compounds and the like.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. "Hydrates" are formed when the solvent is water, or "alcoholates" are formed when the solvent is alcohol. Solvates of compounds described herein are conveniently prepared or formed during the processes described herein. The compounds provided herein optionally exist in either unsolvated as well as solvated forms.

The compounds disclosed herein, in some embodiments, are used in different enriched isotopic forms, e.g., enriched in the content of $^2H$, $^3H$, $^{11}C$, $^{13}C$ and/or $^{14}C$. In some embodiments, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^3H$, $^{11}C$, $^{13}C$, $^{14}C$, $^{15}C$, $^{12}N$, $^{13}N$, $^{15}N$, $^{16}N$, $^{17}O$, $^{18}O$, $^{14}F$, $^{15}F$, $^{16}F$, $^{17}F$, $^{18}F$, $^{33}S$, $^{34}S$, $^{35}S$, $^{36}S$, $^{35}C$, $^{37}C$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art. In some embodiments deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

In some embodiments, the compounds described herein are labeled by other means, including, but not limited to, the use of chromophores or fluorescent moieties, bioluminescent labels, or chemiluminescent labels.

In certain embodiments, the compounds described herein, or a pharmaceutically acceptable salt, solvate, stereoisomer, or prodrug thereof, as described herein are substantially pure, in that it contains less than about 5%, or less than about 1%, or less than about 0.1%, of other organic small molecules, such as contaminating intermediates or by-products that are created, for example, in one or more of the steps of a synthesis method.

Preparation of the Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as described as outlined in the Examples.

Pharmaceutical Compositions

In some embodiments, disclosed herein is a pharmaceutical composition comprising a GPR119 agonist described herein, or a pharmaceutically acceptable salt, solvate, stereoisomer, or prodrug thereof, and a pharmaceutically acceptable excipient. In some embodiments, the GPR119 agonist is combined with a pharmaceutically suitable (or acceptable) carrier (also referred to herein as a pharmaceutically suitable (or acceptable) excipient, physiologically suitable (or acceptable) excipient, or physiologically suitable (or acceptable) carrier) selected on the basis of a chosen route of administration, e.g., oral administration, and standard pharmaceutical practice as described, for example, in Remington: The Science and Practice of Pharmacy (Gennaro, 21$^{st}$ Ed. Mack Pub. Co., Easton, Pa. (2005)).

Accordingly, provided herein is a pharmaceutical composition comprising a compound described herein, or a pharmaceutically acceptable salt or solvate thereof, together with a pharmaceutically acceptable excipient.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants.

Combination Therapies

In certain embodiments, it is appropriate to administer at least one compound described herein, or a pharmaceutically acceptable salt, solvate, stereoisomer, or prodrug thereof, in combination with one or more other therapeutic agents. In some embodiments, a compound described herein, or a pharmaceutically acceptable salt, solvate, stereoisomer, or prodrug thereof, is administered in combination with a TGR5 agonist, a GPR40 agonist, an SSTR5 antagonist, an SSTR5 inverse agonist, a CCK1 agonist, a PDE4 inhibitor, a DPP-4 inhibitor, a GLP-1 receptor agonist, metformin, or combinations thereof. In certain embodiments, the pharmaceutical composition further comprises one or more anti-diabetic agents. In certain embodiments, the pharmaceutical composition further comprises one or more anti-obesity agents. In certain embodiments, the pharmaceutical composition further comprises one or more agents to treat nutritional disorders.

Examples of a TGR5 agonist to be used in combination with a compound described herein, or a pharmaceutically acceptable salt, solvate, stereoisomer, or prodrug thereof, include: INT-777, XL-475, SRX-1374, RDX-8940, RDX-98940, SB-756050, and those disclosed in WO-2008091540, WO-2010059853, WO-2011071565, WO-2018005801, WO-2010014739, WO-2018005794, WO-2016054208, WO-2015160772, WO-2013096771, WO-2008067222, WO-2008067219, WO-2009026241, WO-2010016846, WO-2012082947, WO-2012149236, WO-2008097976, WO-2016205475, WO-2015183794, WO-2013054338, WO-2010059859, WO-2010014836, WO-2016086115, WO-2017147159, WO-2017147174, WO-2017106818, WO-2016161003, WO-2014100025, WO-2014100021, WO-2016073767, WO-2016130809, WO-2018226724, WO-2018237350, WO-2010093845, WO-2017147137, WO-2015181275, WO-2017027396, WO-2018222701, WO-2018064441, WO-2017053826, WO-2014066819, WO-2017079062, WO-2014200349, WO-2017180577, WO-2014085474.

Examples of a GPR40 agonist to be used in combination with a compound described herein, or a pharmaceutically acceptable salt, solvate, stereoisomer, or prodrug thereof, include: fasiglifam, MR-1704, SCO-267, SHR-0534, HXP-0057-SS, LY-2922470, P-11187, JTT-851, ASP-4178, AMG-837, ID-11014A, HD-C$_{715}$, CNX-011-67, JNJ-076, TU-5113, HD-6277, MK-8666, LY-2881835, CPL-207-280, ZYDG-2, and those described in U.S. Ser. No. 07/750,048, WO-2005051890, WO-2005095338, WO-2006011615, WO-2006083612, WO-2006083781, WO-2007088857, WO-2007123225, WO-2007136572, WO-2008054674, WO-2008054675, WO-2008063768, WO-2009039942, WO-2009039943, WO-2009054390, WO-2009054423, WO-2009054468, WO-2009054479, WO-2009058237, WO-2010085522, WO-2010085525, WO-2010085528, WO-2010091176, WO-2010123016, WO-2010123017, WO-2010143733, WO-2011046851, WO-2011052756, WO-2011066183, WO-2011078371, WO-2011161030, WO-2012004269, WO-2012004270, WO-2012010413, WO-2012011125, WO-2012046869, WO-2012072691, WO-2012111849, WO-2012147518, WO-2013025424, WO-2013057743, WO-2013104257, WO-2013122028, WO-2013122029, WO-2013128378, WO-2013144097, WO-2013154163, WO-2013164292, WO-2013178575, WO-2014019186, WO-2014073904, WO-2014082918, WO-2014086712, WO-2014122067, WO-2014130608, WO-2014146604, WO-2014169817, WO-2014170842, WO-2014187343, WO-2015000412, WO-2015010655, WO-2015020184, WO-2015024448, WO-2015024526, WO-2015028960, WO-2015032328, WO-2015044073, WO-2015051496, WO-2015062486, WO-2015073342, WO-2015078802, WO-2015084692, WO-2015088868, WO-2015089809, WO-2015097713, WO-2015105779, WO-2015105786, WO-2015119899, WO-2015176267, WO-201600771, WO-2016019587, WO-2016022446, WO-2016022448, WO-2016022742, WO-2016032120, WO-2016057731, WO-2017025368, WO-2017027309, WO-2017027310, WO-2017027312, WO-2017042121, WO-2017172505, WO-2017180571, WO-2018077699, WO-2018081047, WO-2018095877, WO-2018106518, WO-2018111012, WO-2018118670, WO-2018138026, WO-2018138027, WO-2018138028, WO-2018138029, WO-2018138030, WO-2018146008, WO-2018172727, WO-2018181847, WO-2018182050, WO-2018219204, WO-2019099315, and WO-2019134984.

Examples of a SSTR5 antagonist or inverse agonist to be used in combination with a compound described herein, or a pharmaceutically acceptable salt, solvate, stereoisomer, or prodrug thereof, include those described in: WO-03104816, WO-2009050309, WO-2015052910, WO-2011146324, WO-2006128803, WO-2010056717, WO-2012024183, and WO-2016205032.

Examples of a CCK1 agonist to be used in combination with a compound described herein, or a pharmaceutically acceptable salt, solvate, stereoisomer, or prodrug thereof, include: A-70874, A-71378, A-71623, A-74498, CE-326597, GI-248573, GSKI-181771X, NN-9056, PD-149164, PD-134308, PD-135158, PD-170292, PF-04756956, SR-146131, SSR-125180, and those described in EP-00697403, US-20060177438, WO-2000068209, WO-2000177108, WO-2000234743, WO-2000244150, WO-2009119733, WO-2009314066, WO-2009316982, WO-2009424151, WO-2009528391, WO-2009528399, WO-2009528419, WO-2009611691, WO-2009611940, WO-2009851686, WO-2009915525, WO-2005035793, WO-2005116034, WO-2007120655, WO-2007120688, WO-2008091631, WO-2010067233, WO-2012070554, and WO-2017005765.

Examples of a PDE4 inhibitor to be used in combination with a compound described herein, or a pharmaceutically acceptable salt, solvate, stereoisomer, or prodrug thereof, include: apremilast, cilomilast, crisaborole, diazepam, luteolin, piclamilast, and roflumilast.

Examples of a DPP-4 inhibitor to be used in combination with a compound described herein, or a pharmaceutically acceptable salt, solvate, stereoisomer, or prodrug thereof, include: sitagliptin, vildagliptin, saxagliptin, linagliptin, gemigliptin, teneligliptin, alogliptin, trelagliptin, omarigliptin, evogliptin, gosogliptin, and dutogliptin.

Examples of a GLP-1 receptor agonist to be used in combination with a compound described herein, or a pharmaceutically acceptable salt, solvate, stereoisomer, or prodrug thereof, include: albiglutide, dulaglutide, exenatide, extended-release exenatide, liraglutide, lixisenatide, and semaglutide.

Examples of anti-diabetic agents to be used in combination with a compound described herein, or a pharmaceutically acceptable salt, solvate, stereoisomer, or prodrug thereof, include: GLP-1 receptor agonists such as exenatide, liraglutide, taspoglutide, lixisenatide, albiglutide, dulaglutide, semaglutide, OWL833 and ORMD 0901; SGLT2 inhibitors such as dapagliflozin, canagliflozin, empagliflozin, ertugliflozin, ipragliflozin, luseogliflozin, remogliflozin, sergliflozin, sotagliflozin, and tofogliflozin; biguinides such as metformin; insulin and insulin analogs.

Examples of anti-obesity agents to be used in combination with a compound described herein, or a pharmaceutically acceptable salt, solvate, stereoisomer, or prodrug thereof, include: GLP-1 receptor agonists such as liraglutide, semaglutide; SGLT1/2 inhibitors such as LIK066, pramlintide and other amylin analogs such as AM-833, AC2307, and BI 473494; PYY analogs such as NN-9747, NN-9748, AC-162352, AC-163954, GT-001, GT-002, GT-003, and RHS-08; GIP receptor agonists such as APD-668 and APD-597; GLP-1/GIP co-agonists such as tirzepatide (LY329176), BHM-089, LBT-6030, CT-868, SCO-094, NNC-0090-2746, RG-7685, NN-9709, and SAR-438335; GLP-1/glucagon co-agonist such as cotadutide (MED10382), BI 456906, TT-401, G-49, H&D-001A, ZP-2929, and HM-12525A; GLP-1/GIP/glucagon triple agonist such as SAR-441255, HM-15211, and NN-9423; GLP-1/secretin co-agonists such as GUB06-046; leptin analogs such as metreleptin; GDF15 modulators such as those described in WO2012138919, WO2015017710, WO2015198199, WO-2017147742 and WO-2018071493; FGF21 receptor modulators such as NN9499, NGM386, NGM313, BFKB8488A (RG7992), AKR-001, LLF-580, CVX-343, LY-2405319, B1089-100, and BMS-986036; MC4 agonists such as setmelanotide; MetAP2 inhibitors such as ZGN-1061; ghrelin receptor modulators such as HM04 and AZP-531; ghrelin O-acyltransferase inhibitors such as T-3525770 (RM-852) and GLWL-01; and oxytocin analogs such as carbetocin.

Examples of agents for nutritional disorders to be used in combination with a compound described herein, or a pharmaceutically acceptable salt, solvate, stereoisomer, or prodrug thereof, include: GLP-2 receptor agonists such as tedaglutide, glepaglutide (ZP1848), elsiglutide (ZP1846), apraglutide (FE 203799), HM-15912, NB-1002, GX-G8, PE-0503, SAN-134, and those described in WO-2011050174, WO-2012028602, WO-2013164484, WO-2019040399, WO-2018142363, WO-2019090209, WO-2006117565, WO-2019086559, WO-2017002786, WO-2010042145, WO-2008056155, WO-2007067828, WO-2018229252, WO-2013040093, WO-2002066511, WO-2005067368, WO-2009739031, WO-2009632414, and WO2008028117; and GLP-1/GLP-2 receptor co-agonists such as ZP-GG-72 and those described in WO-2018104561, WO-2018104558, WO-2018103868, WO-2018104560, WO-2018104559, WO-2018009778, WO-2016066818, and WO-2014096440.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt, solvate, stereoisomer, or prodrug thereof, is co-administered with one or more additional therapeutic agents, wherein the compound described herein, or a pharmaceutically acceptable salt, solvate, stereoisomer, or prodrug thereof, and the additional therapeutic agent(s) modulate different aspects of the disease, disorder or condition being treated, thereby providing a greater overall benefit than administration of either therapeutic agent alone. In some embodiments, the additional therapeutic agent(s) is a TGR5 agonist, a GPR40 agonist, an SSTR5 antagonist, an SSTR5 inverse agonist, a CCK1 agonist, a PDE4 inhibitor, a DPP-4 inhibitor, a GLP-1 receptor agonist, metformin, or combinations thereof. In some embodiments, the additional therapeutic agent is an anti-diabetic agent. In some embodiments, the additional therapeutic agent is an anti-obesity agent. In some embodiments, the additional therapeutic agent is an agent to treat nutritional disorders.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or pharmaceutically acceptable salts, solvates, stereoisomers, or prodrugs thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease.

In some embodiments, a compound described herein, or a pharmaceutically acceptable salt thereof, is administered in combination with anti-inflammatory agent, anti-cancer agent, immunosuppressive agent, steroid, non-steroidal anti-inflammatory agent, antihistamine, analgesic, hormone blocking therapy, radiation therapy, monoclonal antibodies, or combinations thereof.

EXAMPLES

List of Abbreviations

As used above, and throughout the description of the invention, the following abbreviations, unless otherwise indicated, shall be understood to have the following meanings:
ACN or MeCN acetonitrile
AIBN azobisisobutyronitrile
BPO benzoyl peroxide
Boc or BOC tert-butyloxycarbonyl
Bn benzyl
BnBr benzyl bromide
DCC N,N'-dicyclohexylcarbodiimide
DCM dichloromethane ($CH_2Cl_2$)
DIAD diisopropyl azodicarboxylate
DIPEA or DIEA diisopropylethylamine
DMAP 4-dimethylaminopyridine
DMF dimethylformamide
DMSO dimethylsulfoxide
EDCI l-ethyl-3-(3-dimethylaminopropyl)carbodiimide
eq equivalent(s)
Et ethyl
EtOH ethanol
EtOAc ethyl acetate
FA formic acid
h, hr(s) hour(s)
HATU 1-[bis(dimethylamino)methylene]-1H-1,2,3-triazolo[4,5-b]pyridinium 3-oxid hexafluorophosphate
HPLC high performance liquid chromatography
i-PrOH iso-propanol
LCMS liquid chromatography-mass spectrometry
Me methyl
MeOH methanol
MS mass spectroscopy
Ms methanesulfonyl (mesyl)
MsCl methanesulfonyl chloride (mesyl chloride)
NBS N-bromosuccinimide
NMR nuclear magnetic resonance
Rt or RT room temperature
TEA triethylamine
Tf trifluoromethylsulfonyl (triflyl)
TFA trifluoroacetic acid
THF tetrahydrofuran
TLC thin layer chromatography
Tol or tol toluene
tR retention time
I. Chemical Synthesis
Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Intermediate 1: 2-(4-(3-(1-(5-chloropyrimidin-2-yl)piperidin-4-yl)propoxy)-2-fluorophenyl)acetic acid

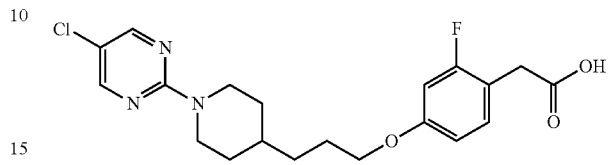

Step 1: 3-(1-(5-chloropyrimidin-2-yl)piperidin-4-yl)propan-1-ol

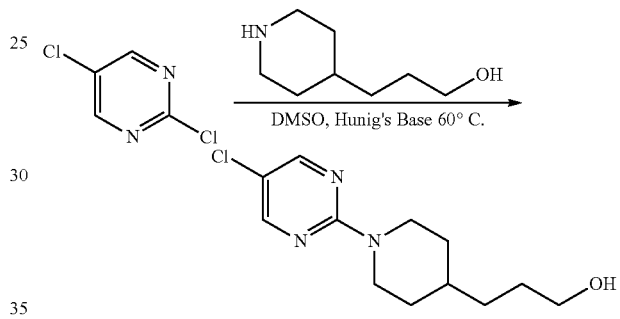

A mixture of 2,5-dichloropyrimidine (2.5 g, 16.78 mmol), 3-(piperidin-4-yl)propan-1-ol (2.4 g, 16.78 mmol) and Hunig's base (5.85 mL, 33.56 mmol) in DMSO (30 mL) was heated at 60° C. overnight. Mixture cooled and poured into water (150 mL) and extracted with EtOAc (3×50 mL); combined EtOAc layers washed with sat. NaCl (50 ML), dried over $Na_2SO_4$, filtered and evaporated. The residue was purified by silica gel column chromatography (Teledyne Isco: SNAP 80 g GOLD) eluent: gradient 0-100% EtOAc in Hexanes to give 3-(1-(5-chloropyrimidin-2-yl)piperidin-4-yl)propan-1-ol (3.56 g, 82%) as a white solid. $^1$H NMR (500 MHz, Chloroform-d) δ 8.19 (s, 2H), 4.67 (ddt, J=13.4, 4.3, 1.9 Hz, 2H), 3.65 (t, J=6.6 Hz, 2H), 2.85 (ddd, J=13.3, 12.3, 2.8 Hz, 2H), 1.80-1.74 (m, 2H), 1.65-1.58 (m, 3H), 1.53 (th, J=10.7, 3.5 Hz, 1H), 1.36-1.30 (m, 3H), 1.16 (tdd, J=13.3, 11.6, 4.2 Hz, 2H). LCMS: tR=0.64, (ES$^+$) m/z (M+H)$^+$=256.2.

Step 2: methyl 2-(4-(3-(1-(5-chloropyrimidin-2-yl)piperidin-4-yl)propoxy)-2-fluorophenyl)acetate

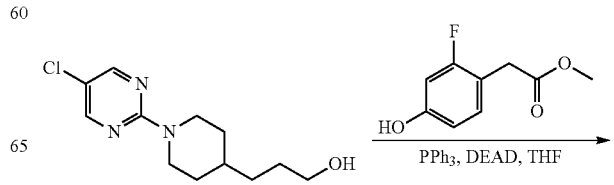

-continued

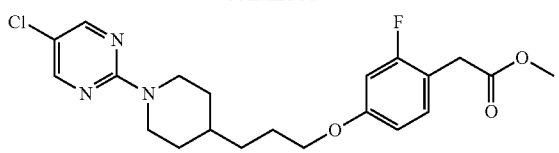

To a mixture of 3-[1-(5-chloropyrimidin-2-yl)-4-piperidyl]propan-1-ol (1.13 g, 4.4 mmol) and methyl-2-fluoro-4-hydroxyphenyl acetate (814 mg, 4.4 mmol) and triphenyl phosphine (2.5 g of polymer bound ~3 mmol/g, 6.6 mmol) in DCM (20 mL) was added DEAD (2.98 mL of a 40% wt solution in toluene, 6.6 mmol) and the resulting mixture stirred at room temperature overnight. Mixture filtered through celite and the filtrate evaporated. The residue was purified by silica gel column chromatography (Teledyne Isco: SNAP 40 g GOLD) eluent: gradient 0-30% EtOAc in Heptane to give 2-(4-(3-(1-(5-chloropyrimidin-2-yl)piperidin-4-yl)propoxy)-2-fluorophenyl)acetate (1.14 g, 61%) as a white solid. $^1$H NMR (500 MHz, Chloroform-d) δ 8.20 (s, 2H), 7.13 (t, J=8.5 Hz, 1H), 6.66-6.63 (m, 1H), 6.61 (dd, J=11.6, 2.5 Hz, 1H), 4.68 (dp, J=13.2, 1.9 Hz, 2H), 3.93 (t, J=6.4 Hz, 2H), 3.70 (s, 3H), 3.61-3.58 (m, 2H), 2.86 (ddd, J=13.3, 12.3, 2.8 Hz, 2H), 1.86-1.77 (m, 4H), 1.56 (ddd, J=11.1, 8.5, 4.8 Hz, 1H), 1.42 (dddd, J=9.3, 7.2, 5.6, 2.5 Hz, 2H), 1.23-1.13 (m, 2H). LCMS: tR=1.59, (ES$^+$) m/z (M+H)$^+$=422.2.

Step 3: 2-(4-(3-(1-(5-chloropyrimidin-2-yl)piperidin-4-yl)propoxy)-2-fluorophenyl)acetic acid

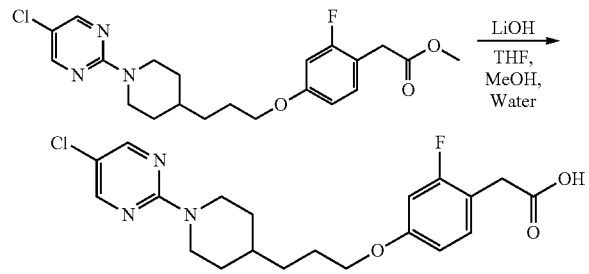

To a solution of methyl 2-[4-[3-[1-(5-chloropyrimidin-2-yl)-4-piperidyl]propoxy]-2-fluoro-phenyl]acetate (1.14 g, 2.7 mmol) in THF (15 mL) and MeOH (5 mL) was added lithium hydroxide (5.4 mL of a 1M aqueous soln, 5.4 mmol) and the resulting mixture stirred at room temperature for 1 hour. Mixture evaporated to remove organic solvents and remaining aqueous diluted with water (20 mL) and acidified by the addition of 1N HCl and extracted with DCM (2×15 mL); combined DCM layers dried over Na$_2$SO$_4$, filtered and evaporated to give 2-(4-(3-(1-(5-chloropyrimidin-2-yl)piperidin-4-yl)propoxy)-2-fluorophenyl)acetic acid (1.1 g, 99%) as a white solid. $^1$H NMR (500 MHz, Chloroform-d) δ 8.20 (s, 2H), 7.13 (t, J=8.5 Hz, 1H), 6.67-6.63 (m, 1H), 6.62 (dd, J=11.5, 2.5 Hz, 1H), 4.67 (dp, J=13.2, 1.9 Hz, 2H), 3.93 (t, J=6.4 Hz, 2H), 3.63 (d, J=1.2 Hz, 2H), 2.86 (ddd, J=13.3, 12.3, 2.7 Hz, 2H), 1.86-1.75 (m, 4H), 1.57 (ddt, J=14.7, 7.0, 3.7 Hz, 1H), 1.45-1.38 (m, 2H), 1.23-1.12 (m, 2H). LCMS: tR=1.28, (ES$^+$) m/z (M+H)$^+$=408.2.

Intermediate 2: 2-(4-(3-(1-(5-chloropyrimidin-2-yl)piperidin-4-yl)propoxy)-2,6-difluorophenyl)acetic acid

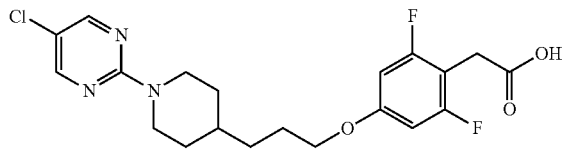 [SMILES: O=C(O)Cc1c(F)cc(OCCCC2CCN(c3ncc(Cl)cn3)CC2)cc1F]

Prepared using procedures outlined in the preparation of intermediate 1; replacing methyl 2-fluoro-4-hydroxyphenyl acetate with methyl 2-(2,6-difluoro-4-hydroxyphenyl)acetate in step 2 to give 2-(4-(3-(1-(5-chloropyrimidin-2-yl)piperidin-4-yl)propoxy)-2,6-difluorophenyl)acetic acid. $^1$H NMR (500 MHz, Chloroform-d) δ 8.20 (s, 2H), 6.49-6.41 (m, 2H), 4.68 (dp, J=13.4, 2.0 Hz, 2H), 3.91 (t, J=6.4 Hz, 2H), 3.67 (d, J=1.3 Hz, 2H), 2.92-2.81 (m, 2H), 1.86-1.75 (m, 4H), 1.56 (ddt, J=14.5, 7.0, 3.6 Hz, 1H), 1.46-1.37 (m, 3H), 1.18 (qd, J=12.5, 4.2 Hz, 2H). LCMS: tR=1.51, (ES$^+$) m/z (M+H)$^+$=426.1.

Intermediate 3: 2-(4-(4-(1-(5-chloropyrimidin-2-yl)piperidin-4-yl)butoxy)-2-fluorophenyl)acetic acid

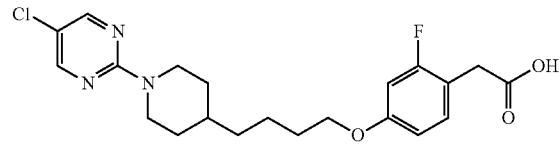 [SMILES: O=C(O)Cc1ccc(OCCCCC2CCN(c3ncc(Cl)cn3)CC2)cc1F]

Prepared using procedures outlined in the preparation of intermediate 1; replacing 3-(piperidin-4-yl)propan-1-ol with 4-(piperidin-4-yl)butan-1-ol in step 1 to give 2-(4-(4-(1-(5-chloropyrimidin-2-yl)piperidin-4-yl)butoxy)-2-fluorophenyl)acetic acid. $^1$H NMR (500 MHz, DMSO-d$_6$) δ 8.36 (s, 2H), 7.14 (t, J=8.7 Hz, 1H), 6.68-6.62 (m, 2H), 4.57 (dt, J=13.8, 3.0 Hz, 2H), 3.93 (t, J=6.5 Hz, 2H), 3.22 (s, 2H), 2.87 (td, J=12.8, 2.7 Hz, 2H), 1.76-1.65 (m, 4H), 1.54 (ddp, J=10.8, 6.8, 3.5 Hz, 1H), 1.48-1.40 (m, 2H), 1.27 (q, J=7.2 Hz, 2H), 1.03 (qd, J=12.6, 4.2 Hz, 2H). LCMS: tR=1.48, (ES$^+$) m/z (M+H)$^+$=422.2.

Intermediate 4: 2-(4-(4-(1-(5-chloropyrimidin-2-yl)piperidin-4-yl)butoxy)-2,6-difluorophenyl)acetic acid

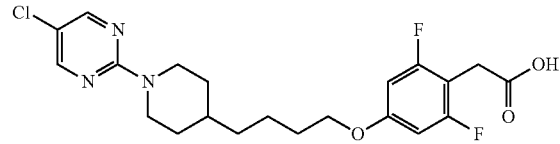 [SMILES: O=C(O)Cc1c(F)cc(OCCCCC2CCN(c3ncc(Cl)cn3)CC2)cc1F]

Prepared using procedures outlined in the preparation of intermediate 1; 3-(piperidin-4-yl)propan-1-ol with 4-(piperidin-4-yl)butan-1-ol in step 1 and methyl 2-fluoro-4-hydroxyphenyl acetate with methyl 2-(2,6-difluoro-4-hydroxyphenyl)acetate in step 2 to give 2-(4-(4-(1-(5- chloropyrimidin-2-yl)piperidin-4-yl)butoxy)-2,6-difluorophenyl)acetic acid. ¹H NMR (500 MHz, Chloroform-d) δ 8.20 (s, 2H), 6.49-6.41 (m, 2H), 4.65 (dq, J=13.4, 2.3 Hz, 2H), 3.92 (t, J=6.3 Hz, 2H), 3.66 (s, 2H), 2.90-2.80 (m, 2H), 1.80-1.73 (m, 4H), 1.57-1.44 (m, 3H), 1.35-1.28 (m, 2H), 1.19-1.09 (m, 2H). LCMS: tR=1.49, (ES⁺) m/z (M+H)⁺=440.1.

Intermediate 5: 2-(4-(3-(1-(5-ethylpyrimidin-2-yl)piperidin-4-yl)propoxy)-2-fluorophenyl)acetic acid

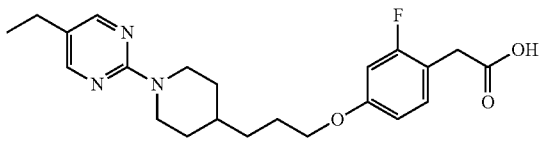

Prepared using procedures outlined in the preparation of intermediate 1; replacing 2,5-dichloropyrimidine with 2-chloro-5-ethylpyrimidine in step 1 to give 2-(4-(3-(1-(5-ethylpyrimidin-2-yl)piperidin-4-yl)propoxy)-2-fluorophenyl)acetic acid. ¹H NMR (500 MHz, Chloroform-d) δ 8.20 (s, 2H), 6.49-6.41 (m, 2H), 4.65 (dq, J=13.4, 2.3 Hz, 2H), 3.92 (t, J=6.3 Hz, 2H), 3.66 (s, 2H), 2.90-2.80 (m, 2H), 1.80-1.73 (m, 4H), 1.57-1.44 (m, 3H), 1.35-1.28 (m, 2H), 1.19-1.09 (m, 2H). LCMS: tR=1.07, (ES⁺) m/z (M+H)⁺=402.3.

Intermediate 6: 2-(4-(3-(1-(5-ethylpyrimidin-2-yl)piperidin-4-yl)propoxy)-2,6-difluorophenyl)acetic acid

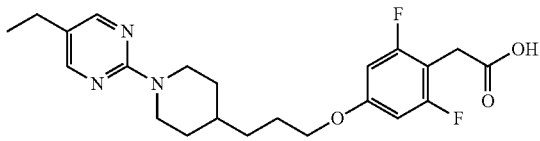 [SMILES: CCc1cnc(N2CCC(CCCOc3cc(F)c(CC(=O)O)c(F)c3)CC2)nc1]

Prepared using procedures outlined in the preparation of intermediate 1; replacing 2,5-dichloropyrimidine with 2-chloro-5-ethylpyrimidine in step 1 and methyl 2-fluoro-4-hydroxyphenyl acetate with methyl 2-(2,6-difluoro-4-hydroxyphenyl)acetate in step 2 to give 2-(4-(3-(1-(5-ethylpyrimidin-2-yl)piperidin-4-yl)propoxy)-2,6-difluorophenyl)acetic acid. ¹H NMR (500 MHz, Chloroform-d) δ 8.20 (s, 2H), 6.49-6.41 (m, 2H), 4.65 (dq, J=13.4, 2.3 Hz, 2H), 3.92 (t, J=6.3 Hz, 2H), 3.66 (s, 2H), 2.90-2.80 (m, 2H), 1.80-1.73 (m, 4H), 1.57-1.44 (m, 3H), 1.35-1.28 (m, 2H), 1.19-1.09 (m, 2H). LCMS: tR=0.96, (ES⁺) m/z (M+H)⁺=420.3.

Intermediate 7: 2-(2-fluoro-4-(3-(1-(5-propylpyrimidin-2-yl)piperidin-4-yl)propoxy)phenyl)acetic acid

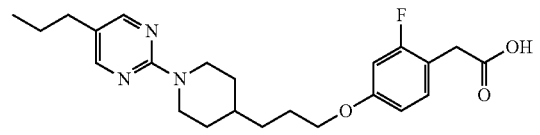 [SMILES: CCCc1cnc(N2CCC(CCCOc3ccc(CC(=O)O)c(F)c3)CC2)nc1]

Prepared using procedures outlined in the preparation of intermediate 1; replacing 2,5-dichloropyrimidine with 2-chloro-5-propylpyrimidine in step 1 to give 2-(2-fluoro-4-(3-(1-(5-propylpyrimidin-2-yl)piperidin-4-yl)propoxy)phenyl)acetic acid. ¹H NMR (500 MHz, Chloroform-d) δ 8.20 (s, 2H), 7.22 (t, J=8.6 Hz, 1H), 6.64 (dd, J=8.5, 2.5 Hz, 1H), 6.58 (dd, J=11.7, 2.5 Hz, 1H), 4.68 (dp, J=13.2, 1.9 Hz, 2H), 4.29-4.21 (m, 1H), 4.16-4.09 (m, 1H), 3.92 (t, J=6.5 Hz, 2H), 3.81 (dd, J=8.5, 5.6 Hz, 1H), 3.73-3.62 (m, 3H), 3.38 (s, 2H), 2.91-2.82 (m, 2H), 2.73 (ddt, J=10.3, 7.9, 4.0 Hz, 1H), 1.86 (dt, J=7.7, 6.3 Hz, 2H), 1.83-1.76 (m, 4H), 1.60-1.53 (m, 1H), 1.45-1.38 (m, 3H), 1.23-1.13 (m, 2H). LCMS: tR=1.26, (ES⁺) m/z (M+H)⁺=416.3.

Intermediate 8: 2-(2,6-difluoro-4-(3-(1-(5-propylpyrimidin-2-yl)piperidin-4-yl)propoxy)phenyl)acetic acid

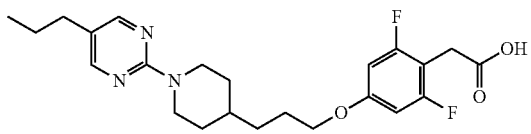

Prepared using procedures outlined in the preparation of intermediate 1; replacing 2,5-dichloropyrimidine with 2-chloro-5-propylpyrimidine in step 1 and methyl 2-fluoro-4-hydroxyphenyl acetate with methyl 2-(2,6-difluoro-4-hydroxyphenyl)acetate in step 2 to give 2-(2,6-difluoro-4-(3-(1-(5-propylpyrimidin-2-yl)piperidin-4-yl)propoxy)phenyl)acetic acid. ¹H NMR (500 MHz, Chloroform-d) δ 8.10 (s, 2H), 6.38 (d, J=9.1 Hz, 2H), 4.61 (dt, J=13.4, 2.8 Hz, 2H), 3.84 (t, J=6.4 Hz, 2H), 3.59 (s, 2H), 2.87-2.76 (m, 2H), 2.32 (t, J=7.5 Hz, 2H), 1.73 (ddd, J=10.5, 8.3, 4.1 Hz, 4H), 1.49 (h, J=7.4 Hz, 3H), 1.34 (ddt, J=12.3, 7.0, 3.4 Hz, 2H), 1.13 (qd, J=12.5, 4.2 Hz, 2H), 0.86 (t, J=7.3 Hz, 3H). LCMS: tR=1.32, (ES⁺) m/z (M+H)⁺=434.3.

Intermediate 9: 2-(2-fluoro-4-(3-(1-(5-methoxypyrimidin-2-yl)piperidin-4-yl)propoxy)phenyl)acetic acid

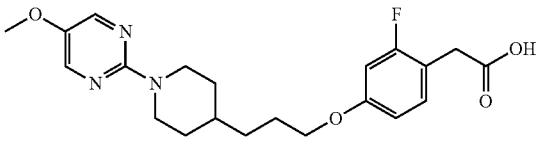 [SMILES: COc1cnc(N2CCC(CCCOc3ccc(CC(=O)O)c(F)c3)CC2)nc1]

Prepared using procedures outlined in the preparation of intermediate 1; replacing 2,5-dichloropyrimidine with 2-chloro-5-methoxypyrimidine in step 1 to give 2-(2-fluoro-4-(3-(1-(5-methoxypyrimidin-2-yl)piperidin-4-yl)propoxy)phenyl)acetic acid. ¹H NMR (500 MHz, Chloroform-d) δ 8.12 (s, 2H), 7.14 (t, J=8.5 Hz, 1H), 6.65 (dd, J=8.5, 2.8 Hz, 1H), 6.62 (dd, J=11.5, 2.5 Hz, 1H), 4.62 (dt, J=13.3, 2.8 Hz, 2H), 3.93 (t, J=6.4 Hz, 2H), 3.80 (s, 3H), 3.63 (d, J=1.1 Hz, 2H), 2.88 (td, J=12.9, 2.7 Hz, 2H), 1.84-1.77 (m, 4H), 1.55 (ddp, J=11.1, 7.1, 3.5 Hz, 1H), 1.47-1.38 (m, 2H), 1.26-1.15 (m, 2H). LCMS: tR=1.95, (ES⁺) m/z (M+H)⁺=404.2.

Intermediate 10: 2-(4-(3-(1-(5-ethoxypyrimidin-2-yl)piperidin-4-yl)propoxy)-2-fluorophenyl)acetic acid

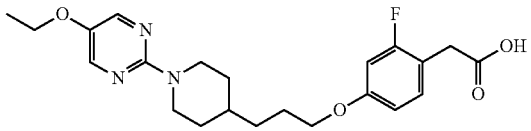 [SMILES: CCOc1cnc(N2CCC(CCCOc3ccc(CC(=O)O)c(F)c3)CC2)nc1]

Prepared using procedures outlined in the preparation of intermediate 1; replacing 2,5-dichloro pyrimidine with 2-chloro-5-ethoxypyrimidine in step 1 to give 2-(4-(3-(1-(5-ethoxypyrimidin-2-yl) piperidin-4-yl)propoxy)-2-fluorophenyl)acetic acid. 1H NMR (500 MHz, Chloroform-d) δ 8.09 (s, 2H), 7.14 (t, J=8.6 Hz, 1H), 6.65 (dd, J=8.4, 2.6 Hz, 1H), 6.62 (dd, J=11.5, 2.5 Hz, 1H), 4.61 (dt, J=12.5, 2.8 Hz, 2H), 3.99 (q, J=7.0 Hz, 2H), 3.93 (t, J=6.5 Hz, 2H), 3.63 (d, J=1.1 Hz, 2H), 2.85 (td, J=12.8, 2.6 Hz, 2H), 1.86-1.76 (m, 4H), 1.54 (dddt, J=14.8, 10.8, 7.0, 3.6 Hz, 1H), 1.45-1.34 (m, 5H), 1.24-1.16 (m, 2H). LCMS: tR=0.96, (ES$^+$) m/z (M+H)$^+$=418.3.

Intermediate 11: 2-(2-fluoro-4-(3-(1-(5-(methoxymethyl)pyrimidin-2-yl)piperidin-4-yl)propoxy) phenyl)acetic acid

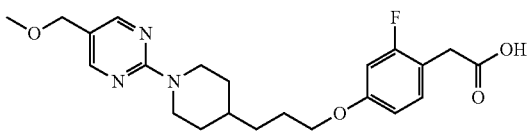 [SMILES: COCc1cnc(N2CCC(CCCOc3ccc(CC(=O)O)c(F)c3)CC2)nc1]

Prepared using procedures outlined in the preparation of intermediate 1; replacing 2,5-dichloropyrimidine with 2-chloro-5-(methoxmethyl)pyrimidine in step 1 to give 2-(2-fluoro-4-(3-(1-(5-(methoxymethyl)pyrimidin-2-yl)piperidin-4-yl)propoxy)phenyl)acetic acid. $^1$H NMR (500 MHz, Chloroform-d) δ 8.29 (s, 2H), 7.14 (t, J=8.6 Hz, 1H), 6.67-6.64 (m, 1H), 6.62 (dd, J=11.5, 2.5 Hz, 1H), 6.47 (s, 1H), 4.78-4.70 (m, 2H), 4.26 (s, 2H), 4.21 (q, J=7.1 Hz, 2H), 3.93 (t, J=6.4 Hz, 2H), 3.63 (d, J=1.2 Hz, 2H), 3.34 (s, 3H), 2.89 (td, J=12.9, 2.7 Hz, 2H), 1.86-1.77 (m, 4H), 1.58 (ddt, J=11.3, 7.8, 4.3 Hz, 1H), 1.45-1.39 (m, 2H), 1.28 (t, J=7.1 Hz, 3H), 1.18 (qd, J=12.3, 4.2 Hz, 2H). LCMS: tR=0.96, (ES$^+$) m/z (M+H)$^+$=418.3.

Intermediate 12: 2-(2,6-difluoro-4-(3-(1-(5-(methoxymethyl)pyrimidin-2-yl)piperidin-4-yl)propoxy) phenyl)acetic acid

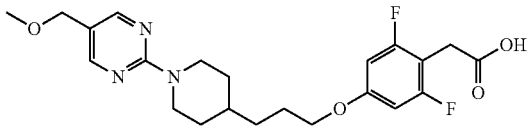

Prepared using procedures outlined in the preparation of intermediate 1; replacing 2,5-dichloropyrimidine with 2-chloro-5-(methoxymethyl)pyrimidine in step 1 and methyl 2-fluoro-4-hydroxyphenyl acetate with methyl 2-(2,6-difluoro-4-hydroxyphenyl)acetate in step 2 to give 2-(2,6-difluoro-4-(3-(1-(5-propylpyrimidin-2-yl)piperidin-4-yl)propoxy)phenyl)acetic acid. $^1$H NMR (500 MHz, Chloroform-d) δ 8.28 (s, 2H), 6.49-6.41 (m, 2H), 4.78-4.70 (m, 2H), 4.26 (s, 2H), 3.91 (t, J=6.4 Hz, 2H), 3.66 (s, 2H), 3.34 (s, 3H), 2.88 (td, J=12.9, 2.7 Hz, 2H), 1.87-1.75 (m, 4H), 1.57 (dtq, J=14.7, 7.0, 3.4 Hz, 1H), 1.45-1.36 (m, 2H), 1.23-1.13 (m, 2H). LCMS: tR=0.86, (ES$^+$) m/z (M+H)$^+$=436.5.

Intermediate 13: 2-(2-fluoro-4-(4-(1-(5-(methoxymethyl)pyrimidin-2-yl)piperidin-4-yl)butoxy)phenyl) acetic acid

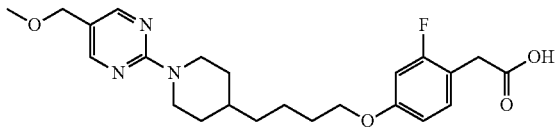 [SMILES: COCc1cnc(N2CCC(CCCCOc3ccc(CC(=O)O)c(F)c3)CC2)nc1]

Prepared using procedures outlined in the preparation of intermediate 1; replacing 2,5-dichloropyrimidine with 2-chloro-5-(methoxymethyl)pyrimidine and 3-(piperidin-4-yl)propan-1-ol with 4-(piperidin-4-yl)butan-1-ol in step 1 to give 2-(2-fluoro-4-(4-(1-(5-(methoxymethyl)pyrimidin-2-yl)piperidin-4-yl)butoxy)phenyl)acetic acid. $^1$H NMR (500 MHz, Chloroform-d) δ 8.27 (s, 2H), 7.22 (t, J=8.6 Hz, 1H), 6.68-6.63 (m, 1H), 6.59 (dd, J=11.7, 2.5 Hz, 1H), 4.76-4.69 (m, 2H), 4.26 (s, 2H), 4.20 (t, J=8.5 Hz, 1H), 4.11-4.03 (m, 1H), 3.98-3.88 (m, 3H), 3.82-3.72 (m, 3H), 3.40 (d, J=1.5 Hz, 2H), 3.34 (s, 3H), 2.87 (td, J=12.9, 2.7 Hz, 2H), 2.82-2.73 (m, 1H), 1.81-1.74 (m, 4H), 1.56-1.46 (m, 2H), 1.32 (dt, J=9.1, 6.8 Hz, 2H), 1.20-1.12 (m, 2H). LCMS: tR=0.86, (ES$^+$) m/z (M+H)$^+$=432.3

Intermediate 14: 2-(2,6-difluoro-4-(4-(1-(5-(methoxymethyl)pyrimidin-2-yl)piperidin-4-yl)butoxy)phenyl)acetic acid

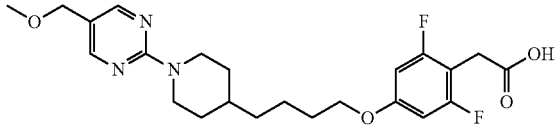

Prepared using procedures outlined in the preparation of intermediate 1; replacing 2,5-dichloropyrimidine with 2-chloro-5-(methoxymethyl)pyrimidine and 3-(piperidin-4-yl)propan-1-ol with 4-(piperidin-4-yl)butan-1-ol in step 1 and methyl 2-fluoro-4-hydroxyphenyl acetate with methyl 2-(2,6-difluoro-4-hydroxyphenyl)acetate in step 2 to 2-(2,6-difluoro-4-(4-(1-(5-(methoxymethyl)pyrimidin-2-yl)piperidin-4-yl)butoxy)phenyl)acetic acid. $^1$H NMR (500 MHz, Chloroform-d) δ 8.27 (s, 2H), 6.44 (d, J=9.2 Hz, 2H), 4.73 (dq, J=13.3, 2.2 Hz, 2H), 4.25 (d, J=8.8 Hz, 3H), 4.08 (dd, J=10.0, 8.5 Hz, 1H), 3.98 (dd, J=8.6, 5.2 Hz, 1H), 3.90 (t, J=6.4 Hz, 2H), 3.79 (ddd, J=11.5, 7.9, 4.9 Hz, 3H), 3.40 (s, 2H), 3.34 (s, 3H), 2.91-2.84 (m, 2H), 2.83-2.76 (m, 1H), 1.81-1.73 (m, 2H), 1.57-1.44 (m, 1H), 1.20-1.11 (m, 1H). LCMS: tR=0.92, (ES$^+$) m/z (M+H)$^+$=450.3

Intermediate 15: tert-butyl 4-((1R,2R)-2-(hydroxymethyl)cyclopropyl)piperidine-1-carboxylate

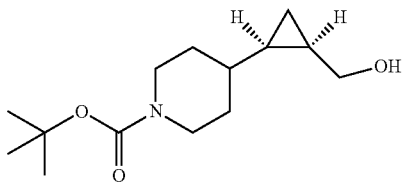 [SMILES: CC(C)(C)OC(=O)N1CCC([C@H]2C[C@H]2CO)CC1]

Step 1: tert-butyl 4-(2,2-dibromovinyl)piperidine-1-carboxylate

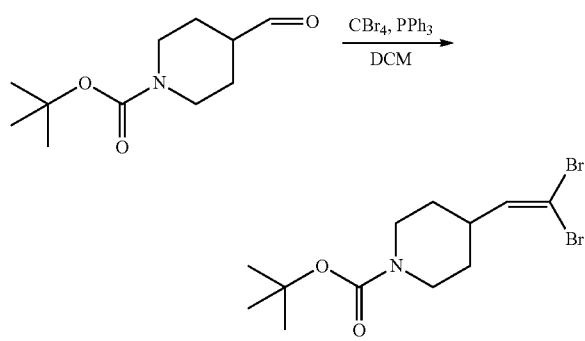

Carbon tetrabromide (11.6 g, 35.1 mmol) in DCM (150 mL) was cooled in an ice bath and triphenylphosphine (18.4 g, 70.2 mmol) added and stirring at 0° C. continued for 25 mins then tert-butyl 4-formylpiperidine-1-carboxylate (5 g, 23.4 mmol) added in one portion. After stirring at ice bath temperature for 50 mins the mixture was evaporated to about ⅓ the original volume to give a suspension. Cyclopentylmethyl ether (150 mL) added causing more precipitation and the mixture filtered washing with more cyclopentylmethyl ether. The filtrate was washed with water (200 mL), 10% aqueous sodium bisulfite, dried over $Na_2SO_4$, filtered and evaporated. The residue was triturated with 40% EtOAc in Heptane and filtered through a pad of silica (washing with further 40% EtOAc in Heptane and filtrate evaporated to give tert-butyl 4-(2,2-dibromovinyl)piperidine-1-carboxylate (7.84 g, 90%) as a white solid. $^1$H NMR (500 MHz, Chloroform-d) δ 6.23 (d, J=8.9 Hz, 1H), 4.06 (s, 2H), 2.88-2.65 (m, 2H), 2.44 (tdt, J=11.4, 8.9, 3.9 Hz, 1H), 1.75-1.67 (m, 2H), 1.46 (s, 9H), 1.37-1.27 (m, 2H).

Step 2 tert-butyl 4-(3-hydroxyprop-1-yn-1-yl)piperidine-1-carboxylate

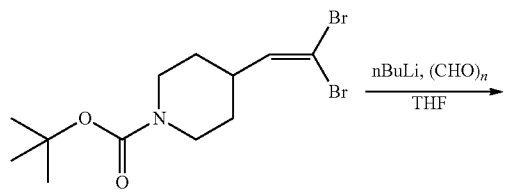

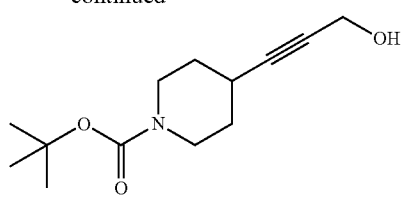

To a solution of tert-butyl 4-(2,2-dibromovinyl)piperidine-1-carboxylate (7.84 g, 21.2 mmol) in THF (100 mL) cooled at −45° C. was added n-butyl lithium (17.4 m of a 2.5M soln in Hexanes, 43.5 mmol) slowly over 10 mins. After complete addition mixture stirred at −45° C. for 45 minutes then paraformaldehyde (1.91 g, 63.6 mmol) added and mixture allowed to warm slowly to warm to room temperature and stirred overnight. Mixture quenched by the addition of sat.$NH_4Cl$ (200 mL) and extracted with EtOAc (300 mL); organic layer washed with water (200 mL), sat. NaCl (100 mL), dried over $MgSO_4$, filtered and evaporated. The residue was purified by silica gel column chromatography (Teledyne Isco: SNAP 80 g GOLD) eluent: gradient 0-100% EtOAc in Heptane (7cv) to give tert-butyl 4-(3-hydroxyprop-1-yn-1-yl)piperidine-1-carboxylate (3.77 g, 74%) as a light yellow oil. $^1$H NMR (500 MHz, Chloroform-d) δ 4.27 (dd, J=6.0, 2.0 Hz, 2H), 3.75-3.66 (m, 2H), 3.14 (ddd, J=13.5, 8.8, 3.4 Hz, 2H), 2.60 (ttq, J=8.2, 4.0, 2.0 Hz, 1H), 1.77 (ddt, J=13.7, 6.3, 3.5 Hz, 2H), 1.56 (dtt, J=12.7, 8.6, 3.7 Hz, 2H), 1.45 (s, 9H).

Step 3: tert-butyl (Z)-4-(3-hydroxyprop-1-en-1-yl)piperidine-1-carboxylate

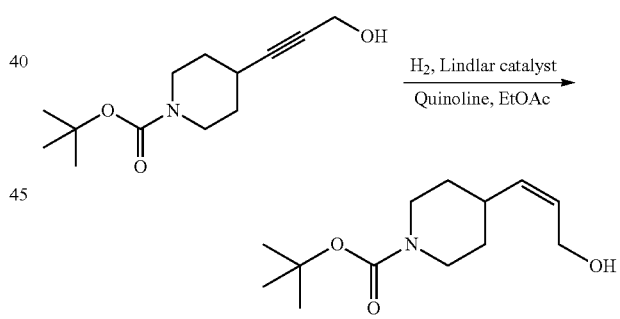

To a solution of alkyne (CM-781, 6.6 g, 27.6 mmol) in EtOAc (120 mL) was added quinoline (0.55 mL) and Lindlar catalyst (750 mg) and the resulting mixture stirred under a balloon of hydrogen for 1 hour. Mixture filtered through celite and the filtrate evaporated. The residue was purified by silica gel column chromatography (Teledyne Isco: SNAP 120 g GOLD) eluent: gradient 0-100% EtOAc in Heptane to give tert-butyl (Z)-4-(3-hydroxyprop-1-en-1-yl)piperidine-1-carboxylate (5 g, 75%) as a light yellow oil. $^1$H NMR (500 MHz, Chloroform-d) δ 5.58 (dtd, J=11.0, 6.8, 1.0 Hz, 1H), 5.37 (ddt, J=11.0, 9.5, 1.4 Hz, 1H), 4.22 (td, J=5.4, 2.7 Hz, 2H), 4.08 (s, 2H), 2.73 (d, J=13.6 Hz, 2H), 2.50-2.40 (m, 1H), 1.59-1.55 (m, 2H), 1.46 (s, 9H), 1.35-1.22 (m, 2H).

Step 4: tert-butyl 4-((1R,2R)-2-(hydroxymethyl)cyclopropyl)piperidine-1-carboxylate

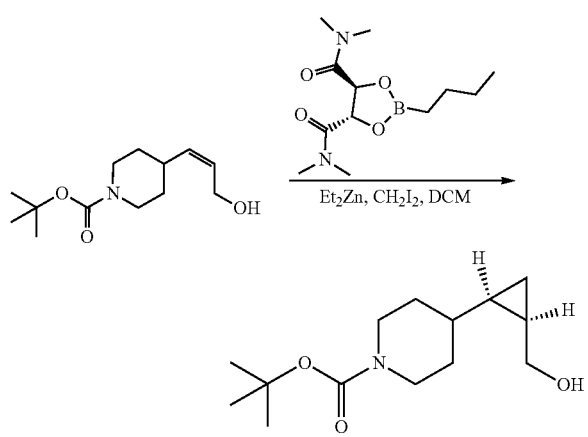

In a 100 mL flask was added dichloromethane (20 mL) cooled to −30° C. and diethyl zinc (10.3 mL of a 1M soln in hexane, 10.3 mmol) added followed by 1,2-dimethoxyethane (1.07 mL, 10.3 mmol) and the resulting mixture stirred at −20° C. for 20 min then diiodomethane (1.67 mL, 20.7 mmol) added slowly over 10 min and the resulting mixture stirred at −20° C. for 45 minutes. To this mixture was added slowly over 45 min a mixture of tert-butyl (Z)-4-(3-hydroxyprop-1-en-1-yl)piperidine-1-carboxylate (1 g, 4.14 mmol) and (4S,5S)-2-butyl-$N^4,N^4,N^5,N^5$-tetramethyl-1,3,2-dioxaborolane-4,5-dicarboxamide (1.22 mL, 4.97 mmol) in DCM (12 mL) and the resulting mixture allowed to warm to room temperature overnight. Mixture quenched by the addition of sat. NH$_4$Cl (30 mL) and mixture decanted into a separating funnel and remaining solids treated with DCM (30 mL) and sat. NH$_4$Cl (30 mL) and stirred until all solids had dissolved, mixture added to separating funnel and organic layer separated and dried over MgSO$_4$, filtered and evaporated. The residue was purified by silica gel column chromatography (Teledyne Isco: SNAP 24 g GOLD) eluent: gradient 0-100% EtOAc in Heptane to give an oil which partially solidified on standing. Mixture treated with heptane and solid filtered and dried to give tert-butyl 4-((1R,2R)-2-(hydroxymethyl)cyclopropyl)piperidine-1-carboxylate (660 mg, 62%) as a white solid. $^1$H NMR (500 MHz, Chloroform-d) δ 4.09 (s, 2H), 3.67 (dd, J=7.5, 3.7 Hz, 2H), 2.68 (s, 2H), 1.84-1.68 (m, 2H), 1.48 (s, 9H), 1.38-1.24 (m, 2H), 1.17 (dddd, J=15.9, 8.5, 7.5, 5.5 Hz, 1H), 0.98 (tdd, J=11.2, 8.2, 4.9 Hz, 1H), 0.77-0.68 (m, 2H), 0.05-0.01 (m, 1H).

Intermediate 16: ((1R,2R)-2-(1-(5-chloropyrimidin-2-yl)piperidin-4-yl)cyclopropyl)methanol

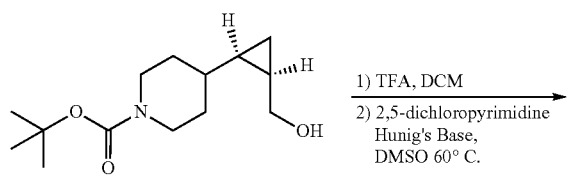

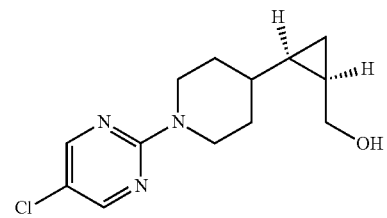

To an ice bath cooled solution of tert-butyl 4-((1R,2R)-2-(hydroxymethyl)cyclopropyl)piperidine-1-carboxylate (2.5 g, 9.79 mmol) in DCM (50 mL) was added TFA (50 mL) slowly over 5 mins and the resulting mixture stirred at ice bath temperature for 1 hour. Mixture evaporated and azeotroped with further DCM. The residue was taken up in DMSO (50 mL) and Hunig's base (8.5 mL, 48.9 mmol) and 2,5-dichloropyrimidine (1.61 g, 10.8 mmol) added and the resulting mixture heated at 60° C. for 72 hours. Mixture cooled and diluted with EtOAc (100 mL) and washed with water (300 mL), aqueous back extracted with EtOAc (100 mL); combined EtOAc layers washed with water (200 mL), sat. NaCl (100 mL), dried over MgSO$_4$, filtered and evaporated. The residue was purified by silica gel column chromatography (Teledyne Isco: SNAP 40 g GOLD) eluent: gradient 0-100% EtOAc in Heptane to give ((1R,2R)-2-(1-(5-chloropyrimidin-2-yl)piperidin-4-yl)cyclopropyl)methanol (1.5 g (Yield 57%). $^1$H NMR (500 MHz, Chloroform-d) δ 8.20 (s, 2H), 4.66 (ddddd, J=16.5, 13.2, 4.7, 2.9, 1.9 Hz, 2H), 3.69 (dd, J=7.4, 3.8 Hz, 2H), 2.85 (dddd, J=13.2, 12.3, 6.1, 2.9 Hz, 2H), 1.92-1.80 (m, 2H), 1.43-1.29 (m, 3H), 1.23-1.14 (m, 1H), 1.14-1.07 (m, 1H), 0.78-0.68 (m, 2H), 0.08-0.03 (m, 1H).

Intermediate 17: ((1R,2R)-2-(1-(5-(methoxymethyl)pyrimidin-2-yl)piperidin-4-yl)cyclopropyl)methanol

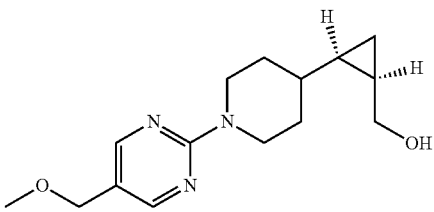 [SMILES: COCc1cnc(N2CCC([C@H]3C[C@H]3CO)CC2)nc1]

Prepared using procedures outlined in the preparation of intermediate 16; replacing 2,5-dichloropyrimidine with 2-chloro-5-(methoxymethyl)pyrimidine to give ((1R,2R)-2-(1-(5-(methoxymethyl)pyrimidin-2-yl)piperidin-4-yl)cyclopropyl)methanol. $^1$H NMR (400 MHz, Chloroform-d) δ 8.28 (s, 2H), 4.77-4.70 (m, 2H), 4.26 (s, 2H), 3.68 (d, J=7.6 Hz, 2H), 3.34 (s, 3H), 2.88-2.84 (m, 2H), 1.84-1.50 (m, 3H), 1.41-1.16 (m, 4H), 0.74-0.71 (m, 2H), 0.07-0.04 (m, 1H).

Intermediate 18: 2-(4-(2-((1S,2R)-2-(1-(5-chloropy-rimidin-2-yl)piperidin-4-yl)cyclopropyl)ethoxy)-2-fluorophenyl)acetic acid

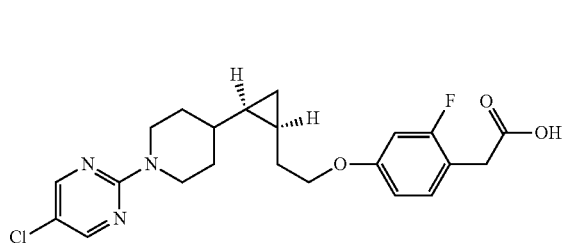 [SMILES: O=C(O)Cc1ccc(OCC[C@@H]2C[C@@H]2C2CCN(c3ncc(Cl)cn3)CC2)cc1F]

Step 1: (1R,2R)-2-(1-(5-chloropyrimidin-2-yl)piperidin-4-yl)cyclopropane-1-carbaldehyde

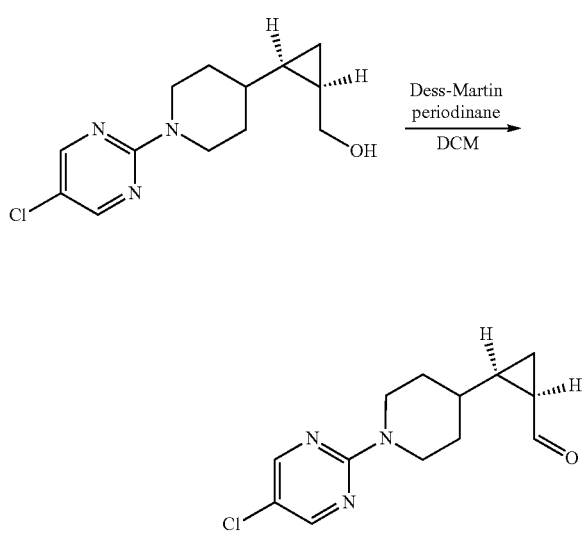

To an ice-bath cooled solution of ((1R,2R)-2-(1-(5-chloropyrimidin-2-yl)piperidin-4-yl)cyclopropyl) methanol intermediate 16 (1.4 g, 5.23 mmol) in DCM (100 mL) was added Dess-Martin periodinane (2.9 g, 6.8 mmol) and the resulting mixture stirred at ice bath temperature for 1 hour then stirred at room temperature overnight. Mixture washed with sat. NaHCO$_3$ (100 mL), dried over MgSO$_4$, filtered and evaporated. The residue was purified by silica gel column chromatography (Teledyne Isco: SNAP 24 g GOLD) eluent: gradient 0-80% EtOAc in Heptane and product recrystallized from MTBE/Heptane to give (1R,2R)-2-(1-(5-chloropyrimidin-2-yl)piperidin-4-yl)cyclopropane-1-carbaldehyde (510 mg, 36%) as a white solid. $^1$H NMR (500 MHz, Chloroform-d) δ 9.56 (d, J=4.7 Hz, 1H), 8.20 (s, 2H), 4.76-4.67 (m, 1H), 4.67-4.59 (m, 1H), 2.87 (ddd, J=13.4, 12.2, 2.8 Hz, 1H), 2.78 (ddd, J=13.3, 12.2, 2.9 Hz, 1H), 2.03-1.95 (m, 1H), 1.94-1.87 (m, 1H), 1.56 (dtd, J=14.5, 4.6, 2.2 Hz, 1H), 1.49 (tdd, J=11.2, 8.1, 5.5 Hz, 1H), 1.42-1.32 (m, 2H), 1.32-1.22 (m, 3H).

Step 2: 5-chloro-2-(4-((1R,2S)-2-vinylcyclopropyl)piperidin-1-yl)pyrimidine

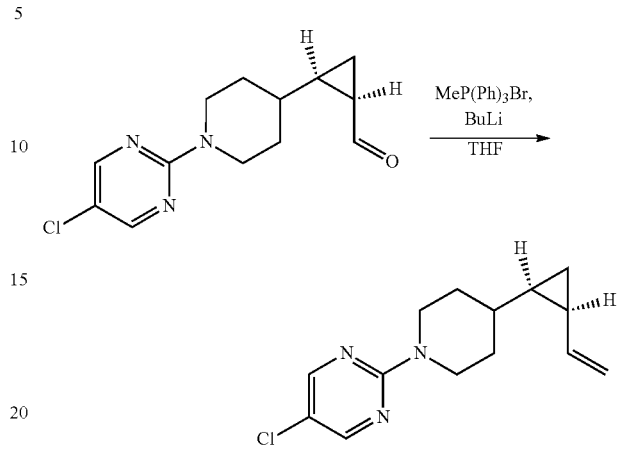

To a solution of methyltriphenylphosphonium bromide (1.34 g, 3.76 mmol) in THF (15 mL) cooled at −78° C. was added dropwise n-butyl lithium (1.43 mL of a 2.5M soln, 3.57 mmol) and the resulting mixture stirred at −78° C. for 45 mins. To this mixture a solution of (1R,2R)-2-(1-(5-chloropyrimidin-2-yl)piperidin-4-yl)cyclopropane-1-carbaldehyde (500 mg, 1.88 mmol) in THF (5 mL) was added dropwise. After complete addition cooling bath removed and mixture stirred at room temperature for 2 hours. Quenched by the addition of sat. NH$_4$Cl (20 mL) and extracted with EtOAc (3×15 mL); combined EtOAc layers washed with sat. NaCl (20 mL), dried over Na$_2$SO$_4$, filtered and evaporated. The residue was purified by silica gel column chromatography (Teledyne Isco: SNAP 12 g GOLD) eluent: gradient 0-20% EtOAc in Heptane to give 5-chloro-2-(4-((1R,2S)-2-vinylcyclopropyl)piperidin-1-yl)pyrimidine (350 mg, 70%) as a white solid. $^1$H NMR (500 MHz, Chloroform-d) δ 8.20 (s, 2H), 5.62 (ddd, J=17.0, 10.2, 8.8 Hz, 1H), 5.15 (ddd, J=16.9, 2.0, 0.7 Hz, 1H), 5.01 (ddd, J=10.2, 1.9, 0.6 Hz, 1H), 4.67 (dddd, J=13.3, 4.6, 2.9, 1.9 Hz, 1H), 4.61 (dddd, J=13.3, 4.7, 2.9, 1.9 Hz, 1H), 2.84 (dddd, J=23.8, 13.3, 12.2, 2.9 Hz, 2H), 1.88-1.74 (m, 2H), 1.60-1.52 (m, 1H), 1.41-1.23 (m, 2H), 1.17-1.06 (m, 1H), 0.89 (td, J=8.3, 4.7 Hz, 1H), 0.75 (dtd, J=10.2, 8.5, 5.9 Hz, 1H), 0.32 (td, J=5.7, 4.7 Hz, 1H).

Step 3: 2-[(1S,2R)-2-[1-(5-chloropyrimidin-2-yl)-4-piperidyl]cyclopropyl]ethanol

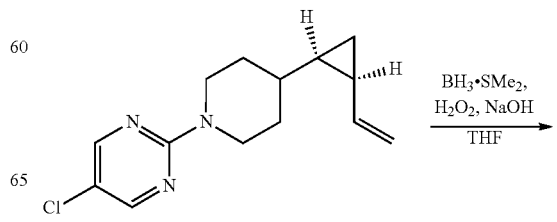

-continued

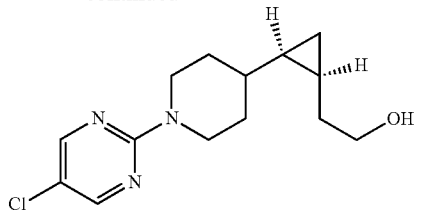

To a solution of 5-chloro-2-[4-[(1R,2S)-2-vinylcyclopropyl]-1-piperidyl]pyrimidine (190 mg, 0.72 mmol) in THF (3 mL) cooled in an ice bath was added borane methyl sulfide (0.36 mL of a 1M soln in THF, 0.36 mmol) and the resulting mixture stirred at room temperature for 2 hours. Mixture treated with NaOH (1.15 mL of a 5N aqueous soln, 5.76 mmol) followed by hydrogen peroxide (1.25 mL of a 30% aqueous soln, 12.25 mmol) and the resulting mixture stirred at room temperature for 1 hour. Mixture diluted with water (10 mL) and extracted with EtOAc (2×10 mL); combined EtOAc layers washed with sat. NaCl (10 mL), dried over Na$_2$SO$_4$, filtered and evaporated. The residue was purified by silica gel column chromatography (Teledyne Isco: SNAP 12 g GOLD) eluent: gradient 0-60% EtOAc in Heptane to give 2-[(1S,2R)-2-[1-(5-chloropyrimidin-2-yl)-4-piperidyl]cyclopropyl]ethanol (90 mg, 44%) as a colorless oil. LCMS: tR=0.85, (ES$^+$) m/z (M+H)$^+$=282.2

Step 4: Methyl 2-(4-(2-((1S,2R)-2-(1-(5-chloropyrimidin-2-yl)piperidin-4-yl)cyclopropyl)ethoxy)-2-fluorophenyl)acetate

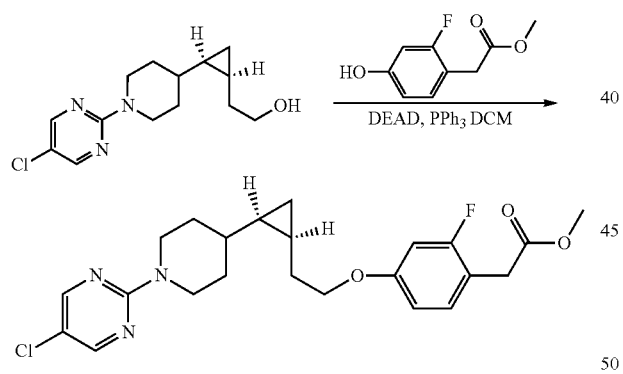

To a mixture of 2-[(1S,2R)-2-[1-(5-chloropyrimidin-2-yl)-4-piperidyl]cyclopropyl]ethanol (90 mg, 0.32 mmol), methyl 2-fluoro-4-hydroxyphenyl acetate (70 mg, 0.38 mmol) and triphenylphosphine (200 mg of polymer bound ~3 mmol/g, 0.5 mmol) in DCM (3 mL) was added diethyl azodicarboxylate (0.215 mL of a 40% wt soln in toluene, 0.48 mmol) and the resulting mixture stirred at room temperature for 2 hours. Mixture filtered through Celite and the filtrate evaporated. The residue was purified by silica gel column chromatography (Teledyne Isco: SNAP 12 g GOLD) eluent: gradient 0-30% EtOAc in Heptane to give methyl 2-(4-(2-((1S,2R)-2-(1-(5-chloropyrimidin-2-yl)piperidin-4-yl)cyclopropyl)ethoxy)-2-fluorophenyl) acetate (115 mg, 80%) as a clear oil. LCMS: tR=1.70, (ES$^+$) m/z (M+H)$^+$=448.2.

Step 5: 2-(4-(2-((1S,2R)-2-(1-(5-chloropyrimidin-2-yl)piperidin-4-yl)cyclopropyl)ethoxy)-2-fluorophenyl) acetic acid

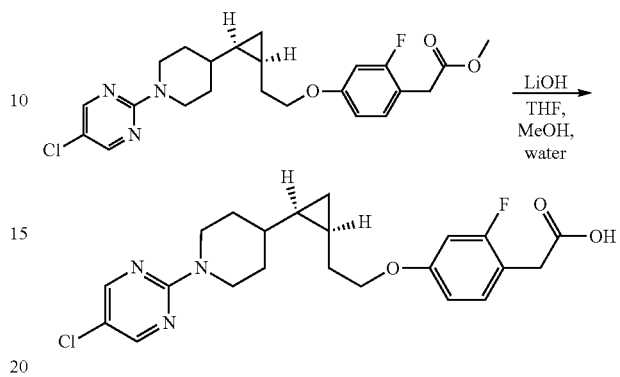

To a solution of methyl 2-[4-[2-[(1S,2R)-2-[1-(5-chloropyrimidin-2-yl)-4-piperidyl]cyclopropyl]ethoxy]-2-fluorophenyl]acetate (115 mg, 0.257 mol) in a mixture of THF (1.5 mL) and MeOH (0.5 mL) was added lithium hydroxide (0.5 mL of a 1M aqueous solution, 0.5 ml) and the resulting mixture stirred at room temperature for 1 hour after which UPLC_MS indicated complete conversion. Mixture evaporated to remove organic solvents and the remaining aqueous acidified by the addition of 1N HCl. Extracted with DCM (2×5 mL); combined DCM layers dried over Na$_2$SO$_4$, filtered and evaporated to give 2-(4-(2-((1S,2R)-2-(1-(5-chloropyrimidin-2-yl)piperidin-4-yl)cyclopropyl)ethoxy)-2-fluorophenyl)acetic acid (110 mg, 99%) as a white solid. LCMS: tR=1.38, (ES$^+$) m/z (M+H)$^+$=434.2.

Intermediate 19: 2-(2-fluoro-4-(2-((1S,2R)-2-(1-(5-(methoxymethyl)pyrimidin-2-yl)piperidin-4-yl)cyclopropyl)ethoxy) phenyl)acetic acid

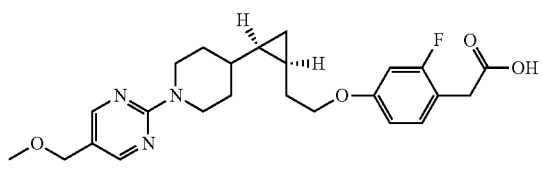 [SMILES: COCc1cnc(N2CCC([C@H]3C[C@H]3CCOc3ccc(CC(=O)O)c(F)c3)CC2)nc1]

Step 1: tert-butyl 4-((1R,2R)-2-formylcyclopropyl)piperidine-1-carboxylate

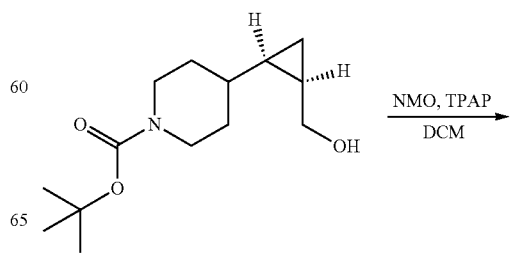

-continued

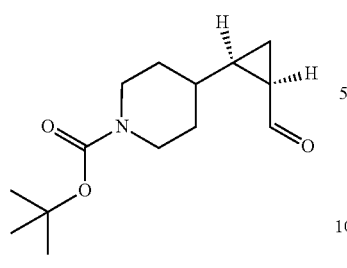

To a solution of tert-butyl 4-((1R,2R)-2-(hydroxymethyl)cyclopropyl)piperidine-1-carboxylate (2 g, 7.8 mmol) in DCM (40 mL) was treated with N-methyl-morpholine-N-oxide (2.8 g, 24 mmol) and the resulting mixture stirred at room temperature for 15 mins. The mixture was cooled to 0° C. and tetrapropylammonium perruthenate (28 mg, 0.078 mmol) and molecular sieves (2 g) added and the resulting mixture stirred at room temperature for 1 hour. The mixture was filtered and the filtrate washed with water (50 mL), DCM layer evaporated and the residue purified by silica gel column chromatography eluting with petroleum ether:ethyl acetate 3:1 to give tert-butyl 4-((1R,2R)-2-formylcyclopropyl)piperidine-1-carboxylate (1.6 g, 81%) as a yellow solid.

Step 2: tert-butyl 4-((1R,2R)-2-(oxiran-2-yl)cyclopropyl)piperidine-1-carboxylate

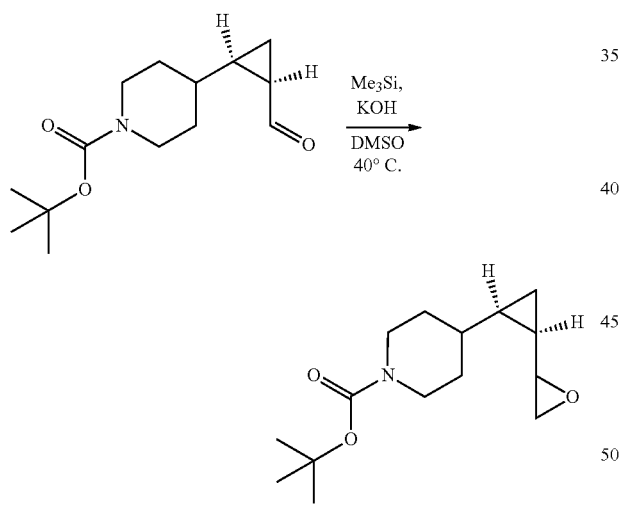

To a solution of tert-butyl 4-((1R,2R)-2-formylcyclopropyl)piperidine-1-carboxylate (1.6 g, 6.3 mmol) and trimethylsulfonium iodide (1.8, 8.8 mmol) in DMSO (20 mL) was added KOH (0.5 g, 8.8 mmol) and the resulting mixture stirred at 40° C. for 3 hours. Water (30 mL) was added and extracted with EtOAc (2×40 mL); combined ETOAC layers dried over MgSO₄, filtered and evaporated. The residue was purified by silica gel column chromatography eluent: petroleum ether:ethyl acetate 5:1 to give tert-butyl 4-((1R,2R)-2-(oxiran-2-yl)cyclopropyl)piperidine-1-carboxylate (0.7 g, 41%) as a yellow solid. LCMS: tR=0.176, (ES⁺) m/z (M−55)⁺=212.1.

Step 3: tert-butyl 4-((1R,2S)-2-(2-hydroxyethyl)cyclopropyl)piperidine-1-carboxylate

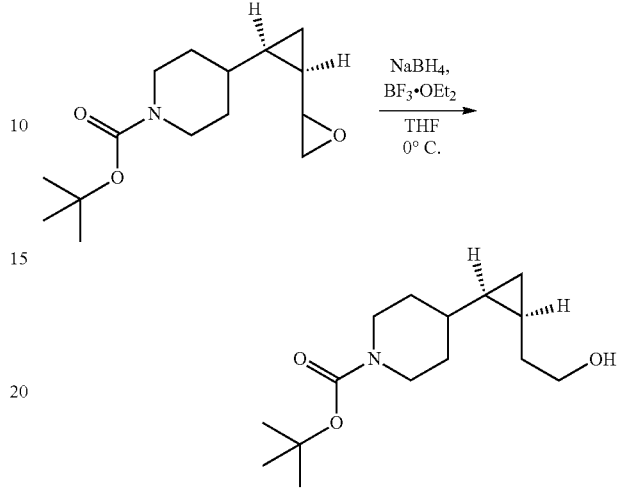

To a solution of NaBH₄ (57 mg, 1.5 mmol) in THF (5 mL) was added BF₃.Et₂O (0.24 mL, 2.0 mmol) and the resulting mixture stirred at room temperature for 30 mins. The mixture was cooled to 0° C. and a solution of tert-butyl 4-((1R,2R)-2-(oxiran-2-yl)cyclopropyl)piperidine-1-carboxylate (0.8 g, 3.0 mmol) in THF (5 ml) added dropwise over 10 mins. After complete addition the mixture was stirred at room temperature for 3 hours. The mixture was quenched by the addition of water (30 mL) and extracted with EtOAc (2×40 mL); combined EtOAc layers washed with sat. NaCl (20 mL), dried over MgSO₄, filtered and evaporated. The residue was purified by silica gel column chromatography eluent petroleum ether:ethyl acetate 4:1 to give tert-butyl 4-((1R,2S)-2-(2-hydroxyethyl)cyclopropyl)piperidine-1-carboxylate (680 mg, 84%) as a yellow solid. ¹H NMR (400 MHz, MeOD-d) δ 4.22-4.16 (m, 2H), 3.81-3.77 (m, 2H), 2.75 (m, 1H), 1.96-1.88 (m, 3H), 1.60 (s, 9H), 1.44-1.37 (m, 3H), 1.20 (m, 1H), 1.00-0.98 (m, 1H) 0.86-0.70 (m, 2H), 0.01--0.02 (m, 1H).

Step 4: tert-butyl 4-((1R,2S)-2-(2-(3-fluoro-4-(2-methoxy-2-oxoethyl)phenoxy)ethyl)cyclopropyl)piperidine-1-carboxylate

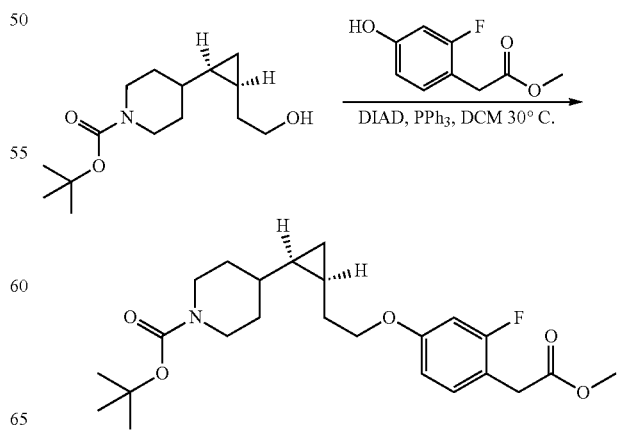

To a mixture of tert-butyl 4-((1R,2S)-2-(2-hydroxyethyl)cyclopropyl)piperidine-1-carboxylate (680 mg, 2.5 mmol) and methyl (2-fluoro-4-hydroxy-phenyl)acetate (470 mg, 2.5 mmol) in DCM (60 mL) was added di-isopropylazodicarboxylate (0.74 mL, 3.8 mmol) and triphenylphosphine (990 mg, 3.8 mmol) and the resulting mixture stirred at 30° C. for 12 hours. The mixture was quenched by the addition of water (50 mL) and extracted with EtOAc (2×70 mL); combined EtOAc layers washed with sat. NaCl (30 mL), dried over MgSO$_4$, filtered and evaporated. The residue was purified by silica gel column chromatography eluent petroleum ether:ethyl acetate 5:1 to give tert-butyl 4-((1R,2S)-2-(2-(3-fluoro-4-(2-methoxy-2-oxoethyl)phenoxy)ethyl)cyclopropyl) piperidine-1-carboxylate (740 mg, 66%) as a yellow solid. LCMS: tR=1.121, (ES$^+$) m/z (M−55)$^+$=380.2

Step 5: methyl 2-(2-fluoro-4-(2-((1S,2R)-2-(1-(5-(methoxymethyl)pyrimidin-2-yl)piperidin-4-yl)cyclopropyl)ethoxy)phenyl)acetate

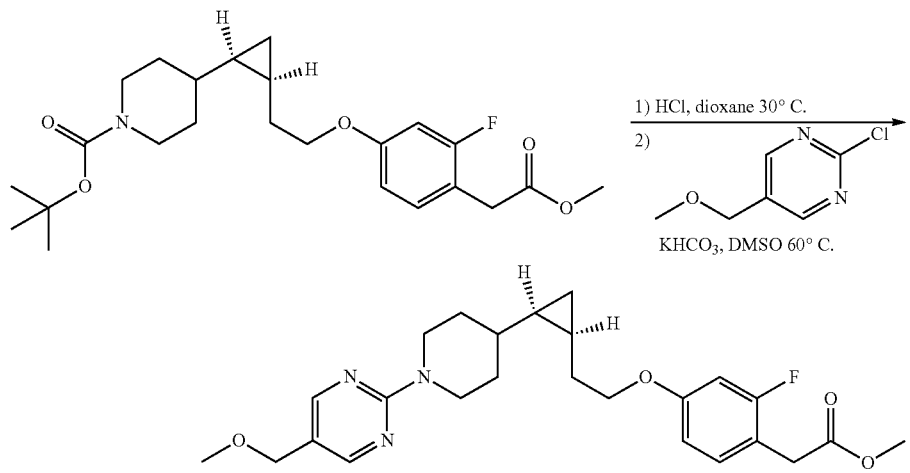

A mixture of tert-butyl 4-((1R,2S)-2-(2-(3-fluoro-4-(2-methoxy-2-oxoethyl)phenoxy)ethyl)cyclopropyl) piperidine-1-carboxylate (730 mg, 1.7 mmol) and 4M HCl in dioxane (20 mL) was stirred at 30° C. for 3 hours and then evaporated. The residue was mixed with 2-chloro-5-(methoxymethyl)pyrimidine (270 mg, 1.7 mmol), KHCO$_3$ (330 mg, 3.3 mmol) in DMSO (30 mL) and heated at 60° C. for 12 hours. The cooled mixture was treated with water (50 mL) and extracted with EtOAc (2×80 mL); combined EtOAc layers washed with sat. NaCl (20 mL), dried over MgSO$_4$, filtered and evaporated. The residue was purified by silica gel column chromatography eluent petroleum ether: ethylacetate 3:1 to give methyl 2-(2-fluoro-4-(2-((1S,2R)-2-(1-(5-(methoxymethyl)pyrimidin-2-yl)piperidin-4-yl)cyclopropyl)ethoxy)phenyl)acetate 680 mg, 89%) as a yellow solid. $^1$H NMR (400 MHz, MeOD-d) δ 8.30 (d, J=4.0 Hz, 2H), 7.23-7.19 (m, 1H), 6.76-670 (m, 2H), 4.76-4.73 (m, 2H), 4.31 (s, 2H), 4.11-4.09 (m, 2H), 3.72 (s, 3H), 3.65 (s, 2H), 3.47 (s, 3H), 2.95-2.93 (m, 2H), 2.16-2.14 (m, 1H), 1.89-1.86 (m, 2H), 1.62 (m, 1H), 1.39-1.23 (m, 3H), 1.02-1.00 (m, 1H) 0.72-0.65 (m, 2H), 0.01--0.01 (m, 1H). LCMS: tR=1.014, (ES$^+$) m/z (M+H)$^+$=458.2.

Step 6: 2-(2-fluoro-4-(2-((1S,2R)-2-(1-(5-(methoxymethyl)pyrimidin-2-yl)piperidin-4-yl)cyclopropyl)ethoxy) phenyl)acetic acid

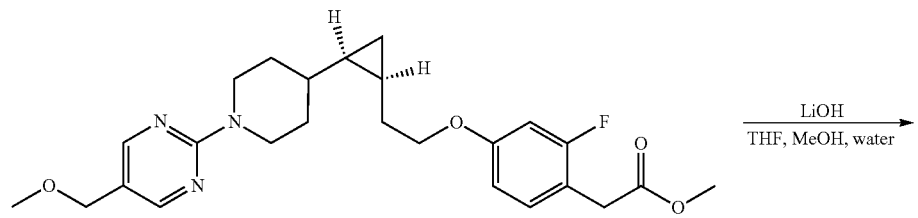

-continued

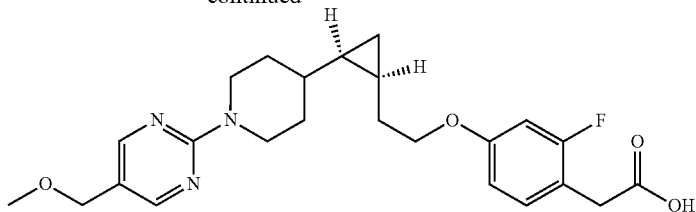

To a mixture of methyl 2-(2-fluoro-4-(2-((1S,2R)-2-(1-(5-(methoxymethyl)pyrimidin-2-yl)piperidin-4-yl)cyclopropyl)ethoxy)phenyl)acetate (300 mg, 0.66 mmol) in THF (10 mL), MeOH (10 mL) and water (10 mL) was added lithium hydroxide monohydrate (55 mg, 1.3 mmol) and stirred at 30° C. for 5 hours. Mixture evaporated to remove organic solvents and diluted with water (20 ml) and extracted with EtOAc (2×20 mL). The aqueous layer was acidified to pH ~2 by the addition of HCl and extracted with EtOAc (2×20 mL). The combined EtOAc layers were washed with sat. NaCl (20 mL0, dried over MgSO₄, filtered and evaporated to give 2-(2-fluoro-4-(2-((1S,2R)-2-(1-(5-(methoxymethyl)pyrimidin-2-yl)piperidin-4-yl)cyclopropyl)ethoxy) phenyl)acetic acid (200 mg, 68%) as a yellow solid.

Intermediate 20: 2-(4-(3-(1-(5-(((tert-butyldimethylsilyl)oxy)methyl)pyrimidin-2-yl)piperidin-4-yl)propoxy)-2-fluorophenyl)acetic acid

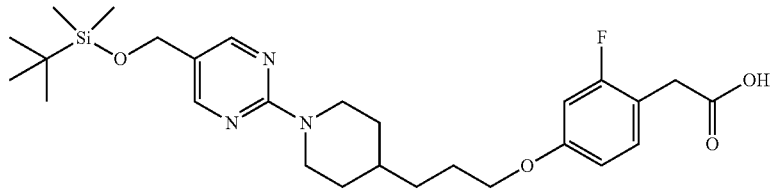 [SMILES: CC(C)(C)[Si](C)(C)OCc1cnc(N2CCC(CCCOc3ccc(CC(=O)O)c(F)c3)CC2)nc1]

Prepared using procedures outlined in the preparation of intermediate 1; replacing 2,5-dichloropyrimidine with 5-(((tert-Butyldimethylsilyl)oxy) methyl)-2-chloropyrimidine in step 1 to give 2-(4-(3-(1-(5-(((tert-butyldimethylsilyl)oxy)methyl)pyrimidin-2-yl)piperidin-4-yl)propoxy)-2-fluorophenyl)acetic acid LCMS: tR=1.76, (ES⁺) m/z (M+H)⁺=518.5.

Intermediate 21: 6-[[2-[4-[3-[1-(5-chloropyrimidin-2-yl)-4-piperidyl]propoxy]-2-fluoro-phenyl]acetyl]amino]hexanoic acid

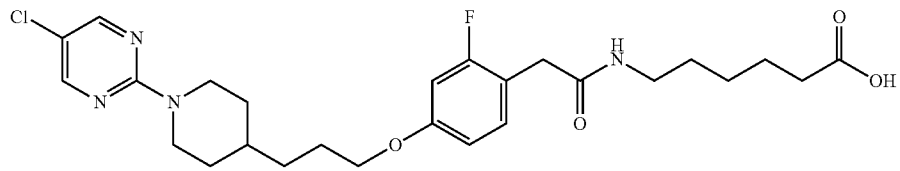 [SMILES: O=C(O)CCCCCNC(=O)Cc1ccc(OCCCC2CCN(c3ncc(Cl)cn3)CC2)cc1F]

Step 1: Methyl 6-(2-(4-(3-(1-(5-chloropyrimidin-2-yl)piperidin-4-yl)propoxy)-2-fluorophenyl)acetamido) hexanoate

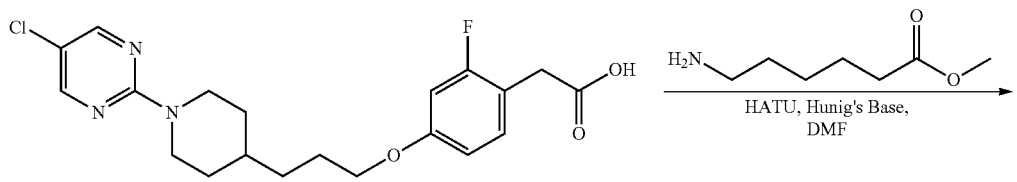

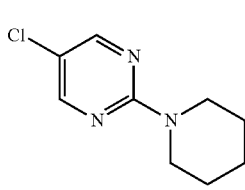
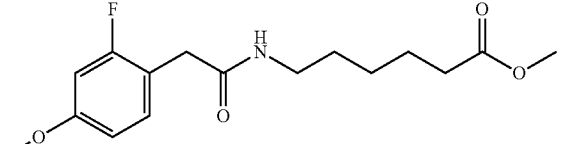

To a solution of 2-(4-(3-(1-(5-chloropyrimidin-2-yl)piperidin-4-yl)propoxy)-2-fluorophenyl)acetic acid intermediate 1 (200 mg, 0.49 mmol) in DMF (3 mL) was added methyl 6-amino-hexanoate hydrochloride (133 mg, 0.74 mmol), HATU (280 mg, 0.74 mmol) and Hunig's base (256 mL, 1.47 mmol) and the resulting mixture stirred at room temperature overnight. The mixture was diluted with EtOAc (20 mL) and washed with water (70 mL), sat. NaCl (40 mL), dried over MgSO$_4$, filtered and evaporated. The residue was purified by silica gel column chromatography (Teledyne Isco: SNAP 12 g Gold) eluent: gradient 2-8% MeOH in DCM to give methyl 6-(2-(4-(3-(1-(5-chloropyrimidin-2-yl)piperidin-4-yl)propoxy)-2-fluorophenyl)acetamido)hexanoate (189 mg, 72%) as a white solid. $^1$H NMR (500 MHz, Chloroform-d) δ 8.20 (s, 2H), 7.16 (t, J=8.6 Hz, 1H), 6.67 (dd, J=8.5, 2.6 Hz, 1H), 6.63 (dd, J=11.7, 2.5 Hz, 1H), 5.46 (s, 1H), 4.73-4.63 (m, 2H), 3.94 (t, J=6.4 Hz, 2H), 3.66 (s, 3H), 3.49 (d, J=1.4 Hz, 2H), 3.21 (td, J=7.2, 5.8 Hz, 2H), 2.91-2.82 (m, 2H), 2.28 (t, J=7.4 Hz, 2H), 1.87-1.76 (m, 4H), 1.66-1.54 (m, 5H), 1.50-1.39 (m, 4H), 1.33-1.24 (m, 2H), 1.23-1.13 (m, 2H). LCMS: tR=1.45, (ES$^+$) m/z (M+H)$^+$=535.3.

Step 2: 6-[[2-[4-[3-[1-(5-chloropyrimidin-2-yl)-4-piperidyl]propoxy]-2-fluoro-phenyl]acetyl]amino]hexanoic acid

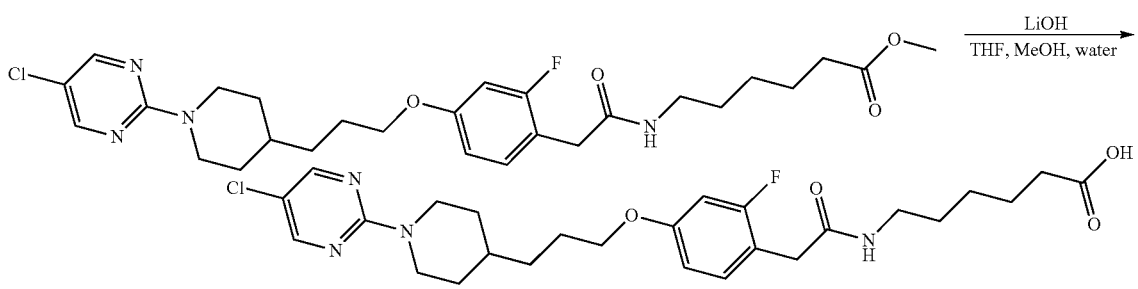

To a solution of methyl 6-(2-(4-(3-(1-(5-chloropyrimidin-2-yl)piperidin-4-yl)propoxy)-2-fluorophenyl) acetamido)hexanoate (155 mg, 0.29 mmol) in a mixture of MeOH (4 mL) and THF (2 mL) was added lithium hydroxide (0.58 mL of a 1N aqueous solution, 0.58 mmol) and the resulting mixture stirred at room temperature overnight. Mixture evaporated and the residue suspended in water (20 mL) and acidified by the addition of 1N HCl and extracted with DCM (3×20 mL); combined DCM layers dried over MgSO$_4$, filtered and evaporated to give 6-[[2-[4-[3-[1-(5-chloropyrimidin-2-yl)-4-piperidyl]propoxy]-2-fluoro-phenyl]acetyl]amino]hexanoic acid (114 mg, 76%) as a white solid. $^1$H NMR (500 MHz, Chloroform-d) δ 8.20 (s, 2H), 7.16 (t, J=8.6 Hz, 1H), 6.67 (dd, J=8.5, 2.6 Hz, 1H), 6.63 (dd, J=11.7, 2.5 Hz, 1H), 5.48 (s, 1H), 4.67 (dq, J=13.4, 2.2 Hz, 2H), 3.94 (t, J=6.4 Hz, 2H), 3.49 (d, J=1.3 Hz, 2H), 3.22 (td, J=7.1, 5.8 Hz, 2H), 2.91-2.80 (m, 2H), 2.32 (t, J=7.4 Hz, 2H), 1.86-1.76 (m, 4H), 1.67-1.53 (m, 3H), 1.51-1.39 (m, 4H), 1.35-1.24 (m, 2H), 1.24-1.13 (m, 2H). LCMS: tR=1.56, (ES$^+$) m/z (M+H)$^+$=521.3

Intermediate 22: 5-[[2-[4-[3-[1-(5-chloropyrimidin-2-yl)-4-piperidyl]propoxy]-2-fluoro-phenyl]acetyl]amino]pentanoic acid

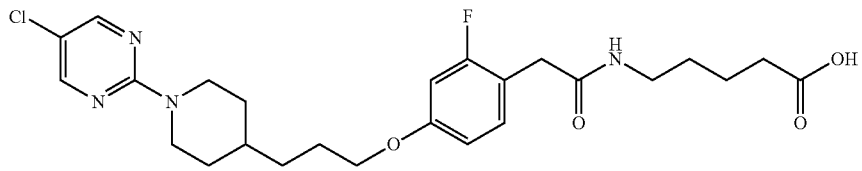 [SMILES: O=C(O)CCCCNC(=O)Cc1ccc(OCCCC2CCN(c3ncc(Cl)cn3)CC2)cc1F]

Prepared using procedures outlined in the preparation of intermediate 21; replacing methyl 6-amino-hexanoate hydrochloride with methyl 5-amino-pentanoate hydrochloride in step 1 to give 5-[[2-[4-[3-[1-(5-chloropyrimidin-2-yl)-4-piperidyl]propoxy]-2-fluoro-phenyl]acetyl]amino] pentanoic acid. $^1$H NMR (500 MHz, DMSO-$d_6$) δ 11.98 (s, 1H), 8.38 (s, 2H), 7.95 (t, J=5.6 Hz, 1H), 7.18 (t, J=8.7 Hz, 1H), 6.75 (dd, J=11.9, 2.5 Hz, 1H), 6.71 (dd, J=8.5, 2.5 Hz, 1H), 4.58 (dt, J=12.1, 3.3 Hz, 2H), 3.95 (t, J=6.5 Hz, 2H), 3.35 (s, 2H), 3.04 (q, J=6.7 Hz, 2H), 2.88 (td, J=12.9, 2.7 Hz, 2H), 2.21 (t, J=7.3 Hz, 2H), 1.80-1.69 (m, 4H), 1.58 (ddp, J=11.0, 7.1, 3.6 Hz, 1H), 1.53-1.45 (m, 2H), 1.45-1.38 (m, 2H), 1.38-1.33 (m, 2H), 1.06 (qd, J=12.4, 4.2 Hz, 2H). LCMS: tR=1.22, (ES$^+$) m/z (M+H)$^+$=507.2.

Intermediate 23: 4-[[2-[4-[3-[1-(5-chloropyrimidin-2-yl)-4-piperidyl]propoxy]-2-fluoro-phenyl]acetyl]amino]butanoic acid

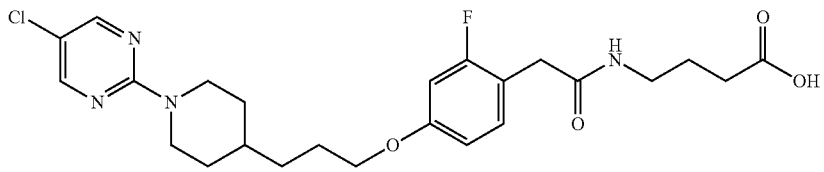 [SMILES: O=C(O)CCCNC(=O)Cc1ccc(OCCCC2CCN(c3ncc(Cl)cn3)CC2)cc1F]

Prepared using procedures outlined in the preparation of intermediate 21; replacing methyl 6-amino-hexanoate hydrochloride with methyl 4-amino-butanoate hydrochloride in step 1 to give 4-[[2-[4-[3-[1-(5-chloropyrimidin-2-yl)-4-piperidyl]propoxy]-2-fluoro-phenyl]acetyl]amino]butanoic acid. $^1$H NMR (500 MHz, DMSO-$d_6$) δ 12.00 (s, 1H), 8.38 (s, 2H), 7.18 (t, J=8.8 Hz, 1H), 6.75 (dd, J=11.9, 2.5 Hz, 1H), 6.71 (dd, J=8.5, 2.6 Hz, 1H), 4.58 (dq, J=13.5, 2.6, 1.9 Hz, 2H), 3.95 (t, J=6.5 Hz, 2H), 3.36 (s, 2H), 3.06 (td, J=6.9, 5.5 Hz, 2H), 2.88 (td, J=12.8, 2.7 Hz, 2H), 2.21 (t, J=7.4 Hz, 2H), 1.75 (ddd, J=15.6, 5.8, 3.3 Hz, 4H), 1.61 (tt, J=13.5, 7.2 Hz, 3H), 1.39-1.31 (m, 2H), 1.06 (qd, J=12.5, 4.2 Hz, 2H). LCMS: tR=1.17, (ES$^+$) m/z (M+H)$^+$=493.2.

Intermediate 24: 3-[[2-[4-[3-[1-(5-chloropyrimidin-2-yl)-4-piperidyl]propoxy]-2-fluoro-phenyl]acetyl]amino]propanoic acid

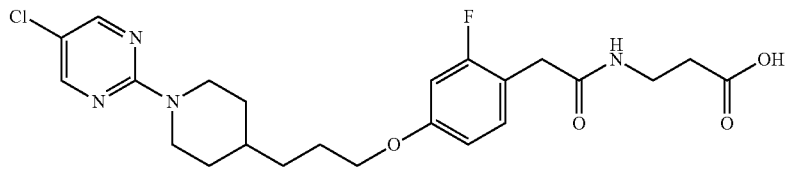 [SMILES: O=C(O)CCNC(=O)Cc1ccc(OCCCC2CCN(c3ncc(Cl)cn3)CC2)cc1F]

Prepared using procedures outlined in the preparation of intermediate 21; replacing methyl 6-amino-hexanoate hydrochloride with beta alanine methyl ester hydrochloride in step 1 to give 3-[[2-[4-[3-[1-(5-chloropyrimidin-2-yl)-4-piperidyl]propoxy]-2-fluoro-phenyl]acetyl]amino]propanoic acid. LCMS: tR=1.14, (ES$^+$) m/z (M+H)$^+$=479.2.

Intermediate 25: 1-[2-[4-[3-[1-(5-chloropyrimidin-2-yl)-4-piperidyl]propoxy]-2-fluoro-phenyl]acetyl]azetidine-3-carboxylic acid

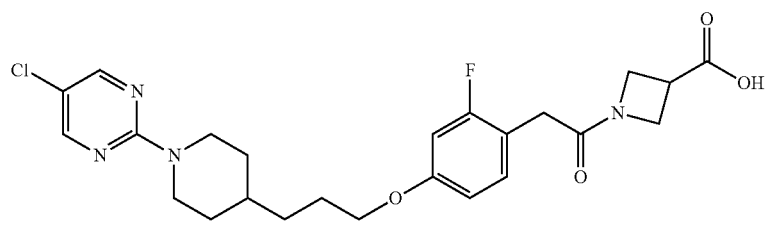 [SMILES: O=C(O)C1CN(C(=O)Cc2ccc(OCCCC3CCN(c4ncc(Cl)cn4)CC3)cc2F)C1]

Prepared using procedures outlined in the preparation of intermediate 21; replacing methyl 6-amino-hexanoate hydrochloride with methyl 3-azetidine carboxylate hydrochloride in step 1 to give 1-[2-[4-[3-[1-(5-chloropyrimidin-2-yl)-4-piperidyl]propoxy]-2-fluoro-phenyl]acetyl]azetidine-3-carboxylic acid. $^1$H NMR (500 MHz, Chloroform-d) δ 8.15 (s, 2H), 7.13 (t, J=8.6 Hz, 1H), 6.58 (dd, J=8.5, 2.6 Hz, 1H), 6.52 (dd, J=11.7, 2.4 Hz, 1H), 4.63-4.53 (m, 2H), 4.24 (p, J=8.7 Hz, 2H), 4.19-4.08 (m, 2H), 3.86 (t, J=6.3 Hz, 2H), 3.34 (dd, J=15.1, 5.3 Hz, 3H), 2.80 (td, J=12.9, 2.6 Hz, 2H), 1.73 (ddt, J=16.5, 11.8, 5.3 Hz, 4H), 1.51 (th, J=11.2, 3.1 Hz, 1H), 1.34 (q, J=7.2 Hz, 2H), 1.10 (qd, J=12.5, 4.1 Hz, 2H). LCMS: tR=1.20, (ES$^+$) m/z (M+H)$^+$=491.2.

Intermediate 26: 1-[2-[4-[3-[1-(5-chloropyrimidin-2-yl)-4-piperidyl]propoxy]-2,6-difluoro-phenyl]acetyl]azetidine-3-carboxylic acid Prepared using procedures outlined in the preparation of intermediate 21; replacing intermediate 1 with intermediate 2 and methyl 6-amino-hexanoate hydrochloride with methyl 3-azetidine carboxylate hydrochloride in step 1 to give 1-[2-[4-[3-[1-(5-chloropyrimidin-2-yl)-4-piperidyl]propoxy]-2,6-difluoro-phenyl]acetyl]azetidine-3-carboxylic acid. $^1$H NMR (500 MHz, DMSO-d$_6$) δ 12.74 (s, 1H), 8.38 (s, 2H), 6.81-6.60 (m, 2H), 4.58 (dt, J=13.2, 3.3 Hz, 2H), 4.38 (t, J=8.8 Hz, 1H), 4.27 (dd, J=8.4, 5.8 Hz, 1H), 4.03 (t, J=9.3 Hz, 1H), 3.98 (t, J=6.5 Hz, 2H), 3.89 (dd, J=9.5, 5.9 Hz, 1H), 3.44 (ddd, J=9.1, 7.5, 4.5 Hz, 1H), 3.39 (s, 2H), 2.88 (td, J=12.9, 2.7 Hz, 2H), 1.74 (p, J=7.1, 6.1 Hz, 4H), 1.58 (dqt, J=10.8, 6.8, 3.6 Hz, 1H), 1.35 (q, J=7.4 Hz, 2H), 1.05 (qd, J=12.5, 4.2 Hz, 2H). LCMS: tR=1.11, (ES$^+$) m/z (M+H)$^+$=509.3

Intermediate 27: 1-[2-[4-[3-[1-(5-ethylpyrimidin-2-yl)-4-piperidyl]propoxy]-2,6-difluoro-phenyl]acetyl]azetidine-3-carboxylic acid Prepared using procedures outlined in the preparation of intermediate 21; replacing intermediate 1 with intermediate 6 and methyl 6-amino-hexanoate hydrochloride with methyl 3-azetidine carboxylate hydrochloride in step 1 to give 1-[2-[4-[3-[1-(5-ethylpyrimidin-2-yl)-4-piperidyl]propoxy]-2,6-difluoro-phenyl]acetyl]azetidine-3-carboxylic acid. LCMS: tR=0.74, (ES$^+$) m/z (M+H)$^+$=503.5.

Intermediate 28: 1-[2-[2,6-difluoro-4-[3-[1-(5-propylpyrimidin-2-yl)-4-piperidyl]propoxy]phenyl]acetyl]azetidine-3-carboxylic acid

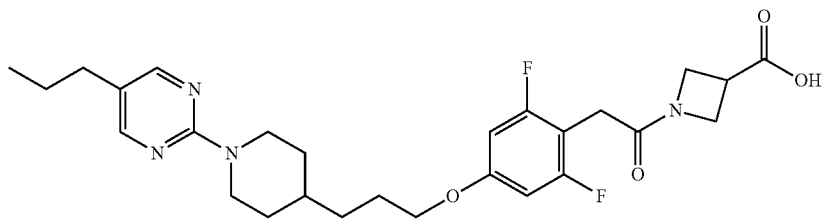 [SMILES: CCCc1cnc(N2CCC(CCCOc3cc(F)c(CC(=O)N4CC(C(=O)O)C4)c(F)c3)CC2)nc1]

Prepared using procedures outlined in the preparation of intermediate 21; replacing intermediate 1 with intermediate 8 and methyl 6-amino-hexanoate hydrochloride with methyl 3-azetidine carboxylate hydrochloride in step 1 to give 1-[2-[2,6-difluoro-4-[3-[1-(5-propylpyrimidin-2-yl)-4-piperidyl]propoxy]phenyl]acetyl]azetidine-3-carboxylic acid. $^1$H NMR (500 MHz, Chloroform-d) δ 8.29 (s, 2H), 6.52-6.38 (m, 2H), 4.76 (s, 2H), 4.32 (t, J=8.9 Hz, 1H), 4.27 (t, J=9.7 Hz, 1H), 4.24-4.18 (m, 2H), 4.00 (t, J=6.2 Hz, 2H), 3.52 (d, J=15.9 Hz, 1H), 3.48-3.41 (m, 2H), 3.01 (d, J=15.8 Hz, 2H), 2.47 (t, J=7.6 Hz, 2H), 1.91-1.76 (m, 2H), 1.62 (dt, J=14.9, 7.4 Hz, 2H), 1.44 (q, J=7.6 Hz, 2H), 1.33-1.18 (m, 2H), 0.97 (t, J=7.3 Hz, 3H). LCMS: tR=0.91, (ES$^+$) m/z (M+H)$^+$=517.3.

Intermediate 29: 2-[1-[2-[4-[3-[1-(5-chloropyrimidin-2-yl)-4-piperidyl]propoxy]-2-fluoro-phenyl]acetyl]azetidin-3-yl]acetic acid

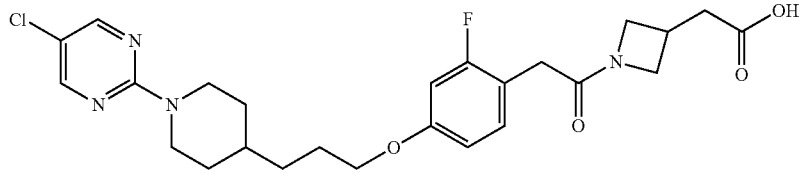 [SMILES: O=C(O)CC1CN(C(=O)Cc2ccc(OCCCC3CCN(c4ncc(Cl)cn4)CC3)cc2F)C1]

Prepared using procedures outlined in the preparation of intermediate 21; replacing methyl 6-amino-hexanoate hydrochloride with methyl 3-azetidine acetate trifluoroacetate to give in step 1. $^1$H NMR (500 MHz, DMSO-d$_6$) δ 12.24 (s, 1H), 8.38 (s, 2H), 7.16 (t, J=8.7 Hz, 1H), 6.76 (dd, J=12.0, 2.5 Hz, 1H), 6.71 (dd, J=8.5, 2.5 Hz, 1H), 4.58 (dq, J=13.5, 2.7, 1.8 Hz, 2H), 4.26 (t, J=8.4 Hz, 1H), 3.98-3.91 (m, 3H), 3.84 (dd, J=8.5, 5.7 Hz, 1H), 3.52 (dd, J=9.6, 5.8 Hz, 1H), 3.38-3.28 (m, 2H), 2.93-2.79 (m, 3H), 2.59 (d, J=7.8 Hz, 2H), 1.80-1.69 (m, 4H), 1.58 (dqd, J=10.9, 7.0, 3.2 Hz, 1H), 1.40-1.31 (m, 2H), 1.06 (qd, J=12.5, 4.2 Hz, 2H). LCMS: tR=1.07, (ES$^+$) m/z (M+H)$^+$=505.2.

Intermediate 30: 2-[1-[2-[4-[3-[1-(5-chloropyrimidin-2-yl)-4-piperidyl]propoxy]-2,6-difluoro-phenyl]acetyl]azetidin-3-yl]acetic acid

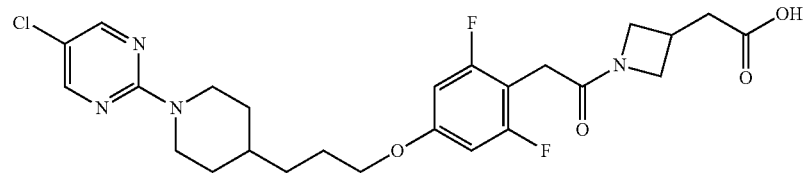 [SMILES: O=C(O)CC1CN(C(=O)Cc2c(F)cc(OCCCC3CCN(c4ncc(Cl)cn4)CC3)cc2F)C1]

Prepared using procedures outlined in the preparation of intermediate 21; replacing intermediate 1 with intermediate 2 and methyl 6-amino-hexanoate hydrochloride with methyl 3-azetidine acetate trifluoroacetate to give 2-[1-[2-[4-[3-[1-(5-chloropyrimidin-2-yl)-4-piperidyl]propoxy]-2,6-difluoro-phenyl]acetyl]azetidin-3-yl]acetic acid. $^1$H NMR (500 MHz, Chloroform-d) δ 8.21 (s, 2H), 6.47-6.39 (m, 2H), 4.66 (ddq, J=13.4, 4.6, 2.2 Hz, 2H), 4.35 (t, J=8.5 Hz, 1H), 4.23-4.17 (m, 1H), 3.91 (t, J=6.4 Hz, 2H), 3.87 (dd, J=8.8, 5.5 Hz, 1H), 3.72 (dd, J=10.2, 5.7 Hz, 1H), 3.40 (s, 2H), 3.03-2.94 (m, 1H), 2.87 (td, J=12.9, 2.7 Hz, 2H), 2.69 (dd, J=7.8, 2.6 Hz, 2H), 1.87-1.74 (m, 4H), 1.57 (ttt, J=10.6, 6.9, 3.6 Hz, 1H), 1.41 (ddt, J=12.2, 7.0, 3.6 Hz, 2H), 1.23-1.11 (m, 2H). LCMS: tR=1.14, (ES$^+$) m/z (M+H)$^+$=523.2.

Intermediate 31: 1-[2-[4-[3-[1-(5-chloropyrimidin-2-yl)-4-piperidyl]propoxy]-2-fluoro-phenyl]acetyl]piperidine-4-carboxylic acid

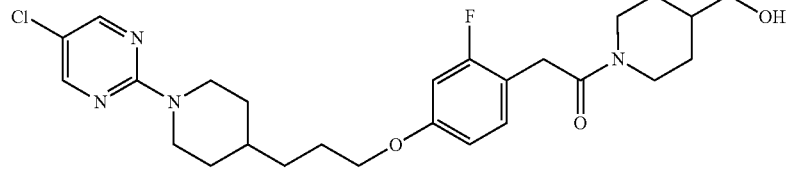

Prepared using procedures outlined in the preparation of intermediate 21; replacing methyl 6-amino-hexanoate hydrochloride with methyl-4-piperidine carboxylate in step 1 to give 1-[2-[4-[3-[1-(5-chloropyrimidin-2-yl)-4-piperidyl]propoxy]-2-fluoro-phenyl]acetyl]piperidine-4-carboxylic acid. LCMS: tR=1.40, (ES$^+$) m/z (M+H)$^+$=519.3.

Intermediate 32: 3-(1-(2-(4-(3-(1-(5-chloropyrimidin-2-yl)piperidin-4-yl)propoxy)-2-fluorophenyl)acetyl)azetidin-3-yl)propanoic acid

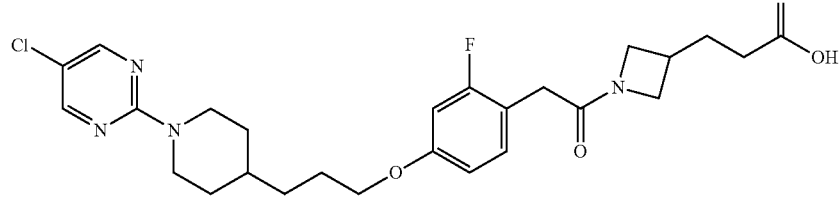

Step 1: tert-butyl (E)-3-(3-ethoxy-3-oxoprop-1-en-1-yl)azetidine-1-carboxylate

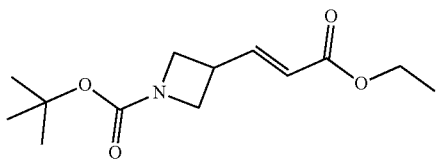

To a solution of triethyl phosphonoacetate (2.6 mL, 12.9 mmol) in THF (30 mL) cooled in an ice bath was added sodium hydride (518 mg of a 60% dispersion, 12.9 mmol) and the resulting mixture stirred at room temperature for 15 mins. To this mixture was added a solution of 3-formyl BOC azetidine (1.5 g, 8.1 mmol) in THF (10 mL) and the resulting mixture stirred at room temperature for 1 hour. Quenched by the addition of 1N HCl (100 mL) and extracted with EtOAc (2×50 mL), dried over MgSO$_4$, filtered and evaporated. The residue was purified by silica gel column chromatography (Teledyne Isco: SNAP 24 g GOLD) eluent: 0-100% EtOAc in Hexanes to give tert-butyl (E)-3-(3-ethoxy-3-oxoprop-1-en-1-yl)azetidine-1-carboxylate (868 mg, 42%) as a colorless oil. $^1$H NMR (500 MHz, Chloroform-d) δ 7.08 (dd, J=15.6, 8.1 Hz, 1H), 5.87 (dd, J=15.7, 1.2 Hz, 1H), 4.21 (q, J=7.1 Hz, 2H), 4.14 (t, J=8.6 Hz, 2H), 3.81 (dd, J=8.6, 5.8 Hz, 2H), 3.33 (qtd, J=8.4, 5.8, 1.2 Hz, 1H), 1.44 (s, 9H), 1.30 (t, J=7.1 Hz, 3H).

Step 2: tert-butyl 3-(3-ethoxy-3-oxopropyl)azetidine-1-carboxylate

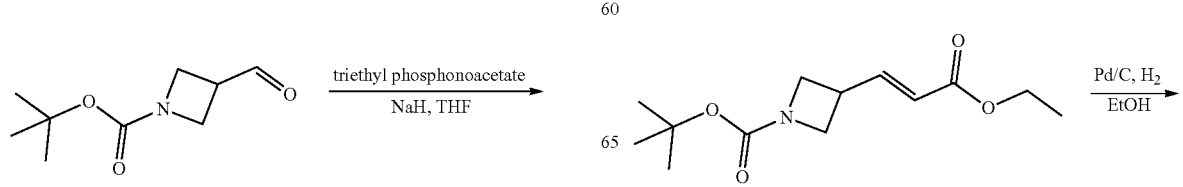

-continued

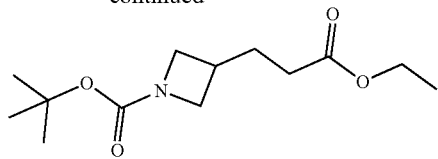

To a nitrogen flushed solution of tert-butyl (E)-3-(3-ethoxy-3-oxoprop-1-en-1-yl)azetidine-1-carboxylate (868 mg, 3.4 mmol) in ethanol (30 mL) was added 10% palladium on carbon (100 mg) and the resulting mixture stirred under a balloon of hydrogen overnight. Mixture filtered through celite and the filtrate evaporated to give tert-butyl 3-(3-ethoxy-3-oxopropyl)azetidine-1-carboxylate (768 mg, 88%) as a colorless oil. $^1$H NMR (500 MHz, Chloroform-d) δ 4.13 (q, J=7.2 Hz, 2H), 4.00 (dd, J=8.7, 8.1 Hz, 2H), 3.54 (dd, J=8.7, 5.6 Hz, 2H), 2.52 (tt, J=7.9, 5.5 Hz, 1H), 2.26 (t, J=7.5 Hz, 2H), 1.91 (q, J=7.6 Hz, 2H), 1.43 (s, 9H), 1.26 (t, J=7.1 Hz, 3H).

Step 3: ethyl 3-(azetidin-3-yl)propanoate hydrochloride

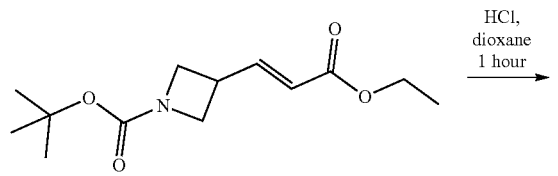

To tert-butyl 3-(3-ethoxy-3-oxopropyl)azetidine-1-carboxylate (5.5 g, 21.4 mmol) was added hydrogen chloride solution (50 mL of 4M in dioxanes, 214 mmol) and the resulting mixture stirred at room temperature for 1 hour. Mixture evaporated to give ethyl 3-(azetidin-3-yl)propanoate hydrochloride (4.3 g, 100%).

Step 4: Ethyl 3-(1-(2-(4-(3-(1-(5-chloropyrimidin-2-yl)piperidin-4-yl)propoxy)-2-fluorophenyl) acetyl)azetidin-3-yl)propanoate

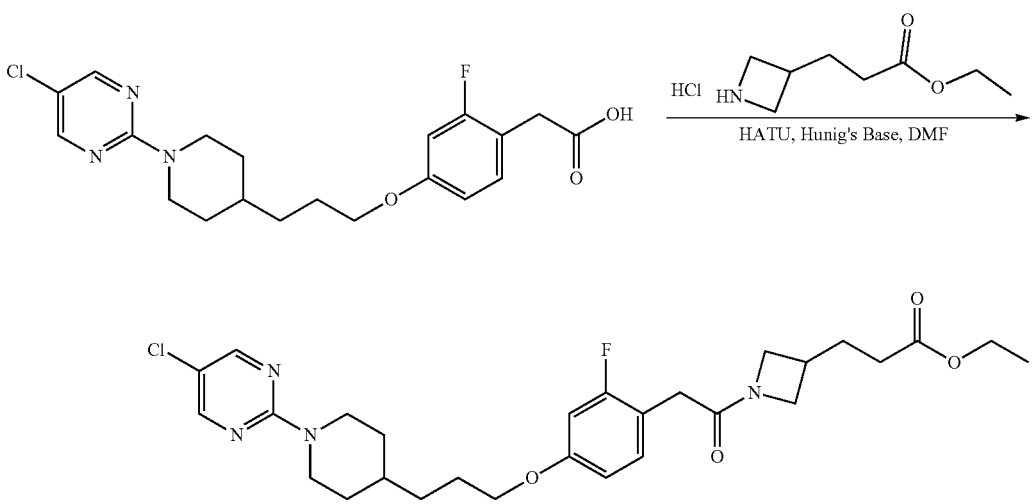

To a solution of 2-(4-(3-(1-(5-chloropyrimidin-2-yl)piperidin-4-yl)propoxy)-2-fluorophenyl)acetic acid intermediate 1 (80 mg, 0.2 mmol) in DMF (1 mL) was added ethyl 3-(azetidin-3-yl)propanoate hydrochloride (76 mg, 0.4 mmol), HATU (112 mg, 0.3 mmol) and Hunig's base (136 mL, 0.79 mmol) and the resulting mixture stirred at room temperature for 90 mins. Diluted with EtOAc (20 mL) and washed with water (80 mL), sat. NaCl (30 mL), dried over MgSO$_4$, filtered and evaporated. The residue was purified by silica gel column chromatography (Teledyne Isco: SNAP 12 g Gold) eluent: gradient 1-4% MeOH in DCM to give ethyl 3-(1-(2-(4-(3-(1-(5-chloropyrimidin-2-yl)piperidin-4-yl)propoxy)-2-fluorophenyl) acetyl)azetidin-3-yl)propanoate (67 mg, 61%) as a waxy solid. $^1$H NMR (500 MHz, Chloroform-d) δ 8.20 (s, 2H), 7.22 (t, J=8.6 Hz, 1H), 6.64 (dd, J=8.5, 2.5 Hz, 1H), 6.58 (dd, J=11.7, 2.5 Hz, 1H), 4.71-4.65 (m, 2H), 4.21 (t, J=8.4 Hz, 1H), 4.13 (q, J=7.1 Hz, 2H), 4.08 (dd, J=9.9, 8.5 Hz, 1H), 3.92 (t, J=6.4 Hz, 2H), 3.74 (dd, J=8.5, 5.5 Hz, 1H), 3.63 (dd, J=9.9, 5.6 Hz, 1H), 3.37 (s, 2H), 2.86 (td, J=12.9, 2.7 Hz, 2H), 2.59 (tt, J=8.0, 5.5 Hz, 1H), 2.26 (td, J=7.4, 1.8 Hz, 2H), 1.92 (q, J=7.5 Hz, 2H), 1.80 (ddd, J=11.9, 9.3, 4.6 Hz, 4H), 1.61-1.57 (m, 1H), 1.45-1.38 (m, 2H), 1.26 (t, J=7.1 Hz, 3H), 1.18 (qd, J=12.5, 4.2 Hz, 2H). LCMS: tR=1.45, (ES$^+$) m/z (M+H)$^+$=547.3.

Step 5: 3-(1-(2-(4-(3-(1-(5-chloropyrimidin-2-yl)piperidin-4-yl)propoxy)-2-fluorophenyl)acetyl)azetidin-3-yl)propanoic acid

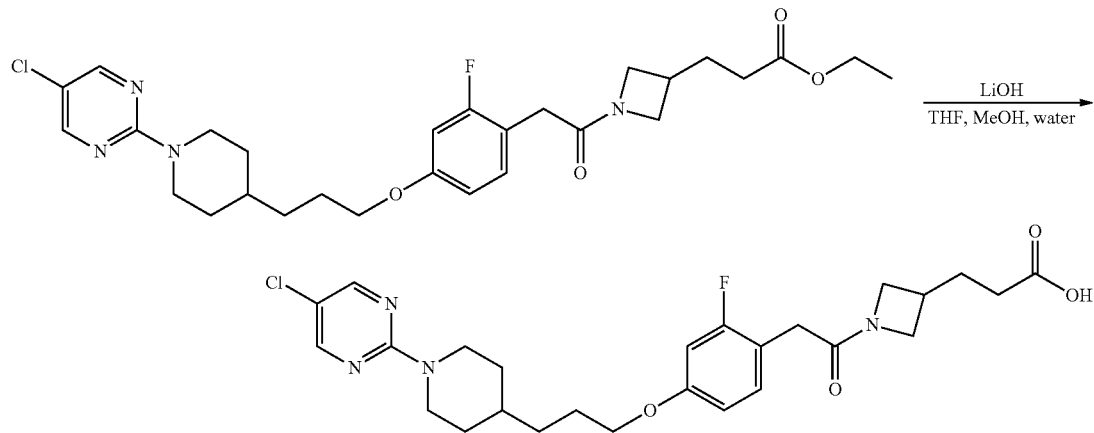

To a solution of ethyl 3-(1-(2-(4-(3-(1-(5-chloropyrimidin-2-yl)piperidin-4-yl)propoxy)-2-fluorophenyl) acetyl)azetidin-3-yl)propanoate (60 mg, 0.11 mmol) in a mixture of methanol (0.25 mL) and THF (0.75 mL) was added lithium hydroxide (0.22 mL of a 1M aqueous solution, 0.22 mmol) and the resulting mixture stirred at room temperature for 2 hours. Mixture acidified by the addition of TN HCl (1 mL) and the organic solvents removed by evaporation. The remaining aqueous was diluted with water (20 mL) and extracted with DCM (20 mL); dried over MgSO$_4$, filtered and evaporated to give 3-(1-(2-(4-(3-(1-(5-chloropyrimidin-2-yl)piperidin-4-yl)propoxy)-2-fluorophenyl)acetyl)azetidin-3-yl)propanoic acid (53 mg, 93%) as a white solid. LCMS: tR=1.12, (ES$^+$) m/z (M+H)$^+$=519.2.

Intermediate 33: 3-(1-(2-(4-(3-(1-(5-chloropyrimidin-2-yl)piperidin-4-yl)propoxy)-2,6-difluorophenyl)acetyl)azetidin-3-yl)propanoic acid

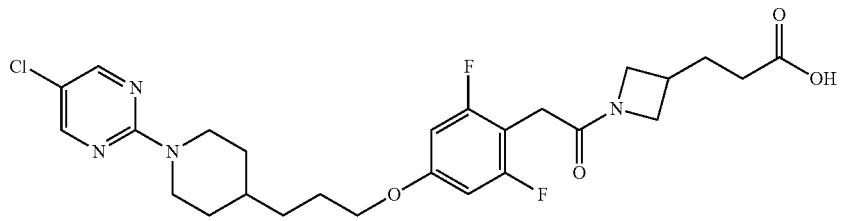 [SMILES: O=C(O)CCC1CN(C(=O)Cc2c(F)cc(OCCCC3CCN(c4ncc(Cl)cn4)CC3)cc2F)C1]

Prepared using procedures outlined in the preparation of intermediate 32; replacing intermediate 1 with intermediate 2 in step 4 and methyl 6-amino-hexanoate hydrochloride with ethyl 3-(azetidin-3-yl)propanoate hydrochloride to give 3-(1-(2-(4-(3-(1-(5-chloropyrimidin-2-yl)piperidin-4-yl)propoxy)-2,6-difluorophenyl)acetyl)azetidin-3-yl)propanoic acid LCMS: tR=1.19, (ES$^+$) m/z (M+H)$^+$=537.3.

Intermediate 34: 2-(4-(3-(1-(5-chloropyrimidin-2-yl)piperidin-4-yl)propoxy)-2-fluorophenyl)-N-(5-hydroxypentyl) acetamide

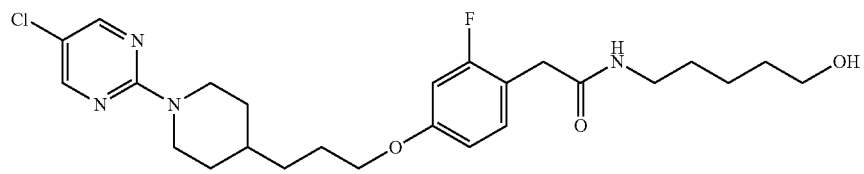 [SMILES: O=C(Cc1ccc(OCCCC2CCN(c3ncc(Cl)cn3)CC2)cc1F)NCCCCCO]

215

To a solution of 2-(4-(3-(1-(5-chloropyrimidin-2-yl)piperidin-4-yl)propoxy)-2-fluorophenyl)acetic acid intermediate 1 (400 mg, 0.98 mmol) in DMF (4 mL) was added 5-amino-1-pentanol (152 mg, 1.47 mmol), HATU (560 mg, 1.47 mmol) and Hunig's base (342 mL, 1.96 mmol) and the resulting mixture stirred at room temperature overnight. Diluted with EtOAc (50 mL) and washed with water (100 mL), sat. NaCl (50 mL), dried over MgSO$_4$, filtered and evaporated. The residue was purified by silica gel column chromatography (Teledyne Isco: SNAP 24 g Gold) eluent: gradient 2-10% MeOH in DCM to give 2-(4-(3-(1-(5-chloropyrimidin-2-yl)piperidin-4-yl)propoxy)-2-fluorophenyl)-N-(5-hydroxypentyl)acetamide (426 mg, 88%) as a white solid. $^1$H NMR (500 MHz, Chloroform-d) δ 8.20 (s, 2H), 7.17 (t, J=8.6 Hz, 1H), 6.67 (dd, J=8.4, 2.6 Hz, 1H), 6.63 (dd, J=11.7, 2.5 Hz, 1H), 5.48 (s, 1H), 4.73-4.63 (m, 2H), 3.94 (t, J=6.4 Hz, 2H), 3.61 (q, J=5.9 Hz, 2H), 3.49 (d, J=1.3 Hz, 2H), 3.23 (td, J=7.1, 5.9 Hz, 2H), 2.87 (td, J=12.9, 2.7 Hz, 2H), 1.87-1.76 (m, 4H), 1.55 (dq, J=8.1, 6.5 Hz, 2H), 1.51-1.40 (m, 3H), 1.40-1.29 (m, 2H), 1.23-1.13 (m, 2H). LCMS: tR=1.08, (ES$^+$) m/z (M+H)$^+$=493.2.

Intermediate 35: 2-(2,6-difluoro-4-(3-(1-(5-propylpyrimidin-2-yl)piperidin-4-yl)propoxy)phenyl)-N-(5-hydroxypentyl) acetamide

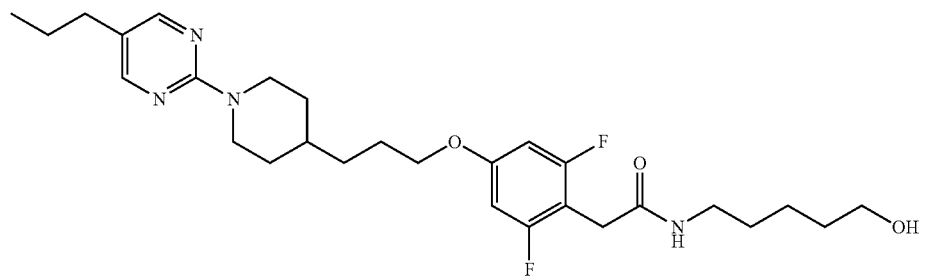 [SMILES: CCCc1cnc(N2CCC(CCCOc3cc(F)c(CC(=O)NCCCCCO)c(F)c3)CC2)nc1]

Prepared using procedures outlined in the preparation of intermediate 33; replacing intermediate 1 with intermediate 8 to give 2-(4-(3-(1-(5-chloropyrimidin-2-yl)piperidin-4-yl)propoxy)-2-fluorophenyl)-N-(5-hydroxypentyl)acetamide. 1H NMR (500 MHz, Chloroform-d) δ 8.15 (s, 2H), 6.51-6.43 (m, 2H), 5.49 (s, 1H), 4.69 (d, J=13.1 Hz, 2H), 3.92 (t, J=6.4 Hz, 2H), 3.63 (t, J=6.5 Hz, 2H), 3.51 (s, 2H), 3.25 (td, J=7.1, 5.8 Hz, 2H), 2.87 (td, J=12.9, 2.7 Hz, 2H), 2.39 (t, J=7.5 Hz, 2H), 1.87-1.77 (m, 5H), 1.59-1.52 (m, 25H), 1.53-1.46 (m, 2H), 1.45-1.38 (m, 3H), 1.38-1.32 (m, 2H), 1.24-1.16 (m, 2H), 0.93 (t, J=7.3 Hz, 3H). LCMS: tR=0.94, (ES$^+$) m/z (M+H)$^+$=519.4.

Intermediate 36: 1-(2-aminoethyl)-3-(1,3-dihydroxy-2-(hydroxymethyl)propan-2-yl)urea naphthalene-1,5-disulfonate

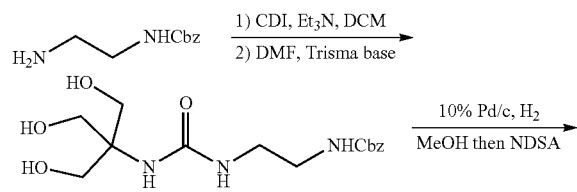

216

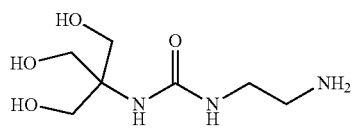

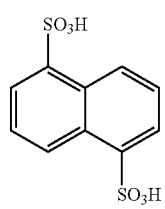

To a solution of benzyl 2-aminoethylcarbamate (1.00 g, 5.15 mmol) and triethylamine (1.00 mL, 7.21 mmol) in DCM (5 mL) was added a solution of carbonyldiimidazole (1.17 g, 7.21 mmol) in DCM (5 mL) dropwise at room temperature and stirred for 1 hr. The mixture was quenched with water (10 mL) and the layers were separated. The organic solution was dried over MgSO$_4$ and concentrated. The residue was dissolved in DMF (5 mL) and 2-amino-2-(hydroxymethyl)-1,3-propanediol (1.25 g, 10.3 mmol) was added and the mixture was heated to 50° C. for 12 hr. The mixture was quenched with 1M aq citric acid and extracted with DCM (2×20 mL). The organic layer was dried over MgSO$_4$ and concentrated. The residue was dissolved in methanol (20 mL) and 10 wt % Pd/C was added to the solution. Hydrogen was bubbled into the mixture and the reaction stirred under hydrogen balloon for 12 hr. The mixture was filtered through Celite and the cake was washed with MeOH (40 mL). The solution was concentrated to 20 mL and naphthalene-1,5-disulfonic acid tetrahydrate (3.71 g, 10.3 mmol, 2 eq) was added and the mixture stirred. After 10 min, solids precipitated and continued to stir for 1 hr. The solids were filtered and washed with methanol (10 mL) to give 1-(2-aminoethyl)-3-(1,3-dihydroxy-2-(hydroxymethyl)propan-2-yl)urea naphthalene-1,5-disulfonate (2.30 g, 90%) as a white solid. $^1$H NMR (500 MHz, DMSO-d$_6$) δ 8.92-8.85 (m, 2H), 7.97 (dd, J=7.1, 1.2 Hz, 2H), 7.70 (s, 3H), 7.45 (dd, J=8.6, 7.1 Hz, 2H), 6.02 (s, 7H), 3.47 (s, 6H), 3.23-3.14 (m, 2H), 2.81 (h, J=5.9 Hz, 2H).

Intermediate 37: 2-(4-(3-(1-(5-chloropyrimidin-2-yl)piperidin-4-yl)propoxy)-2-fluorophen)-1-(3-(hydroxymethyl)azetidin-1-yl)ethan-1-one

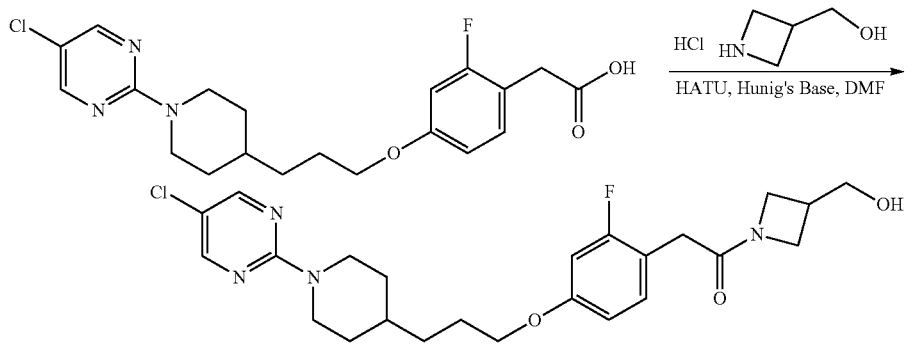

To a solution of 2-(4-(3-(1-(5-chloropyrimidin-2-yl)piperidin-4-yl)propoxy)-2-fluorophenyl)acetic acid intermediate 1 (500 mg, 1.23 mmol) in DMF (10 mL) was added HATU (700 mg, 1.84 mmol) and Hunig's base (640 mL, 3.69 mmol) followed by azetidine-3-methanol hydrochloride (196 mg, 1.6 mmol), and the resulting mixture stirred at room temperature for 90 mins. The mixture was diluted with EtOAc (50 mL) and washed with water (100 mL), sat. NaCl (80 mL), dried over MgSO$_4$, filtered and evaporated. The residue was purified by silica gel column chromatography (Teledyne Isco: SNAP 24 g Gold) eluent: gradient 2-10% MeOH in DCM to give 2-(4-(3-(1-(5-chloropyrimidin-2-yl)piperidin-4-yl)propoxy)-2-fluorophenyl)-1-(3-(hydroxymethyl)azetidin-1-yl)ethan-1-one (508 mg, 86%) as a white solid. $^1$H NMR (500 MHz, Chloroform-d) δ 8.22 (s, 2H), 7.24 (t, J=8.6 Hz, 1H), 6.67 (ddd, J=8.5, 2.6, 0.7 Hz, 1H), 6.61 (dd, J=11.8, 2.5 Hz, 1H), 4.70 (dp, J=13.3, 2.0 Hz, 2H), 4.21 (t, J=8.5 Hz, 1H), 4.12-4.05 (m, 1H), 3.99-3.91 (m, 3H), 3.84-3.72 (m, 3H), 3.43-3.39 (m, 2H), 2.89 (ddd, J=13.3, 12.3, 2.7 Hz, 2H), 2.83-2.74 (m, 1H), 1.88-1.77 (m, 5H), 1.60 (ddq, J=14.8, 7.7, 3.5 Hz, 1H), 1.46-1.41 (m, 2H), 1.25-1.15 (m, 2H). LCMS: tR=1.01, (ES$^+$) m/z (M+H)$^+$=477.2.

Intermediate 38: 2-(4-(3-(1-(5-chloropyrimidin-2-yl)piperidin-4-yl)propoxy)-2-fluorophenyl)-1-(3-(2-hydroxyethyl)azetidin-1-yl)ethan-1-one

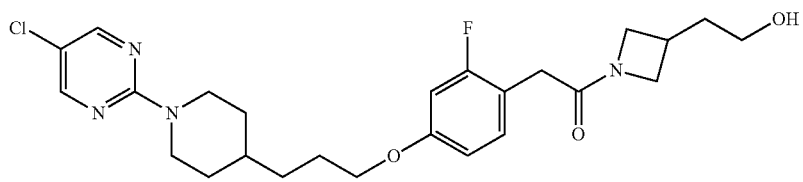 [SMILES: O=C(Cc1ccc(OCCCC2CCN(c3ncc(Cl)cn3)CC2)cc1F)N1CC(CCO)C1]

Prepared using procedures outlined in the preparation of intermediate 37; replacing azetidine-3-methanol hydrochloride with 2-(azetidin-3-yl)ethanol hydrochloride to give 2-(4-(3-(1-(5-chloropyrimidin-2-yl)piperidin-4-yl)propoxy)-2-fluorophenyl)-1-(3-(2-hydroxyethyl)azetidin-1-yl)ethan-1-one. $^1$H NMR (500 MHz, Chloroform-d) δ 8.20 (s, 2H), 7.22 (t, J=8.6 Hz, 1H), 6.64 (dd, J=8.5, 2.5 Hz, 1H), 6.58 (dd, J=11.7, 2.5 Hz, 1H), 4.68 (dp, J=13.2, 1.9 Hz, 2H), 4.29-4.21 (m, 1H), 4.16-4.09 (m, 1H), 3.92 (t, J=6.5 Hz, 2H), 3.81 (dd, J=8.5, 5.6 Hz, 1H), 3.73-3.61 (m, 3H), 3.38 (s, 2H), 2.92-2.82 (m, 2H), 2.73 (tt, J=8.0, 5.7 Hz, 1H), 1.91-1.74 (m, 6H), 1.56 (dtd, J=14.7, 7.8, 7.0, 4.5 Hz, 1H), 1.45-1.37 (m, 3H), 1.23-1.12 (m, 2H). LCMS: tR=1.08, (ES$^+$) m/z (M+H)$^+$=491.3.

Intermediate 39: 2-(4-(3-(1-(5-chloropyrimidin-2-yl)piperidin-4-yl)propoxy)-2,6-difluorophenyl)-1-(3-(hydroxymethyl)_azetidin-1-yl)ethan-1-one

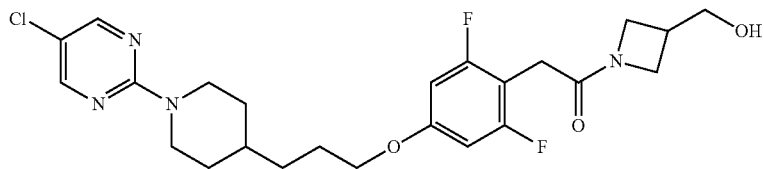 [SMILES: O=C(Cc1c(F)cc(OCCCC2CCN(c3ncc(Cl)cn3)CC2)cc1F)N1CC(CO)C1]

Prepared using procedures outlined in the preparation of intermediate 37; replacing intermediate 1 with intermediate 2 to give 2-(4-(3-(1-(5-chloropyrimidin-2-yl)piperidin-4-yl)propoxy)-2,6-difluorophenyl)-1-(3-(hydroxymethyl)azetidin-1-yl)ethan-1-one. $^1$H NMR (500 MHz, Chloroform-d) δ 8.20 (s, 2H), 7.22 (t, J=8.6 Hz, 1H), 6.64 (dd, J=8.5, 2.5 Hz, 1H), 6.58 (dd, J=11.7, 2.5 Hz, 1H), 4.68 (dp, J=13.2, 1.9 Hz, 2H), 4.29-4.21 (m, 1H), 4.16-4.09 (m, 1H), 3.92 (t, J=6.5 Hz, 2H), 3.81 (dd, J=8.5, 5.6 Hz, 1H), 3.73-3.61 (m, 3H), 3.38 (s, 2H), 2.92-2.82 (m, 2H), 2.73 (tt, J=8.0, 5.7 Hz, 1H), 1.91-1.74 (m, 6H), 1.56 (dtd, J=14.7, 7.8, 7.0, 4.5 Hz, 1H), 1.45-1.37 (m, 3H), 1.23-1.12 (m, 2H). LCMS: tR=1.11, (ES$^+$) m/z (M+H)+=495.3.

Intermediate 40: 2-(4-(4-(1-(5-chloropyrimidin-2-yl)piperidin-4-yl)butoxy)-2-fluorophenyl)-1-(3-(hydroxymethyl)azetidin-1-yl)ethan-1-one Prepared using procedures outlined in the preparation of intermediate 37; replacing intermediate 1 with intermediate 3 to give 2-(4-(4-(1-(5-chloropyrimidin-2-yl)piperidin-4-yl)butoxy)-2-fluorophenyl)-1-(3-(hydroxymethyl)azetidin-1-yl)ethan-1-one. $^1$H NMR (500 MHz, Chloroform-d) δ 8.19 (s, 2H), 7.22 (t, J=8.6 Hz, 1H), 6.65 (dd, J=8.4, 2.6 Hz, 1H), 6.59 (dd, J=11.8, 2.5 Hz, 1H), 4.66 (dp, J=13.3, 1.9 Hz, 2H), 4.19 (t, J=8.5 Hz, 1H), 4.10-4.03 (m, 1H), 3.93 (q, J=6.5 Hz, 3H), 3.77 (dp, J=8.6, 4.2, 3.1 Hz, 3H), 3.39 (t, J=1.7 Hz, 2H), 2.90-2.81 (m, 2H), 2.81-2.73 (m, 1H), 1.80-1.72 (m, 5H), 1.69 (t, J=5.1 Hz, 1H), 1.57-1.45 (m, 2H), 1.35-1.28 (m, 2H), 1.20-1.10 (m, 2H). LCMS: tR=1.17, (ES$^+$) m/z (M+H)$^+$=491.3.

Intermediate 41: 2-(4-(4-(1-(5-chloropyrimidin-2-yl)piperidin-4-yl)butoxy)-2,6-difluorophenyl)-1-(3-(hydroxymethyl)_azetidin-1-yl)ethan-1-one Prepared using procedures outlined in the preparation of intermediate 37; replacing intermediate 1 with intermediate 4 to give 2-(4-(4-(1-(5-chloropyrimidin-2-yl)piperidin-4-yl)butoxy)-2,6-difluorophenyl)-1-(3-(hydroxymethyl) azetidin-1-yl)ethan-1-one. $^1$H NMR (500 MHz, Chloroform-d) δ 8.20 (s, 2H), 6.44 (d, J=9.3 Hz, 2H), 4.67 (dp, J=13.3, 1.9 Hz, 2H), 4.24 (t, J=8.4 Hz, 1H), 4.08 (dd, J=10.0, 8.5 Hz, 1H), 3.98 (dd, J=8.5, 5.2 Hz, 1H), 3.90 (t, J=6.4 Hz, 2H), 3.85-3.75 (m, 3H), 3.40 (s, 2H), 2.89-2.82 (m, 2H), 2.82-2.77 (m, 1H), 1.81-1.73 (m, 4H), 1.58-1.44 (m, 3H), 1.35-1.28 (m, 2H), 1.21-1.10 (m, 2H). LCMS: tR=1.17, (ES$^+$) m/z (M+H)$^+$=509.3.

Intermediate 42: 2-(4-(3-(1-(5-ethylpyrimidin-2-yl)piperidin-4-yl)propoxy)-2-fluorophenyl)-1-(3-(hydroxymethyl)azetidin-1-yl)ethan-1-one

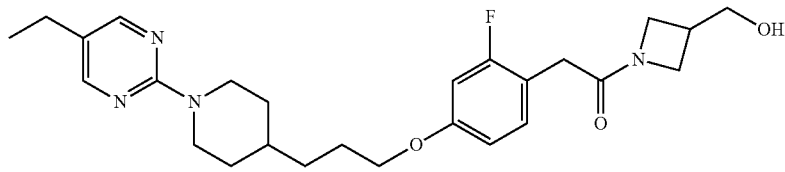 [SMILES: CCc1cnc(N2CCC(CCCOc3ccc(CC(=O)N4CC(CO)C4)c(F)c3)CC2)nc1]

Prepared using procedures outlined in the preparation of intermediate 37; replacing intermediate 1 with intermediate 5 to give 2-(4-(3-(1-(5-ethylpyrimidin-2-yl)piperidin-4-yl)propoxy)-2-fluorophenyl)-1-(3-(hydroxymethyl)azetidin-1-yl)ethan-1-one. $^1$H NMR (500 MHz, Chloroform-d) δ 8.19 (s, 2H), 7.22 (t, J=8.6 Hz, 1H), 6.65 (dd, J=8.4, 2.6 Hz, 1H), 6.59 (dd, J=11.8, 2.5 Hz, 1H), 4.66 (dp, J=13.3, 1.9 Hz, 2H), 4.19 (t, J=8.5 Hz, 1H), 4.10-4.03 (m, 1H), 3.93 (q, J=6.5 Hz, 3H), 3.77 (dp, J=8.6, 4.2, 3.1 Hz, 3H), 3.39 (t, J=1.7 Hz, 2H), 2.90-2.81 (m, 2H), 2.81-2.73 (m, 1H), 1.80-1.72 (m, 5H), 1.69 (t, J=5.1 Hz, 1H), 1.57-1.45 (m, 2H), 1.35-1.28 (m, 2H), 1.20-1.10 (m, 2H). LCMS: tR=0.63, (ES$^+$) m/z (M+H)$^+$=471.4.

Intermediate 43: 2-(4-(3-(1-(5-ethylpyrimidin-2-yl)piperidin-4-yl)propoxy)-2,6-difluorophenyl)-1-(3-(hydroxymethyl) azetidin-1-yl)ethan-1-one

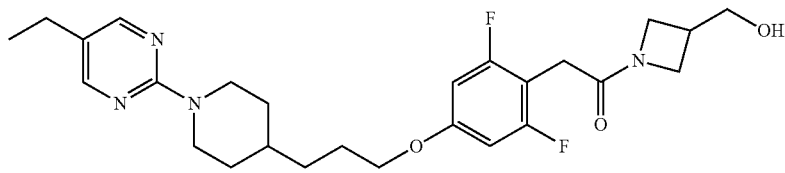 [SMILES: CCc1cnc(N2CCC(CCCOc3cc(F)c(CC(=O)N4CC(CO)C4)c(F)c3)CC2)nc1]

Prepared using procedures outlined in the preparation of intermediate 37; replacing intermediate 1 with intermediate 6 to give 2-(4-(3-(1-(5-ethylpyrimidin-2-yl)piperidin-4-yl)propoxy)-2,6-difluorophenyl)-1-(3-(hydroxymethyl) azetidin-1-yl)ethan-1-one. $^1$H NMR (500 MHz, Chloroform-d) δ 8.16 (s, 2H), 6.43 (d, J=9.3 Hz, 2H), 4.69 (dt, J=13.0, 2.5 Hz, 2H), 4.23 (t, J=8.4 Hz, 1H), 4.10-4.04 (m, 1H), 3.98 (dd, J=8.6, 5.3 Hz, 1H), 3.90 (t, J=6.4 Hz, 2H), 3.81-3.75 (m, 3H), 3.40 (s, 2H), 2.89-2.76 (m, 3H), 2.45 (q, J=7.6 Hz, 2H), 1.85-1.76 (m, 5H), 1.55 (th, J=10.7, 3.4 Hz, 1H), 1.44-1.37 (m, 3H), 1.18 (t, J=7.6 Hz, 6H). LCMS: tR=0.71, (ES$^+$) m/z (M+H)$^+$=489.4.

Intermediate 44: 2-(2-fluoro-4-(3-(1-(5-propylpyrimidin-2-yl)piperidin-4-yl)propoxy)phenyl)-1-(3-(hydroxymethyl)azetidin-1-yl)ethan-1-one

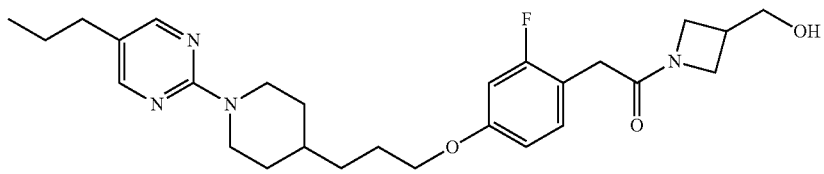 [SMILES: CCCc1cnc(N2CCC(CCCOc3ccc(CC(=O)N4CC(CO)C4)c(F)c3)CC2)nc1]

Prepared using procedures outlined in the preparation of intermediate 37; replacing intermediate 1 with intermediate 7 to give 2-(2-fluoro-4-(3-(1-(5-propylpyrimidin-2-yl)piperidin-4-yl)propoxy)phenyl)-1-(3-(hydroxymethyl)azetidin-1-yl)ethan-1-one. ¹H NMR (500 MHz, Chloroform-d) δ 8.14 (s, 2H), 7.21 (t, J=8.6 Hz, 1H), 6.68-6.62 (m, 1H), 6.59 (dd, J=11.8, 2.5 Hz, 1H), 4.68 (dt, J=13.0, 2.5 Hz, 2H), 4.19 (t, J=8.5 Hz, 1H), 4.10-4.02 (m, 1H), 3.93 (td, J=6.5, 5.9, 3.2 Hz, 3H), 3.77 (ddd, J=7.9, 5.5, 2.3 Hz, 3H), 3.39 (t, J=1.4 Hz, 2H), 2.89-2.81 (m, 2H), 2.81-2.72 (m, 1H), 2.41-2.35 (m, 2H), 1.98 (t, J=5.0 Hz, 1H), 1.86-1.75 (m, 4H), 1.56 (h, J=7.3 Hz, 3H), 1.46-1.37 (m, 3H), 1.24-1.15 (m, 2H), 0.93 (t, J=7.3 Hz, 3H). LCMS: tR=0.80, (ES⁺) m/z (M+H)⁺=485.4.

Intermediate 45: 2-(2,6-difluoro-4-(3-(1-(5-propylpyrimidin-2-yl)piperidin-4-yl)propoxy)phenyl)-1-(3-(hydroxymethyl) azetidin-1-yl)ethan-1-one

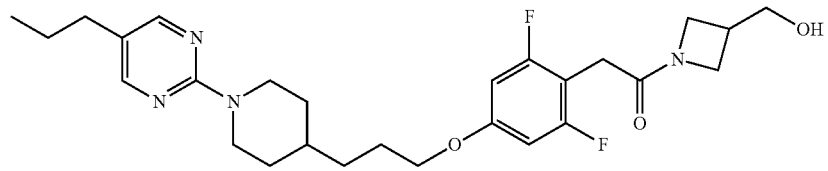 [SMILES: CCCc1cnc(N2CCC(CCCOc3cc(F)c(CC(=O)N4CC(CO)C4)c(F)c3)CC2)nc1]

Prepared using procedures outlined in the preparation of intermediate 37; replacing intermediate 1 with intermediate 8 to give 2-(2,6-difluoro-4-(3-(1-(5-propylpyrimidin-2-yl)piperidin-4-yl)propoxy)phenyl)-1-(3-(hydroxymethyl) azetidin-1-yl)ethan-1-one. ¹H NMR (500 MHz, Chloroform-d) δ 8.14 (s, 2H), 6.43 (d, J=9.1 Hz, 2H), 4.69 (dp, J=13.2, 2.0 Hz, 2H), 4.23 (t, J=8.4 Hz, 1H), 4.07 (dd, J=10.0, 8.4 Hz, 1H), 3.98 (dd, J=8.6, 5.3 Hz, 1H), 3.90 (t, J=6.5 Hz, 2H), 3.82-3.75 (m, 3H), 3.40 (s, 2H), 2.89-2.76 (m, 3H), 2.38 (t, J=7.5 Hz, 2H), 1.86-1.76 (m, 5H), 1.56 (h, J=7.4 Hz, 3H), 1.40 (dt, J=8.8, 7.1 Hz, 3H), 1.24-1.15 (m, 2H), 0.93 (t, J=7.3 Hz, 3H). LCMS: tR=0.88, (ES⁺) m/z (M+H)⁺=503.5.

Intermediate 46: 2-(2-fluoro-4-(3-(1-(5-methoxypyrimidin-2-yl)piperidin-4-yl)propoxy)phenyl)-1-(3-(hydroxymethyl) azetidin-1-yl)ethan-1-one

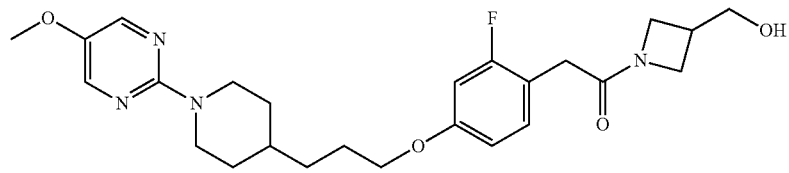

Prepared using procedures outlined in the preparation of intermediate 37; replacing intermediate 1 with intermediate 9 to give 2-(2-fluoro-4-(3-(1-(5-methoxypyrimidin-2-yl)piperidin-4-yl)propoxy)phenyl)-1-(3-(hydroxymethyl) azetidin-1-yl)ethan-1-one. ¹H NMR (500 MHz, Chloroform-d) δ 8.09 (s, 2H), 7.22 (t, J=8.7 Hz, 1H), 6.65 (dd, J=8.4, 2.6 Hz, 1H), 6.59 (dd, J=11.8, 2.5 Hz, 1H), 4.60 (d, J=13.1 Hz, 1H), 4.20 (t, J=8.5 Hz, 1H), 4.11-4.03 (m, 1H), 3.93 (t, J=6.4 Hz, 3H), 3.80 (s, 6H), 3.40 (s, 2H), 2.84 (td, J=12.7, 2.6 Hz, 2H), 2.77 (p, J=8.2 Hz, 1H) 1.85-1.75 (m, 4H), 1.50-1.38 (m, 4H), 1.24-1.15 (m, 2H). LCMS: tR=1.61, (ES⁺) m/z (M+H)⁺=473.3.

Intermediate 47: 2-(4-(3-(1-(5-ethoxypyrimidin-2-yl)piperidin-4-yl)propoxy)-2-fluorophenyl)-1-(3-(hydroxymethyl)azetidin-1-yl)ethan-1-one

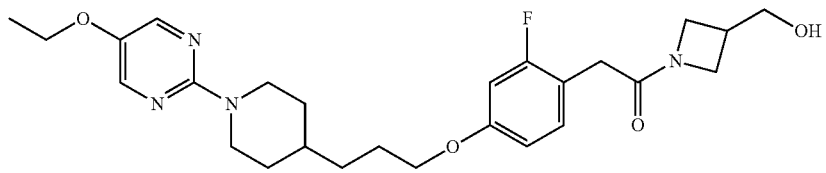 [SMILES: CCOc1cnc(N2CCC(CCCOc3ccc(CC(=O)N4CC(CO)C4)c(F)c3)CC2)nc1]

Prepared using procedures outlined in the preparation of intermediate 37 replacing intermediate 1 with intermediate 10 to give 2-(4-(3-(1-(5-ethoxypyrimidin-2-yl)piperidin-4-yl)propoxy)-2-fluorophenyl)-1-(3-(hydroxymethyl)azetidin-1-yl)ethan-1-one. H NMR (500 MHz, Chloroform-d) δ 8.09 (s, 2H), 7.21 (t, J=8.6 Hz, 1H), 6.68-6.62 (m, 1H), 6.58 (dd, J=11.7, 2.5 Hz, 1H), 4.64-4.56 (m, 2H), 4.20 (t, J=8.5 Hz, 1H), 4.07 (dd, J=10.0, 8.6 Hz, 1H), 4.00 (q, J=6.9 Hz, 2H), 3.93 (q, J=6.3 Hz, 3H), 3.82-3.74 (m, 3H), 3.40 (s, 2H), 2.91-2.83 (m, 2H), 2.82-2.74 (m, 1H), 1.88-1.78 (m, 4H), 1.53-1.48 (m, 3H), 1.44 (d, J=6.7 Hz, 2H), 1.39 (t, J=7.0 Hz, 3H), 1.19 (td, J=12.3, 4.2 Hz, 2H). LCMS: tR=1.71, (ES$^+$) m/z (M+H)$^+$=487.4.

Intermediate 48: 2-(2-fluoro-4-(3-(1-(5-(methoxymethyl)pyrimidin-2-yl)piperidin-4-yl)propoxy)phenyl)-1-(3-(hydroxyl methyl)azetidin-1-yl)ethan-1-one

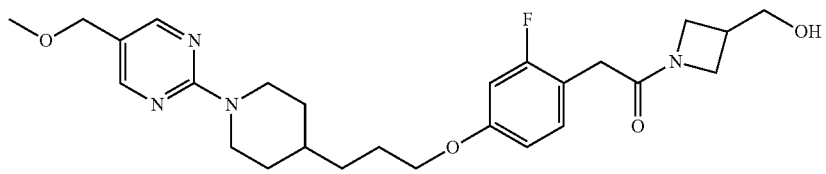 [SMILES: COCc1cnc(N2CCC(CCCOc3ccc(CC(=O)N4CC(CO)C4)c(F)c3)CC2)nc1]

Prepared using procedures outlined in the preparation of intermediate 37; replacing intermediate 1 with intermediate 11 to give 2-(2-fluoro-4-(3-(1-(5-(methoxymethyl)pyrimidin-2-yl)piperidin-4-yl)propoxy)phenyl)-1-(3-(hydroxyl methyl)azetidin-1-yl)ethan-1-one. $^1$H NMR (500 MHz, Chloroform-d) δ 8.27 (s, 2H), 7.21 (t, J=8.6 Hz, 1H), 6.68-6.62 (m, 1H), 6.59 (dd, J=11.7, 2.5 Hz, 1H), 4.74 (dp, J=13.3, 1.9 Hz, 2H), 4.26 (s, 2H), 4.19 (t, J=8.5 Hz, 1H), 4.09-4.03 (m, 1H), 3.93 (q, J=6.4 Hz, 3H), 3.82-3.74 (m, 3H), 3.39 (t, J=1.6 Hz, 2H), 3.34 (s, 3H), 2.91-2.83 (m, 2H), 2.80-2.73 (m, 1H), 1.80 (tdd, J=9.8, 7.7, 3.8 Hz, 2H), 1.59 (dddt, J=14.5, 10.7, 7.0, 4.1 Hz, 1H), 1.45-1.38 (m, 2H), 1.32-1.27 (m, 2H), 1.22-1.14 (m, 2H), LCMS: tR=0.69, (ES$^+$) m/z (M+H)$^+$=487.3.

Intermediate 49: 2-(2-fluoro-4-(4-(1-(5-(methoxymethyl)pyrimidin-2-yl)piperidin-4-yl)butoxy)phenyl)-1-(3-(hydroxymethyl)azetidin-1-yl)ethan-1-one

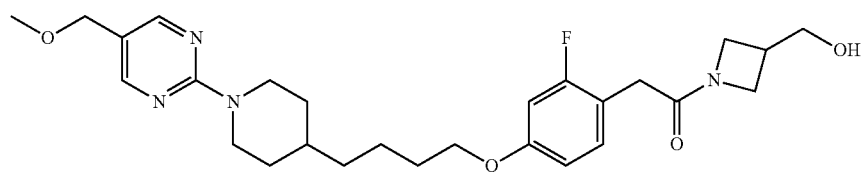 [SMILES: COCc1cnc(N2CCC(CCCCOc3ccc(CC(=O)N4CC(CO)C4)c(F)c3)CC2)nc1]

Prepared using procedures outlined in the preparation of intermediate 37; replacing intermediate 1 with intermediate 13 to give 2-(2-fluoro-4-(4-(1-(5-(methoxymethyl)pyrimidin-2-yl)piperidin-4-yl)butoxy)phenyl)-1-(3-(hydroxymethyl)azetidin-1-yl)ethan-1-one. LCMS: tR=0.62, (ES⁺) m/z (M+H)⁺=501.4.

Intermediate 50: 2-(2,6-difluoro-4-(4-(1-(5-(methoxymethyl)pyrimidin-2-yl)piperidin-4-yl)butoxy)phenyl)-1-(3-(hydroxymethyl)azetidin-1-yl)ethan-1-one

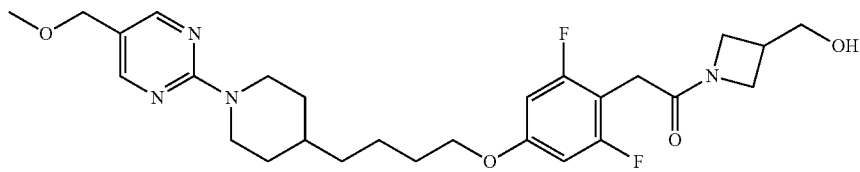 [SMILES: COCc1cnc(N2CCC(CCCCOc3cc(F)c(CC(=O)N4CC(CO)C4)c(F)c3)CC2)nc1]

Prepared using procedures outlined in the preparation of intermediate 37; replacing intermediate 1 with intermediate 14 to give 2-(2,6-difluoro-4-(4-(1-(5-(methoxymethyl)pyrimidin-2-yl)piperidin-4-yl)butoxy)phenyl)-1-(3-(hydroxymethyl)azetidin-1-yl)ethan-1-one. LCMS: tR=0.69, (ES⁺) m/z (M+H)⁺=519.4.

Intermediate 51: 2-(4-(2-(((1S,2R)-2-(1-(5-chloropyrimidin-2-yl)piperidin-4-yl)cyclopropyl)ethoxy)-2-fluorophenyl)-1-(3-(hydroxymethyl)azetidin-1-yl)ethan-1-one

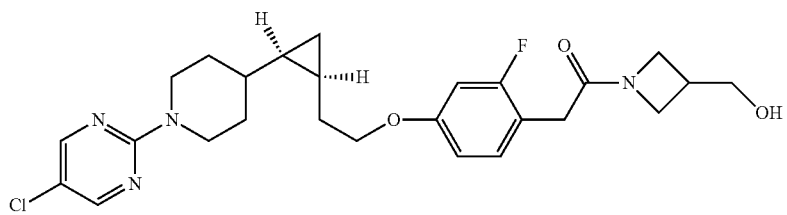 [SMILES: O=C(Cc1ccc(OCC[C@@H]2C[C@@H]2C2CCN(c3ncc(Cl)cn3)CC2)cc1F)N1CC(CO)C1]

Prepared using procedures outlined in the preparation of intermediate 37; replacing intermediate 1 with intermediate 18 to give 2-(4-(2-(((1S,2R)-2-(1-(5-chloropyrimidin-2-yl)piperidin-4-yl)cyclopropyl) ethoxy)-2-fluorophenyl)-1-(3-(hydroxymethyl)azetidin-1-yl)ethan-1-one. LCMS: tR=1.16, (ES⁺) m/z (M+H)⁺=503.5.

Intermediate 52: 2-(4-(3-(1-(5-(((tert-butyldimethylsilyl)oxy)methyl)pyrimidin-2-yl)piperidin-4-yl)propoxy)-2-fluorophenyl)-1-(3-(hydroxymethyl)azetidin-1-yl)ethan-1-one

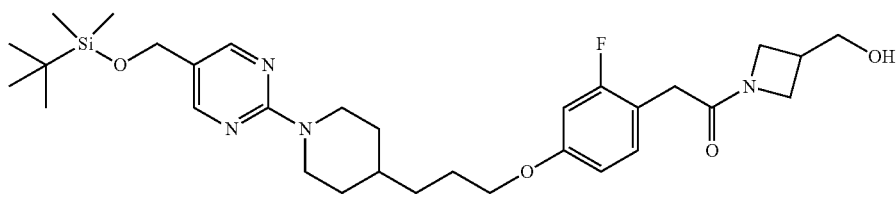 [SMILES: CC(C)(C)[Si](C)(C)OCc1cnc(N2CCC(CCCOc3ccc(CC(=O)N4CC(CO)C4)c(F)c3)CC2)nc1]

Prepared using procedures outlined in the preparation of intermediate 37; replacing intermediate 1 with intermediate 20 to give 2-(4-(3-(1-(5-(((tert-butyldimethylsilyl)oxy)methyl)pyrimidin-2-yl)piperidin-4-yl)propoxy)-2-fluorophenyl)-1-(3-(hydroxymethyl)azetidin-1-yl)ethan-1-one. LCMS: tR=1.56, (ES+) m/z (M+H)+=587.5.

Intermediate 53: Methyl 2-(4-(3-(3-fluoro-4-(2-(3-(hydroxymethyl)azetidin-1-yl)-2-oxoethyl)phenoxy)propyl)piperidin-1-yl)pyrimidine-5-carboxylate

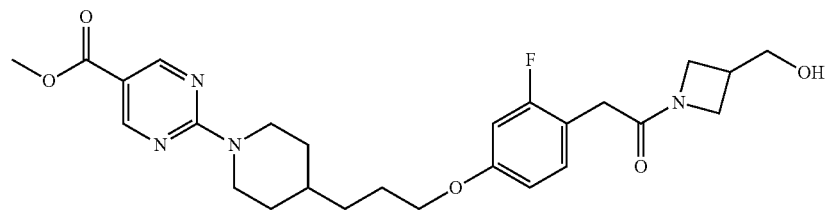 [SMILES: COC(=O)c1cnc(N2CCC(CCCOc3ccc(CC(=O)N4CC(CO)C4)c(F)c3)CC2)nc1]

Step 1: tert-butyl 4-(3-(3-fluoro-4-(2-methoxy-2-oxoethyl)phenoxy)propyl)piperidine-1-carboxylate

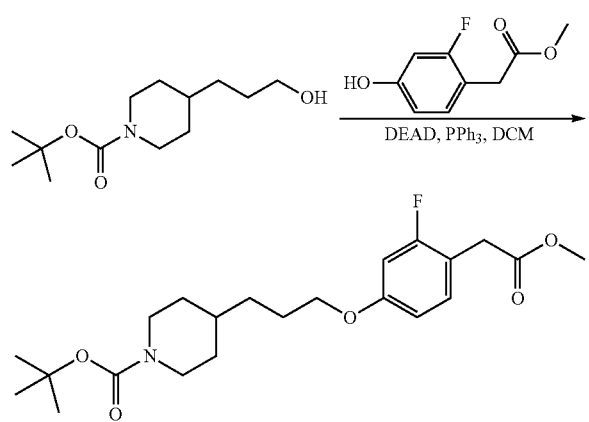

To a mixture of tert-butyl 4-(3-hydroxypropyl)piperidine-1-carboxylate (500 mg, 2.05 mmol), methyl 2-(2-fluoro-4-hydroxyphenyl)acetate (378 mg, 2.05 mmol) and triphenyl phosphine (1 g of 3 mmol/g polymer bound, 3 mmol) in DCM (10 mL) was added diethyl azodicarboxylate (1.4 mL of a 40% wt soln in toluene, 3.07 mmol) and the resulting mixture stirred at room temperature overnight. Mixture filtered through celite and the filtrate evaporated. The residue was purified by silica gel column chromatography (Teledyne Isco: SNAP 24G GOLD) eluent: gradient 0-100% EtOAc in Heptane to give tert-butyl 4-(3-(3-fluoro-4-(2-methoxy-2-oxoethyl)phenoxy)propyl)piperidine-1-carboxylate_(550 mg, 65%) as a colorless oil. LCMS: tR=1.35, (ES+) m/z (M−55)+=354.3.

Step 2: 2-(4-(3-(1-(tert-butoxycarbonyl)piperidin-4-yl)propoxy)-2-fluorophenyl)acetic acid

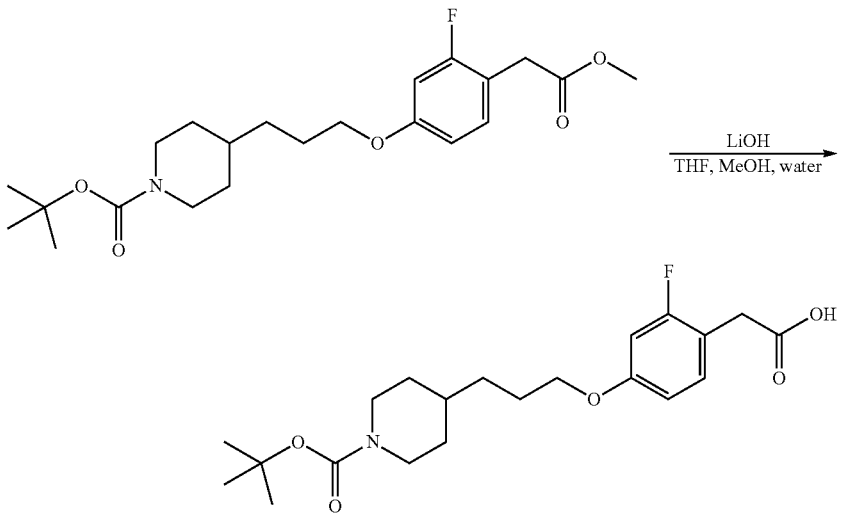

To a solution of tert-butyl 4-(3-(3-fluoro-4-(2-methoxy-2-oxoethyl)phenoxy)propyl)piperidine-1-carboxylate (550 mg, 1.34 mmol) in THF (8 mL) and methanol (3 mL) was added lithium hydroxide (2.7 mL of a 1M aqueous solution, 2.7 mmol) and the resulting mixture stirred at room temperature overnight Mixture evaporated to remove organic solvents and remaining aqueous acidified by the addition of 1N HCl and extracted with EtOAc (3×50 mL); combined EtOAc layers washed with sat. NaCl (30 mL), dried over MgSO$_4$, filtered and evaporated to give 2-(4-(3-(1-(tert-butoxycarbonyl)piperidin-4-yl)propoxy)-2-fluorophenyl) acetic acid (495 mg, 93%) as a clear oil. LCMS: tR=1.05, (ES$^+$) m/z (M−55)$^+$=340.2.

Step 3: tert-butyl 4-(3-(3-fluoro-4-(2-(3-(hydroxymethyl)azetidin-1-yl)-2-oxoethyl)phenoxy) propyl) piperidine-1-carboxylate

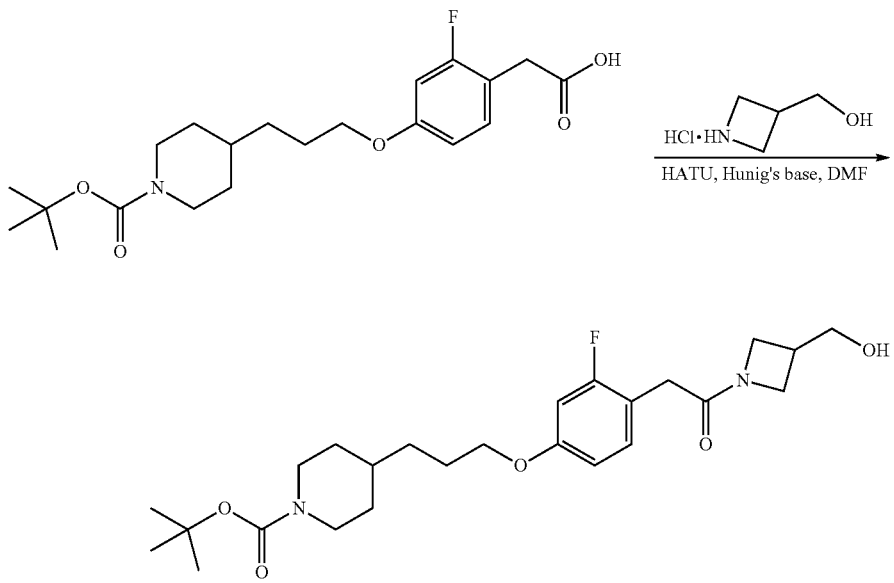

To a mixture of 2-(4-(3-(1-(tert-butoxycarbonyl)piperidin-4-yl)propoxy)-2-fluorophenyl)acetic acid (495 mg, 1.25 mmol) and azetidine-3-methanol. HCl (185 mg, 1.5 mmol) in DMF (5 mL) was added HATU (717 mg, 1.88 mmol) and Hunig's Base (0.654 mL, 3.75 mmol) and the resulting mixture stirred at room temperature for 30 min. Mixture diluted with EtOAc (30 mL) and washed with water (50 mL), sat. NaCl (25 mL), dried over Na$_2$SO$_4$, filtered and evaporated. The residue was purified by silica gel column chromatography (Teledyne Isco: SNAP 12 g GOLD) eluent: gradient 2-10% MeOH in DCM to give tert-butyl 4-(3-(3-fluoro-4-(2-(3-(hydroxymethyl)azetidin-1-yl)-2-oxoethyl) phenoxy) propyl)piperidine-1-carboxylate (470 mg, 80%) as a clear oil. LCMS: tR=0.85, (ES$^+$) m/z (M+H)$^+$=485.3.

Step 4: Methyl 2-(4-(3-(3-fluoro-4-(2-(3-(hydroxymethyl)azetidin-1-yl)-2-oxoethyl)phenoxy) propyl) piperidin-1-yl)pyrimidine-5-carboxylate

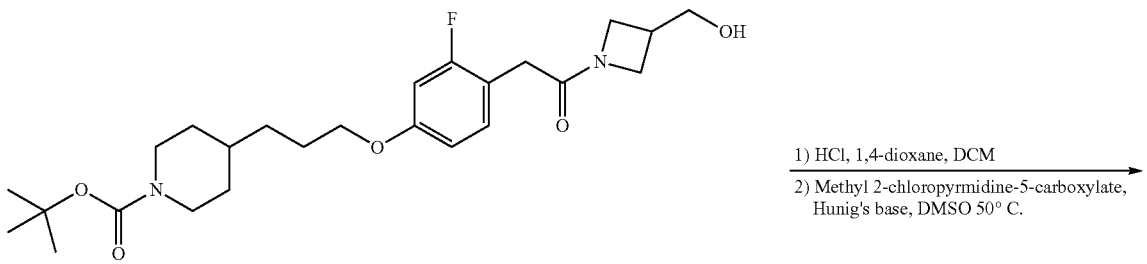

1) HCl, 1,4-dioxane, DCM
2) Methyl 2-chloropyrimidine-5-carboxylate, Hunig's base, DMSO 50° C.

-continued

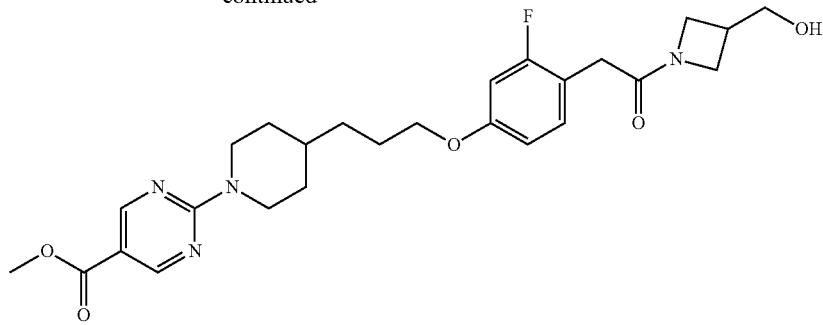

To a solution of tert-butyl 4-(3-(3-fluoro-4-(2-(3-(hydroxymethyl)azetidin-1-yl)-2-oxoethyl)phenoxy) propyl)piperidine-1-carboxylate (470 mg, 1 mmol) in DCM (5 mL) was added hydrogen chloride (5 mL of a 4M solution in dioxane, 20 mmol) and the resulting mixture stirred at room temperature overnight and evaporated. Residue partitioned between DCM and sat. NaHCO$_3$, however product stayed in aqueous layer. Aqueous layer evaporated and resultant solid extracted with MeOH filtered and evaporated to give an oily white solid. A mixture of this solid (350 mg, 0.96 mmol), methyl 2-chloropyrimidine-5-carboxylate (166 mg, 0.96 mmol) and Hunig's Base (0.248 mL, 1.92 mmol) in DMSO (5 mL) was heated at 50° C. for 2 hours. Mixture cooled and diluted with EtOAc (40 mL) and washed with water (100 mL), sat. NaCl (50 ML), dried over Na$_2$SO$_4$, filtered and evaporated. The residue was purified by silica gel column chromatography (Teledyne Isco:SNAP 24 g GOLD) eluent: gradient 2-8% MeOH in DCM to give methyl 2-(4-(3-(3-fluoro-4-(2-(3-(hydroxymethyl)azetidin-1-yl)-2-oxoethyl) phenoxy)propyl) piperidin-1-yl)pyrimidine-5-carboxylate (287 mg, 59%) as a white solid. LCMS: tR=0.76, (ES$^+$) m/z (M+H)$^+$=501.4.

Intermediate 54: 2-(4-((2-(1-(5-ethylpyrimidin-2-yl) piperidin-4-yl)ethoxy)methyl)-2-fluorophenyl)-1-(3-(hydroxymethyl) azetidin-1-yl)ethan-1-one

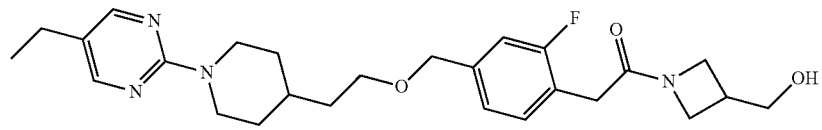 [SMILES: CCc1cnc(N2CCC(CCOCc3ccc(CC(=O)N4CC(CO)C4)c(F)c3)CC2)nc1]

Step 1: 2-(1-(5-ethylpyrimidin-2-yl)piperidin-4-yl) ethan-1-ol

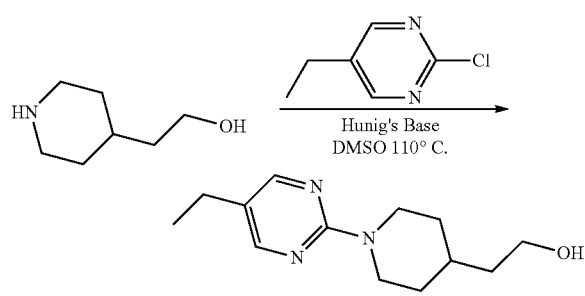

A mixture of 2-(piperidin-4-yl)ethan-1-ol (730 mg, 5.65 mmol), 2-chloro-5-ethylpyrimidine (846 mg, 5.93 mmol), and Hunig's base (1.48 mL, 8.48 mmol) in DMSO (10 mL) was heated at 110° C. overnight. Mixture cooled and poured into water (100 mL) and extracted with EtOAc (3×25 mL); combined EtOAc layers were washed with sat. NaCl (50 mL), dried over MgSO$_4$, filtered and evaporated. The residue was purified by silica gel column chromatography (Teledyne Isco: SNAP 40 g GOLD) eluent: gradient 0-100% EtOAc in Heptanes (6cv) then hold 100% EtOAc (4cv) to give 2-(1-(5-ethylpyrimidin-2-yl)piperidin-4-yl)ethan-1-ol (1.3 g, 97%) as a yellow solid. $^1$H NMR (500 MHz, Chloroform-d) δ 8.17 (s, 2H), 4.70 (d, J=13.3 Hz, 2H), 3.74 (t, J=6.7 Hz, 2H), 2.87 (t, J=12.9 Hz, 2H), 2.46 (q, J=7.6 Hz, 2H), 1.79 (d, J=13.8 Hz, 2H), 1.72 (dtt, J=11.1, 7.1, 3.9 Hz, 1H), 1.55 (m, 2H), 1.25-1.15 (m, 5H). LCMS: tR=1.17, (ES$^+$) m/z (M+H)$^+$=236.2.

Step 2: 2-(4-(2-((4-bromo-3-fluorobenzyl)oxy)ethyl)piperidin-1-yl)-5-ethylpyrimidine

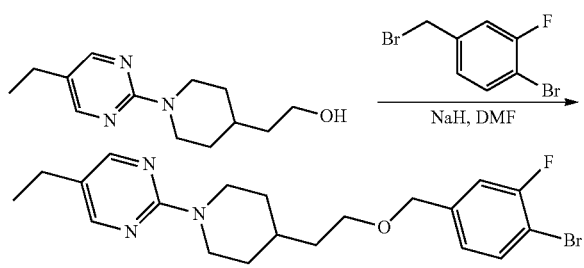

To a solution of 2-(1-(5-ethylpyrimidin-2-yl)piperidin-4-yl)ethan-1-ol (600 mg, 2.55 mmol) in DMF (5 mL) was added sodium hydride (132 mg of a 60% dispersion in oil, 3.3 mmol) and the resulting mixture stirred at room temperature for 10 mins. To this mixture was added 4-bromo-3-fluorobenzyl bromide (750 mg, 2.81 mmol) and the resulting mixture stirred at room temperature for 3 hours. Poured into water (50 mL) and extracted with EtOAc (40 mL); organic layer washed with sat. NaCl (30 mL), dried over MgSO$_4$, filtered and evaporated. The residue was purified by silica gel column chromatography (Teledyne Isco: SNAP 24 g GOLD) eluent: gradient 0-20% EtOAc in Heptanes to give 2-(4-(2-((4-bromo-3-fluorobenzyl)oxy)ethyl)piperidin-1-yl)-5-ethylpyrimidine (615 mg, 57%) as a white solid. LCMS: tR=1.42, (ES$^+$) m/z (M+H)$^+$=422.2/424.2.

Step 3: tert-butyl 2-(4-((2-(1-(5-ethylpyrimidin-2-yl)piperidin-4-yl)ethoxy)methyl)-2-fluorophenyl)acetate

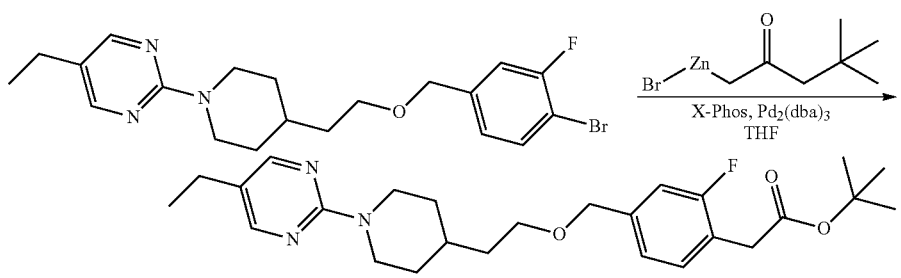

A mixture of 2-(4-(2-((4-bromo-3-fluorobenzyl)oxy)ethyl)piperidin-1-yl)-5-ethylpyrimidine (615 mg, 1.46 mmol) and 2-tert-butoxy-2-oxoethylzinc bromide (8.8 mL of a 0.5M soln in diethyl ether, 4.38 mmol) was de-gassed by bubbling nitrogen through for 10 mins then dicyclohexyl({2-[2,4,6-tris(propan-2-yl)phenyl]phenyl})phosphane (X-PHOS) (70 mg, 0.146 mmol) and Pd$_2$(dba)$_3$ (67 mg, 0.073 mmol) and de-gassing continued for 10 mins. Mixture heated at 50° C. overnight then cooled to room temperature. Mixture quenched by the addition of methanol (3 mL) and evaporated. The residue was purified by silica gel column chromatography (Teledyne Isco: SNAP 24 g GOLD) eluent: gradient 0-20% EtOAc in Heptanes (8cv) then hold 20% EtOAc in Heptanes (5cv) to give tert-butyl 2-(4-((2-(1-(5-ethylpyrimidin-2-yl)piperidin-4-yl)ethoxy)methyl)-2-fluorophenyl)acetate (460 mg, 69%) as a yellow oil. LCMS: tR=1.48, (ES$^+$) m/z (M+H)$^+$=458.4.

Step 4: 2-(4-((2-(1-(5-ethylpyrimidin-2-yl)piperidin-4-yl)ethoxy)methyl)-2-fluorophenyl)acetic acid

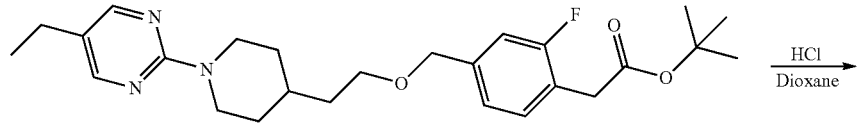

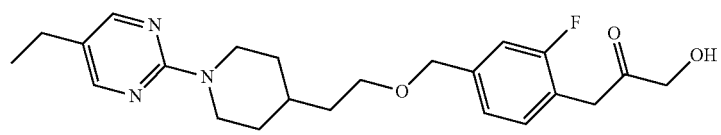

A mixture of tert-butyl 2-(4-((2-(1-(5-ethylpyrimidin-2-yl)piperidin-4-yl)ethoxy)methyl)-2-fluorophenyl)acetate (460 mg, 1 mmol) and hydrogen chloride (10 mL of a 4M solution in dioxane, 40 mmol) was stirred at room temperature overnight and mixture evaporated to give 2-(4-((2-(1-(5-ethylpyrimidin-2-yl)piperidin-4-yl)ethoxy)methyl)-2-fluorophenyl)acetic acid (405 mg, 100%). LCMS: tR=0.69, (ES+) m/z (M+H)+=402.3.

Step 5: 2-(4-((2-(1-(5-ethylpyrimidin-2-yl)piperidin-4-yl)ethoxy)methyl)-2-fluorophenyl)-1-(3-(hydroxymethyl) azetidin-1-yl)ethan-1-one

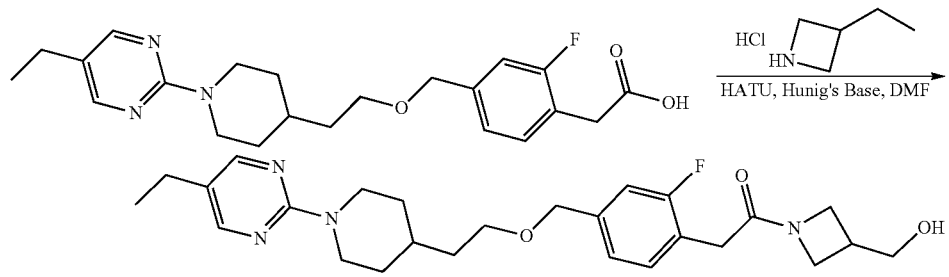

To a solution of 2-(4-((2-(1-(5-ethylpyrimidin-2-yl)piperidin-4-yl)ethoxy)methyl)-2-fluorophenyl)acetic acid (405 mg, 1 mmol) and azetidine-3-methanol hydrochloride (188 mg, 1.5 mmol) in DMF (4 mL) was added HATU (578 mg, 1.5 mmol) and Hunig's base (0.7 mL, 4 mmol) and the resulting mixture stirred at room temperature for 60 mins. Mixture diluted with EtOAc (40 mL) and washed with water (50 mL), sat. NaCl (30 mL), dried over MgSO4, filtered and evaporated. The residue was purified by silica gel column chromatography (Teledyne Isco: SNAP 24 g GOLD) eluent: gradient 2-10% MeOH in DCM (8cv) then hold 10% MeOH in DCM (5cv) to give 2-(4-((2-(1-(5-ethylpyrimidin-2-yl)piperidin-4-yl)ethoxy)methyl)-2-fluorophenyl)-1-(3-(hydroxymethyl) azetidin-1-yl)ethan-1-one (440 mg, 92%) as an off white solid. LCMS: tR=1.52, (ES+) m/z (M+H)+=471.4.

Intermediate 55: 2-(4-((2-(1-(5-ethylpyrimidin-2-yl) piperidin-4-yl)ethoxy)methyl)-3-fluorophenyl)-1-(3-(hydroxymethyl) azetidin-1-yl)ethan-1-one

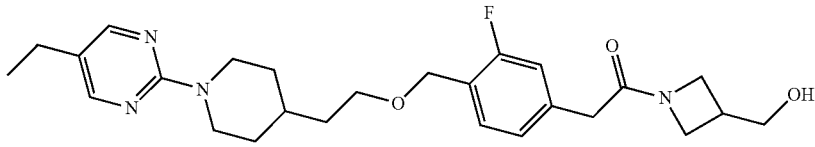 [SMILES: CCc1cnc(N2CCC(CCOCc3ccc(CC(=O)N4CC(CO)C4)cc3F)CC2)nc1]

Prepared using procedures outlined in the preparation of intermediate 54; replacing 4-bromo-3-fluorobenzyl bromide with 4-bromo-2-fluorobenzyl bromide in step 2 to give 2-(4-((2-(1-(5-ethylpyrimidin-2-yl)piperidin-4-yl)ethoxy) methyl)-3-fluorophenyl)-1-(3-(hydroxymethyl) azetidin-1-yl)ethan-1-one. LCMS: tR=1.51, (ES+) m/z (M+H)+=471.4.

Intermediate 56: 2-(4-((3-(1-(5-chloropyrimidin-2-yl)piperidin-4-yl)propoxy)methyl)-2-fluorophenyl)-1-(3-(hydroxymethyl) azetidin-1-yl)ethan-1-one

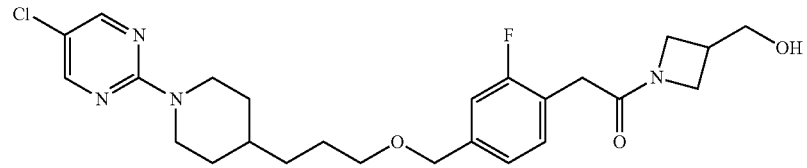 [SMILES: O=C(Cc1ccc(COCCCC2CCN(c3ncc(Cl)cn3)CC2)cc1F)N1CC(CO)C1]

Prepared using procedures outlined in the preparation of intermediate 54; replacing 2-(1-(5-ethylpyrimidin-2-yl)piperidin-4-yl)ethan-1-ol with 3-(1-(5-chloropyrimidin-2-yl)piperidin-4-yl)propan-1-ol in step 2 to give 2-(4-((3-(1-(5-chloropyrimidin-2-yl)piperidin-4-yl)propoxy)methyl)-2-fluorophenyl)-1-(3-(hydroxymethyl) azetidin-1-yl)ethan-1-one. LCMS: tR=1.51, (ES+) m/z (M+H)+=471.4.

Intermediate 57: 2-(1-(5-chloropyrimidin-2-yl)piperidin-4-yl)ethyl 3-fluoro-4-(2-(3-(hydroxymethyl) azetidin-1-yl)-2-oxoethyl)benzoate 2-yl)piperidin-4-yl)ethan-1-ol (1.48 g, 79%) as a white solid. ¹H NMR (500 MHz, Chloroform-d) δ 8.20 (s, 2H), 4.67 (ddt, J=13.4, 4.5, 2.0 Hz, 2H), 3.73 (td, J=6.6, 4.9 Hz, 2H), 2.87 (ddd, J=13.3, 12.3, 2.7 Hz, 2H), 1.82-1.76 (m, 2H), 1.73 (ddt, J=11.1, 7.0, 3.3 Hz, 1H), 1.55 (q, J=6.6 Hz, 2H), 1.34 (t, J=5.0 Hz, 1H), 1.19 (tdd, J=12.8, 11.1, 4.1 Hz, 2H).

Step 2: 2-(1-(5-chloropyrimidin-2-yl)piperidin-4-yl) ethyl 4-bromo-3-fluorobenzoate

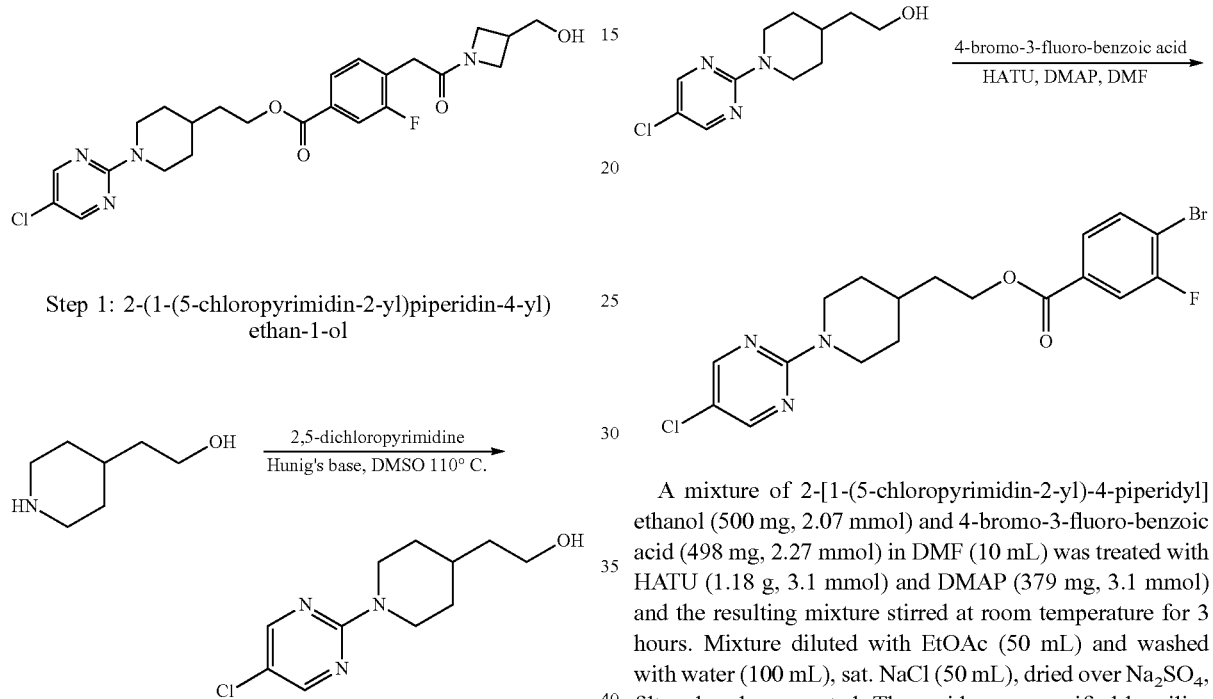

Step 1: 2-(1-(5-chloropyrimidin-2-yl)piperidin-4-yl)ethan-1-ol

A mixture of 2-(piperidin-4-yl)ethan-1-ol (1 g, 7.74 mmol), 2,5-dichloropyrimidine (1.15 g, 7.74 mmol) and Hunig's Base (2.02 mL, 11.6 mmol) in DMSO (10 mL) was warmed at 50° C. for 72 hours. Mixture cooled and diluted with EtOAc (40 mL) and washed with water (100 mL), sat. NaCl (50 mL), dried over Na₂SO₄, filtered and evaporated. The residue was purified by silica gel column chromatography (Teledyne Isco: SNAP 40 g GOLD) eluent: gradient 0-100% EtOAc in Heptane to give 2-(1-(5-chloropyrimidin- A mixture of 2-[1-(5-chloropyrimidin-2-yl)-4-piperidyl] ethanol (500 mg, 2.07 mmol) and 4-bromo-3-fluoro-benzoic acid (498 mg, 2.27 mmol) in DMF (10 mL) was treated with HATU (1.18 g, 3.1 mmol) and DMAP (379 mg, 3.1 mmol) and the resulting mixture stirred at room temperature for 3 hours. Mixture diluted with EtOAc (50 mL) and washed with water (100 mL), sat. NaCl (50 mL), dried over Na₂SO₄, filtered and evaporated. The residue was purified by silica gel column chromatography (Teledyne Isco: SNAP 40 g GOLD) eluent: gradient 0-100% EtOAc in Heptane to give 2-(1-(5-chloropyrimidin-2-yl)piperidin-4-yl)ethyl 4-bromo-3-fluorobenzoate (500 mg, 55%). LCMS: tR=1.69, (ES+) m/z (M+H)+=442.1/444.1.

Step 3: 2-(1-(5-chloropyrimidin-2-yl)piperidin-4-yl) ethyl 4-(2-(tert-butoxy)-2-oxoethyl)-3-fluorobenzoate

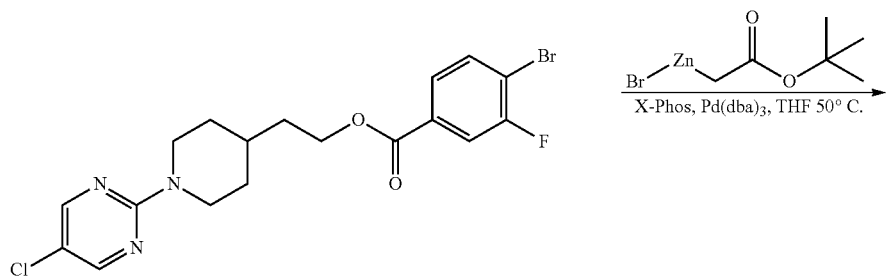

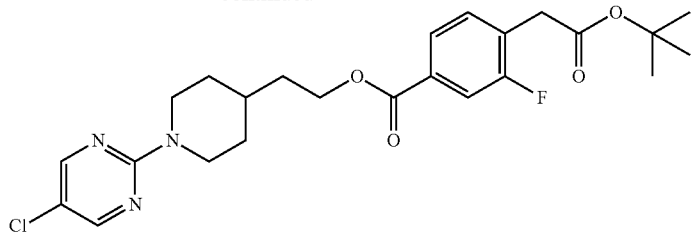

A mixture of (4-bromo-3-fluoro-phenyl) 3-[1-(5-chloro-pyrimidin-2-yl)-4-piperidyl]propanoate (N32-27, 208 mg, 0.47 mmol) and 2-tert butoxy-2-oxoethyl zinc bromide (2.8 mL of a 0.5M soln in diethyl ether, 1.41 mmol) was de-oxygenated by bubbling nitrogen gas through for 10 mins then $Pd_2(dba)_3$ (21 mg, 0.024 mmol) and X-phos (22 mg, 0.047 mmol) added and nitrogen gas bubbling continued for a further 10 mins. Mixture heated to 50° C. for 5 hours then stirred at room temperature for 72 hours. Mixture evaporated and the residue purified by silica gel column chromatography (Teledyne Isco: SNAP 40G GOLD) eluent: gradient 0-30% EtOAc in Heptane to give 2-(1-(5-chloropyrimidin-2-yl)piperidin-4-yl)ethyl 4-(2-(tert-butoxy)-2-oxoethyl)-3-fluorobenzoate (269 mg, 49%) as a light yellow oil which solidified on standing. LCMS: tR=1.74, (ES$^+$) m/z (M+H)$^+$=478.4.

Step 4: 2-(4-((2-(1-(5-chloropyrimidin-2-yl)piperi-din-4-yl)ethoxy)carbonyl)-2-fluorophenyl)acetic acid

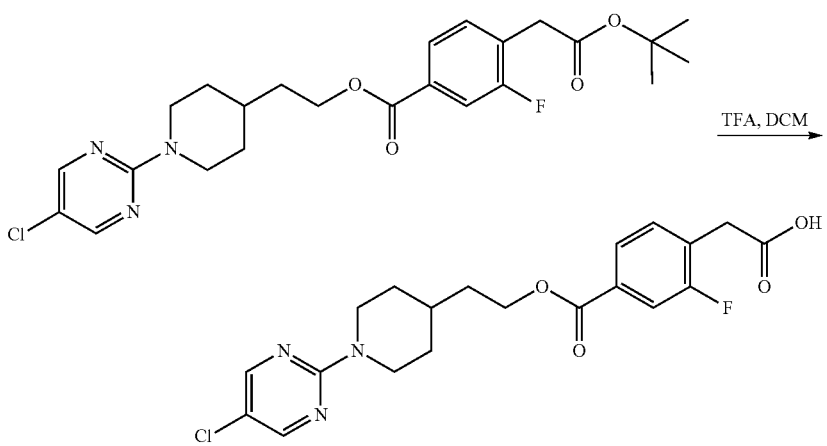

To a solution of 2-[1-(5-chloropyrimidin-2-yl)-4-piperidyl]ethyl 4-(2-tert-butoxy-2-oxo-ethyl)-3-fluoro-benzoate (269 mg, 0.563 mmol) in DCM (3 mL) was added TFA (0.862 mL, 11.26 mmol) and the resulting mixture stirred at room temperature for 30 mins then mixture evaporated to give 2-(4-((2-(1-(5-chloropyrimidin-2-yl)piperidin-4-yl)ethoxy)carbonyl)-2-fluorophenyl)acetic acid (237 mg, 100%). LCMS: tR=1.06, (ES$^+$) m/z (M+H)$^+$=422.2.

Step 5: 2-(1-(5-chloropyrimidin-2-yl)piperidin-4-yl)ethyl 3-fluoro-4-(2-(3-(hydroxymethyl)azetidin-1-yl)-2-oxoethyl)benzoate

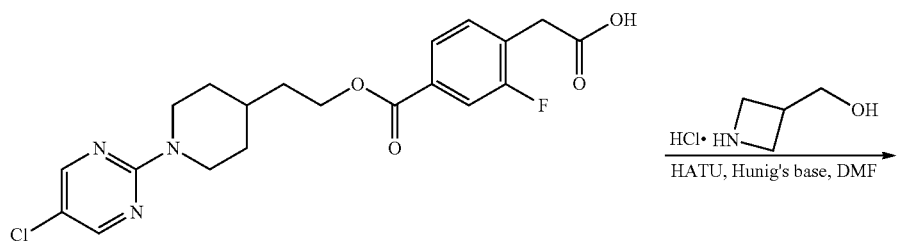

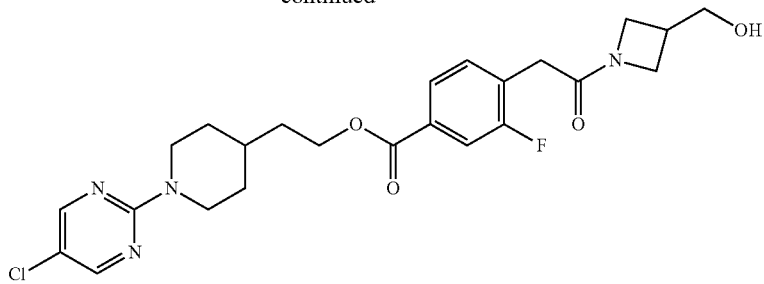

To a mixture of 2-[4-[2-[1-(5-chloropyrimidin-2-yl)-4-piperidyl]ethoxycarbonyl]-2-fluoro-phenyl]acetic acid (237 mg, 0.562 mmol) and azetidine-3-methanol hydrochloride (104 mg, 0.843 mmol) in DMF (3 mL) was added HATU (320 mg, 0.843 mmol) and Hunig's base (0.491 mL, 2.81 mmol) and the resulting mixture stirred at room temperature for 2 hours. Mixture diluted with EtOAc (20 mL) and washed with water (30 mL), sat. NaCl (10 ml), dried over Na$_2$SO$_4$, filtered and evaporated. The residue was purified by silica gel column chromatography (Teledyne Isco: SNAP 24 g GOLD) eluent: gradient 2-10% MeOH in DCM to give 2-(1-(5-chloropyrimidin-2-yl)piperidin-4-yl)ethyl 3-fluoro-4-(2-(3-(hydroxymethyl)azetidin-1-yl)-2-oxoethyl)benzoate (264 mg, 95%) as a white solid. LCMS: tR=1.80, (ES$^+$) m/z (M+H)$^+$=491.3.

Intermediate 58: 2-(1-(5-chloropyrimidin-2-yl)piperidin-4-yl)ethyl 2-(3-fluoro-4-(2-(3-(hydroxymethyl)azetidin-1-yl)-2-oxoethyl)phenyl)acetate

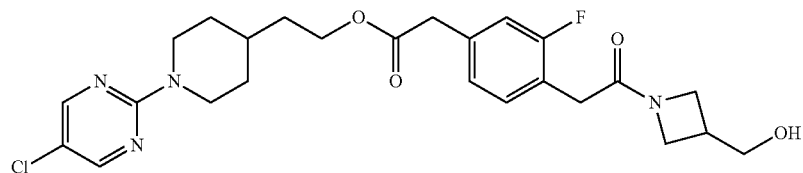 [SMILES: O=C(Cc1ccc(CC(=O)N2CC(CO)C2)c(F)c1)OCCC1CCN(c2ncc(Cl)cn2)CC1]

Prepared using procedures outlined in the preparation of intermediate 57; replacing 4-bromo-3-fluoro-benzoic acid 2-(4-bromo-3-fluoro-phenyl)acetic acid in step 2 to give 2-(1-(5-chloropyrimidin-2-yl)piperidin-4-yl)ethyl 2-(3-fluoro-4-(2-(3-(hydroxymethyl)azetidin-1-yl)-2-oxoethyl)phenyl)acetate. LCMS: tR=0.78, (ES$^+$) m/z (M+H)$^+$=505.3.

Intermediate 59: 2-(4-(((((1R,2R)-2-(1-(5-chloropyrimidin-2-yl)piperidin-4-yl)cyclopropyl)methoxy)carbonyl)-2-fluorophenyl)acetic acid

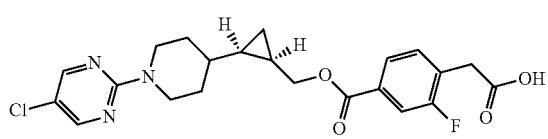 [SMILES: O=C(O)Cc1ccc(C(=O)OC[C@@H]2C[C@@H]2C2CCN(c3ncc(Cl)cn3)CC2)cc1F]

Step 1: ethyl 4-allyl-3-fluorobenzoate

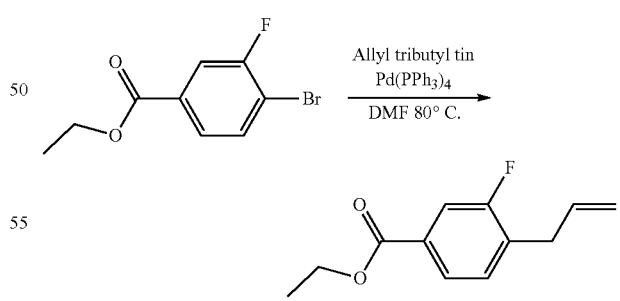

To a solution of ethyl 4-bromo-3-fluorobenzoate (7.0 g, 28 mmol) in DMF (180 mL) was added allyl tributyltin (11 g, 34 mmol) and Pd(PPh$_3$)$_4$ (1.6 g, 1.4 mmol). The mixture was heated at 80° C. for 12 hours. The cooled reaction mixture was quenched by the addition of CsF (7.0 g) and water (200 mL), then diluted with water (100 mL) and extracted with EtOAc (200 mL). The organic layer was washed with sat. NaCl (2×200 mL), dried over Na$_2$SO$_4$, filtered and evaporated. The residue was purified by silica gel column chromatography (eluent: Petroleum ether/ethyl acetate 50:1 to 40:1) to give ethyl 4-allyl-3-fluorobenzoate (4.8 g, 80%) as yellow oil. $^1$H NMR (400 MHz, Chloroform-d) δ 7.78 (dd, J=1.6, 1.2 Hz, 1H), 7.69 (dd, J=1.2, 1.2 Hz, 1H), 7.27 (m, 1H), 5.95 (m, 1H), 5.11 (m, 2H), 4.38 (m, 2H), 3.46 (d, J=6.4 Hz, 2H), 1.4 (m, 3H).

Step 2: 2-(4-(ethoxycarbonyl)-2-fluorophenyl)acetic acid

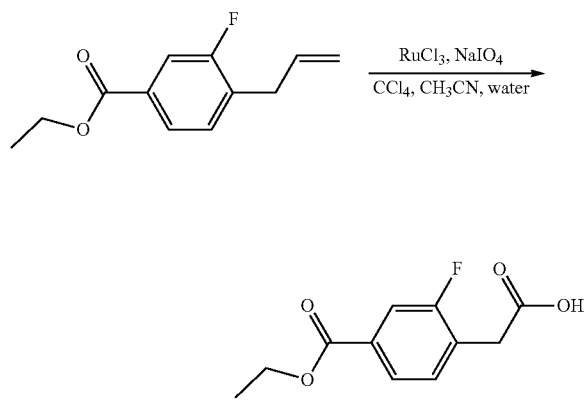

To a solution of ethyl 4-allyl-3-fluorobenzoate (4.8 g, 23 mmol) in CCl$_4$ (20 mL), CH$_3$CN (20 mL) and water (30 mL) was added NaIO$_4$ (25 g, 0.12 mol) and RuCl$_3$ (0.70 g, 3.5 mmol) and the resulting mixture stirred at room temperature for 20 mins. The reaction was quenched by the addition of Na$_2$SO$_3$ (100 mL) and acidified to pH 5 by the addition of 1N HCl. The resulting mixture was filtered and the filtrate diluted with water (150 mL) and extracted with DCM+MeOH (10:1) (2×100 mL). The combined organic layers dried over Na$_2$SO$_4$, filtered and evaporated. The residue was purified by PREP_HPLC to give 2-(4-(ethoxycarbonyl)-2-fluorophenyl)acetic acid (3.2 g, 61%) as a yellow solid. $^1$H NMR (400 MHz, Chloroform-d) δ 7.82 (dd, J=1.6, 1.2 Hz, 1H), 7.74 (dd, J=1.6, 1.2 Hz, 1H), 7.35 (t, J=15.2 Hz, 1H), 4.38 (m, 2H), 3.78 (s, 2H), 1.4 (m, 3H).

Step 3: ethyl-4-(2-(tert-butoxy)-2-oxoethyl)-3-fluorobenzoate

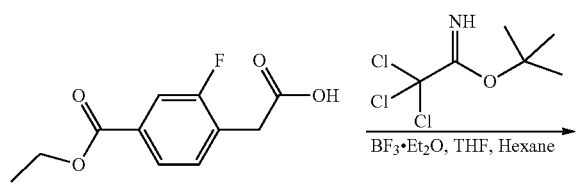

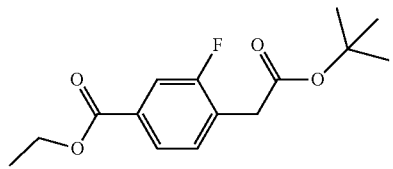

To a solution of 2-(4-(ethoxycarbonyl)-2-fluorophenyl) acetic acid (1.1 g, 4.9 mmol) in THF (15 mL) and Hexane (15 mL) cooled in an ice bath was added tert-butyl 2,2,2-trichloroacetimidate (2.1 g, 9.7 mmol) and the resulting mixture stirred at 0° C. for 15 mins. To this mixture was added BF$_3$.Et$_2$O (69 mg, 0.49 mmol) and the resulting mixture stirred at 15° C. for 12 hours. The reaction was quenched by the addition of sat. NaHCO$_3$ (20 mL) and water (20 mL) at 0° C. The mixture was extracted with EtOAc (2×20 mL); combined EtOAc layers washed with sat. NaCl (2×15 mL), dried over Na$_2$SO$_4$, filtered and evaporated. The residue was suspended in petroleum ether, filtered and the filtrate evaporated to give ethyl-4-(2-(tert-butoxy)-2-oxoethyl)-3-fluorobenzoate (1.3 g, 93%) as a yellow oil. $^1$H NMR (400 MHz, Chloroform-d) δ 7.80 (dd, J=1.2, 1.2 Hz, 1H), 7.72 (dd, J=1.6, 1.6 Hz, 1H), 7.34 (t, J=15.2 Hz, 1H), 4.39 (m, 2H), 3.64 (s, 2H), 1.44 (s, 9H), 1.40 (m, 3H).

Step 4: 4-(2-(tert-butoxy)-2-oxoethyl)-3-fluorobenzoic acid

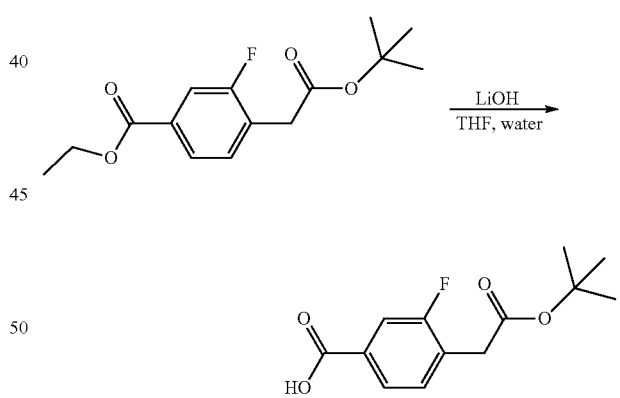

To a solution of ethyl-4-(2-(tert-butoxy)-2-oxoethyl)-3-fluorobenzoate (1.3 g, 4.6 mmol) in THF (12 mL) and water (3 mL) was added LiOH monohydrate (480 mg, 12 mmol) and the resulting mixture stirred at room temperature for 12 hours. The mixture was diluted with water (20 mL) and extracted with EtOAc (2×20 mL). The aqueous phase was acidified to pH 5 by the addition of 1N HCl and extracted with EtOAc (2×20 mL); combined EtOAc layers dried over Na$_2$SO$_4$, filtered and evaporated to give 4-(2-(tert-butoxy)-2-oxoethyl)-3-fluorobenzoic acid (590 mg, 50%) as a yellow solid. $^1$H NMR (400 MHz, Chloroform-d) δ 7.87 (d, J=8.0 Hz, 1H), 7.79 (d, J=10.0 Hz, 1H), 7.39 (t, J=14.8 Hz, 1H), 3.67 (s, 2H), 1.46 (s, 9H).

Step 5: ((1R,2R)-2-(1-(5-chloropyrimidin-2-yl)piperidin-4-yl)cyclopropyl)methyl 4-(2-(tert-butoxy)-2-oxoethyl)-3-fluorobenzoate

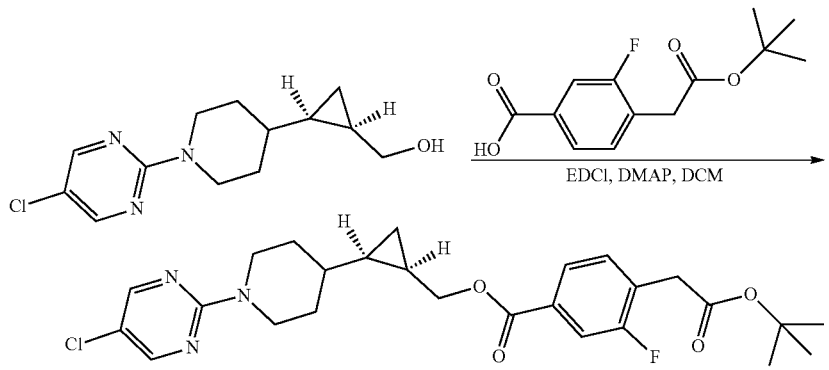

To a solution of ((1R,2R)-2-(1-(5-chloropyrimidin-2-yl)piperidin-4-yl)cyclopropyl)methanol intermediate 16 (270 mg, 1.0 mmol) in DCM (5 mL) was added DMAP (250 mg, 2.0 mmol), EDCI (390 mg, 2.0 mmol) and 4-(2-(tert-butoxy)-2-oxoethyl)-3-fluorobenzoic acid (260 mg, 1.0 mmol) and the resulting mixture stirred at room temperature for 2 hours. The reaction was poured into water (30 mL) and extracted with EtOAc (2×20 mL); combined EtOAc layers washed with sat. NaCl (30 mL), dried over $Na_2SO_4$ filtered and evaporated. The residue was purified by reversed phase PREP-HPLC to give ((1R,2R)-2-(1-(5-chloropyrimidin-2-yl)piperidin-4-yl)cyclopropyl)methyl 4-(2-(tert-butoxy)-2-oxoethyl)-3-fluorobenzoate (310 mg, 60%) as a yellow oil. LCMS: tR=1.103, (ES$^+$) m/z (M+H)$^+$=504.1.

Step 6: 2-(4-((((1R,2R)-2-(1-(5-chloropyrimidin-2-yl)piperidin-4-yl)cyclopropyl)methoxy)carbonyl)-2-fluorophenyl)acetic acid

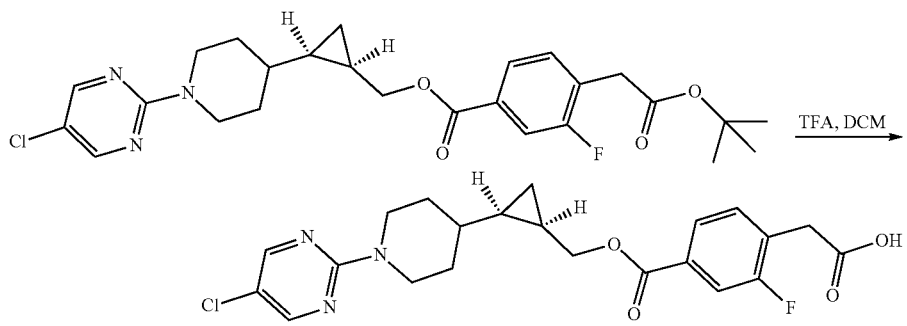

To a solution of ((1R,2R)-2-(1-(5-chloropyrimidin-2-yl)piperidin-4-yl)cyclopropyl)methyl 4-(2-(tert-butoxy)-2-oxoethyl)-3-fluorobenzoate (320 mg, 0.62 mmol) in DCM (9.3 mL) was added TFA (4.8 g, 42 mmol) and the resulting mixture stirred at room temperature for 1 hour. The reaction was quenched with water (20 mL) and extracted with DCM (2×30 mL); combined DCM layers dried over $Na_2SO_4$, filtered and evaporated. The residue was purified by reversed phase PREP-HPLC to give 2-(4-((((1R,2R)-2-(1-(5-chloropyrimidin-2-yl)piperidin-4-yl)cyclopropyl)methoxy)carbonyl)-2-fluorophenyl)acetic acid (220 mg, 80%) as a yellow oil. $^1$H NMR (400 MHz, MeOD) δ 8.24 (s, 2H), 7.83 (dd, J=1.6, 1.6 Hz, 1H), 7.71 (dd, J=1.6, 1.2 Hz, 1H), 7.47 (t, J=15.2 Hz, 1H), 4.69 (m, 1H), 4.57 (m, 2H), 4.26 (m, 1H), 3.76 (s, 2H), 2.88 (m, 2H), 1.88 (m, 2H), 1.36 (m, 4H), 0.81 (m, 2H), 0.25 (m, 1H).

Intermediate 60: 2-(2-fluoro-4-((((1R,2R)-2-(1-(5-(methoxymethyl)pyrimidin-2-yl)piperidin-4-yl)cyclopropyl)methoxy) methyl)phenyl)acetic acid

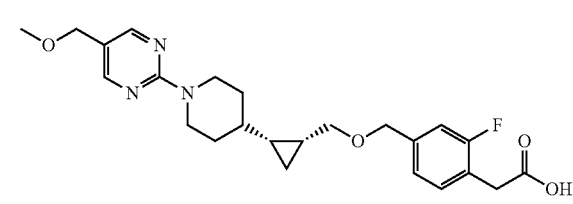 [SMILES: COCc1cnc(N2CCC([C@H]3C[C@H]3COCc3ccc(CC(=O)O)c(F)c3)CC2)nc1]

Step 1: 2-(4-((1R,2R)-2-(((4-bromo-3-fluorobenzyl)oxy)methyl)cyclopropyl)piperidin-1-yl)-5-(methoxymethyl)pyrimidine

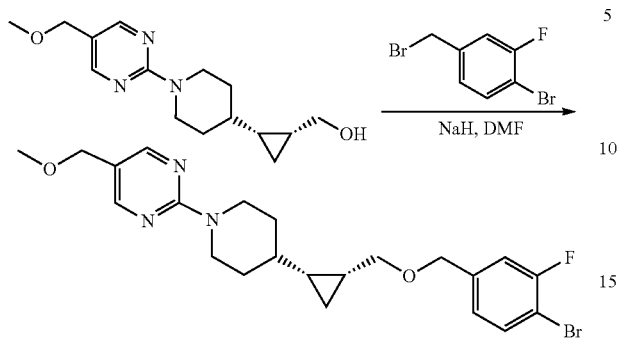

To a solution of ((1R,2R)-2-(1-(5-(methoxymethyl)pyrimidin-2-yl)piperidin-4-yl)cyclopropyl)methanol intermediate 17 (2 g, 7.2 mmol) in DMF (20 mL) cooled at 0° C. was added sodium hydride (430 mg of a 60% dispersion, 11 mmol) followed by dropwise addition of a solution of 1-bromo-4-(bromomethyl)-2-fluoro-benzene (3.9 g, 14 mmol) in DMF (40 mL). After complete addition mixture stirred at 0° C. for 30 mins then at room temperature for 12 hours. Mixture quenched by the addition of sat. NH$_4$Cl (200 mL) and extracted with EtOAc (2×200 mL); combined EtOAc layers washed with sat. NaCl (2×100 mL), dried over Na$_2$SO$_4$, filtered and evaporated. The residue was purified by reversed phase PREP-HPLC to give 2-(4-((1R,2R)-2-(((4-bromo-3-fluorobenzyl)oxy)methyl)cyclopropyl)piperidin-1-yl)-5-(methoxymethyl) pyrimidine (2.0 g, 60%) as a white solid. LCMS: tR=0.939, (ES$^+$) m/z (M+H)$^+$=464.2.

Step 2: ethyl 2-(2-fluoro-4-((((1R,2R)-2-(1-(5-(methoxymethyl)pyrimidin-2-yl)piperidin-4-yl)cyclopropyl)methoxy)methyl)phenyl)acetate

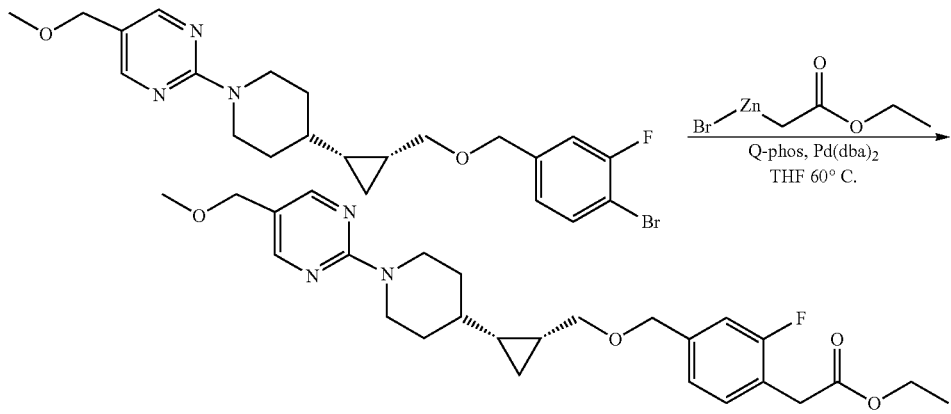

To a solution of 2-(4-((1R,2R)-2-(((4-bromo-3-fluorobenzyl)oxy)methyl)cyclopropyl)piperidin-1-yl)-5-(methoxymethyl)pyrimidine (0.9 g, 1.9 mmol) in THF (10 mL) was added Pd(dba)$_2$ (170 mg, 0.29 mmol), Q-phos (140 mg, 0.19 mmol) and bromo-(2-ethoxy-2-oxo-ethyl)zinc (4.8 mL of a 1.2M soln, 5.7 mmol) under a nitrogen atmosphere. And the resulting mixture heated at 60° C. for 12 hours. The cooled reaction mixture was filtered and the filtrate diluted with water (50 mL) and extracted with EtOAc (2×50 mL). The combined EtOAc layers were washed with sat. NaCl (2×40 mL), dried over Na$_2$SO$_4$, filtered and evaporated. The residue was purified by silica gel column chromatography (eluent: Petroleum ether:ethyl acetate=10:1 to 3:1). Product further purified by reversed phase PREP-HPLC to give ethyl 2-(2-fluoro-4-((((1R,2R)-2-(1-(5-(methoxymethyl)pyrimidin-2-yl)piperidin-4-yl)cyclopropyl)methoxy) methyl)phenyl)acetate (0.8 g, 70%) as a red oil. $^1$H NMR (400 MHz, MeOD) δ 8.27 (s, 2H), 7.31 7.26 (m 1H), 7.14-7.09 (m, 2H), 4.71-4.62 (m, 2H), 4.60-4.45 (m, 2H), 4.28 (s, 2H), 4.16-4.11 (m, 2H), 3.72-3.64 (m, 3H), 3.45-3.41 (m, 1H), 3.35 (s, 3H), 2.91-2.77 (m, 2H), 2.00-1.95 (m, 1H), 1.84-1.74 (m, 1H), 1.36-1.25 (m, 4H), 1.23-1.21 (m, 3H), 1.15-1.05 (m, 1H), 0.73-0.68 (m, 1H), 0.12-0.02 (m, 1H).

Step 3: 2-(2-fluoro-4-((((1R,2R)-2-(1-(5-(methoxymethyl)pyrimidin-2-yl)piperidin-4-yl)cyclopropyl)methoxy) methyl)phenyl)acetic acid

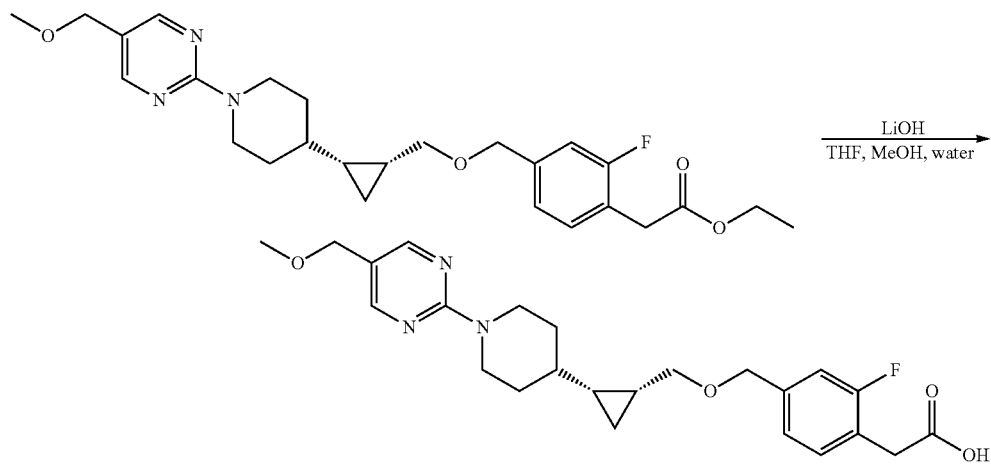

To a solution of ethyl 2-(2-fluoro-4-((((1R,2R)-2-(1-(5-(methoxymethyl)pyrimidin-2-yl)piperidin-4-yl)cyclopropyl)methoxy) methyl)phenyl)acetate (70 mg, 0.15 mmol) in THF (1 mL), MeOH (1 mL) and water (1 mL) was added lithium hydroxide (12 mg, 0.50 mmol) and the resulting mixture stirred at room temperature for 1 hour. The mixture was evaporated and the residue acidified to pH 6-7 by the addition of 1N HCl and extracted with EtOAc (2×25 mL). The combined EtOAc layers were washed with sat. NaCl (2×20 mL), dried over Na$_2$SO$_4$, filtered and evaporated to give 2-(2-fluoro-4-((((1R,2R)-2-(1-(5-(methoxymethyl)pyrimidin-2-yl)piperidin-4-yl)cyclopropyl)methoxy) methyl) phenyl)acetic acid (0.1 g, crude) as a red oil. LCMS: tR=0.890, (ES$^+$) m/z (M+H)$^+$=444.2.

Example 1: 2-[4-[3-[1-(5-chloropyrimidin-2-yl)-4-piperidyl]propoxy]-2-fluoro-phenyl]-N-[5-[[2-hydroxy-1-(hydroxymethyl)ethyl]amino]pentyl]acetamide

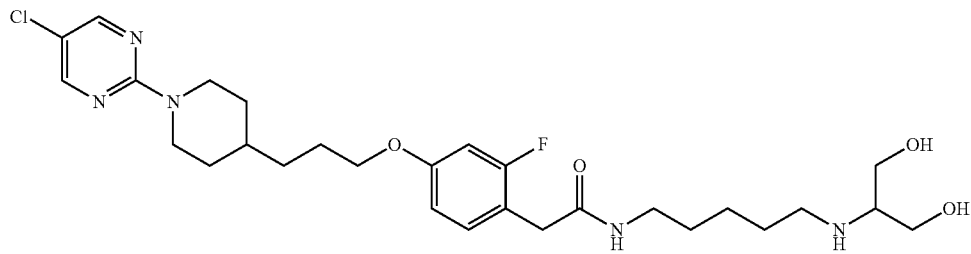 [SMILES: O=C(Cc1ccc(OCCCC2CCN(c3ncc(Cl)cn3)CC2)cc1F)NCCCCCNC(CO)CO]

Step 1: 5-(2-(4-(3-(1-(5-chloropyrimidin-2-yl)piperidin-4-yl)propoxy)-2-fluorophenyl) acetamido)pentyl methanesulfonate

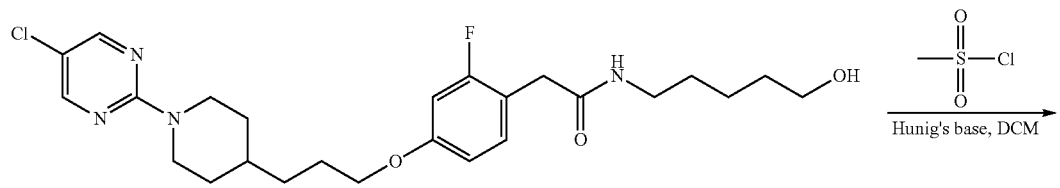

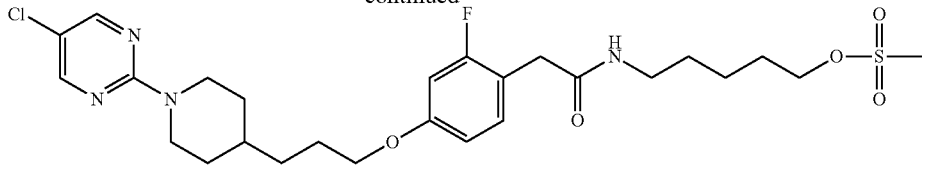

To a solution of 2-(4-(3-(1-(5-chloropyrimidin-2-yl)piperidin-4-yl)propoxy)-2-fluorophenyl)-N-(5-hydroxypentyl)acetamide intermediate 32 (426 mg, 0.87 mmol) in DCM (10 mL) was added Hunig's base (181 µL, 1.04 mmol) followed by methane sulfonyl chloride (74 µL, 0.95 mmol) and the resulting mixture stirred at room temperature overnight. Mixture diluted with further DCM (20 mL) and washed with water (30 mL), sat NaCl (20 mL), dried over MgSO$_4$, filtered and evaporated to give 5-(2-(4-(3-(1-(5-chloropyrimidin-2-yl)piperidin-4-yl)propoxy)-2-fluorophenyl) acetamido)pentyl methanesulfonate (486 mg, 98%) as a white solid. LCMS: tR=1.28, (ES$^+$) m/z (M+H)$^+$=571.3.

Step 2: 2-[4-[3-[1-(5-chloropyrimidin-2-yl)-4-piperidyl]propoxy]-2-fluoro-phenyl]-N-[5-[[2-hydroxy-1-(hydroxymethyl)ethyl]amino]pentyl]acetamide

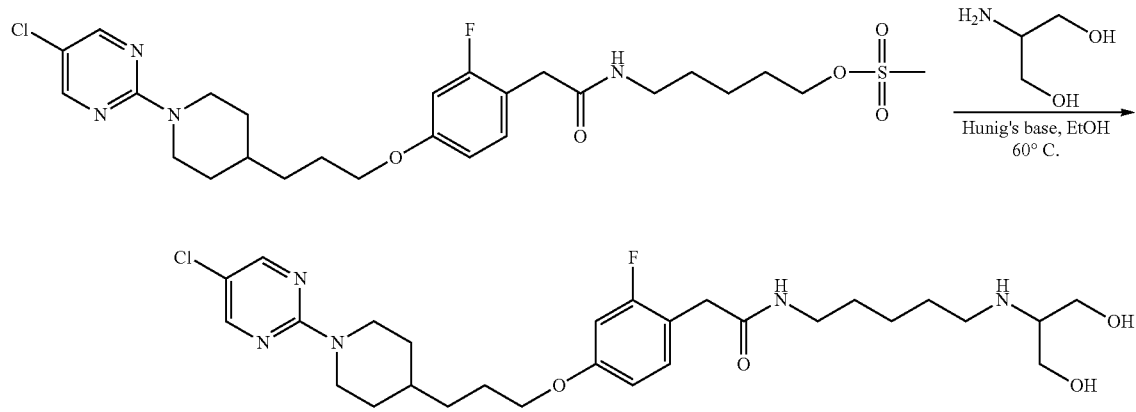

A mixture of 5-(2-(4-(3-(1-(5-chloropyrimidin-2-yl)piperidin-4-yl)propoxy)-2-fluorophenyl) acetamido)pentyl methanesulfonate (60 mg, 0.105 mmol), 2-amino-1,3-propanediol (48 mg, 0.525 mmol) and Hunig's base (18.3 µL, 0.105 mmol) in EtOH (2 mL) was heated at 80° C. for 72 hours. Mixture cooled and treated with formic acid (100 mL) and evaporated. The residue was purified by reverse phase silica gel column chromatography (Teledyne Isco: SNAP 15.5 g C18 gold) eluent: gradient 10-100% CH$_3$CN in water+0.5% formic acid to give 2-[4-[3-[1-(5-chloropyrimidin-2-yl)-4-piperidyl]propoxy]-2-fluoro-phenyl]-N-[5-[[2-hydroxy-1-(hydroxymethyl)ethyl]amino]pentyl]acetamide (33 mg, 55%) as a white solid. $^1$H NMR (500 MHz, DMSO-d$_6$) δ 8.38 (s, 2H), 8.31 (s, 1H), 7.96 (t, J=5.6 Hz, 1H), 7.18 (t, J=8.7 Hz, 1H), 6.75 (dd, J=11.9, 2.5 Hz, 1H), 6.71 (dd, J=8.4, 2.5 Hz, 1H), 4.58 (dt, J=13.3, 3.2 Hz, 2H), 3.95 (t, J=6.5 Hz, 2H), 3.53 (dd, J=11.4, 5.1 Hz, 2H), 3.48 (dd, J=11.3, 5.5 Hz, 2H), 3.35 (s, 2H), 3.04 (q, J=6.6 Hz, 2H), 2.88 (td, J=12.8, 2.6 Hz, 2H), 2.81 (p, J=5.3 Hz, 1H), 2.76 (t, J=7.6 Hz, 2H), 2.51 (p, J=1.9 Hz, 2H), 1.79-1.70 (m, 4H), 1.58 (ddt, J=11.1, 7.5, 3.9 Hz, 0H), 1.52 (p, J=7.8 Hz, 2H), 1.45-1.33 (m, 4H), 1.28 (qd, J=12.1, 10.1, 5.5 Hz, 2H), 1.06 (qd, J=12.3, 4.1 Hz, 2H). LCMS: tR=1.56, (ES$^+$) m/z (M+H)$^+$=566.4.

The following compounds in Table P1 were prepared using procedures similar to those described in Example 1 using appropriate starting materials.

TABLE P1

| Ex # | [M + H]$^+$ |
|---|---|
| 2 | 576.4 |
| 3 | 656.5 |
| 4 | 602.6 |

Example 5: 2-[4-[3-[1-(5-chloropyrimidin-2-yl)-4-piperidyl]propoxy]-2-fluoro-phenyl]-N-[2-hydroxy-1,1-bis(hydroxymethyl)ethyl]acetamide

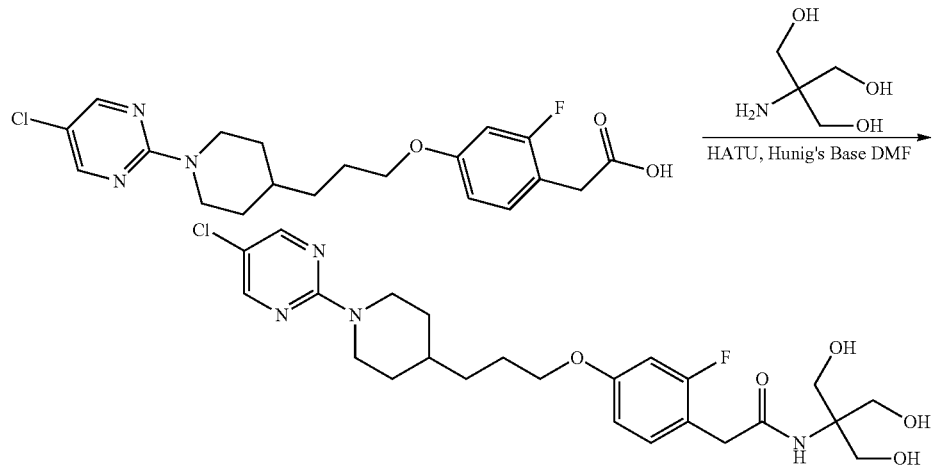

To a solution of 2-(4-(3-(1-(5-chloropyrimidin-2-yl)piperidin-4-yl)propoxy)-2-fluorophenyl)acetic acid intermediate 1 (70 mg, 0.17 mmol) in DMF (1 mL) was added 2-amino-2-(hydroxymethyl)-1,3-propanediol (31 mg, 0.25 mmol), HATU (98 mg, 0.25 mmol) and Hunig's base (90 μL, 0.5 mmol) and the resulting mixture stirred at room temperature for 1 hour. Reaction mixture diluted with EtOAc (20 mL) and washed with water (80 mL), sat. NaCl (30 mL), dried over MgSO₄, filtered and evaporated. The residue was purified by silica gel column chromatography (Teledyne Isco: SNAP 12 g Gold) eluent: 2-8% MeOH in DCM to give 2-[4-[3-[1-(5-chloropyrimidin-2-yl)-4-piperidyl]propoxy]-2-fluoro-phenyl]-N-[2-hydroxy-1,1-bis(hydroxymethyl) ethyl]acetamide (15 mg, 17%) as a white solid. $^1$H NMR (500 MHz, Chloroform-d) 8.20 (s, 2H), 7.15 (t, J=8.6 Hz, TH), 6.67 (dd, J=8.4, 2.6 Hz, TH), 6.63 (dd, J=11.7, 2.5 Hz, 1H), 6.58 (s, 1H), 4.67 (dp, J=13.4, 2.0 Hz, 2H) 3.94 (t J=6.4 Hz, 2H), 3.76 (t, J=6.3 Hz, 3H), 3.61 (d, J=6.2 Hz, 6H), 3.56-3.54 (m, 2H), 2.86 (td, J=13.0, 12.6, 2.7 Hz, 2H), 1.86-1.74 (m, 4H), 1.57 (dtt, J=10.7, 6.9, 3.9 Hz, 1H), 1.47-1.39 (m, 2H), 1.23-1.13 (m, 2H). LCMS: tR=0.91, (ES⁺) m/z (M+H)⁺=511.3.

The following compounds in Table P2 were prepared using procedures similar to those described in Example 5 using appropriate starting materials.

TABLE P2

| Ex # | [M + H]⁺ |
|------|----------|
| 6 | 529.3 |
| 7 | 523.3 |
| 8 | 537.4 |
| 9 | 507.2 |

Example 10: 2-[[2-[4-[3-[1-(5-chloropyrimidin-2-yl)-4-piperidyl]propoxy]-2-fluoro-phenyl]acetyl]amino]ethanesulfonic acid

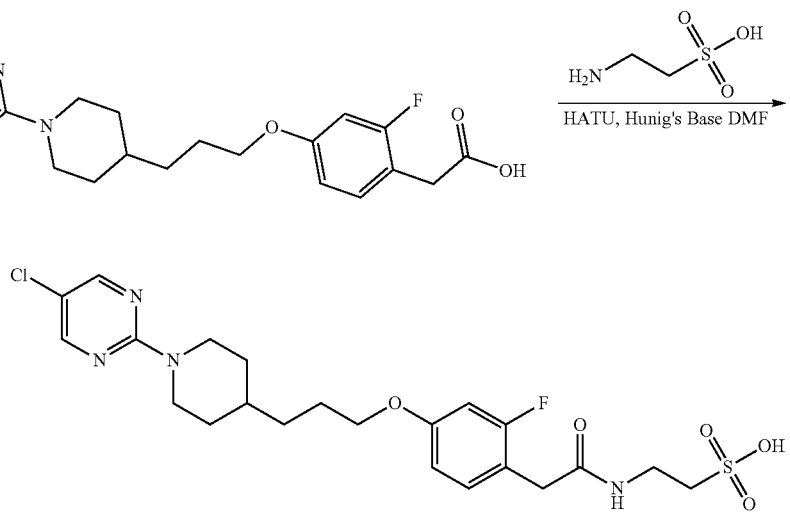

To a solution of 2-(4-(3-(1-(5-chloropyrimidin-2-yl)piperidin-4-yl)propoxy)-2-fluorophenyl)acetic acid intermediate 1 (50 mg, 0.12 mmol) in DMF (0.5 mL) was added 3-aminopropane sulfonic acid (23 mg, 0.18 mmol), HATU (73 mg, 0.18 mmol) and Hunig's base (44 µL, 0.25 mmol) and the resulting mixture stirred at room temperature overnight. Mixture acidified by the addition of formic acid (0.2 mL) and purified directly by reverse phase silica gel chromatography (Teledyne Isco: SNAP C18 15.5 g) eluent: gradient 10-100% acetonitrile in water+0.1% formic acid to give 2-[[2-[4-[3-[1-(5-chloropyrimidin-2-yl)-4-piperidyl]propoxy]-2-fluoro-phenyl]acetyl]amino]ethanesulfonic acid (15 mg, 24%). LCMS: tR=0.79, (ES$^+$) m/z (M+H)$^+$=515.2.

The following compounds in Table P3 were prepared using procedures similar to those described in Example 10 using appropriate starting materials

TABLE P3

| Ex # | [M + H]$^+$ |
|---|---|
| 11 | 529.2 |
| 12 | 543.3 |
| 13 | 528.2 |
| 14 | 542.3 |
| 15 | 500.4 |
| 16 | 613.5 |

Example 17: 6-[[2-[4-[3-[1-(5-chloropyrimidin-2-yl)-4-piperidyl]propoxy]-2-fluoro-phenyl]acetyl]amino]-N-[2-hydroxy-1-(hydroxymethyl)ethyl]hexanamide propoxy]-2-fluoro-phenyl]acetyl]amino]-N-[2-hydroxy-1-(hydroxymethyl)ethyl]hexanamide (12 mg, 21%) as a white solid. $^1$H NMR (500 MHz, DMSO-d$_6$) δ 8.38 (s, 2H), 7.93 (t, J=5.7 Hz, 1H), 7.42 (d, J=8.1 Hz, 1H), 7.18 (t, J=8.7 Hz, 1H), 6.75 (dd, J=11.9, 2.5 Hz, 1H), 6.71 (dd, J=8.5, 2.6 Hz, 1H), 4.62-4.53 (m, 4H), 3.95 (t, J=6.5 Hz, 2H), 3.70 (dt, J=7.9, 5.5 Hz, 1H), 3.39 (t, J=5.6 Hz, 4H), 3.35 (s, 2H), 3.02 (q, J=6.6 Hz, 2H), 2.88 (td, J=12.8, 2.7 Hz, 2H), 2.07 (t, J=7.5 Hz, 2H), 1.74 (ddd, J=14.8, 8.7, 4.9 Hz, 4H), 1.58 (m, 1H), 1.48 (p, J=7.6 Hz, 2H), 1.37 (dp, J=14.9, 7.1 Hz, 4H), 1.23 (td, J=8.5, 3.8 Hz, 2H), 1.06 (qd, J=12.3, 4.1 Hz, 2H). LCMS: tR=0.94, (ES$^+$) m/z (M+H)$^+$=594.4.

The following compounds in Table P4 were prepared using procedures similar to those described in Example 17 using appropriate starting materials

TABLE P4

| Ex # | [M + H]$^+$ |
|---|---|
| 18 | 624.4 |
| 19 | 552.3 |
| 20 | 582.24 |
| 21 | 566.3 |
| 22 | 596.3 |
| 23 | 580.3 |
| 24 | 610.3 |
| 25 | 606.3 |
| 26 | 612.4 |
| 27 | 690.4 |
| 28 | 564.5 |
| 29 | 594.5 |
| 30 | 594.5 |
| 31 | 696.4 |
| 32 | 608.5 |
| 33 | 608.5 |

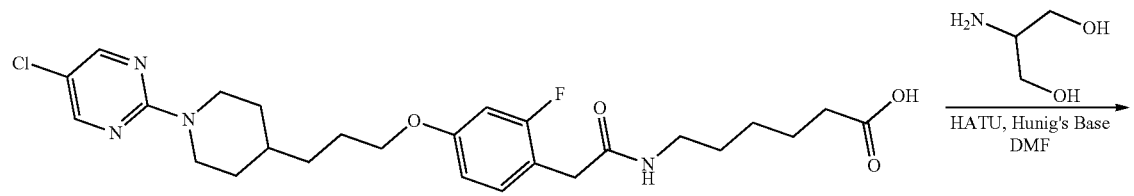

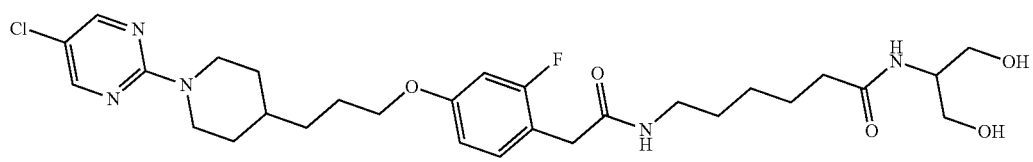

To a solution of 6-[[2-[4-[3-[1-(5-chloropyrimidin-2-yl)-4-piperidyl]propoxy]-2-fluoro-phenyl]acetyl]amino]hexanoic acid intermediate 21 (50 mg, 0.096 mmol) in DMF (1.5 mL) was added 2-amino-1,3-propanediol (13 mg, 0.144 mmol), HATU (55 mg, 0.144 mmol) and Hunig's base (33 µL, 0.19 mmol) and the resulting mixture stirred at room temperature for overnight. Diluted with EtOAc (20 mL) and washed with water (70 mL), sat. NaCl (40 mL), dried over MgSO$_4$, filtered and evaporated. The residue was purified by silica gel column chromatography (Teledyne Isco: SNAP 4 g Gold) eluent: gradient 2-8% MeOH in DCM to give 6-[[2-[4-[3-[1-(5-chloropyrimidin-2-yl)-4-piperidyl]

TABLE P4-continued

| Ex # | [M + H]$^+$ |
|---|---|
| 34 | 626.4 |
| 35 | 622.4 |
| 36 | 640.4 |
| 37 | 654.4 |
| 38 | 668.5 |
| 39 | 664.5 |
| 40 | 615.5 |
| 41 | 622.5 |

Example 42: 2-[4-[3-[1-(5-chloropyrimidin-2-yl)-4-piperidyl]propoxy]-2-fluoro-phenyl]-1-[3-[[[(2S,3R,4R,5R)-2,3,4,5,6-pentahydroxyhexyl]amino]methyl]azetidin-1-yl]ethanone

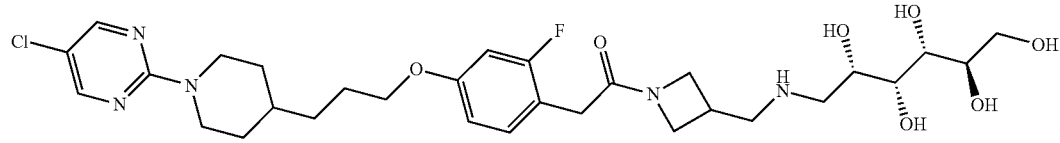 [SMILES: O=C(Cc1ccc(OCCCC2CCN(c3ncc(Cl)cn3)CC2)cc1F)N1CC(CNC[C@H](O)[C@@H](O)[C@H](O)[C@H](O)CO)C1]

Step 1: 1-(2-(4-(3-(1-(5-chloropyrimidin-2-yl)piperidin-4-yl)propoxy)-2-fluorophenyl)acetyl)azetidine-3-carbaldehyde

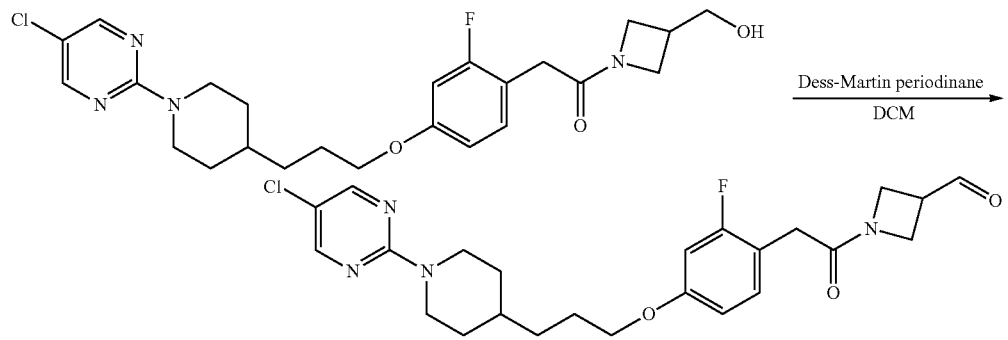

To a solution of 2-(4-(3-(1-(5-chloropyrimidin-2-yl)piperidin-4-yl)propoxy)-2-fluorophenyl)-1-(3-(hydroxymethyl)azetidin-1-yl)ethan-1-one intermediate 37 (150 mg, 0.315 mmol) in DCM (5 mL) was added Dess Martin periodinane (200 mg, 0.473 mmol) and the resulting mixture stirred at room temperature for 90 mins. Diluted with DCM (10 mL) and washed with sat. NaHCO$_3$(80 mL), sat. NaCl (30 mL), dried over MgSO$_4$, filtered and evaporated. The residue was purified by silica gel column chromatography (Teledyne Isco: SNAP 12 g Gold) eluent: 2% MeOH in DCM to give 1-(2-(4-(3-(1-(5-chloropyrimidin-2-yl)piperidin-4-yl)propoxy)-2-fluorophenyl)acetyl)azetidine-3-carbaldehyde (150 mg, 100%). LCMS: tR=1.01, (ES$^+$) m/z (M+18)$^+$=493.2.

Step 2: 2-[4-[3-[1-(5-chloropyrimidin-2-yl)-4-piperidyl]propoxy]-2-fluoro-phenyl]-1-[3-[[[(2S,3R,4R,5R)-2,3,4,5,6-pentahydroxyhexyl]amino]methyl]azetidin-1-yl]ethanone formate

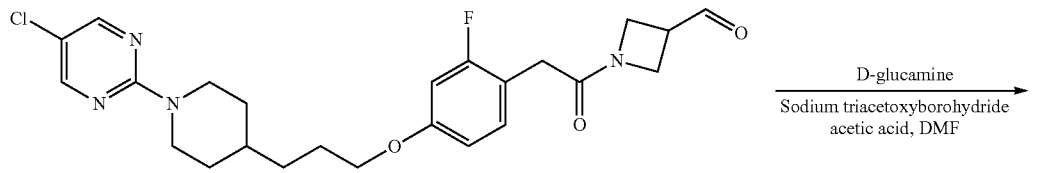

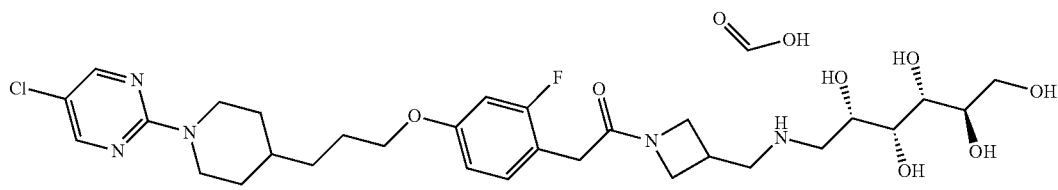

To a solution of 1-(2-(4-(3-(1-(5-chloropyrimidin-2-yl)piperidin-4-yl)propoxy)-2-fluorophenyl)acetyl) azetidine-3-carbaldehyde (150 mg, 0.3 mmol) in DMF (2 mL) was added D-glucamine (57 mg, 0.3 mmol), acetic acid (30 µL, 0.5 mmol) and sodium triacetoxyborohydride (100 mg, 0.475 mmol) and the resulting mixture stirred at room temperature overnight. The mixture was treated with formic acid (100 µL) and purified directly by reverse phase silica gel column chromatography (Teledyne Isco: 15.5 g C18 column) eluent: gradient 10-100% acetonitrile in water+ 0.05% formic acid to give 2-[4-[3-[1-(5-chloropyrimidin-2-yl)-4-piperidyl]propoxy]-2-fluoro-phenyl]-1-[3-[[[(2S,3R,4R,5R)-2,3,4,5,6-pentahydroxyhexyl]amino] methyl] azetidin-1-yl]ethanone formate (36 mg, 19%). $^1$H NMR (500 MHz, DMSO-$d_6$) δ 8.36 (s, 2H), 8.34 (s, 1H), 7.16 (t, J=8.8 Hz, 1H), 6.75 (dd, J=11.9, 2.5 Hz, 1H), 6.70 (dd, J=8.4, 2.5 Hz, 1H), 4.58 (dt, J=13.9, 2.8 Hz, 2H), 4.23 (t, J=8.5 Hz, 1H), 3.98-3.89 (m, 4H), 3.83 (dq, J=8.7, 3.9 Hz, 1H), 3.67 (dd, J=5.0, 1.7 Hz, 1H), 3.61 (ddd, J=11.0, 7.5, 4.2 Hz, 2H), 3.50 (ddd, J=8.8, 5.7, 3.4 Hz, 1H), 3.46-3.39 (m, 2H), 3.38-3.30 (m, 2H), 1.78-1.68 (m, 4H), 1.56 (ddp, J=10.8, 6.9, 3.5 Hz, 1H), 1.39-1.30 (m, 2H), 1.04 (qd, J=12.5, 4.1 Hz, 2H). LCMS: tR=1.47, (ES$^+$) m/z (M+H)$^+$=640.4.

The following compounds in Table P5 were prepared using procedures similar to those described in Example 42 using appropriate starting materials

TABLE P5

| Ex # | [M + H]$^+$ |
|---|---|
| 43 | 580.4 |
| 44 | 580.5 |
| 45 | 564.5 |
| 46 | 562.4 |
| 47 | 562.5 |
| 48 | 562.5 |
| 49 | 592.5 |
| 50 | 592.5 |
| 51 | 608.1 |
| 52 | 607.2 |
| 53 | 658.4 |
| 54 | 654.4 |
| 55 | 672.4 |
| 56 | 564.5 |
| 57 | 578.5 |
| 58 | 594.5 |
| 59 | 594.5 |
| 60 | 680.5 |
| 61 | 654.5 |
| 62 | 558.6 |
| 63 | 574.6 |
| 64 | 574.6 |
| 65 | 660.5 |
| 66 | 648.5 |
| 67 | 592.6 |
| 68 | 678.5 |
| 69 | 652.6 |
| 70 | 572.6 |
| 71 | 588.6 |
| 72 | 588.6 |
| 73 | 674.6 |
| 74 | 648.6 |
| 75 | 606.6 |
| 76 | 606.5 |
| 77 | 692.5 |
| 78 | 666.6 |
| 79 | 636.6 |
| 80 | 650.5 |
| 81 | 676.5 |
| 82 | 646.2 |
| 83 | 650.5 |
| 84 | 664.5 |
| 85 | 682.5 |
| 86 | 666.4 |
| 87 | 664.5 |
| 88 | 634.5 |
| 89 | 634.5 |
| 90 | 654.5 |
| 91 | 654.4 |
| 92 | 668.4 |

Example 93: 2-[2-fluoro-4-[3-[1-[5-(hydroxymethyl)pyrimidin-2-yl]-4-piperidyl]propoxy]phenyl]-1-[3-[[[(2S,3R,4R,5R)-2,3,4,5,6-pentahydroxyhexyl]amino]methyl]azetidin-1-yl]ethanone

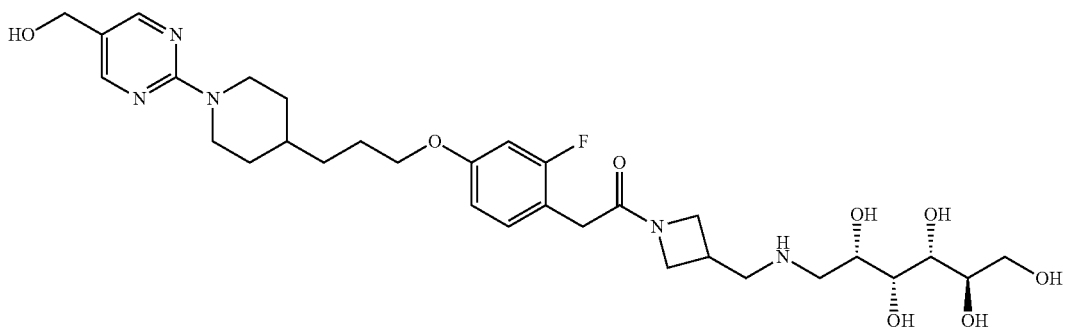 [SMILES: O=C(Cc1ccc(OCCCC2CCN(c3ncc(CO)cn3)CC2)cc1F)N1CC(CNC[C@H](O)[C@@H](O)[C@H](O)[C@H](O)CO)C1]

Prepared using procedures outlined in the preparation of example 42; replacing intermediate 37 with intermediate 52 in step 1 and with the addition of aqueous lithium hydroxide (8 eq) before purification in step 2 to remove the tert-butyldimethylsilyl group to give 2-[2-fluoro-4-[3-[1-[5-(hydroxymethyl)pyrimidin-2-yl]-4-piperidyl]propoxy]phenyl]-1-[3-[[[(2S,3R,4R,5R)-2,3,4,5,6-pentahydroxyhexyl]amino]methyl]azetidin-1-yl]ethanone. LCMS: tR=1.17, (ES$^+$) m/z (M+H)$^+$=636.5.

Example 94: 2-(2,6-difluoro-4-(3-(1-(5-(methoxymethyl)pyrimidin-2-yl)piperidin-4-yl)propoxy)phenyl)-1-(3-((((2S,3R,4R,5R)-2,3,4,5,6-pentahydroxyhexyl)amino)methyl)azetidin-1-yl)ethan-1-one

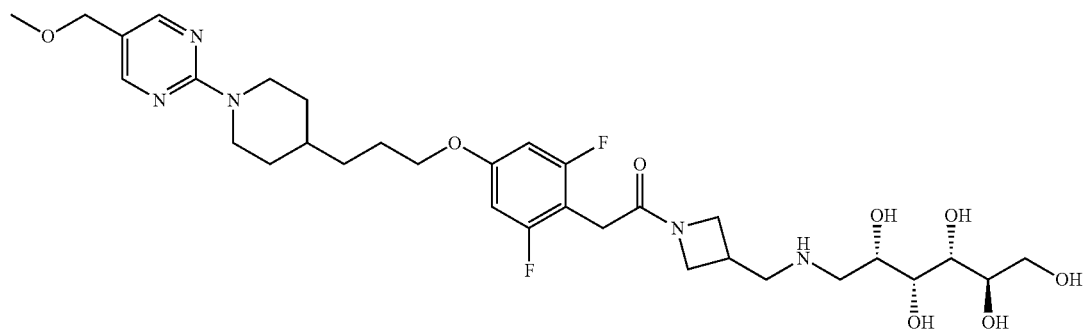 [SMILES: COCc1cnc(N2CCC(CCCOc3cc(F)c(CC(=O)N4CC(CNC[C@H](O)[C@@H](O)[C@H](O)[C@H](O)CO)C4)c(F)c3)CC2)nc1]

Step 1: azetidine-3-carbaldehyde hydrochloride

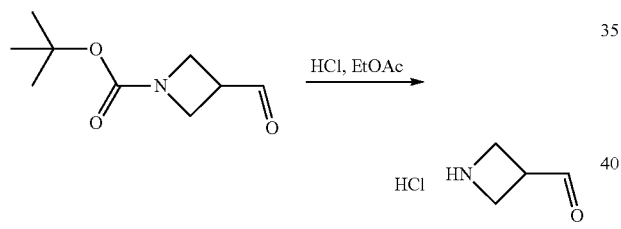

To a solution of tert-butyl 3-formyazetidine-1-carboxylate (0.25 g, 1.4 mmol) in EtOAc (2.5 mL) was added HCl (2.5 mL of a 4M solution in EtOAc) and the resulting mixture stirred at room temperature for 1 hour. The mixture was evaporated to give azetidine-3-carbaldehyde hydrochloride (160 mg, crude) as a yellow oil.

Step 2: 1-(2-(2,6-difluoro-4-(3-(1-(5-(methoxymethyl)pyrimidin-2-yl)piperidin-4-yl)propoxy) phenyl)acetyl) azetidine-3-carbaldehyde

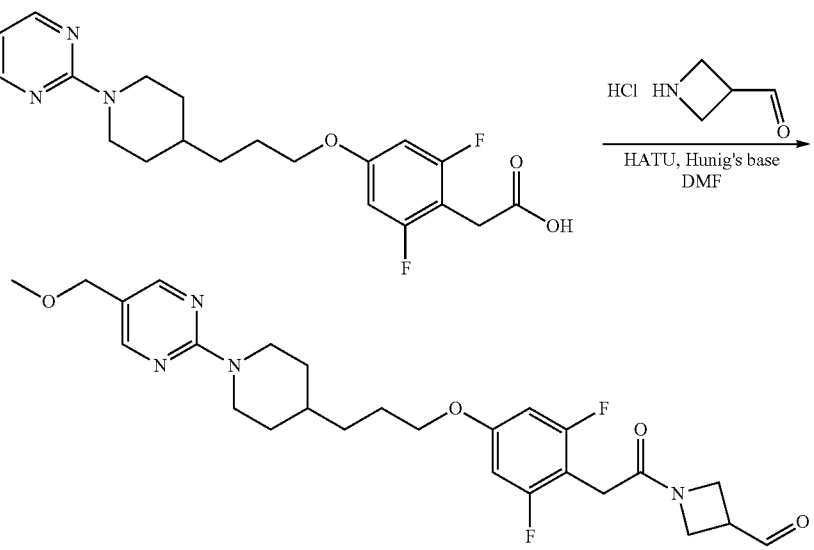

To a solution of 2-(2,6-difluoro-4-(3-(1-(5-(methoxymethyl)pyrimidin-2-yl)piperidin-4-yl)propoxy) phenyl)acetic acid intermediate 12 (170 mg, 0.39 mmol) in DMF (2 mL) was added HATU (180 mg, 0.47 mmol), Hunig's base (200 mg, 1.6 mmol) and azetidine-3-carbaldehyde hydrochloride (95 mg, 0.78 mmol) and the resulting mixture stirred at room temperature for 12 hours. Mixture poured into water (10 mL) and extracted with EtOAc (10 mL), the organic layer was evaporated and purified directly by PREP-TLC (eluent: ethyl acetate) to give 1-(2-(2,6-difluoro-4-(3-(1-(5-(methoxymethyl)pyrimidin-2-yl)piperidin-4-yl)propoxy) phenyl)acetyl) azetidine-3-carbaldehyde (20 mg, 6%) as a white solid. LCMS: tR=0.814, (ES$^+$) m/z (M+H)$^+$=503.2.

Step 3: 2-(2,6-difluoro-4-(3-(1-(5-(methoxymethyl)pyrimidin-2-yl)piperidin-4-yl)propoxy)phenyl)-1-(3-((((2S,3R,4R,5R)-2,3,4,5,6-pentahydroxyhexyl)amino)methyl)azetidin-1-yl)ethan-1-one

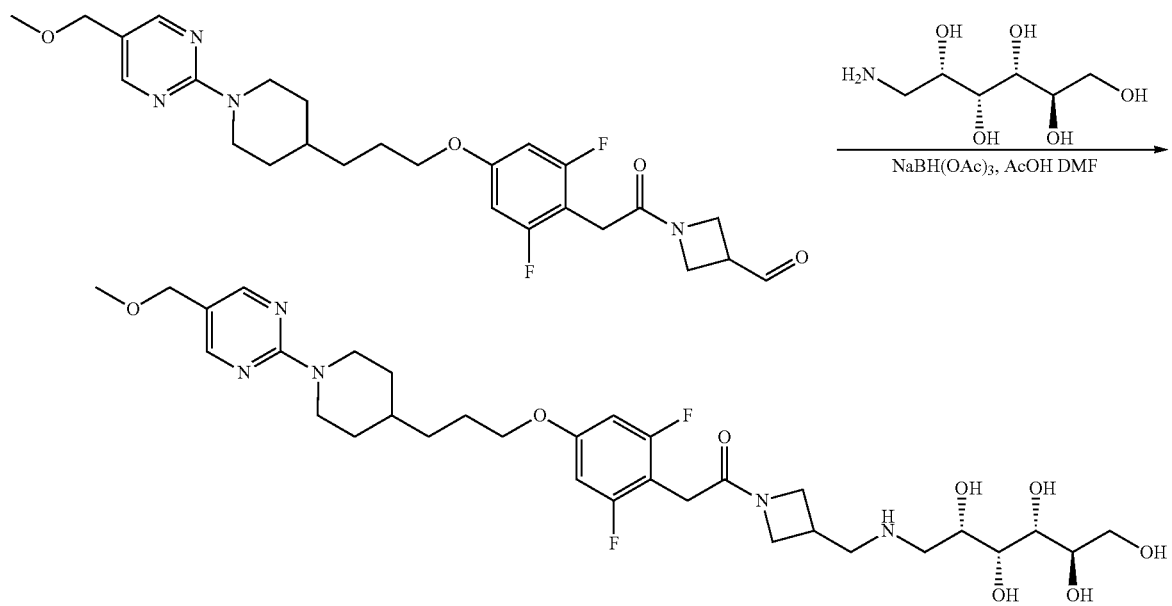

To a mixture of 1-(2-(2,6-difluoro-4-(3-(1-(5-(methoxymethyl)pyrimidin-2-yl)piperidin-4-yl)propoxy)phenyl)acetyl) azetidine-3-carbaldehyde (20 mg, 40 μmol) and D-glucamine (11 mg, 60 μmol) in DMF (0.3 mL) was added acetic acid (12 mg. 0.2 mmol) and the resulting mixture stirred at room temperature for 10 mins then sodium triacetoxyborohydride ((13 mg, 60 μmol) added and stirring continued for 12 hours. The mixture was filtered and the filtrate purified directly by reversed phase PREP-HPLC to give 2-(2,6-difluoro-4-(3-(1-(5-(methoxymethyl)pyrimidin-2-yl)piperidin-4-yl)propoxy)phenyl)-1-(3-((((2S,3R,4R,5R)-2,3,4,5,6-pentahydroxyhexyl)amino)methyl)azetidin-1-yl)ethan-1-one (3.9 mg, 11%) as a white solid. $^1$H NMR (400 MHz, MeOD) δ 8.27 (s, 2H), 6.57 (br d, J=9.3 Hz, 2H), 4.72 (br d, J=14.1 Hz, 2H), 4.58 (br s, 1H), 4.45 (t, J=8.3 Hz, 1H), 4.28 (s, 2H), 4.16 (br t, J=9.2 Hz, 1H), 4.04 (br s, 2H), 3.97 (t, J=6.4 Hz, 2H), 3.85 (br d, J=4.5 Hz, 1H), 3.79 (br d, J=9.7 Hz, 2H), 3.73-3.61 (m, 3H), 3.47 (s, 2H), 3.35 (s, 3H), 3.27-3.23 (m, 1H), 3.15 (br s, 2H), 3.02 (br s, 1H), 2.90 (br t, J=12.2 Hz, 2H), 1.88-1.76 (m, 4H), 1.61 (br s, 1H), 1.50-1.38 (m, 2H), 1.21-1.09 (m, 2H). LCMS: tR=0.704, (ES$^+$) m/z (M+H)$^+$=668.3.

Example 95: (1R,2R)-2-[1-(5-chloropyrimidin-2-yl)-4-piperidyl]cyclopropyl]methyl 3-fluoro-4-[2-oxo-2-[3-[[[rac-(2S,3R,4R,5R)-2,3,4,5,6-pentahydroxyhexyl]amino]methyl]azetidin-1-yl]ethyl]benzoate

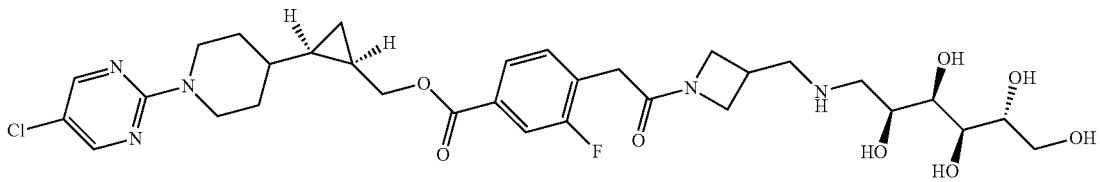 [SMILES: O=C(OC[C@@H]1C[C@@H]1C1CCN(c2ncc(Cl)cn2)CC1)c1ccc(CC(=O)N2CC(CNC[C@H](O)[C@@H](O)[C@H](O)[C@H](O)CO)C2)c(F)c1]

Prepared using procedures outlined in the preparation of example 94; replacing intermediate 12 with intermediate 59 in step 2 to give (1R,2R)-2-[1-(5-chloropyrimidin-2-yl)-4-piperidyl]cyclopropyl]methyl 3-fluoro-4-[2-oxo-2-[3-[[[rac-(2S,3R,4R,5R)-2,3,4,5,6-pentahydroxyhexyl]amino]methyl]azetidin-1-yl]ethyl]benzoate. $^1$H NMR (400 MHz, MeOD) δ 8.48 (s, 1H), 8.24 (s, 2H), 7.83 (dd, J=1.6, 1.2 Hz, 1H), 7.71 (dd, J=1.6, 1.2 Hz, 1H), 7.47 (t, J=15.2 Hz, 1H), 4.69 ((m, 1H), 4.58 (m, 3H), 4.07 (m, 2H), 3.82 (m, 4H), 3.66 (m, 5H), 3.35 (m, 2H), 3.17 (m, 2H), 3.04 (m, 4H), 1.88 (m, 2H), 1.32 (m, 5H), 0.82 (m, 2H), 0.25 (m, 1H).

Example 96: 2-[2-fluoro-4-[[(1R,2R)-2-[1-[5-(methoxymethyl)pyrimidin-2-yl]-4-piperidyl]cyclopropyl]methoxy methyl]phenyl]-1-[3-[[[(2S,3R,4R,5R)-2,3,4,5,6-pentahydroxyhexyl]amino]methyl]azetidin-1-yl]ethanone Step 1: 2-[2-fluoro-4-[[(1R,2R)-2-[1-[5-(methoxymethyl)pyrimidin-2-yl]-4-piperidyl]cyclopropyl]methoxy methyl]phenyl]-1-[3-[[[(2S,3R,4R,5R)-2,3,4,5,6-pentahydroxyhexyl]amino]methyl]azetidin-1-yl]ethanone To a solution of 2-(2-fluoro-4-((((1R,2R)-2-(1-(5-(methoxymethyl)pyrimidin-2-yl)piperidin-4-yl)cyclopropyl)methoxy) methyl)phenyl)acetic acid intermediate 60 (64 mg, 0.14 mmol) and (2R,3R,4R,5S)-6-((azetidin-3-ylmethyl)amino)hexane-1,2,3,4,5-pentayl pentaacetate (44 mg, 96 μmol) in DMF (1 mL) was added HATU ((44 mg, 0.11 mmol) and Hunig's base (25 mg, 0.19 mmol) and the resulting mixture stirred at room temperature for 2 hours. Mixture diluted with MeOH (1 mL) and water (1 mL)) and sodium hydroxide (19 mg, 0.48 mmol) added and the resulting mixture stirred at room temperature for 96 hours. The mixture was evaporated and the residue treated with 1N HCl (6 mL), filtered and the filtrate purified by PREP-HPLC to give 2-[2-fluoro-4-[[(1R,2R)-2-[1-[5-(methoxymethyl)pyrimidin-2-yl]-4-piperidyl]cyclopropyl]methoxy methyl]phenyl]-1-[3-[[[(2S,3R,4R,5R)-2,3,4,5,6-pentahydroxyhexyl]amino]methyl]azetidin-1-yl]ethanone (23 mg, 35%) as a white solid. $^1$H NMR (400 MHz, MeOD) δ 8.27 (s, 2H), 7.35-7.25 (m, 1H), 7.20-7.05 (m, 2H), 4.75-4.55 (m, 3H), 4.53-4.38 (m, 2H), 4.28 (s, 2H), 4.20-4.12 (m, 1H), 4.10-4.00 (m, 2H), 3.87-3.83 (m, 1H), 3.82-3.72 (m, 2H), 3.74-3.62 (m, 4H), 3.55-3.50 (m, 2H), 3.47-3.39 (m, 1H), 3.35 (s, 3H), 3.30-3.20 (m, 2H), 3.18-3.10 (m, 2H), 3.07-2.95 (m, 1H), 2.94-2.73 (m, 2H), 2.06-1.93 (m, 1H), 1.83-1.74 (m, 1H), 1.37-0.97 (m, 4H), 0.82-0.55 (m, 2H), 0.09-0.03 (m, 1H). LCMS: tR=0.789, (ES$^+$) m/z (M+H)$^+$=676.5

Example 97: 2-[2-fluoro-4-[2-[rac-(1S,2R)-2-[1-[5-(methoxymethyl)pyrimidin-2-yl]-4-piperidyl]cyclopropyl]ethoxy] phenyl]-1-[3-[[[(2S,3R,4R,5R)-2,3,4,5,6-pentahydroxyhexyl]amino]methyl]azetidin-1-yl]ethanone 322 mmol) followed by sodium cyanoborohydride (33.74 g, 537 mmol) and the resulting mixture stirred at room temperature for 12 hours. The mixture was evaporated to give tert-butyl 3-((((2S,3R,4R,5R)-2,3,4,5,6-pentahydroxyhexyl)amino)methyl)azetidine-1-carboxylate used in the next step without purification. $^1$H NMR (400 MHz, deuterium oxide) δ 4.25-4.05 (s, 3H), 3.91-3.71 (6H), 3.68-3.60 (m, 2H), 3.39 (br d, J=6.38 Hz, 2H), 3.30-3.11 (m, 2H), 3.01 (br d, J=6.25 Hz, 1H), 1.42 (s, 9H).

Step 2: tert-butyl 3-(((((9H-fluoren-9-yl)methoxy)carbonyl)((2S,3R,4R,5R)-2,3,4,5,6-pentahydroxyhexyl) amino)methyl)azetidine-1-carboxylate

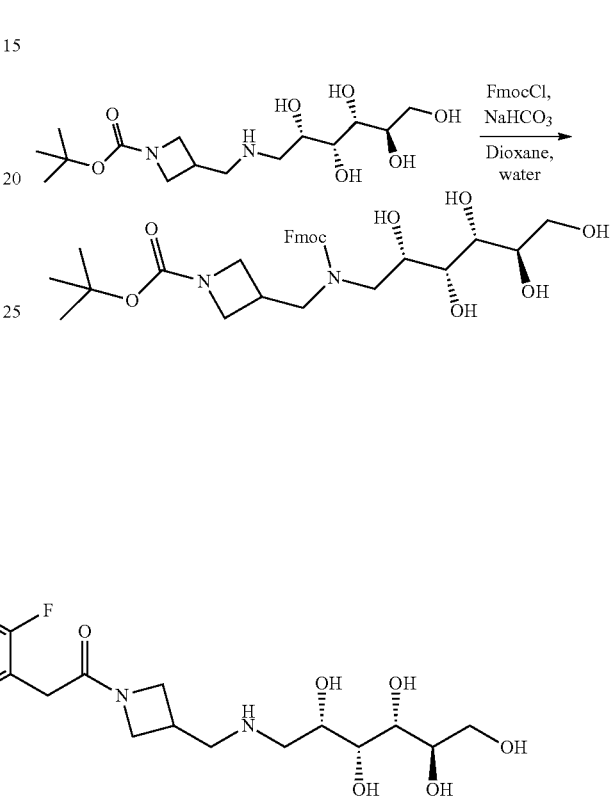

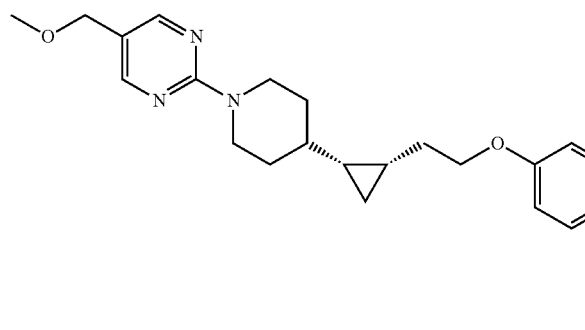

Step 1: tert-butyl 3-((((2S,3R,4R,5R)-2,3,4,5,6-pentahydroxyhexyl)amino)methyl)azetidine-1-carboxylate

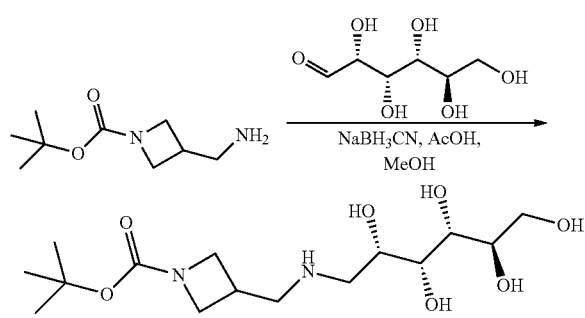

To a solution of tert-butyl-(3-aminomethyl)azetidine-1-carboxylate (50 g, 269 mmol) in a mixture of MeOH (500 mL) and acetic acid (25 mL) was added D-glucose (58.04 g, To a solution of tert-butyl 3-((((2S,3R,4R,5R)-2,3,4,5,6-pentahydroxyhexyl) amino)methyl)azetidine-1-carboxylate (94.07 g, 269 mmol) in a mixture of water (1 L) and 1,4-dioxane (1.2 L) was added NaHCO$_3$ (47.95 g, 571 mmol) followed by 9-fluorenylmethoxycarbonyl chloride (88.59 g, 342 mmol) and the resulting mixture stirred at room temperature for 4 hours. The mixture was filtered and the filtrate evaporated to remove the organic solvents. The remaining aqueous was extracted with EtOAc (3×500 mL); the combined EtOAc layers washed with sat. NaCl (2×500 mL), dried over Na$_2$SO$_4$, filtered and evaporated. The residue was triturated with MTBE:Petroleum ether (1:1) filtered and dried to give tert-butyl 3-(((((9H-fluoren-9-yl)methoxy)carbonyl)((2S,3R,4R,5R)-2,3,4,5,6-pentahydroxyhexyl) amino)methyl)azetidine-1-carboxylate (100 g, 60%) as a white solid. $^1$H NMR (400 MHz, MeOD) δ 7.81 (br d, J=7.0 Hz, 2H), 7.61 (br d, J=7.13 Hz, 2H), 7.43-7.27 (m, 4H), 4.73-4.36 (m, 2H), 4.25 (br t, J=4.82 Hz, 1H), 3.96-3.49 (m, 9H), 3.23-3.06 (m, 3H), 2.85 (br s, 1H), 2.35 (br s, 1H), 1.43 s, 8H).

Step 3: (H-fluoren-9-ylmethyl N-(azetidin-3-ylmethyl)-N-[(2S,3R,4R,5R)-2,3,4,5,6-pentahydroxylhexyl]carbamate hydrochloride

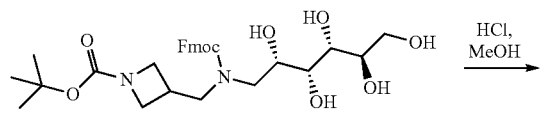

Step 4: 2-[2-fluoro-4-[2-[rac-(1S,2R)-2-[1-[5-(methoxymethyl)pyrimidin-2-yl]-4-piperidyl]cyclopropyl]ethoxy]phenyl]-1-[3-[[[(2S,3R,4R,5R)-2,3,4,5,6-pentahydroxyhexyl]amino]methyl]azetidin-1-yl]ethanone

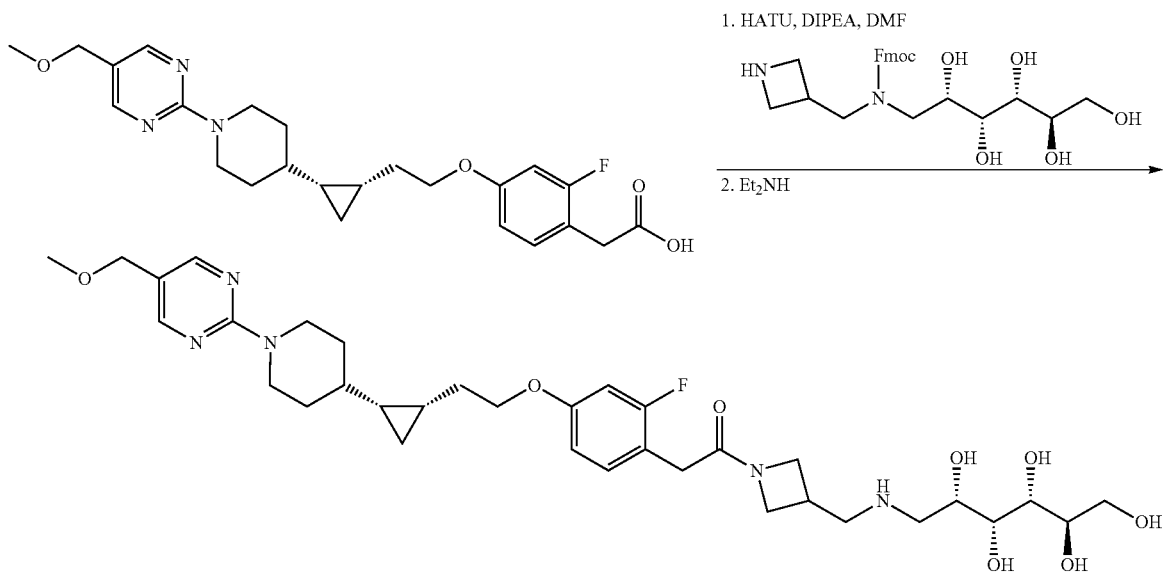

-continued

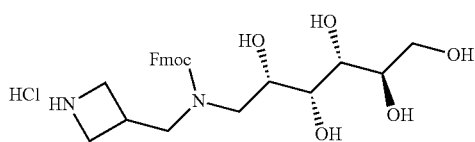

To a mixture of MeOH (125 mL) and 12M HCl (125 mL) at 20° C. was added portionwise tert-butyl 3-(((((9H-fluoren-9-yl)methoxy)carbonyl)((2S,3R,4R,5R)-2,3,4,5,6-pentahydroxyhexyl) amino)methyl)azetidine-1-carboxylate (100 g, 175 mmol). After complete addition the resulting mixture was stirred at 20° C. for 1 hour. The mixture was diluted with water (500 mL) and extracted with DCM (3×300 mL), and the aqueous layer was evaporated. The residue was dissolved in MeOH (150 mL) and EtOAc (300 ml) added to form an oil. The oil was collected and the operation repeated whereupon the oil solidified. The solid was diluted with EtOH (5 l) and heated at 80° C. for 30 min. The EtOH layer was collected and evaporated to give a solid. The operation was repeated one time to give (H-fluoren-9-ylmethyl N-(azetidin-3-ylmethyl)-N-[(2S,3R,4R,5R)-2,3,4,5,6-pentahydroxylhexyl] carbamate hydrochloride (50 g, 57%) as a light yellow solid. $^1$H NMR (400 MHz, deuterium oxide) δ 7.70 (br s, 2H), 7.54-7.41 (m, 2H), 7.40-7.20 (m, 4H), 4.70-4.48 (m, 2H), 4.10-3.42 (m, 9H), 3.29-3.03 (m, 3H), 3.02-2.70 (m, 2H), 2.68-2.49 (m, 1H), 2.45-2.27 (m, 1H).

To a solution of 2-(2-fluoro-4-(2-((1S,2R)-2-(1-(5-(methoxymethyl)pyrimidin-2-yl)piperidin-4-yl)cyclopropyl)ethoxy) phenyl)acetic acid intermediate 19 (100 mg, 0.23 mmol) and (H-fluoren-9-ylmethyl N-(azetidin-3-ylmethyl)-N-[(2S,3R,4R,5R)-2,3,4,5,6-pentahydroxylhexyl] carbamate hydrochloride (110 mg, 0.23 mmol) in DMF (1 mL) was added HATU (130 mmg, 0.34 mmol) and Hunig's base (87 mg, 0.68 mmol) and the resulting mixture stirred at room temperature for 12 hours. To this mixture was added diethylamine (69 μL, 0.67 mmol) and stirring continued for 30 minutes. The mixture was filtered and the filtrate purified directly by reversed phase PREP-HPLC to give 2-[2-fluoro-4-[2-[rac-(1S,2R)-2-[1-[5-(methoxymethyl)pyrimidin-2-yl]-4-piperidyl]cyclopropyl] ethoxy]phenyl]-1-[3-[[[(2S,3R,4R,5R)-2,3,4,5,6-pentahydroxyhexyl]amino]methyl] azetidin-1-yl]ethanone (81.2 mg, 49%) as an orange solid. $^1$H NMR (400 MHz, MeOD) δ 8.50 (s, 1H), 8.28 (s, 2H), 7.19 (t, J=8.7 Hz, 1H), 6.72 (d, J=2.4 Hz, 2H), 4.74-4.66 (m, 2H), 4.41 (t, J=8.8 Hz, 1H), 4.28 (s, 2H), 4.16 (t, J=9.2 Hz, 1H), 4.11-3.98 (m, 4H), 3.85 (d, J=4.8 Hz, 1H), 3.82-3.74 (m, 2H), 3.74-3.61 (m, 3H), 3.45 (s, 2H), 3.35 (s, 3H), 3.35 (s, 3H), 3.30-3.23 (m, 2H), 3.19-3.09 (m, 2H), 3.06-2.96 (m, 1H), 2.96-2.83 (m, 2H), 2.16-2.06 (m, 1H), 1.92-1.80 (m, 2H), 1.59 (d, J=5.2 Hz, 1H), 1.41-1.26 (m, 2H), 1.24-1.12 (m 1H), 1.03-0.90 (m 1H), 0.73-0.56 (m, 2H), -0.03 (d, J=4.4 Hz, 1H). LCMS: tR=0.781, (ES$^+$) m/z (M+H)$^+$=676.4.

The following compounds in Table P6 were prepared using procedures similar to those described in Examples 1-97 using appropriate starting materials.

TABLE P6

| Ex # | [M + H]+ |
|---|---|
| 98 | 654.4 |
| 99 | 594.5 |
| 100 | 654.5 |
| 101 | 594.5 |
| 102 | 608.5 |
| 103 | 608.5 |
| 104 | 666.4 |
| 105 | 680.4 |
| 106 | 694.4 |
| 107 | 666.4 |
| 108 | 618.5 |
| 109 | 668.5 |
| 110 | 652.4 |
| 111 | 652.5 |
| 112 | 614.5 |
| 113 | 638.5 |
| 114 | 668.5 |
| 115 | 684.5 |
| 116 | 698.5 |
| 117 | 654.5 |
| 118 | 640.6 |
| 119 | 626.5 |
| 120 | 666.5 |
| 121 | 698.4 |
| 122 | 652.4 |
| 123 | 680.4 |
| 124 | 698.4 |
| 125 | 696.5 |
| 126 | 714.4 |
| 127 | 668.5 |
| 128 | 686.4 |
| 129 | 678.5 |
| 130 | 696.5 |
| 131 | 696.4 |
| 132 | 672.4 |
| 133 | 664.5 |
| 134 | 682.5 |
| 135 | 682.5 |
| 136 | 712.4 |
| 137 | 666.4 |
| 138 | 666.4 |
| 139 | 684.5 |
| 140 | 640.5 |
| 141 | 658.5 |
| 142 | 666.4 |
| 143 | 684.4 |
| 144 | 680.4 |
| 145 | 640.5 |
| 146 | 658.5 |
| 147 | 608.5 |
| 148 | 594.5 |
| 149 | 612.5 |
| 150 | 612.4 |
| 151 | 626.5 |
| 152 | 604.6 |
| 153 | 604.6 |
| 154 | 618.5 |
| 155 | 622.5 |
| 156 | 622.5 |
| 157 | 636.5 |
| 158 | 622.5 |
| 159 | 622.5 |
| 160 | 636.5 |
| 161 | 630.6 |
| 162 | 630.6 |
| 163 | 644.5 |
| 164 | 624.5 |
| 165 | 610.5 |
| 166 | 610.5 |
| 167 | 610.5 |
| 168 | 624.5 |
| 169 | 623.4 |
| 170 | 641.4 |
| 171 | 598.5 |
| 172 | 612.4 |
| 173 | 626.4 |
| 174 | 640.4 |
| 175 | 654.4 |
| 176 | 612.4 |
| 177 | 626.4 |
| 178 | 640.4 |
| 179 | 623.4 |
| 180 | 624.5 |
| 181 | 684.4 |
| 182 | 638.5 |
| 183 | 638.5 |
| 184 | 638.5 |
| 185 | 626.4 |
| 186 | 640.5 |
| 187 | 654.4 |
| 188 | 642.5 |
| 189 | 652.5 |
| 190 | 652.5 |

II. Biological Evaluation

Example A-1: In Vitro Activity Assay

Cell Line Expressing GPR119

CHO-K1 cells stably expressing human GPR119 (hGPR119) were prepared by transfection of a GPR119-carrying plasmid using Lipofectamine 2000 (following manufacturer instructions). A stable cell line was established using the limiting dilution method with geneticine selection. Assay-ready frozen (ARF) cells were prepared and used throughout the study.

cAMP Accumulation Assay

The assay was performed in a 384-well plate format using the cAMP Gs dynamic assay kit from Cisbio. ARF cells expressing hGPR119 were thawed, washed and then resuspended in cAMP stimulation buffer at a cell density of $1.1 \times 10^6$ cells/mL. Cells were plated at a density of ~10,000 cells/well (9 μL/well). Dose response curves for the tested compounds were prepared in a cAMP stimulation buffer, containing 0.1% Tween 80 at 4 fold the final concentration. The compounds were then transferred to the cell plates using BRAVO (3 μL/well) and the plates were incubated for 60 minutes at 37° C./5% $CO_2$. Detection buffer (10 μL, prepared as described in the cAMP Gs dynamic kit) were added to each well, and the plates were incubated at ambient temperature for 1 hr.

RT-FRET was measured using a ClarioSTAR plate reader, calculating the ratio between emissions at 665 nm and 620 nm (HTRF ratio). The HTRF ratio for positive (Max) and negative (Min) controls were used to normalize HTRF data and generate values for % activity. $EC_{50}$ and Max activity values were determined using a standard 4-parameter fit.

Results for exemplary compounds are shown in Table 2.

TABLE 2

| Compound | Max Activity[a] | $EC_{50}$[b] |
|---|---|---|
| 1 | +++ | B |
| 2 | +++ | B |
| 3 | +++ | B |
| 4 | −+ | B |
| 5 | −+ | B |
| 6 | −+ | B |
| 7 | −+ | A |
| 8 | −+ | A |
| 9 | −+ | A |
| 10 | +++ | C |
| 11 | +++ | C |

TABLE 2-continued

| Compound | Max Activity$^a$ | EC$_{50}$$^b$ |
|---|---|---|
| 12 | +++ | C |
| 13 | +++ | A |
| 14 | +++ | A |
| 15 | ++ | B |
| 16 | ++ | B |
| 17 | +++ | B |
| 18 | ++ | B |
| 19 | ++ | B |
| 20 | +++ | B |
| 21 | +++ | B |
| 22 | +++ | B |
| 23 | +++ | B |
| 24 | +++ | B |
| 25 | +++ | B |
| 26 | +++ | A |
| 27 | −+ | B |
| 28 | −+ | B |
| 29 | +++ | A |
| 30 | −+ | A |
| 31 | −+ | B |
| 32 | −+ | B |
| 33 | +++ | B |
| 34 | +++ | A |
| 35 | +++ | A |
| 36 | −+ | A |
| 37 | −+ | B |
| 38 | +++ | B |
| 39 | −+ | B |
| 40 | −+ | B |
| 41 | −+ | B |
| 42 | −+ | B |
| 43 | −+ | A |
| 44 | +++ | A |
| 45 | −+ | A |
| 46 | −+ | A |
| 47 | −+ | A |
| 48 | −+ | A |
| 49 | +++ | B |
| 50 | −+ | A |
| 51 | + | A |
| 52 | −+ | B |
| 53 | +++ | A |
| 54 | +++ | B |
| 55 | +++ | B |
| 56 | −+ | A |
| 57 | −+ | A |
| 58 | +++ | B |
| 59 | −+ | B |
| 60 | +++ | B |
| 61 | −+ | B |
| 62 | +++ | B |
| 63 | +++ | A |
| 64 | +++ | A |
| 65 | −+ | A |
| 67 | ++ | A |
| 68 | +++ | A |
| 69 | ++ | A |
| 70 | ++ | A |
| 71 | ++ | A |
| 72 | +++ | A |
| 73 | ++ | B |
| 74 | +++ | B |
| 75 | ++ | A |
| 76 | +++ | A |
| 77 | +++ | B |
| 78 | ++ | A |
| 79 | ++ | B |
| 80 | ++ | B |
| 81 | ++ | B |
| 82 | + | B |
| 83 | ++ | B |
| 84 | ++ | B |
| 85 | ++ | B |
| 86 | ++ | B |
| 87 | ++ | B |
| 88 | + | C |
| 89 | + | C |
| 90 | + | B |
| 91 | ++ | C |
| 92 | ++ | B |
| 93 | + | C |
| 94 | ++ | B |
| 95 | ++ | B |
| 96 | ++ | B |
| 97 | ++ | B |
| 98 | ++ | A |
| 99 | +++ | A |
| 100 | ++ | A |
| 101 | ++ | A |
| 102 | ++ | A |
| 103 | ++ | A |
| 104 | ++ | B |
| 105 | ++ | A |
| 106 | ++ | B |
| 107 | ++ | C |
| 108 | ++ | A |
| 109 | −+ | B |
| 110 | −+ | B |
| 111 | + | C |
| 112 | −+ | B |
| 113 | −+ | B |
| 114 | −+ | A |
| 115 | −+ | B |
| 116 | +++ | A |
| 117 | −+ | B |
| 118 | −+ | B |
| 119 | −+ | B |
| 120 | −+ | A |
| 121 | −+ | A |
| 122 | −+ | A |
| 123 | −+ | B |
| 124 | −+ | A |
| 125 | −+ | B |
| 126 | −+ | B |
| 127 | +++ | A |
| 128 | +++ | A |
| 129 | −+ | A |
| 130 | −+ | A |
| 131 | −+ | A |
| 132 | −+ | A |
| 133 | −+ | A |
| 134 | −+ | A |
| 135 | −+ | A |
| 136 | −+ | A |
| 137 | −+ | A |
| 138 | + | C |
| 139 | −+ | B |
| 140 | − | D |
| 141 | + | C |
| 142 | −+ | B |
| 143 | −+ | B |
| 144 | −+ | C |
| 145 | + | C |
| 146 | −+ | B |
| 147 | −+ | A |
| 148 | +++ | A |
| 149 | +++ | A |
| 150 | ++ | A |
| 151 | +++ | A |
| 152 | +++ | A |
| 153 | +++ | A |
| 154 | ++ | A |
| 155 | +++ | A |
| 156 | +++ | A |
| 157 | +++ | A |
| 158 | ++ | A |
| 159 | ++ | A |
| 160 | +++ | A |
| 161 | +++ | A |
| 162 | ++ | A |
| 163 | ++ | A |
| 164 | ++ | A |
| 165 | ++ | A |
| 166 | ++ | A |

TABLE 2-continued

| Compound | Max Activity[a] | EC50[b] |
|---|---|---|
| 167 | ++ | A |
| 168 | ++ | A |
| 169 | ++ | C |
| 170 | ++ | B |
| 171 | ++ | B |
| 172 | ++ | A |
| 173 | ++ | B |
| 174 | ++ | B |
| 175 | ++ | B |
| 176 | ++ | B |
| 177 | ++ | B |
| 178 | ++ | B |
| 179 | ++ | C |
| 180 | ++ | A |
| 181 | ++ | A |
| 182 | ++ | A |
| 183 | ++ | A |
| 184 | ++ | A |
| 185 | ++ | A |
| 186 | +++ | A |
| 187 | ++ | A |
| 188 | ++ | A |
| 189 | ++ | A |
| 190 | ++ | A |

[a]+++ ≥ 130%; 130% > ++ ≥ 100%; 100% > + ≥ 50%; − < 50%; NT = not tested
[b]A ≤ 100 nM; 100 nM < B ≤ 1000 nM; 1000 nM < C ≤ 10000 nM; D > 10000 nM.

Example A-2: In Vivo Plasma Levels in Mice

Male C57BL/6J mice 10-12 weeks old were dosed with test article or vehicle [0.25% (w/v) methylcellulose, 5% (v/v) Polysorbate 80, and 0.02% (w/v) sodium lauryl sulfate in Hanks' Balanced Salt solution (all final concentrations)] by oral gavage at a volume of 10 mL/kg. Animals were euthanized with carbon dioxide 7-8 h post dose. Blood was collected for measurement of plasma concentrations of test article. Unbound exposure was calculated by multiplying the measured total exposure by the free fraction as assessed from plasma protein binding.

Plasma protein binding to isotonic phosphate buffer (PBS) containing 10% C57 BL/6 mouse plasma was determined using equilibrium dialysis of plasma spiked with test article (2 µM) against a dialysis buffer (100 mM sodium phosphate and 150 mM NaCl). At the end of the dialysis (4 hr), aliquots of the plasma and buffer were processed by protein precipitation for LC-MS/MS analysis to quantitate the test article.

Results for exemplary compounds (total exposure in plasma and unbound exposure in plasma) are shown in Table 3.

TABLE 3

| Compound | Dose (mpk) | Exposure (nM) Total (unbound) | Time post-dose (h) |
|---|---|---|---|
| 42 | 30 | 806 (2.4) | 2 |
| 42 | 30 | 369 (1.1) | 8 |
| 86 | 30 | 67 (0.1) | 7 |
| 37 | 30 | 551 (1.1) | 7 |
| 44 | 30 | 668 (0 7) | 7 |

TABLE 3-continued

| Compound | Dose (mpk) | Exposure (nM) Total (unbound) | Time post-dose (h) |
|---|---|---|---|
| 29 | 30 | 354 (0.7) | 7 |
| 38 | 30 | 76 (0.2) | 7 |
| 3-isopropyl-5-(4-(((6-(4-(methylsulfonyl)phenyl)pyridin-3-yl)oxy)methyl)piperidin-1-yl)-1,2,4-oxadiazole (GSK1292263) | 30 | 7840 (n.d.) | 2 |
| isopropyl 4-((5-methoxy-6-((2-methyl-6-(methylsulfonyl)pyridin-3-yl)amino)pyrimidin-4-yl)oxy)piperidine-1-carboxylate (APD597; JNJ-38431055) | 30 | 16,200 (n.d) | 2 |

As demonstrated in Table 3, compounds of the instant disclosure do not have high systemic exposure. This is in contrast to previously described GPR119 compounds, such as GSK1292263 and APD597.

Example A-3: Oral Bioavailability in Mice

Compounds 42 and 83 were tested for oral bioavailability in C57BL/6 mice. Compounds were dosed IV at 1 mg/kg as a formulation of 0.5 mg/mL in 5% DMSO+30% PEG400+65% water and PO at 30 mg/kg as a formulation of 6 mg/mL in 0.25% methylcellulose+5% Tween 80+0.02% SDS in water (Compound 42) or 0.5% methylcellulose+0.5% Tween 80 in water (Compound 83).

Compounds 42 and 83 were shown to have oral bioavailabilities of 2.4% and 1.4%, respectively. This is in contrast to 1-(azetidin-1-yl)-2-(2,6-difluoro-4-(2-((1S,2R)-2-(1-(5-(methoxymethyl)pyrimidin-2-yl)piperidin-4-yl)cyclopropyl)ethoxy)phenyl)ethan-1-one, which has high bioavailability (80% in rats), as described in *Bioorganic & Medicinal Chemistry Letters*, Volume 27, Issue 5, 1 Mar. 2017, Pages 1124-1128 (Compound 17 in the reference).

We claim:
1. A compound of Formula (IIa):

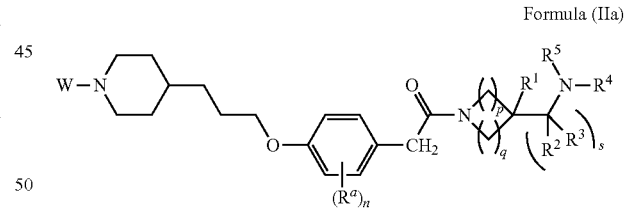

Formula (IIa)

or a pharmaceutically acceptable salt, solvate, or stereoisomer thereof,
wherein:
$R^1$ is hydrogen, —OH, or $C_{1-8}$ alkyl, wherein the alkyl is unsubstituted or substituted by —OH or —O($C_{1-6}$ alkyl);
each $R^2$ and $R^3$ is hydrogen;
or $R^2$ and $R^3$ on the same carbon atom are taken together to form =O;
$R^4$ is hydrogen or $C_{1-6}$ alkyl;
$R^5$ is $C_{1-8}$ alkyl, $C_{3-8}$ cycloalkyl, 4- to 8-membered heterocycloalkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$; wherein each alkyl, cycloalkyl, and 4- to 8-membered heterocycloalkyl is substituted by 1-6 R$^c$ groups each Z is independently —CH$_2$O—, —CH$_2$NR$^d$—, —CH$_2$N$^+$(R$^d$)$_2$—, or —NH—C(=O)—NH—;
each r is independently 1-6;
each t is independently 1-6;
R$^6$ is hydrogen, C$_{1-8}$ alkyl, C$_{3-8}$ cycloalkyl, or 4- to 8-membered heterocycloalkyl, wherein the alkyl, cycloalkyl, or 4- to 8-membered heterocycloalkyl is unsubstituted or substituted by 1-6 R$^c$ groups;
or R$^4$ and R$^5$ are taken together with the nitrogen to which they are attached to form a 4- to 8-membered heterocycloalkyl, which is unsubstituted or substituted by 1-6 R$^c$ groups;
each R$^c$ is independently —OH, —CH$_2$OH, —NH$_2$, —N(R$^d$)$_3^+$, —C(=O)OH, —S(=O)$_2$OH, —S(=O)$_2$NH$_2$, —P(=O)(OH)$_2$, —P(=O)(OH)(R$^d$), —P(=O)(OH)(OR$^d$),

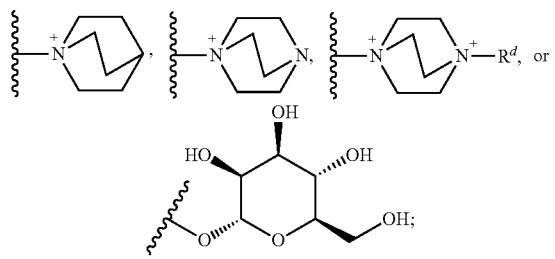

each R$^d$ is independently C$_{1-6}$ alkyl;
each R$^a$ is independently halogen, —CN, C$_{1-6}$ alkyl, C$_{1-6}$ fluoroalkyl, or C$_{3-6}$ cycloalkyl;
W is phenyl or 5-6 membered monocyclic heteroaryl, wherein the phenyl or heteroaryl is unsubstituted or substituted with 1, 2, or 3 substituents selected from R$^b$;
each R$^b$ is independently halogen, —OH, —CN, —C(O)OH, —C(O)O(C$_{1-6}$ alkyl), C$_{1-6}$ alkyl, C$_{1-6}$ alkoxy, C$_{3-6}$ cycloalkyl, phenyl, or 5- to 6-membered heteroaryl; wherein each alkyl, alkoxy, and cycloalkyl is unsubstituted or substituted with 1, 2, or 3 substituents selected from halogen, —OH, C$_{1-6}$ alkyl, and C$_{1-6}$ alkoxy;
or W is —C(=O)O—R$^{22}$;
R$^{22}$ is C$_{1-6}$ alkyl, C$_{3-6}$ cycloalkyl, or 3- to 6-membered heterocycloalkyl, wherein the alkyl, cycloalkyl, and heterocycloalkyl are unsubstituted or substituted by 1-3 substituents independently selected from fluorine, —OH, C$_{1-6}$ alkyl, C$_{1-6}$ haloalkyl or C$_{3-6}$ cycloalkyl;
n is 0-4;
p is 1 or 2;
q is 1 or 2; and
s is 1 or 2.

2. The compound of claim 1, or a pharmaceutically acceptable salt, solvate, or stereoisomer thereof, wherein:
W is phenyl or 5- or 6-membered monocyclic heteroaryl, wherein the phenyl or heteroaryl is unsubstituted or substituted with 1, 2, or 3 substituents selected from R$^b$.

3. The compound of claim 2, or a pharmaceutically acceptable salt, solvate, or stereoisomer thereof, wherein:
W is phenyl or 6-membered monocyclic heteroaryl, wherein the heteroaryl is unsubstituted or substituted with 1 or 2 substituents selected from R$^b$; and
each R$^b$ is independently halogen, —C(O)OH, —C(O)O (C$_{1-6}$ alkyl), C$_{1-6}$ alkyl, C$_{1-6}$ alkoxy, or C$_{3-6}$ cycloalkyl; wherein each alkyl, alkoxy, and cycloalkyl is unsubstituted or substituted with 1, 2, or 3 substituents selected from halogen, —OH, C$_{1-6}$ alkyl, and C$_{1-6}$ alkoxy.

4. The compound of claim 2, or a pharmaceutically acceptable salt, solvate, or stereoisomer thereof, wherein:
W is 6-membered monocyclic heteroaryl, wherein the heteroaryl is unsubstituted or substituted with 1 or 2 substituents selected from R$^b$; and
each R$^b$ is independently —F, —Cl, —CH$_3$, —CH$_2$CH$_3$, —CH$_2$CH$_2$CH$_3$, —CH$_2$OH, —CH$_2$OCH$_3$, —OCH$_3$, —OCH$_2$CH$_3$, —C(O)OH, or —C(O)OCH$_3$.

5. The compound of claim 1, wherein the compound has the structure of Formula (IIb):

Formula (IIb)

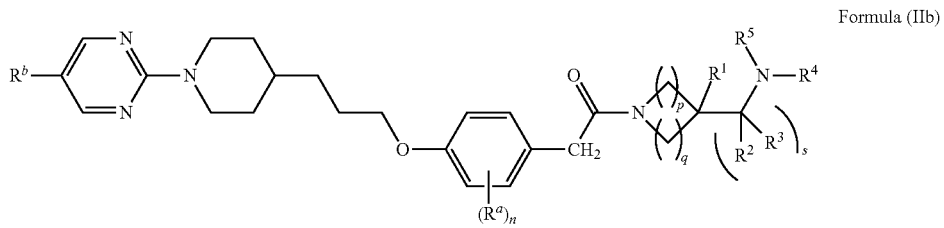

or a pharmaceutically acceptable salt, solvate, or stereoisomer thereof.

6. The compound of claim 1, or a pharmaceutically acceptable salt, solvate, or stereoisomer thereof, wherein:
W is —C(=O)O—R$^{22}$; and
R$^{22}$ is C$_{1-6}$ alkyl, C$_{3-6}$ cycloalkyl, or 3- to 6-membered heterocycloalkyl, wherein the alkyl, cycloalkyl, or heterocycloalkyl is unsubstituted or substituted by 1-3 substituents independently selected from C$_{1-6}$ alkyl and C$_{1-6}$ haloalkyl.

7. The compound of claim 1, or a pharmaceutically acceptable salt, solvate, or stereoisomer thereof, wherein:
p is 1; and
q is 1.

8. The compound of claim 1, or a pharmaceutically acceptable salt, solvate, or stereoisomer thereof, wherein:
R$^4$ is hydrogen or C$_{1-4}$ alkyl;
R$^5$ is C$_{1-8}$ alkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$;
wherein the alkyl is substituted by 1-6 R$^c$ groups;
each Z is independently —CH$_2$O—, —CH$_2$NR$^d$—, or —NH—C(=O)—NH—;
r is 1-3;
t is 1-3; and
R$^6$ is hydrogen or C$_{1-8}$ alkyl, wherein the alkyl is substituted by 1-6 R$^c$ groups.

9. The compound of claim 1, or a pharmaceutically acceptable salt, solvate, or stereoisomer thereof, wherein: each $R^c$ is independently —OH, —CH$_2$OH, —NH$_2$, —N(R$^d$)$_3^+$, —C(=O)OH, or

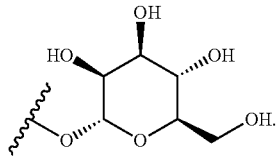 [SMILES: *O[C@H]1O[C@H](CO)[C@@H](O)[C@H](O)[C@@H]1O]

10. The compound of claim 1, or a pharmaceutically acceptable salt, solvate, or stereoisomer thereof, wherein: $R^5$ is C$_{1-8}$ alkyl which is substituted by 1-6 $R^c$ groups; and each $R^c$ is independently —OH, —CH$_2$OH, —N(R$^d$)$_3^+$, —C(=O)OH, or

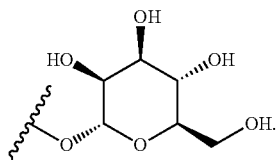 [SMILES: *O[C@H]1O[C@H](CO)[C@@H](O)[C@H](O)[C@@H]1O]

11. The compound of claim 1, or a pharmaceutically acceptable salt, solvate, or stereoisomer thereof, wherein: $R^4$ and $R^5$ are taken together with the nitrogen to which they are attached to form a 5- or 6-membered heterocycloalkyl, which is unsubstituted or substituted by 1-3 —OH groups.

12. The compound of claim 1, wherein the compound has the structure of Formula (IIc) or (IId):

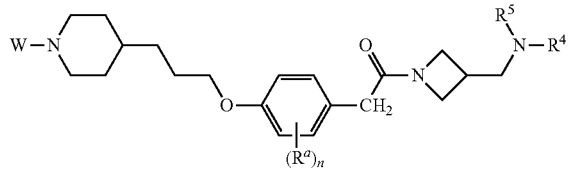

Formula (IIc)

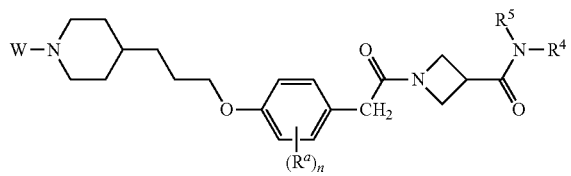

Formula (IId)

or a pharmaceutically acceptable salt, solvate, or stereoisomer thereof.

13. The compound of claim 12, or a pharmaceutically acceptable salt, solvate, or stereoisomer thereof, wherein:
W is phenyl or 6-membered monocyclic heteroaryl, wherein the heteroaryl is unsubstituted or substituted with 1 or 2 substituents selected from $R^b$;
each $R^b$ is independently halogen, —C(O)OH, —C(O)O(C$_{1-6}$ alkyl), C$_{1-6}$ alkyl, C$_{1-6}$ alkoxy, or C$_{3-6}$ cycloalkyl; wherein each alkyl, alkoxy, and cycloalkyl is unsubstituted or substituted with 1, 2, or 3 substituents selected from halogen, —OH, C$_{1-6}$ alkyl, and C$_{1-6}$ alkoxy;

$R^4$ is hydrogen or C$_{1-4}$ alkyl;
$R^5$ is C$_{1-8}$ alkyl, —[(CH$_2$)$_r$—Z]$_t$—R$^6$, —[(CHR$^d$)$_r$—Z]$_t$—R$^6$, or —[(C(R$^d$)$_2$)$_r$—Z]$_t$—R$^6$;
wherein the alkyl is substituted by 1-6 $R^c$ groups;
each Z is independently —CH$_2$O—, —CH$_2$NR$^d$—, or —NH—C(=O)—NH—;
r is 1-3;
t is 1-3; and
$R^6$ is hydrogen or C$_{1-8}$ alkyl, wherein the alkyl is substituted by 1-6 $R^c$ groups.

14. The compound of claim 12, or a pharmaceutically acceptable salt, solvate, or stereoisomer thereof, wherein:
W is 6-membered monocyclic heteroaryl, wherein the heteroaryl is unsubstituted or substituted with 1 or 2 substituents selected from $R^b$;
each $R^b$ is independently —F, —Cl, —CH$_3$, —CH$_2$CH$_3$, —CH$_2$CH$_2$CH$_3$, —CH$_2$OH, —CH$_2$OCH$_3$, —OCH$_3$, —OCH$_2$CH$_3$, —C(O)OH, or —C(O)OCH$_3$;
$R^4$ is hydrogen or C$_{1-4}$ alkyl;
$R^5$ is C$_{1-8}$ alkyl which is substituted by 1-6 $R^c$ groups; and each $R^c$ is independently —OH, —CH$_2$OH, —N(R$^d$)$_3^+$, —C(=O)OH, or

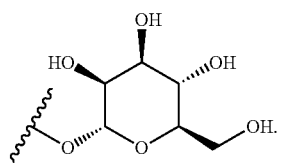 [SMILES: *O[C@H]1O[C@H](CO)[C@@H](O)[C@H](O)[C@@H]1O]

15. The compound of claim 1, or a pharmaceutically acceptable salt, solvate, or stereoisomer thereof, selected from:
1-[2-[4-[3-[1-(5-chloropyrimidin-2-yl)-4-piperidyl]propoxy]-2,6-difluoro-phenyl]acetyl]-N-[2-hydroxy-1,1-bis(hydroxymethyl)ethyl]azetidine-3-carboxamide;
1-[2-[2-fluoro-4-[3-[1-[5-(methoxymethyl)pyrimidin-2-yl]-4-piperidyl]propoxy]phenyl]acetyl]-N-[2-[[2-hydroxy-1,1-bis(hydroxymethyl)ethyl]carbamoylamino]ethyl]azetidine-3-carboxamide;
1-[2-[4-[3-[1-(5-chloropyrimidin-2-yl)-4-piperidyl]propoxy]-2-fluoro-phenyl]acetyl]-N-[2-hydroxy-1-(hydroxymethyl)ethyl]azetidine-3-carboxamide;
1-[2-[4-[3-[1-(5-chloropyrimidin-2-yl)-4-piperidyl]propoxy]-2-fluoro-phenyl]acetyl]-N-[2-hydroxy-1,1-bis(hydroxymethyl)ethyl]azetidine-3-carboxamide;
1-[2-[4-[3-[1-(5-chloropyrimidin-2-yl)-4-piperidyl]propoxy]-2-fluoro-phenyl]acetyl]-N-[2,3-dihydroxy-2-(hydroxymethyl)propyl]azetidine-3-carboxamide;
1-[2-[4-[3-[1-(5-chloropyrimidin-2-yl)-4-piperidyl]propoxy]-2-fluoro-phenyl]acetyl]-N-[2-[rac-(2S,3S,4S,5S,6R)-3,4,5-trihydroxy-6-(hydroxymethyl)tetrahydropyran-2-yl]oxyethyl]azetidine-3-carboxamide;
2-[1-[2-[4-[3-[1-(5-chloropyrimidin-2-yl)-4-piperidyl]propoxy]-2-fluoro-phenyl]acetyl]azetidin-3-yl]-N-[2-hydroxy-1,1-bis(hydroxymethyl)ethyl]acetamide;
2-[1-[2-[4-[3-[1-(5-chloropyrimidin-2-yl)-4-piperidyl]propoxy]-2-fluoro-phenyl]acetyl]azetidin-3-yl]-N-[2,3-dihydroxy-2-(hydroxymethyl)propyl]acetamide;
2-[1-[2-[4-[3-[1-(5-chloropyrimidin-2-yl)-4-piperidyl]propoxy]-2,6-difluoro-phenyl]acetyl]azetidin-3-yl]-N-[2,3-dihydroxy-2-(hydroxymethyl)propyl]acetamide;
1-[2-[4-[3-[1-(5-chloropyrimidin-2-yl)-4-piperidyl]propoxy]-2-fluoro-phenyl]acetyl]-N-[rac-(2S,3R,4R,5R)-2,3,4,5,6-pentahydroxyhexyl]azetidine-3-carboxamide;

2-[1-[2-[4-[3-[1-(5-chloropyrimidin-2-yl)-4-piperidyl]
propoxy]-2-fluoro-phenyl]acetyl]azetidin-3-yl]-N-
[rac-(2S,3R,4R,5R)-2,3,4,5,6-pentahydroxyhexyl]ac-
etamide;

1-[2-[2-fluoro-4-[3-[1-[5-(methoxymethyl)pyrimidin-2-
yl]-4-piperidyl]propoxy]phenyl]acetyl]-N-[rac-(2S,3R,
4R,5R)-2,3,4,5,6-pentahydroxyhexyl]azetidine-3-car-
boxamide;

3-[[1-[2-[2,6-difluoro-4-[3-[1-(5-propylpyrimidin-2-yl)-
4-piperidyl]propoxy]phenyl]acetyl]azetidine-3-carbo-
nyl]amino]propyl-trimethyl-ammonium formate;

1-[2-[4-[3-[1-(5-chloropyrimidin-2-yl)-4-piperidyl]
propoxy]-2-fluoro-phenyl]acetyl]-N-[2,3-dihydroxy-2-
(hydroxymethyl)propyl]piperidine-4-carboxamide;

2-[4-[3-[1-(5-chloropyrimidin-2-yl)-4-piperidyl]
propoxy]-2-fluoro-phenyl]-1-[3-[[[(2S,3R,4R,5R)-2,3,
4,5,6-pentahydroxyhexyl]amino]methyl]azetidin-1-yl]
ethanone;

2-[4-[3-[1-(5-chloropyrimidin-2-yl)-4-piperidyl]
propoxy]-2-fluoro-phenyl]-1-[3-[[[2,3-dihydroxy-2-
(hydroxymethyl)propyl]amino]methyl]azetidin-1-yl]
ethanone;

2-[4-[3-[1-(5-chloropyrimidin-2-yl)-4-piperidyl]
propoxy]-2-fluoro-phenyl]-1-[3-[[[2-hydroxy-1,1-bis
(hydroxymethyl)ethyl]amino]methyl]azetidin-1-yl]
ethanone;

2-[4-[3-[1-(5-chloropyrimidin-2-yl)-4-piperidyl]
propoxy]-2-fluoro-phenyl]-1-[3-[[[3-hydroxy-2-(hy-
droxymethyl)propyl]amino]methyl]azetidin-1-yl]etha-
none;

2-[4-[3-[1-(5-chloropyrimidin-2-yl)-4-piperidyl]
propoxy]-2-fluoro-phenyl]-1-[3-[[rac-(3S,4S)-3,4-di-
hydroxypyrrolidin-1-yl]methyl]azetidin-1-yl]etha-
none;

2-[4-[3-[1-(5-chloropyrimidin-2-yl)-4-piperidyl]
propoxy]-2-fluoro-phenyl]-1-[3-[[rac-(3R,4R)-3,4-di-
hydroxypyrrolidin-1-yl]methyl]azetidin-1-yl]etha-
none;

2-[4-[3-[1-(5-chloropyrimidin-2-yl)-4-piperidyl]
propoxy]-2-fluoro-phenyl]-1-[3-[[rac-(3S,4R)-3,4-di-
hydroxypyrrolidin-1-yl]methyl]azetidin-1-yl]etha-
none;

2-[4-[3-[1-(5-chloropyrimidin-2-yl)-4-piperidyl]
propoxy]-2-fluoro-phenyl]-1-[3-[[[rac-(1R,2S,3R,4S)-
2,3,4-trihydroxycyclopentyl]amino]methyl]azetidin-1-
yl]ethanone;

2-[4-[3-[1-(5-chloropyrimidin-2-yl)-4-piperidyl]
propoxy]-2-fluoro-phenyl]-1-[3-[[rac-(3R,5S)-3,4,5-
trihydroxy-1-piperidyl]methyl]azetidin-1-yl]ethanone;

2-[4-[3-[1-(5-chloropyrimidin-2-yl)-4-piperidyl]
propoxy]-2-fluoro-phenyl]-1-[3-[[2-[2-(2-hydroxy-
ethoxy)ethoxy]ethylamino]methyl]azetidin-1-yl]etha-
none;

1-[3-[[2-[2-(2-aminoethoxy)ethoxy]ethylamino]methyl]
azetidin-1-yl]-2-[4-[3-[1-(5-chloropyrimidin-2-yl)-4-
piperidyl]propoxy]-2-fluoro-phenyl]ethanone;

2-[4-[3-[1-(5-chloropyrimidin-2-yl)-4-piperidyl]
propoxy]-2,6-difluoro-phenyl]-1-[3-[[[(2S,3R,4R,5R)-
2,3,4,5,6-pentahydroxyhexyl]amino]methyl]azetidin-
1-yl]ethanone;

2-(4-(3-(1-(5-chloropyrimidin-2-yl)piperidin-4-yl)
propoxy)-2-fluorophenyl)-1-(3-(2-((1,3-dihydroxypro-
pan-2-yl)amino)ethyl)azetidin-1-yl)ethan-1-one;

2-(4-(3-(1-(5-chloropyrimidin-2-yl)piperidin-4-yl)
propoxy)-2-fluorophenyl)-1-(3-(2-((3-hydroxy-2-(hy-
droxymethyl)propyl)amino)ethyl)azetidin-1-yl)ethan-
1-one;

2-(4-(3-(1-(5-chloropyrimidin-2-yl)piperidin-4-yl)
propoxy)-2-fluorophenyl)-1-(3-(2-((2,3-dihydroxy-2-
(hydroxymethyl)propyl)amino)ethyl)azetidin-1-yl)
ethan-1-one;

2-(4-(3-(1-(5-chloropyrimidin-2-yl)piperidin-4-yl)
propoxy)-2-fluorophenyl)-1-(3-(2-((1,3-dihydroxy-2-
(hydroxymethyl)propan-2-yl)amino)ethyl)azetidin-1-
yl)ethan-1-one;

1-(2-((2-(1-(2-(4-(3-(1-(5-chloropyrimidin-2-yl)piperi-
din-4-yl)propoxy)-2-fluorophenyl)acetyl)azetidin-3-
yl)ethyl)amino)ethyl)-3-(1,3-dihydroxy-2-(hydroxym-
ethyl)propan-2-yl)urea;

2-[4-[3-[1-(5-chloropyrimidin-2-yl)-4-piperidyl]
propoxy]-2-fluoro-phenyl]-1-[3-[2-[[[(2S,3R,4R,5R)-2,
3,4,5,6-pentahydroxyhexyl]amino]ethyl]azetidin-1-yl]
ethanone;

2-(4-(3-(1-(5-ethylpyrimidin-2-yl)piperidin-4-yl)
propoxy)-2-fluorophenyl)-1-(3-(((3-hydroxy-2-(hy-
droxymethyl)propyl)amino)methyl)azetidin-1-yl)
ethan-1-one;

1-(3-(((2,3-dihydroxy-2-(hydroxymethyl)propyl)amino)
methyl)azetidin-1-yl)-2-(4-(3-(1-(5-ethylpyrimidin-2-
yl)piperidin-4-yl)propoxy)-2-fluorophenyl)ethan-1-
one;

1-(3-(((1,3-dihydroxy-2-(hydroxymethyl)propan-2-yl)
amino)methyl)azetidin-1-yl)-2-(4-(3-(1-(5-ethylpy-
rimidin-2-yl)piperidin-4-yl)propoxy)-2-fluorophenyl)
ethan-1-one;

1-(1,3-dihydroxy-2-(hydroxymethyl)propan-2-yl)-3-(2-
(((1-(2-(4-(3-(1-(5-ethylpyrimidin-2-yl)piperidin-4-yl)
propoxy)-2-fluorophenyl)acetyl)azetidin-3-yl)methyl)
amino)ethyl)urea;

(2S,3R,4S,5S)-6-[[[1-[2-[4-[3-[1-(5-ethylpyrimidin-2-yl)-
4-piperidyl]propoxy]-2-fluoro-phenyl]acetyl]azetidin-
3-yl]methylamino]-2,3,4,5-tetrahydroxy-hexanoic
acid;

1-(3-(((2,3-dihydroxy-2-(hydroxymethyl)propyl)amino)
methyl)azetidin-1-yl)-2-(4-(3-(1-(5-ethylpyrimidin-2-
yl)piperidin-4-yl)propoxy)-2,6-difluorophenyl)ethan-
1-one;

1-(1,3-dihydroxy-2-(hydroxymethyl)propan-2-yl)-3-(2-
(((1-(2-(4-(3-(1-(5-ethylpyrimidin-2-yl)piperidin-4-yl)
propoxy)-2,6-difluorophenyl)acetyl)azetidin-3-yl)
methyl)amino)ethyl)urea;

2-(4-(3-(1-(5-ethylpyrimidin-2-yl)piperidin-4-yl)
propoxy)-2,6-difluorophenyl)-1-(3-((((2S,3R,4R,5R)-
2,3,4,5,6-pentahydroxyhexyl)amino)methyl)azetidin-
1-yl)ethan-1-one;

2-(2-fluoro-4-(3-(1-(5-propylpyrimidin-2-yl)piperidin-4-
yl)propoxy)phenyl)-1-(3-(((3-hydroxy-2-(hydroxym-
ethyl)propyl)amino)methyl)azetidin-1-yl)ethan-1-one;

1-(3-(((2,3-dihydroxy-2-(hydroxymethyl)propyl)amino)
methyl)azetidin-1-yl)-2-(2-fluoro-4-(3-(1-(5-propylpy-
rimidin-2-yl)piperidin-4-yl)propoxy)phenyl)ethan-1-
one;

1-(3-(((1,3-dihydroxy-2-(hydroxymethyl)propan-2-yl)
amino)methyl)azetidin-1-yl)-2-(2-fluoro-4-(3-(1-(5-
propylpyrimidin-2-yl)piperidin-4-yl)propoxy)phenyl)
ethan-1-one;

1-(1,3-dihydroxy-2-(hydroxymethyl)propan-2-yl)-3-(2-
(((1-(2-(2-fluoro-4-(3-(1-(5-propylpyrimidin-2-yl)pip-
eridin-4-yl)propoxy)phenyl)acetyl)azetidin-3-yl)
methyl)amino)ethyl)urea;

2-(2-fluoro-4-(3-(1-(5-propylpyrimidin-2-yl)piperidin-4-
yl)propoxy)phenyl)-1-(3-((((2S,3R,4R,5R)-2,3,4,5,6-
pentahydroxyhexyl)amino)methyl)azetidin-1-yl)ethan-
1-one;

2-(2,6-difluoro-4-(3-(1-(5-propylpyrimidin-2-yl)piperidin-4-yl)propoxy)phenyl)-1-(3-(((2,3-dihydroxy-2-(hydroxymethyl)propyl)amino)methyl)azetidin-1-yl)ethan-1-one;

2-(2,6-difluoro-4-(3-(1-(5-propylpyrimidin-2-yl)piperidin-4-yl)propoxy)phenyl)-1-(3-(((1,3-dihydroxy-2-(hydroxymethyl)propan-2-yl)amino)methyl)azetidin-1-yl)ethan-1-one;

1-(2-(((1-(2-(2,6-difluoro-4-(3-(1-(5-propylpyrimidin-2-yl)piperidin-4-yl)propoxy)phenyl)acetyl)azetidin-3-yl)methyl)amino)ethyl)-3-(1,3-dihydroxy-2-(hydroxymethyl)propan-2-yl)urea;

2-(2,6-difluoro-4-(3-(1-(5-propylpyrimidin-2-yl)piperidin-4-yl)propoxy)phenyl)-1-(3-((((2S,3R,4R,5R)-2,3,4,5,6-pentahydroxyhexyl)amino)methyl)azetidin-1-yl)ethan-1-one;

2-[2-fluoro-4-[3-[1-(5-methoxypyrimidin-2-yl)-4-piperidyl]propoxy]phenyl]-1-[3-[[[rac-(2S,3R,4R,5R)-2,3,4,5,6-pentahydroxyhexyl]amino]methyl]azetidin-1-yl]ethanone;

2-[4-[3-[1-(5-ethoxypyrimidin-2-yl)-4-piperidyl]propoxy]-2-fluoro-phenyl]-1-[3-[[[rac-(2S,3R,4R,5R)-2,3,4,5,6-pentahydroxyhexyl]amino]methyl]azetidin-1-yl]ethanone;

1-[2-[[1-[2-[2-fluoro-4-[3-[1-[5-(methoxymethyl)pyrimidin-2-yl]-4-piperidyl]propoxy]phenyl]acetyl]azetidin-3-yl]methylamino]ethyl]-3-[2-hydroxy-1,1-bis(hydroxymethyl)ethyl]urea;

(3R,5R)-7-[[1-[2-[2-fluoro-4-[3-[1-[5-(methoxymethyl)pyrimidin-2-yl]-4-piperidyl]propoxy]phenyl]acetyl]azetidin-3-yl]methylamino]-3,5-dihydroxy-heptanoic acid;

2-[2-fluoro-4-[3-[1-[5-(methoxymethyl)pyrimidin-2-yl]-4-piperidyl]propoxy]phenyl]-1-[3-[[[(2S,3R,4R,5R)-2,3,4,5,6-pentahydroxyhexyl]amino]methyl]azetidin-1-yl]ethanone;

methyl 2-[4-[3-[3-fluoro-4-[2-oxo-2-[3-[[[(2S,3R,4R,5R)-2,3,4,5,6-pentahydroxyhexyl]amino]methyl]azetidin-1-yl]ethyl]phenoxy]propyl]-1-piperidyl]pyrimidine-5-carboxylate;

2-[2-fluoro-4-[3-[1-[5-(hydroxymethyl)pyrimidin-2-yl]-4-piperidyl]propoxy]phenyl]-1-[3-[[[(2S,3R,4R,5R)-2,3,4,5,6-pentahydroxyhexyl]amino]methyl]azetidin-1-yl]ethanone;

2-[2,6-difluoro-4-[3-[1-[5-(methoxymethyl)pyrimidin-2-yl]-4-piperidyl]propoxy]phenyl]-1-[3-[[[(2S,3R,4R,5R)-2,3,4,5,6-pentahydroxyhexyl]amino]methyl]azetidin-1-yl]ethanone;

2-[4-[3-[1-(5-chloropyrimidin-2-yl)-4-piperidyl]propoxy]-2-fluoro-phenyl]-1-[(3S)-3-[[[(2S,3R,4R,5R)-2,3,4,5,6-pentahydroxyhexyl]amino]methyl]pyrrolidin-1-yl]ethanone;

2-[4-[3-[1-(5-chloropyrimidin-2-yl)-4-piperidyl]propoxy]-2-fluoro-phenyl]-1-[(3S)-3-[[[2,3-dihydroxy-2-(hydroxymethyl)propyl]amino]methyl]pyrrolidin-1-yl]ethanone;

2-[4-[3-[1-(5-chloropyrimidin-2-yl)-4-piperidyl]propoxy]-2-fluoro-phenyl]-1-[(3R)-3-[[[(2S,3R,4R,5R)-2,3,4,5,6-pentahydroxyhexyl]amino]methyl]pyrrolidin-1-yl]ethanone;

2-[4-[3-[1-(5-chloropyrimidin-2-yl)-4-piperidyl]propoxy]-2-fluoro-phenyl]-1-[(3R)-3-[[[2,3-dihydroxy-2-(hydroxymethyl)propyl]amino]methyl]pyrrolidin-1-yl]ethanone;

(3R)-1-[2-[4-[3-[1-(5-chloropyrimidin-2-yl)-4-piperidyl]propoxy]-2-fluoro-phenyl]acetyl]-N-[2-hydroxy-1,1-bis(hydroxymethyl)ethyl]pyrrolidine-3-carboxamide;

(3S)-1-[2-[4-[3-[1-(5-chloropyrimidin-2-yl)-4-piperidyl]propoxy]-2-fluoro-phenyl]acetyl]-N-[2-hydroxy-1,1-bis(hydroxymethyl)ethyl]pyrrolidine-3-carboxamide;

N-[2,3-dihydroxy-2-(hydroxymethyl)propyl]-2-[1-[2-[4-[3-[1-(5-ethoxypyrimidin-2-yl)-4-piperidyl]propoxy]-2-fluoro-phenyl]acetyl]azetidin-3-yl]acetamide;

isopropyl 4-[3-[3-fluoro-4-[2-oxo-2-[3-[[[(2S,3R,4R,5R)-2,3,4,5,6-pentahydroxyhexyl]amino]methyl]azetidin-1-yl]ethyl]phenoxy]propyl]piperidine-1-carboxylate;

2-[4-[3-[1-(5-ethoxypyrimidin-2-yl)-4-piperidyl]propoxy]-2,6-difluoro-phenyl]-1-[3-[[[(2S,3R,4R,5R)-2,3,4,5,6-pentahydroxyhexyl]amino]methyl]azetidin-1-yl]ethanone;

(1-methylcyclopropyl) 4-[3-[3-fluoro-4-[2-oxo-2-[3-[[[rac-(2S,3R,4R,5R)-2,3,4,5,6-pentahydroxyhexyl]amino]methyl]azetidin-1-yl]ethyl]phenoxy]propyl]piperidine-1-carboxylate;

2-[4-[3-[1-(5-chloropyrimidin-2-yl)-4-piperidyl]propoxy]-2-fluoro-phenyl]-1-[3-(methoxymethyl)-3-[[[r(2S,3R,4R,5R)-2,3,4,5,6-pentahydroxyhexyl]amino]methyl]pyrrolidin-1-yl]ethanone;

2-[4-[3-[1-(5-chloropyrimidin-2-yl)-4-piperidyl]propoxy]-2-fluoro-phenyl]-1-[3-[[[3-hydroxy-2,2-bis(hydroxymethyl)propyl]amino]methyl]-3-(methoxymethyl)pyrrolidin-1-yl]ethanone;

[3-(trifluoromethyl)oxetan-3-yl] 4-[3-[3-fluoro-4-[2-oxo-2-[3-[[[(2S,3R,4R,5R)-2,3,4,5,6-pentahydroxyhexyl]amino]methyl]azetidin-1-yl]ethyl]phenoxy]propyl]piperidine-1-carboxylate;

[3-(trifluoromethyl)oxetan-3-yl] 4-[3-[3,5-difluoro-4-[2-oxo-2-[3-[[[(2S,3R,4R,5R)-2,3,4,5,6-pentahydroxyhexyl]amino]methyl]azetidin-1-yl]ethyl]phenoxy]propyl]piperidine-1-carboxylate;

(3S)-1-[2-[4-[3-[1-(5-chloropyrimidin-2-yl)-4-piperidyl]propoxy]-2-fluoro-phenyl]acetyl]-N-[(2S,3R,4R,5R)-2,3,4,5,6-pentahydroxyhexyl]pyrrolidine-3-carboxamide;

(3S)-1-[2-[4-[3-[1-(5-chloropyrimidin-2-yl)-4-piperidyl]propoxy]-2,6-difluoro-phenyl]acetyl]-N-[(2S,3R,4R,5R)-2,3,4,5,6-pentahydroxyhexyl]pyrrolidine-3-carboxamide;

(3S)-1-[2-[4-[3-[1-(5-ethoxypyrimidin-2-yl)-4-piperidyl]propoxy]-2-fluoro-phenyl]acetyl]-N-[(2S,3R,4R,5R)-2,3,4,5,6-pentahydroxyhexyl]pyrrolidine-3-carboxamide;

(3S)-1-[2-[4-[3-[1-(5-ethoxypyrimidin-2-yl)-4-piperidyl]propoxy]-2,6-difluoro-phenyl]acetyl]-N-[(2S,3R,4R,5R)-2,3,4,5,6-pentahydroxyhexyl]pyrrolidine-3-carboxamide;

(3S)-1-[2-[2,6-difluoro-4-[3-[1-[5-(methoxymethyl)pyrimidin-2-yl]-4-piperidyl]propoxy]phenyl]acetyl]-N-[(2S,3R,4R,5R)-2,3,4,5,6-pentahydroxyhexyl]pyrrolidine-3-carboxamide;

2-[4-[3-[1-(5-chloropyrimidin-2-yl)-4-piperidyl]propoxy]-2,6-difluoro-phenyl]-1-[(3S)-3-[[[(2S,3R,4R,5R)-2,3,4,5,6-pentahydroxyhexyl]amino]methyl]pyrrolidin-1-yl]ethanone;

2-[4-[3-[1-(5-ethoxypyrimidin-2-yl)-4-piperidyl]propoxy]-2-fluoro-phenyl]-1-[(3S)-3-[[[(2S,3R,4R,5R)-2,3,4,5,6-pentahydroxyhexyl]amino]methyl]pyrrolidin-1-yl]ethanone;

2-[4-[3-[1-(5-ethoxypyrimidin-2-yl)-4-piperidyl]propoxy]-2,6-difluoro-phenyl]-1-[(3S)-3-[[[(2S,3R,4R,5R)-2,3,4,5,6-pentahydroxyhexyl]amino]methyl]pyrrolidin-1-yl]ethanone;

2-[2,6-difluoro-4-[3-[1-[5-(methoxymethyl)pyrimidin-2-yl]-4-piperidyl]propoxy]phenyl]-1-[(3S)-3-[[[(2S,3R,4R,5R)-2,3,4,5,6-pentahydroxyhexyl]amino]methyl]pyrrolidin-1-yl]ethanone;

1-[2-[4-[3-[1-(5-chloropyrimidin-2-yl)-4-piperidyl]propoxy]-2-fluoro-phenyl]acetyl]-3-(methoxymethyl)-N-[(2S,3R,4R,5R)-2,3,4,5,6-pentahydroxyhexyl]pyrrolidine-3-carboxamide;

1-[2-[4-[3-[1-(5-chloropyrimidin-2-yl)-4-piperidyl]propoxy]-2-fluoro-phenyl]acetyl]-N-[3-hydroxy-2,2-bis(hydroxymethyl)propyl]-3-(methoxymethyl)pyrrolidine-3-carboxamide;

2-[4-[3-[1-(5-chloropyrimidin-2-yl)-4-piperidyl]propoxy]-2-fluoro-phenyl]-1-[(3S)-3-[[[3-hydroxy-2,2-bis(hydroxymethyl)propyl]amino]methyl]pyrrolidin-1-yl]ethanone;

2-[4-[3-[1-(5-chloropyrimidin-2-yl)-4-piperidyl]propoxy]-2-fluoro-phenyl]-1-[(3S)-3-[[[2-hydroxy-1,1-bis(hydroxymethyl)ethyl]amino]methyl]pyrrolidin-1-yl]ethanone;

2-[4-[3-[1-(5-chloropyrimidin-2-yl)-4-piperidyl]propoxy]-2,6-difluoro-phenyl]-1-[(3S)-3-[[[2-hydroxy-1,1-bis(hydroxymethyl)ethyl]amino]methyl]pyrrolidin-1-yl]ethanone;

2-[4-[3-[1-(5-chloropyrimidin-2-yl)-4-piperidyl]propoxy]-2,6-difluoro-phenyl]-1-[(3S)-3-[[[2,3-dihydroxy-2-(hydroxymethyl)propyl]amino]methyl]pyrrolidin-1-yl]ethanone;

2-[4-[3-[1-(5-chloropyrimidin-2-yl)-4-piperidyl]propoxy]-2,6-difluoro-phenyl]-1-[(3S)-3-[[[3-hydroxy-2,2-bis(hydroxymethyl)propyl]amino]methyl]pyrrolidin-1-yl]ethanone;

2-[4-[3-[1-(5-ethoxypyrimidin-2-yl)-4-piperidyl]propoxy]-2-fluoro-phenyl]-1-[(3S)-3-[[[2-hydroxy-1,1-bis(hydroxymethyl)ethyl]amino]methyl]pyrrolidin-1-yl]ethanone;

2-[4-[3-[1-(5-ethoxypyrimidin-2-yl)-4-piperidyl]propoxy]-2-fluoro-phenyl]-1-[(3S)-3-[[[2,3-dihydroxy-2-(hydroxymethyl)propyl]amino]methyl]pyrrolidin-1-yl]ethanone;

2-[4-[3-[1-(5-ethoxypyrimidin-2-yl)-4-piperidyl]propoxy]-2-fluoro-phenyl]-1-[(3S)-3-[[[3-hydroxy-2,2-bis(hydroxymethyl)propyl]amino]methyl]pyrrolidin-1-yl]ethanone;

2-[4-[3-[1-(5-ethoxypyrimidin-2-yl)-4-piperidyl]propoxy]-2,6-difluoro-phenyl]-1-[(3S)-3-[[[2-hydroxy-1,1-bis(hydroxymethyl)ethyl]amino]methyl]pyrrolidin-1-yl]ethanone;

2-[4-[3-[1-(5-ethoxypyrimidin-2-yl)-4-piperidyl]propoxy]-2,6-difluoro-phenyl]-1-[(3S)-3-[[[2,3-dihydroxy-2-(hydroxymethyl)propyl]amino]methyl]pyrrolidin-1-yl]ethanone;

2-[4-[3-[1-(5-ethoxypyrimidin-2-yl)-4-piperidyl]propoxy]-2,6-difluoro-phenyl]-1-[(3S)-3-[[[3-hydroxy-2,2-bis(hydroxymethyl)propyl]amino]methyl]pyrrolidin-1-yl]ethanone;

2-[2,6-difluoro-4-[3-[1-[5-(methoxymethyl)pyrimidin-2-yl]-4-piperidyl]propoxy]phenyl]-1-[(3S)-3-[[[2-hydroxy-1,1-bis(hydroxymethyl)ethyl]amino]methyl]pyrrolidin-1-yl]ethanone;

2-[2,6-difluoro-4-[3-[1-[5-(methoxymethyl)pyrimidin-2-yl]-4-piperidyl]propoxy]phenyl]-1-[(3S)-3-[[[2,3-dihydroxy-2-(hydroxymethyl)propyl]amino]methyl]pyrrolidin-1-yl]ethanone;

2-[2,6-difluoro-4-[3-[1-[5-(methoxymethyl)pyrimidin-2-yl]-4-piperidyl]propoxy]phenyl]-1-[(3S)-3-[[[3-hydroxy-2,2-bis(hydroxymethyl)propyl]amino]methyl]pyrrolidin-1-yl]ethanone;

2-[4-[3-[1-(5-chloropyrimidin-2-yl)-4-piperidyl]propoxy]-2-fluoro-phenyl]-1-[3-[2-[[(2S,3S,4R)-2,3,4,5-tetrahydroxypentyl]amino]ethyl]azetidin-1-yl]ethanone;

2-[4-[3-[1-(5-chloropyrimidin-2-yl)-4-piperidyl]propoxy]-2-fluoro-phenyl]-1-[3-[[[(2S,3S,4R)-2,3,4,5-tetrahydroxypentyl]amino]methyl]azetidin-1-yl]ethanone;

2-[4-[3-[1-(5-chloropyrimidin-2-yl)-4-piperidyl]propoxy]-2-fluoro-phenyl]-1-[3-[[[(2S,3R,4R)-2,3,4,5-tetrahydroxypentyl]amino]methyl]azetidin-1-yl]ethanone;

2-[4-[3-[1-(5-chloropyrimidin-2-yl)-4-piperidyl]propoxy]-2-fluoro-phenyl]-1-[3-[[[(2R,3S,4R)-2,3,4,5-tetrahydroxypentyl]amino]methyl]azetidin-1-yl]ethanone;

2-[4-[3-[1-(5-chloropyrimidin-2-yl)-4-piperidyl]propoxy]-2-fluoro-phenyl]-1-[(3R)-3-[[[(2S,3S,4R)-2,3,4,5-tetrahydroxypentyl]amino]methyl]pyrrolidin-1-yl]ethanone;

2-[[1-[2-[4-[3-[1-(5-chloropyrimidin-2-yl)-4-piperidyl]propoxy]-2-fluoro-phenyl]acetyl]azetidine-3-carbonyl]amino]ethanesulfonic acid;

3-[[1-[2-[4-[3-[1-(5-chloropyrimidin-2-yl)-4-piperidyl]propoxy]-2-fluoro-phenyl]acetyl]azetidine-3-carbonyl]amino]propane-1-sulfonic acid;

4-[[1-[2-[4-[3-[1-(5-chloropyrimidin-2-yl)-4-piperidyl]propoxy]-2-fluoro-phenyl]acetyl]azetidine-3-carbonyl]amino]butane-1-sulfonic acid;

5-[[1-[2-[4-[3-[1-(5-chloropyrimidin-2-yl)-4-piperidyl]propoxy]-2-fluoro-phenyl]acetyl]azetidine-3-carbonyl]amino]pentane-1-sulfonic acid;

6-[[1-[2-[4-[3-[1-(5-chloropyrimidin-2-yl)-4-piperidyl]propoxy]-2-fluoro-phenyl]acetyl]azetidine-3-carbonyl]amino]hexane-1-sulfonic acid;

2-[[2-[1-[2-[4-[3-[1-(5-chloropyrimidin-2-yl)-4-piperidyl]propoxy]-2-fluoro-phenyl]acetyl]azetidin-3-yl]acetyl]amino]ethanesulfonic acid;

3-[[2-[1-[2-[4-[3-[1-(5-chloropyrimidin-2-yl)-4-piperidyl]propoxy]-2-fluoro-phenyl]acetyl]azetidin-3-yl]acetyl]amino]propane-1-sulfonic acid;

4-[[2-[1-[2-[4-[3-[1-(5-chloropyrimidin-2-yl)-4-piperidyl]propoxy]-2-fluoro-phenyl]acetyl]azetidin-3-yl]acetyl]amino]butane-1-sulfonic acid;

2-[4-[3-[1-(5-chloropyrimidin-2-yl)-4-piperidyl]propoxy]-2-fluoro-phenyl]-1-[3-hydroxy-3-[[[3-hydroxy-2,2-bis(hydroxymethyl)propyl]amino]methyl]pyrrolidin-1-yl]ethanone;

1-[2-[4-[3-[1-(5-chloropyrimidin-2-yl)-4-piperidyl]propoxy]-2-fluoro-phenyl]acetyl]-3-hydroxy-N-[(2S,3R,4R,5R)-2,3,4,5,6-pentahydroxyhexyl]pyrrolidine-3-carboxamide;

1-[2-[4-[3-[1-(5-chloropyrimidin-2-yl)-4-piperidyl]propoxy]-2-fluoro-phenyl]acetyl]-3-hydroxy-N-[3-hydroxy-2,2-bis(hydroxymethyl)propyl]pyrrolidine-3-carboxamide;

2-[4-[3-[1-(5-chloropyrimidin-2-yl)-4-piperidyl]propoxy]-2-fluoro-phenyl]-1-[4-hydroxy-4-[[[3-hydroxy-2,2-bis(hydroxymethyl)propyl]amino]methyl]-1-piperidyl]ethanone;

2-[1-[2-[4-[3-[1-(5-chloropyrimidin-2-yl)-4-piperidyl]propoxy]-2-fluoro-phenyl]acetyl]-3-hydroxy-azetidin-3-yl]-N-[3-hydroxy-2,2-bis(hydroxymethyl)propyl]acetamide;

2-[4-[3-[1-(5-chloropyrimidin-2-yl)-4-piperidyl]propoxy]-2-fluoro-phenyl]-1-[3-hydroxy-3-[[[(2S,3S,4R)-2,3,4,5-tetrahydroxypentyl]amino]methyl]azetidin-1-yl]ethanone;

2-[4-[3-[1-(5-chloropyrimidin-2-yl)-4-piperidyl]propoxy]-2-fluoro-phenyl]-1-[3-hydroxy-3-[[[(2S,3S,4R)-2,3,4,5-tetrahydroxypentyl]amino]methyl]pyrrolidin-1-yl]ethanone;

2-[4-[3-[1-(5-chloropyrimidin-2-yl)-4-piperidyl]propoxy]-2-fluoro-phenyl]-1-[4-hydroxy-4-[[[(2S,3S,4R)-2,3,4,5-tetrahydroxypentyl]amino]methyl]-1-piperidyl]ethanone;

2-[4-[3-[1-(5-chloropyrimidin-2-yl)-4-piperidyl]propoxy]-2,6-difluoro-phenyl]-1-[3-hydroxy-3-[[[3-hydroxy-2,2-bis(hydroxymethyl)propyl]amino]methyl]pyrrolidin-1-yl]ethanone;

2-[4-[3-[1-(5-ethoxypyrimidin-2-yl)-4-piperidyl]propoxy]-2,6-difluoro-phenyl]-1-[3-hydroxy-3-[[[3-hydroxy-2,2-bis(hydroxymethyl)propyl]amino]methyl]pyrrolidin-1-yl]ethanone; and 2-[2,6-difluoro-4-[3-[1-[5-(methoxymethyl)pyrimidin-2-yl]-4-piperidyl]propoxy]phenyl]-1-[3-hydroxy-3-[[[3-hydroxy-2,2-bis(hydroxymethyl)propyl]amino]methyl]pyrrolidin-1-yl]ethanone;

or a pharmaceutically acceptable salt, solvate, or stereoisomer thereof.

16. A pharmaceutical composition comprising a compound of claim 1, or a pharmaceutically acceptable salt, solvate, or stereoisomer thereof, and at least one pharmaceutically acceptable excipient.

17. A method of treating a condition or disorder involving the gut-brain axis in a subject in need thereof, the method comprising administering to the subject a therapeutically effective amount of a compound of claim 1, or a pharmaceutically acceptable salt, solvate, or stereoisomer thereof; wherein the condition or disorder is associated with GPR119 activity.

18. The method of claim 17, wherein the condition or disorder is a metabolic disorder or a nutritional disorder.

19. The method of claim 17, wherein the condition or disorder is type 2 diabetes, hyperglycemia, metabolic syndrome, obesity, hypercholesterolemia, nonalcoholic steatohepatitis, hypertension, short bowel syndrome, intestinal failure, intestinal insufficiency, chemotherapy-induced enteritis or radiation-induced enteritis.

20. The method of claim 17, further comprising administering one or more additional therapeutic agents to the subject; wherein the one or more additional therapeutic agents are selected from a TGR5 agonist, a GPR40 agonist, an SSTR5 antagonist, an SSTR5 inverse agonist, a CCK1 agonist, a PDE4 inhibitor, a DPP-4 inhibitor, a GLP-1 receptor agonist, metformin, or a combination thereof.

* * * * *